US011338007B2

(12) United States Patent
Chal et al.

(10) Patent No.: US 11,338,007 B2
(45) Date of Patent: *May 24, 2022

(54) COMBINATION FORMULATION OF THREE ANTIVIRAL COMPOUNDS

(71) Applicant: Gilead Sciences, Inc., Foster City, CA (US)

(72) Inventors: Ben Chal, Millbrae, CA (US); Elham Nejati, San Mateo, CA (US); Rowchanak Pakdaman, San Carlos, CA (US); Dimitrios Stefanidis, Saratoga, CA (US)

(73) Assignee: Gilead Sciences, Inc., Foster City, CA (US)

( * ) Notice: Subject to any disclaimer, the term of this patent is extended or adjusted under 35 U.S.C. 154(b) by 306 days.

This patent is subject to a terminal disclaimer.

(21) Appl. No.: 16/306,424

(22) PCT Filed: Jun. 1, 2017

(86) PCT No.: PCT/US2017/035539
§ 371 (c)(1),
(2) Date: Nov. 30, 2018

(87) PCT Pub. No.: WO2017/210483
PCT Pub. Date: Dec. 7, 2017

(65) Prior Publication Data
US 2020/0323894 A1 Oct. 15, 2020

Related U.S. Application Data

(60) Provisional application No. 62/344,904, filed on Jun. 2, 2016.

(51) Int. Cl.
| | | |
|---|---|---|
| *A61K 38/06* | (2006.01) | |
| *A61K 9/20* | (2006.01) | |
| *A61K 31/4188* | (2006.01) | |
| *A61K 31/7072* | (2006.01) | |
| *A61K 31/4985* | (2006.01) | |
| *A61K 9/14* | (2006.01) | |
| *A61K 31/4178* | (2006.01) | |
| *A61K 47/32* | (2006.01) | |
| *A61K 47/38* | (2006.01) | |
| *A61K 9/16* | (2006.01) | |

(52) U.S. Cl.
CPC ............ *A61K 38/06* (2013.01); *A61K 9/146* (2013.01); *A61K 9/1611* (2013.01); *A61K 9/1617* (2013.01); *A61K 9/1635* (2013.01); *A61K 9/1652* (2013.01); *A61K 9/2009* (2013.01); *A61K 9/2013* (2013.01); *A61K 9/2027* (2013.01); *A61K 9/2054* (2013.01); *A61K 31/4178* (2013.01); *A61K 31/4188* (2013.01); *A61K 31/4985* (2013.01); *A61K 31/7072* (2013.01); *A61K 47/32* (2013.01); *A61K 47/38* (2013.01)

(58) Field of Classification Search
CPC .... A61K 38/06; A61K 31/4178; A61K 47/32; A61K 47/38; A61K 31/4985; A61K 9/146; A61K 9/1611; A61K 9/1617; A61K 9/1635; A61K 9/1652; A61K 9/2009; A61K 9/2013; A61K 9/2027; A61K 9/2054; A61K 31/4188; A61K 31/7072; A61K 9/2077; A61K 31/498; A61K 31/661; A61K 2300/00; A61P 43/00; A61P 31/14; A61P 31/12
See application file for complete search history.

(56) References Cited

U.S. PATENT DOCUMENTS

| | | | |
|---|---|---|---|
| 7,964,580 | B2 | 6/2011 | Sofia et al. |
| 8,334,270 | B2 | 12/2012 | Sofia et al. |
| 8,575,135 | B2 | 11/2013 | Bacon et al. |
| 8,580,765 | B2 | 11/2013 | Sofia et al. |
| 8,618,076 | B2 | 12/2013 | Ross et al. |
| 8,735,372 | B2 | 5/2014 | Du et al. |
| 8,735,569 | B2 | 5/2014 | Ross et al. |
| 8,906,880 | B2 | 12/2014 | Du et al. |
| 8,921,341 | B2 | 12/2014 | Bacon et al. |
| 8,940,718 | B2 | 1/2015 | Bacon et al. |
| 8,957,046 | B2 | 2/2015 | Du et al. |

(Continued)

FOREIGN PATENT DOCUMENTS

| | | |
|---|---|---|
| WO | WO 2008/121634 | 10/2008 |
| WO | WO 2011/123645 | 10/2011 |

(Continued)

OTHER PUBLICATIONS

Anonymous, "Effect of Sofosbuvir/Velpatasvir/GS-9857 Fixed-Dose Combination on the Pharmacokinetics of a Representative Hormonal Contraceptive Medication, Norgestimate/Ethinyl Estradiol", Tabular View—Clinical Trials.gov, Retrieved from the Internet: https://web.archive.org/web/20151010022854/https://clinicaltrials.gov/ct2/show/record/NCT02533 427, retrieved on Aug. 1, 2017, p. 3, paragraph Intervention.

(Continued)

*Primary Examiner* — Snigdha Maewall
(74) *Attorney, Agent, or Firm* — Sheppard Mullin Richter & Hampton LLP

(57) ABSTRACT

Disclosed are pharmaceutical compositions comprising three antiviral compounds. In particular, the pharmaceutical compositions comprise an effective amount of velpatasvir, an effective amount of sofosbuvir, and an effective amount of voxilaprevir. Also disclosed are methods of use for the pharmaceutical composition.

44 Claims, 34 Drawing Sheets

(56) References Cited

U.S. PATENT DOCUMENTS

| | | | |
|---|---|---|---|
| 9,085,573 | B2 | 7/2015 | Du et al. |
| 9,284,342 | B2 | 3/2016 | Ross et al. |
| 9,296,782 | B2 | 3/2016 | Bjornson et al. |
| 9,562,058 | B2 | 2/2017 | Bringley et al. |
| 9,585,906 | B2 | 3/2017 | Du et al. |
| 9,630,972 | B2 | 4/2017 | Lapina et al. |
| 9,655,944 | B2 | 5/2017 | Bjornson et al. |
| 9,757,406 | B2 | 9/2017 | Gorman et al. |
| 9,862,728 | B2 | 1/2018 | Bringley et al. |
| 9,868,745 | B2 | 1/2018 | Bacon et al. |
| 9,884,873 | B2 | 2/2018 | Lapina et al. |
| 10,086,011 | B2 | 10/2018 | Gorman et al. |
| 2013/0136776 | A1* | 5/2013 | Cleary ................ A61K 9/2009 424/400 |
| 2013/0172239 | A1* | 7/2013 | Gao ................... A61K 31/4178 514/4.3 |
| 2014/0017198 | A1* | 1/2014 | Bjornson ............ C07D 241/36 424/85.4 |
| 2015/0064252 | A1 | 3/2015 | Gorman et al. |
| 2015/0064253 | A1 | 3/2015 | Gorman et al. |
| 2015/0150896 | A1 | 6/2015 | Cleary et al. |
| 2015/0175655 | A1 | 6/2015 | Bjornson et al. |
| 2016/0130300 | A1 | 5/2016 | Bjornson et al. |
| 2016/0354400 | A1 | 12/2016 | Ross et al. |
| 2017/0290827 | A1 | 10/2017 | Bjornson et al. |
| 2017/0360874 | A1 | 12/2017 | Chal et al. |
| 2018/0000855 | A1 | 1/2018 | Du et al. |
| 2018/0021362 | A1 | 1/2018 | Gorman et al. |
| 2018/0186806 | A1 | 7/2018 | Bacon et al. |
| 2019/0008858 | A1 | 1/2019 | Bjornson et al. |

FOREIGN PATENT DOCUMENTS

| | | | |
|---|---|---|---|
| WO | WO 2013/075029 | 5/2013 | |
| WO | WO-2013082003 | 6/2013 | |
| WO | WO 2013/101550 | 7/2013 | |
| WO | WO-2013101550 A1 * | 7/2013 | .......... A61K 31/501 |
| WO | WO 2014/008285 | 1/2014 | |
| WO | WO 2014/120981 | 8/2014 | |
| WO | WO 2015/030853 | 3/2015 | |
| WO | WO 2015/030854 | 3/2015 | |
| WO | WO-2015030853 A1 * | 3/2015 | ......... A61K 31/7056 |
| WO | WO 2015/100144 | 7/2015 | |
| WO | WO 2015/191431 | 12/2015 | |
| WO | WO 2016/055576 | 4/2016 | |

OTHER PUBLICATIONS

International Preliminary Report on Patentability for International Application No. PCT/US2017/035539 dated Dec. 4, 2018. (8 pages).
International Search Report and Written Opinion dated Aug. 16, 2017 for PCT/US2017/035539. (16 pages).
Official Action for Bolivian Patent Application No. SP-00113-2017 dated Oct. 30, 2018. (11 pages).
Anonymous. Study to Evaluate Effect of Sofosbuvir/Velpatasvir/ GS-9857 Fixed-Dose Combination on the Pharmacokinetics of a Representative Hormonal Contraceptive Medication, Norgestimate/ Ethinyl Estradiol. CliniclaTrials.gov, A service of the U.S. National Institutes of health. Identifier: NCT02533427 Aug. 2015. https:// web.archive.org/web/20151010052206/https:/clinicaltrials.gov/ct2/ show/study/NCT02533427; retrieved on Dec. 10, 2021. 4 pages.
Office Action for Mexican Patent Application No. MX/a/2018/ 014790 dated Sep. 13, 2021. 10 pages.

* cited by examiner

COMBINATION FORMULATION OF THREE ANTIVIRAL COMPOUNDS

CROSS REFERENCE TO RELATED APPLICATION

Priority is claimed to U.S. Provisional Application Ser. No. 62/344,904, filed on Jun. 2, 2016, the contents of which are incorporated by reference in its entirety.

BACKGROUND

Hepatitis C is recognized as a chronic viral disease of the liver. Although drugs targeting the liver are in wide use and have shown effectiveness, toxicity and other side effects have limited their usefulness. Inhibitors of hepatitis C virus (HCV) are useful to limit the establishment and progression of infection by HCV as well as in diagnostic assays for HCV.

Velpatasvir, sofosbuvir and voxilaprevir are known to be effective anti-HCV agents, as described for example in U.S. Pat. Nos. 7,964,580, 8,575,135 and 9,296,782. However, the therapeutic benefits of the administration of velpatasvir, sofosbuvir and voxilaprevir, in combination or in a particular co-formulation, were not heretofore known.

SUMMARY

It has now been discovered that three active antiviral agents, i.e., sofosbuvir, velpatasvir and voxilaprevir, may be co-formulated into a fixed dosage composition. The resulting tablet comprising these three active antiviral agents demonstrates surprising and unexpected benefits, e.g., excellent stability and dissolution profiles.

Accordingly, the present disclosure, in one embodiment, provides a pharmaceutical composition comprising:

a) an effective amount of velpatasvir, wherein velpatasvir is substantially amorphous;

b) an effective amount of sofosbuvir, wherein sofosbuvir is substantially crystalline; and c) an effective amount of voxilaprevir, wherein voxilaprevir is substantially amorphous.

In some embodiments, velpatasvir is formulated as a solid dispersion comprising velpatasvir dispersed within a polymer matrix formed by a pharmaceutically acceptable polymer A. In one embodiment, polymer A is hydrophilic. In another embodiment, polymer A is a non-ionic polymer. In yet another embodiment, polymer A is an ionic polymer. In various embodiments, polymer A is hypromellose, copovidone, povidone, polyvinyl caprolactam-polyvinyl acetate-polyethylene glycol, hydroxypropyl methylcellulose acetate-succinate, hydroxypropyl methylcellulose phthalate, or cellulose acetate phthalate. In certain embodiments, the weight ratio of velpatasvir to polymer A in the solid dispersion is from about 5:1 to about 1:5.

In some embodiments, voxilaprevir is formulated as a solid dispersion comprising voxilaprevir dispersed within a polymer matrix formed by a pharmaceutically acceptable polymer B. In one embodiment, polymer B is hydrophilic. In another embodiment, polymer B is a non-ionic polymer. In yet another embodiment, polymer B is an ionic polymer. In various embodiments, polymer B is hypromellose, copovidone, povidone, polyvinyl caprolactam-polyvinyl acetate-polyethylene glycol, hydroxypropyl methylcellulose acetate-succinate, hydroxypropyl methylcellulose phthalate, or cellulose acetate phthalate. In certain embodiments, the weight ratio of velpatasvir to polymer B in the solid dispersion is from about 5:1 to about 1:5.

In some embodiments, the substantially crystalline sofosbuvir has XRPD 2θ-reflections at about: 6.1, 20.1, and 20.8 °2θ±0.2. In one embodiment, the substantially crystalline sofosbuvir has XRPD 2θ-reflections at about: 6.1, 8.2, 10.4, 12.7, 17.2, 17.7, 18.0, 18.8, 19.4, 19.8, 20.1, 20.8, 21.8, and 23.3 °2θ±0.2. In another embodiment, a trace amount of the substantially crystalline sofosbuvir has XRPD 2θ-reflections at about: 12.6 and 13.5 °2θ±0.2.

In some embodiments, the pharmaceutical compositions disclosed herein comprise from about 20% to about 80% w/w of sofosbuvir. In certain embodiments, the pharmaceutical compositions disclosed herein comprise from about 20% to about 55% w/w of sofosbuvir. In one embodiment, the pharmaceutical compositions disclosed herein comprise about 31% w/w of sofosbuvir.

In some embodiments, the pharmaceutical compositions disclosed herein comprise from about 1% to about 45% w/w of the solid dispersion comprising velpatasvir. In certain embodiments, the pharmaceutical compositions disclosed herein comprise from about 5% to about 25% w/w of the solid dispersion comprising velpatasvir. In one embodiment, the pharmaceutical compositions disclosed herein comprise about 15% w/w of the solid dispersion comprising velpatasvir.

In some embodiments, the pharmaceutical compositions disclosed herein comprise from about 1% to about 45% w/w of the solid dispersion comprising voxilaprevir. In certain embodiments, the pharmaceutical compositions disclosed herein comprise from about 5% to about 25% w/w of the solid dispersion comprising voxilaprevir. In one embodiment, the pharmaceutical compositions disclosed herein comprise about 15% w/w of the solid dispersion comprising voxilaprevir.

In some embodiments, the pharmaceutical compositions disclosed herein comprise: a) about 20 to about 40% w/w of sofosbuvir; b) about 10 to about 30% w/w of the solid dispersion comprising velpatasvir; and c) about 10 to about 30% w/w of the solid dispersion comprising voxilaprevir. In one embodiment, the pharmaceutical compositions disclosed herein comprise: a) about 31% w/w of sofosbuvir; b) about 15% w/w of the solid dispersion comprising velpatasvir; and c) about 15% w/w of the solid dispersion comprising voxilaprevir.

In some embodiments, the pharmaceutical compositions disclosed herein further comprise a diluent, a disintegrant, a lubricant, a glidant or any combination thereof.

In some embodiments, the diluent is selected from the group consisting of: dicalcium phosphate, cellulose, compressible sugars, dibasic calcium phosphate dehydrate, lactose, lactose monohydrate, mannitol, microcrystalline cellulose, starch, tribasic calcium phosphate, and combinations thereof. In another embodiment, the diluent is a mixture of microcrystalline cellulose and lactose monohydrate and is present in an amount from about 10 to about 40% w/w.

In some embodiments, the disintegrant is selected from the group consisting of: croscarmellose sodium, crospovidone, microcrystalline cellulose, modified corn starch, povidone, pregelatinized starch, sodium starch glycolate, and combinations thereof. In one embodiment, the disintegrant is croscarmellose sodium and is present in an amount from about 1 to about 15% w/w.

In some embodiments, the lubricant is selected from the group consisting of: calcium stearate, magnesium stearate, polyethylene glycol, sodium stearyl fumarate, stearic acid, talc, and combinations thereof. In one embodiment, the lubricant is magnesium stearate and is present in an amount from about 0.5 to about 3% w/w.

In some embodiments, the glidant is selected from the group consisting of: colloidal silicon dioxide, talc, starch, starch derivatives, and combinations thereof. In one embodiment, the glidant is colloidal silicon dioxide and is present in an amount from about 0.5 to about 3% w/w.

In some embodiments, the pharmaceutical compositions disclosed herein further comprise: about 5 to about 25% w/w of microcrystalline cellulose; about 5 to about 15% w/w of lactose monohydrate; about 1 to about 15% w/w of croscarmellose sodium; about 0.5 to about 3% w/w of magnesium stearate; and about 0.5 to about 3% w/w of colloidal silicon dioxide. In one embodiment, the pharmaceutical compositions disclosed herein further comprise: about 19% w/w of microcrystalline cellulose; about 9% w/w of lactose monohydrate; about 8% w/w of croscarmellose sodium; about 2% w/w of magnesium stearate; and about 1% w/w of colloidal silicon dioxide.

In some embodiments, the pharmaceutical compositions disclosed herein may be formulated as a tablet. In one embodiment, the tablet further comprises a diluent as disclosed herein, a disintegrant as disclosed herein, a lubricant as disclosed herein, a glidant as disclosed herein, or any combination thereof. In one embodiment, a tablet comprises:

intragranular components comprising: an effective amount of velpatasvir, wherein velpatasvir is substantially amorphous; an effective amount of sofosbuvir, wherein sofosbuvir is substantially crystalline; an effective amount of voxilaprevir, wherein voxilaprevir is substantially amorphous; a diluent as disclosed herein, a disintegrant as disclosed herein, a lubricant as disclosed herein, and a glident as disclosed herein; and extragranular components comprising: a diluent as disclosed herein, a disintegrant as disclosed herein, and a lubricant as disclosed herein.

In one embodiment, the intragranular and extragranular diluents in the tablet may be the same. In one embodiment, the intragranular and extragranular diluents in the tablet may be different. In one embodiment, the intragranular and extragranular disintegrants in the tablet may be the same. In one embodiment, the intragranular and extragranular disintegrants in the tablet may be different. In one embodiment, the intragranular and extragranular lubricants in the tablet may be the same. In one embodiment, the intragranular and extragranular lubricants in the tablet may be different.

In some embodiments, the pharmaceutical compositions disclosed herein are formulated for immediate release.

The present disclosure, in another embodiment, provides a pharmaceutical dosage form comprising the pharmaceutical compositions disclosed herein, wherein the pharmaceutical dosage form comprises from about 5 to about 500 mg of velpatasvir. In certain embodiments, the pharmaceutical dosage forms disclosed herein comprise from about 5 to about 300 mg of velpatasvir. In one embodiment, the pharmaceutical dosage forms disclosed herein comprise about 100 mg of velpatasvir. In another embodiment, the pharmaceutical dosage forms disclosed herein comprise about 200 mg of the solid dispersion comprising velpatasvir.

In some embodiments, the pharmaceutical dosage forms disclosed herein comprise from about 5 to about 500 mg of voxilaprevir. In certain embodiments, the pharmaceutical dosage forms disclosed herein comprise from about 5 to about 300 mg of voxilaprevir. In one embodiment, the pharmaceutical dosage forms disclosed herein comprise about 100 mg of voxilaprevir. In another embodiment, the pharmaceutical dosage forms disclosed herein comprise about 200 mg of the solid dispersion comprising voxilaprevir.

In some embodiments, the pharmaceutical dosage forms disclosed herein comprise from about 200 to about 600 mg of sofosbuvir. In certain embodiments, the pharmaceutical dosage forms disclosed herein comprise from about 300 to about 500 mg of sofosbuvir. In one embodiment, the pharmaceutical dosage forms disclosed herein comprise about 400 mg of sofosbuvir.

The present disclosure, in another embodiment, provides a pharmaceutical dosage form comprising: a) about 100 mg of velpatasvir; b) about 400 mg of sofosbuvir; and c) about 100 mg of voxilaprevir. In another embodiment, the present disclosure provides a pharmaceutical dosage form comprising: a) about 200 mg of the solid dispersion comprising velpatasvir; b) about 400 mg of sofosbuvir; and c) about 200 mg of the solid dispersion comprising voxilaprevir.

The present disclosure, in yet another embodiment, provides a tablet comprising the pharmaceutical dosage forms disclosed herein. In one embodiment, a tablet comprises: a) about 100 mg of velpatasvir; b) about 400 mg of sofosbuvir; and c) about 100 mg of voxilaprevir. In another embodiment, a tablet comprises: a) about 200 mg of the solid dispersion comprising velpatasvir; b) about 400 mg of sofosbuvir; and c) about 200 mg of the solid dispersion comprising voxilaprevir. In some embodiments, the tablets disclosed herein comprise a film coating.

The present disclosure, in another embodiment, provides a method of treating hepatitis C in a human patient in need thereof, comprising administering to the patient a therapeutically effective amount of a pharmaceutical composition as disclosed herein, a pharmaceutical dosage form as disclosed herein, or a tablet as disclosed herein.

In some embodiments, the pharmaceutical composition as disclosed herein, pharmaceutical dosage form as disclosed herein, or tablet as disclosed herein is administered for about 12 weeks or less. In one embodiment, the pharmaceutical composition as disclosed herein, pharmaceutical dosage form as disclosed herein, or tablet as disclosed herein is administered once daily for about 12 weeks.

In some embodiments, the pharmaceutical composition as disclosed herein, pharmaceutical dosage form as disclosed herein, or tablet as disclosed herein is administered for about 8 weeks or less. In one embodiment, the pharmaceutical composition as disclosed herein, pharmaceutical dosage form as disclosed herein, or tablet as disclosed herein is administered once daily for about 8 weeks.

In some embodiments, the pharmaceutical composition as disclosed herein, pharmaceutical dosage form as disclosed herein, or tablet as disclosed herein is administered for about 6 weeks or less. In one embodiment, the pharmaceutical composition as disclosed herein, pharmaceutical dosage form as disclosed herein, or tablet as disclosed herein is administered once daily for about 6 weeks.

In some embodiments, the pharmaceutical composition as disclosed herein, pharmaceutical dosage form as disclosed herein, or tablet as disclosed herein is administered for about 4 weeks or less. In one embodiment, the pharmaceutical composition as disclosed herein, pharmaceutical dosage form as disclosed herein, or tablet as disclosed herein is administered once daily for about 4 weeks.

In some embodiments, the hepatitis C virus genotype is 1, 2, 3, 4, 5, or 6. In particular embodiments, the hepatitis C virus is genotype 1a, 1b, 2a, 2b, 2c, 2d, 3a, 3b, 3c, 3d, 3e, 3f, 4a, 4b, 4c, 4d, 4e, 4f, 4g, 4h, 4i, 5a, or 6a.

DETAILED DESCRIPTION

1. Definitions

Figure 1:
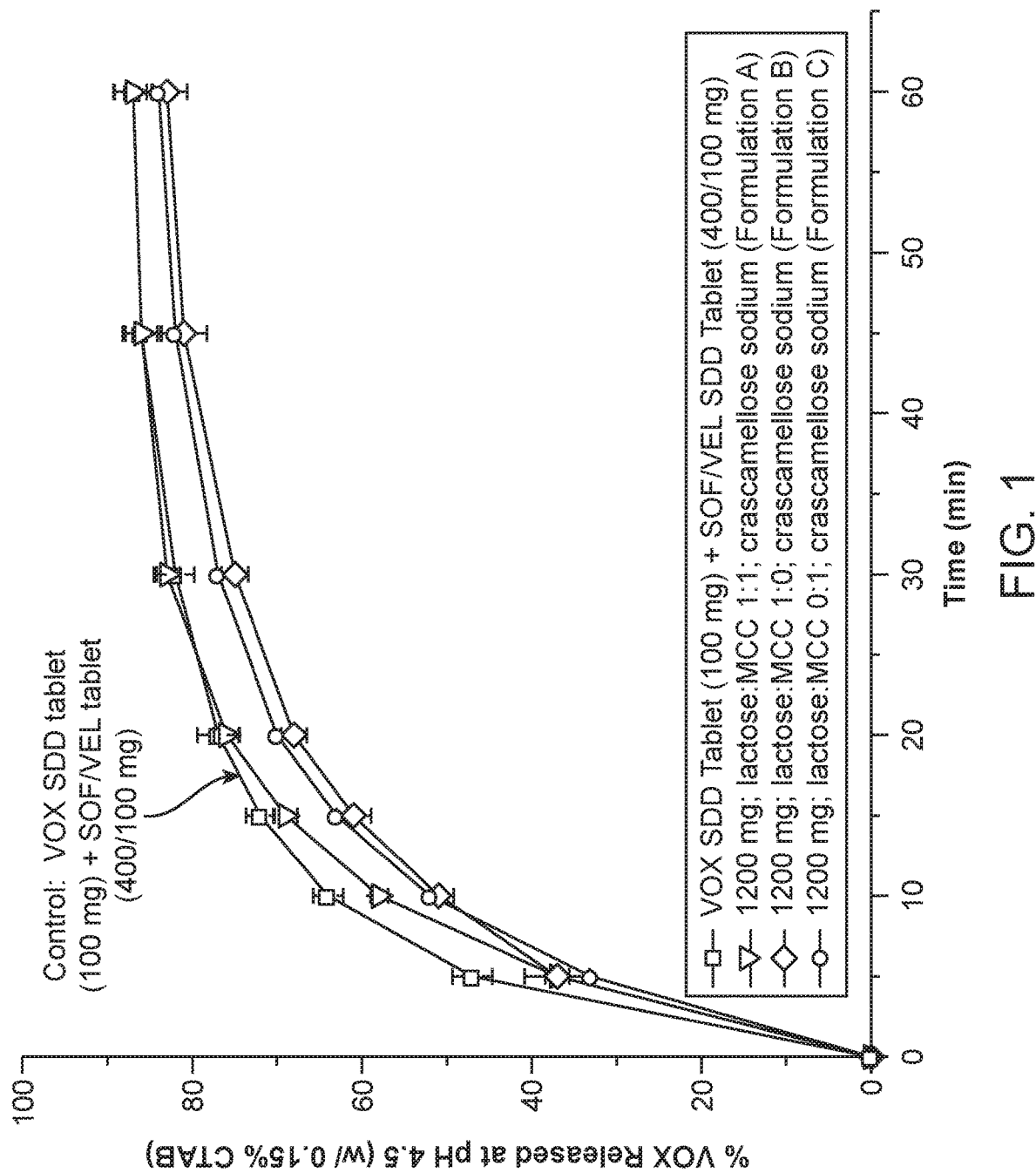
FIG. 1 depicts dissolution profiles of voxilaprevir in co-dry granulation sofosbuvir/velpatasvir/voxilaprevir tablets (400/100/100 mg) as a function of intragranular filler composition.

As used in the present disclosure, the following words and phrases are generally intended to have the meanings as set forth below, except to the extent that the context in which they are used indicates otherwise.

The term "comprise" and variations thereof, such as, "comprises" and "comprising" are to be construed in an open, inclusive sense, that is, as "including, but not limited to." Further, the singular forms "a," "an," and "the" include plural references unless the context clearly dictates otherwise. Thus, reference to "the compound" includes a plurality of such compounds, and reference to "the assay" includes reference to one or more assays and equivalents thereof known to those skilled in the art.

As used herein, the term "about" used in the context of quantitative measurements means the indicated amount±10%. For example, "about 2:8" would mean 1.8-2.2:7.2-8.8.

Recitation of numeric ranges of values throughout the disclosure is intended to serve as a shorthand notation of referring individually to each separate value falling within the range inclusive of the values defining the range, and each separate value is incorporated in the specification as it were individually recited herein.

The term "% w/w" as used herein refers to the weight of a component based on the total weight of a composition comprising the component. For example, if component A is present in an amount of 50% w/w in a 100 mg composition, component A is present in an amount of 50 mg.

The terms "effective amount," "pharmaceutically effective amount" and "therapeutically effective amount" refer to an amount that may be effective to elicit the desired biological or medical response, including the amount of a compound that, when administered to a subject for treating a disease, is sufficient to effect such treatment for the disease. The effective amount will vary depending on the compound, the disease and its severity and the age, weight, etc., of the subject to be treated. The effective amount can include a range of amounts. Further, an effective amount includes amounts of an agent which are effective when combined with other agents.

The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order (glass transition).

The term "substantially amorphous" as used herein is intended to mean that greater than 50%; or greater than 55%; or greater than 60%; or greater than 65%; or greater than 70%; or greater than 75%; or greater than 80%; or greater than 85%; or greater than 90%; or greater than 95%, or greater than 99% of the compound present in a composition is in amorphous form. "Substantially amorphous" can also refer to material which has no more than about 20% crystallinity, or no more than about 10% crystallinity, or no more than about 5% crystallinity, or no more than about 2% crystallinity.

The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order (melting point).

The term "substantially crystalline" as used herein is intended to mean that greater than 50%; or greater than 55%; or greater than 60%; or greater than 65%; or greater than 70%; or greater than 75%; or greater than 80%; or greater than 85%; or greater than 90%; or greater than 95%, or greater than 99% of the compound present in a composition is in crystalline form. "Substantially crystalline" can also refer to material which has no more than about 20%, or no more than about 10%, or no more than about 5%, or no more than about 2% in the amorphous form.

The term "solid dispersion" ("SD") refers to the dispersion of one or more active agents in a polymer matrix at solid state prepared by a variety of methods, including spray drying, the melting (fusion), solvent, or the melting-solvent method. For instance, in some embodiments, the pharmaceutical compositions disclosed herein may comprise a solid dispersion of voxilaprevir, wherein voxilaprevir is dispersed within a polymer matrix formed by a pharmaceutically acceptable polymer such as copovidone. Similarly, in some embodiments, the pharmaceutical compositions disclosed herein may comprise a solid dispersion of velpatasvir, wherein voxilaprevir is dispersed within a polymer matrix formed by a pharmaceutically acceptable polymer such as copovidone.

The term "spray-dried solid dispersion" ("SSD") refers to a solid dispersion prepared by a spray-drying process.

The term "amorphous solid dispersion" as used herein, refers to stable solid dispersions comprising an amorphous active agent and a polymer. By "amorphous active agent," it is meant that the amorphous solid dispersion contains the active agent in a substantially amorphous solid state form. For instance, in some embodiments in which the pharmaceutical compositions disclosed herein comprise a solid dispersion of voxilaprevir, voxilaprevir may be in a substantially amorphous solid state form. Likewise, in some embodiments in which the pharmaceutical compositions disclosed herein comprise a solid dispersion of velpatasvir, velpatasvir may be in a substantially amorphous solid state form.

The term "polymer matrix" as used herein is defined to mean compositions comprising one or more polymers in which the active agent is dispersed or included within the matrix.

The term "polymer" refers to a chemical compound or mixture of compounds consisting of repeating structural units created through a process of polymerization. Suitable polymers useful in this invention are described throughout.

The term "pharmaceutically acceptable" refers to a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable vehicles (e.g., carriers, adjuvants, and/or other excipients) have preferably met the required standards of toxicological and manufacturing testing and/or are included on the Inactive Ingredient Guide prepared by the U.S. Food and Drug administration. For example, it is commonly required that such a material be essentially sterile, e.g., for injectables.

The term "carrier" or "pharmaceutically acceptable carrier" refers to diluents, disintegrants, precipitation inhibitors, surfactants, glidants, binders, lubricants, and other excipients and vehicles with which the compound is administered. Carriers are generally described herein and also in "Remington's Pharmaceutical Sciences" by E. W. Martin. Examples of carriers may include, but are not limited to, aluminum monostearate, aluminum stearate, carboxymethylcellulose, carboxymethylcellulose sodium, croscarmellose sodium, crospovidone, glyceryl isostearate, glyceryl monostearate, hydroxyethyl cellulose, hydroxyethyl cellulose, hydroxymethyl cellulose, hydroxyoctacosanyl hydroxystearate, hydroxypropyl cellulose, hydroxypropyl cellulose, hydroxypropyl methylcellulose, lactose, lactose monohydrate, magnesium stearate, mannitol, microcrystalline cellulose, poloxamer 124, poloxamer 181, poloxamer 182, poloxamer 188, poloxamer 237, poloxamer 407, povidone, silicon dioxide, colloidal silicon dioxide, silicone, silicone adhesive 4102, and silicone emulsion. It should be understood, however, that the carriers selected for the pharmaceutical compositions, and the amounts of such carriers in the composition, may vary depending on the method of formulation (e.g., dry granulation formulation, solid dispersion formulation).

The term "diluent" refers to chemical compounds that are used to dilute the compound of interest prior to delivery. Diluents can also serve to stabilize compounds. Non-limiting examples of diluents include starch, saccharides, disaccharides, sucrose, lactose, lactose monohydrate, polysaccharides, cellulose, cellulose ethers, hydroxypropyl cellulose, microcrystalline cellulose, sugar alcohols, xylitol, sorbitol, maltitol, compressible sugars, calcium or sodium carbonate, dicalcium phosphate, dibasic calcium phosphate dehydrate, mannitol, and tribasic calcium phosphate.

The term "binder" when used herein relates to any pharmaceutically acceptable film which can be used to bind together the active and inert components of the carrier together to maintain cohesive and discrete portions. Non-limiting examples of binders include hydroxypropylcellulose, hydroxypropylmethylcellulose, povidone, copovidone, and ethyl cellulose.

The term "disintegrant" refers to a substance which, upon addition to a solid preparation, facilitates its break-up or disintegration after administration and permits the release of an active ingredient as efficiently as possible to allow for its rapid dissolution. Non-limiting examples of disintegrants include maize starch, sodium starch glycolate, croscarmellose sodium, crospovidone, microcrystalline cellulose, modified corn starch, sodium carboxymethyl starch, povidone, pregelatinized starch, and alginic acid.

The term "lubricant" refers to a substance added to a powder blend to prevent the compacted powder mass from sticking to the equipment during the tableting or encapsulation process. A lubricant can aid the ejection of the tablet form the dies, and can improve powder flow. Non-limiting examples of lubricants include magnesium stearate, stearic acid, silica, fats, calcium stearate, polyethylene glycol, sodium stearyl fumarate, or talc; and solubilizers such as fatty acids including lauric acid, oleic acid, and $C_8/C_{10}$ fatty acid.

The term "film coating" refers to a thin, uniform, film on the surface of a substrate (e.g., tablet). Film coatings are particularly useful for protecting the active ingredient(s) from photolytic degradation. Non-limiting examples of film coatings include polyvinylalcohol based, hydroxyethylcellulose, hydroxypropylmethylcellulose, sodium carboxymethylcellulose, polyethylene glycol 4000 and cellulose acetate phthalate film coatings.

The term "glidant" refers to substances used in tablet and capsule formulations to improve flow-properties during tablet compression and to produce an anti-caking effect. Examples of glidants may include colloidal silicon dioxide, talc, fumed silica, starch, starch derivatives, and bentonite.

"Treating" and "treatment" of a disease or condition include the following: (1) preventing or reducing the risk of developing the disease or condition, i.e., causing the clinical symptoms of the disease or condition not to develop in a subject that may be exposed to or predisposed to the disease or condition but does not yet experience or display symptoms of the disease or condition, (2) inhibiting the disease or condition, i.e., arresting or reducing the development of the disease or condition or the clinical symptoms thereof, and (3) relieving the disease or condition, i.e., causing regression of the disease or condition or the clinical symptoms thereof.

The term "sustained virologic response" refers to the absence of detectable RNA (or wherein the RNA is below the limit of detection) of a virus (i.e., HCV) in a patient sample (i.e., blood sample) for a specific period of time after discontinuation of a treatment. For example, a SVR at 4 weeks indicates that RNA was not detected or was below the limit of detection in the patient at 4 weeks after discontinuing HCV therapy.

"SOF/VEL/VOX fixed-dose combination" or "SOF/VELVOX FDC" refers to a pharmaceutical formulation containing a combination of sofosbuvir, velpatasvir, and voxilaprevir. In specific embodiments, the SOF/VELVOX FDC is a tablet containing about 400 mg of crystalline sofosbuvir, about 200 mg of amorphous VEL SSD (equivalent to 100 mg of velpatasvir), and about 200 mg of amorphous VOX SSD (equivalent to 100 mg of voxilaprevir).

2. Pharmaceutical Compositions

Provided herein are pharmaceutical compositions comprising a combination of an effective amount of velpatasvir (or a solid dispersion comprising velpatasvir), an effective amount of sofosbuvir, and an effective amount of voxilaprevir (or a solid dispersion comprising voxilaprevir), wherein velpatasvir is substantially amorphous, sofosbuvir is substantially crystalline, and voxilaprevir is substantially amorphous.

A. Velpatasvir

Velpatasvir is a selective inhibitor of non-structural 5A (NS5A) protein (see, e.g., WO 2013/075029 and U.S. Pat. No. 8,575,135 describing the synthesis of velpatasvir). The NS5A nonstructural protein is a phosphoprotein, with no apparent enzymatic activity; however, it acts as a multifunctional regulator of cellular pathways, including host cell growth, immunity and innate immunity, and virus replication. NS5A is associated with host cell membranes through its N-terminal amphipathic helix, where it is a part of the replication complex. (Elazar et al., J. Virol. (2004) 78: 11393-11400 and Penin et al., J. Biol. Chem. (2004) 279: 40835-40843.) Recent studies suggest that NS5A is organized into three domains: the first 213 amino acids in the N-terminal domain constitutes domain I and contains a zinc binding motif suggesting that the protein is a zinc metalloprotein and domains II and III are in the C-terminal region of the protein. (Tellinghuisen et al., J. Biol. Chem. (2004) 279: 48576-48587 and Tellinghuisen et al., Nature (2005) 435: 374-379.) NS5A exists in two phosphorylated forms: a basal form of 56 kD and a hyperphosphorylated form of 58 kD. The protein is phosphorylated at specific sites, primarily on serine residue within domains 11 and III, by host cell kinases. (Ide et al., Gene (1997) 201: 151-158; Kaneko et al., Biochem. Biophys. Res. Commun. (1994) 205: 320-326; Katze et al., Virology (2000) 278: 501-513; Reed et al., J. Biol. Chem. (1999) 274: 28011-28018; Reed et al., J. Virol. (1997) 71: 7187-7197; and Tanji et al., J. Virol. (1995) 69: 3980-3986.)

Velpatasvir has the following chemical structure:

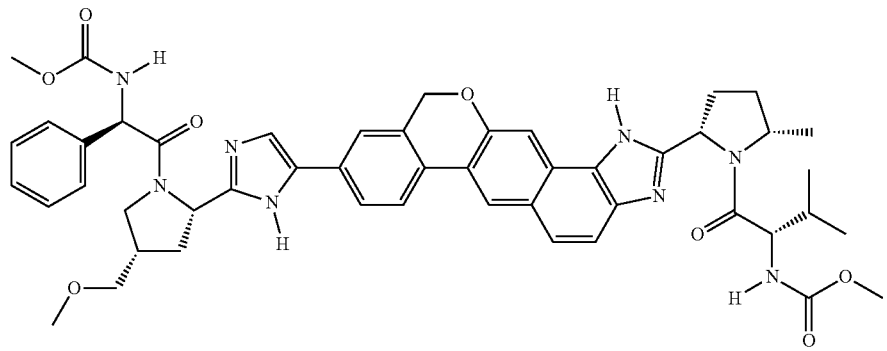

The chemical name of velpatasvir is methyl {(2S)-1-[(2S,5S)-2-(9-{2-[(2S,4S)-1-{(2R)-2-[(methoxycarbonyl)amino]-2-phenylacetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate.

Velpatasvir can have any one of a variety of forms including a free base form, crystalline forms, salts thereof, hydrates thereof, solvates thereof, and an amorphous form. It is within the skill of those in the art to select velpatasvir having a particular form for the pharmaceutical compositions disclosed herein. Crystalline forms I-XVIII of velpatasvir, and methods of preparing the same, are described in U.S. Patent Appl. Pub. No. 2015/0361085, which is incorporated by reference in its entirety. Crystalline forms I-XVIII of velpatasvir, which can serve as the starting materials for making the amorphous version, have the following characteristic XRPD pattern 2θ-values measured according to the XRPD methods disclosed therein (e.g., via a diffractometer using Cu—Kα radiation):
  (a) 4.8, 5.2, 6.0 °2θ±0.2 (Form I);
  (b) 6.1, 7.3, 9.6 °2θ±20.2 (Form II, bis-hydrochloride);
  (c) 7.2, 7.6 °2θ±0.2 (Form III, bis-hydrochloride);
  (d) 7.5, 11.2, 14.5 °2θ (Form IV, bis-hydrochloride);
  (e) 7.1, 10.6, 14.1 °2θ±0.2 (Form V, bis-hydrochloride);
  (f) 3.8, 6.7, 7.6 °2θ±20.2 (Form VI, bis-hydrochloride);
  (g) 7.5, 14.6, 21.6 °2θ±0.2 (Form VII, phosphate);
  (h) 4.2, 8.3, 16.0 °2θ±0.2 (Form VIII, phosphate);
  (i) 8.4, 16.1, 16.3 °2θ (Form IX, phosphate);
  (j) 6.6, 9.5, 10.6 °2θ±0.2 (Form X, phosphate);
  (k) 8.9, 13.1, 18.1 °2θ±0.2 (Form XI, phosphate);
  (l) 3.8, 7.5, 16.9 °2θ±0.2 °2θ (Form XII, phosphate);
  (m) 4.1, 15.9, 22.9 °2θ (Form XIII, phosphate);
  (n) 3.5, 6.9, 8.3 °2θ±0.2 (Form XIV, phosphate);
  (o) 0.8, 15.9 °2θ±0.2 (Form XV, phosphate);
  (p) 4.1, 8.1, 15.6 °2θ±0.2 (Form XVI, L-tartrate);
  (q) 0.2, 15.8, 22.6 °2θ±0.2 (Form XVII, L-tartrate); and
  (r) 6.7, 7.6, 18.9 °2θ±20.2 (Form XVIII, bis-hydrobromide).
It is within the skill of those in the art to select velpatasvir having a particular form for the pharmaceutical compositions disclosed herein.

In one embodiment, the pharmaceutical composition comprises velpatasvir having the free base form. In another embodiment, the pharmaceutical composition comprises velpatasvir having a substantially amorphous form. In a particular embodiment, the pharmaceutical composition comprises velpatasvir having the amorphous free base form.

Velpatasvir may be present in the pharmaceutical composition in a therapeutically effective amount. In some embodiments, the pharmaceutical composition comprises from about 0.1% to about 50% w/w of velpatasvir. In certain embodiments, the pharmaceutical composition comprises from about 0.1% to about 40% w/w, about 0.1% to about 35% w/w, about 0.5% to about 25% w/w, about 0.5% to about 20% w/w, about 0.5% to about 15% w/w, or about 0.5% to about 10% w/w of velpatasvir. In further embodiments, the pharmaceutical composition comprises about 0.1% w/w, about 0.5% w/w, about 1% w/w, about 2% w/w, about 4% w/w, about 5% w/w, about 7% w/w, about 10% w/w, about 12% w/w, about 15% w/w, about 17% w/w, about 20% w/w, about 25% w/w, about 30% w/w, about 35% w/w, about 40% w/w, or about 45% w/w of velpatasvir. In one embodiment, the pharmaceutical composition comprises about 16.7% w/w of velpatasvir. In another embodiment, the pharmaceutical composition comprises about 15.4% w/w of velpatasvir. In yet another embodiment, the pharmaceutical composition comprises about 13.8% w/w of velpatasvir.

In some embodiments, the pharmaceutical composition comprises velpatasvir formulated as a solid dispersion dispersed within a polymer matrix formed by a pharmaceutically acceptable polymer (designated polymer A). The starting material of the solid dispersion can include velpatasvir having any of the forms (e.g., free base, crystalline, salt, hydrate, solvate, amorphous, etc.) described above. In one embodiment, the starting material may include velpatasvir having a substantially amorphous form.

In one embodiment, the resulting solid dispersion comprises velpatasvir having the free base form. In another embodiment, the solid dispersion comprises velpatasvir having a substantially amorphous form. In another embodiment, the solid dispersion comprises velpatasvir having the amorphous free base form.

The selection of the polymer A for the solid dispersion comprising velpatasvir is based on the stability and physical characteristics of velpatasvir in the solution. Polyvinyl caprolactam-polyvinyl acetate-polyethylene glycol (Soluplus®) and copovidone solid dispersions both showed adequate stability and physical characteristics. Accordingly, in some embodiments, polymer A is polyvinyl caprolactam-polyvinyl acetate-polyethylene glycol (Soluplus®) or copovidone. In one embodiment, polymer A is polyvinyl caprolactam-polyvinyl acetate-polyethylene glycol (Soluplus®). In another embodiment, polymer A is copovidone.

In one embodiment, polymer A is hydrophilic. Non-limiting examples of hydrophilic polymers include polysaccharides, polypeptides, cellulose derivatives such as methyl cellulose, sodium carboxymethylcellulose, hydroxyethylcellulose, ethylcellulose, hydroxypropyl methylcellulose acetate-succinate, hydroxypropyl methylcellulose phthalate, cellulose acetate phthalate, hydroxypropylcellulose, povidone, copovidone, hypromellose, pyroxylin, polyethylene oxide, polyvinyl alcohol, and methacrylic acid copolymers.

In another embodiment, polymer A is non-ionic. Non-ionic polymers showed benefits in screening solubility experiments. Non-limiting examples of non-ionic polymers include hypromellose, copovidone, povidone, methyl cellulose, hydroxyethyl cellulose, hydroxypropyl cellulose, ethylcellulose, pyroxylin, polyethylene oxide, polyvinyl alcohol, polyethylene glycol, and polyvinyl caprolactam-polyvinyl acetate-polyethylene glycol (Soluplus®).

In yet another embodiment, polymer A is ionic. Non-limiting examples of ionic polymers include hydroxypropyl methylcellulose acetate-succinate, hydroxypropyl methylcellulose phthalate, cellulose acetate phthalate, and methacrylic acid copolymers.

In a further embodiment, polymer A is selected from the group consisting of hypromellose, hydroxypropyl cellulose, Soluplus®, copovidone, and povidone.

In some embodiments, the weight ratio of velpatasvir to polymer A is from about 5:1 to about 1:5. In certain embodiments, the weight ratio of velpatasvir to polymer A is from about 4:1 to about 1:4, about 3:1 to about 1:3, or about 2:1 to about 1:2. In some embodiments, the weight ratio of velpatasvir to polymer A is about 5:1, 4:1, 3:1, 2:1, 1:1, 1:5, 1:4, 1:3, 1:2, 1:3, 1:4 or 1:5. In one particular embodiment, the weight ratio of velpatasvir to polymer A is about 1:1. In another particular embodiment, the weight ratio of velpatasvir to polymer A is about 1:2. In yet another particular embodiment, the weight ratio of velpatasvir to polymer A is about 2:1.

In some embodiments, polymer A is copovidone. In one embodiment, the weight ratio of velpatasvir to copovidone is from about 5:1 to about 1:5. In certain embodiments, the weight ratio of velpatasvir to copovidone is from about 4:1 to about 1:4, about 3:1 to about 1:3, or about 2:1 to about 1:2. In some embodiments, the weight ratio of velpatasvir to copovidone is about 5:1, 4:1, 3:1, 2:1, 1:1, 1:5, 1:4, 1:3, 1:2, 1:3, 1:4 or 1:5. In one particular embodiment, the weight ratio of velpatasvir to copovidone is about 1:1. In another particular embodiment, the weight ratio of velpatasvir to copovidone is about 1:2. In yet another particular embodiment, the weight ratio of velpatasvir to copovidone is about 2:1.

The solid dispersion comprising velpatasvir may be present in the pharmaceutical composition in a therapeutically effective amount. In some embodiments, the pharmaceutical composition comprises from about 0.1% to about 50% w/w of the solid dispersion comprising velpatasvir. In certain embodiments, the pharmaceutical composition comprises from about 0.1% to about 40% w/w, about 0.1% to about 35% w/w, about 0.5% to about 25% w/w, about 0.5% to about 20% w/w, about 0.5% to about 15% w/w, or about 0.5% to about 10% w/w of the solid dispersion comprising velpatasvir. In further embodiments, the pharmaceutical composition comprises about 0.1% w/w, about 0.5% w/w, about 1% w/w, about 2% w/w, about 4% w/w, about 5% w/w, about 7% w/w, about 10% w/w, about 12% w/w, about 15% w/w, about 17% w/w, about 20% w/w, about 25% w/w, about 30% w/w, about 35% w/w, about 40% w/w, or about 45% w/w of the solid dispersion comprising velpatasvir. In one embodiment, the pharmaceutical composition comprises about 16.7% w/w of the solid dispersion comprising velpatasvir. In another embodiment, the pharmaceutical composition comprises about 15.4% w/w of the solid dispersion comprising velpatasvir. In yet another embodiment, the pharmaceutical composition comprises about 13.8% w/w of the solid dispersion comprising velpatasvir.

In one exemplary embodiment, the pharmaceutical composition comprises about 15.4% w/w of the solid dispersion comprising velpatasvir, wherein the solid dispersion comprises about 7.7% of velpatasvir and about 7.7% of polymer A. In one embodiment, the pharmaceutical composition comprises about 15.4% w/w of the solid dispersion comprising velpatasvir, wherein the solid dispersion comprises about 7.7% of velpatasvir and about 7.7% of polymer A, and wherein polymer A is copovidone.

Various techniques are well known in the art for preparing solid dispersions including, but not limited to, melt-extrusion, spray-drying, lyophilization, and solution-evaporation.

Melt-extrusion methods generally involve embedding a compound in a thermoplastic carrier. The mixture is processed at elevated temperatures and pressures, which disperses the compound in the matrix at a molecular level to form a solid solution. Extruded material can be further processed into a variety of dosage forms, including capsules, tablets and transmucosal systems.

Solution-evaporation methods generally involve dissolving a compound in a suitable liquid solvent and subsequently incorporating the solution directly into the melt of a polymer, which is then evaporated until a clear, solvent free film is left. The film is further dried to constant weight.

Lyophilization methods generally involve co-dissolving a compound and a carrier in a common solvent, frozen and sublimed to obtain a lyophilized molecular dispersion.

Spray drying methods generally involve mixing a compound and polymer in a solvent to provide a feed solution, and spray drying the feed solution to provide the solid dispersion.

In some embodiments, the solid dispersion comprising velpatasvir is a spray dried solid dispersion. Spray dried solid dispersions of velpatasvir provide improved in vivo and in vitro performance and manufacturability/scalability relative to the other formulation approaches, such as wet and dry granulation formulations.

As such, the solid dispersion comprising velpatasvir, in some embodiments, is formulated via a spray drying process involving: a) preparing a feed solution by dissolving, in a suitable solvent, velpatasvir (as the amorphous free base) dispersed within the polymer matrix formed by polymer A; b) spray drying the solution; and c) optionally secondary drying the spray-dried particles of velpatasvir to remove residual solvent. Regarding step a) of the spray drying process, it is within the skill of those in the art to select an appropriate solvent based on the properties of velpatasvir and/or polymer A such as solubility, glass transition temperature, viscosity, and molecular weight. Acceptable solvents include, but are not limited to, water, acetone, methyl acetate, ethyl acetate, chlorinated solvents, ethanol, dichloromethane, and methanol. In some embodiments, the solvent is selected from the group consisting of ethanol, dichloromethane, and methanol. In certain embodiments, the solvent is ethanol or methanol. In one embodiment, the solvent is ethanol.

Per step b) of the spray drying process discussed above, upon solubilization of velpatasvir and polymer A with the solvent, the solution may then be spray dried. Spray drying is a well known process wherein a liquid feedstock is dispersed into droplets into a drying chamber along with a heated process gas stream to aid in solvent removal and to produce a powder product. Suitable spray drying parameters are known in the art, and it is within the knowledge of a skilled artisan in the field to select appropriate parameters for spray drying. For instance, the target feed concentration is generally about 10 to about 50% with a target of about 20% and a viscosity of about 1 to about 300 cP, or about 1 to about 80 cP, or about 4 to 60 cP. The inlet temperature of the spray dry apparatus is typically about 50-190° C., while the outlet temperature is about 30-90° C. A two fluid nozzle and/or hydraulic pressure nozzle can be used to spray dry velpatasvir. The two fluid nozzle gas flow can be about 1-100 kg/hr, the hydraulic pressure nozzle flow can be about 15-300 kg/hr, and the chamber gas flow may be about 25-2500 kg/hr. The spray-dried material typically has a particle size ($D_{90}$) of less than about 500 µm, about 200 µm, about 150 µm, about 100 µm, about 50 µm, or about 25 µm, in some instances. A milling step may be used if desired to further reduce the particle size, in additional instances. Further descriptions of spray drying methods and other techniques for forming amorphous dispersions are provided in U.S. Pat. No. 6,763,607 and U.S. Pat. Pub. No. 2006-0189633, the entirety of each of which is incorporated herein by reference.

In some embodiments, the spray-dried solid dispersion comprising velpatasvir has a particle size ($D_{90}$) of less than about 500 µm, about 450 µm, about 400 µm, about 350 µm, about 300 µm, about 250 µm, about 200 µm, about 150 µm, about 100 µm, about 75 µm, about 50 µm, or about 25 µm. In certain embodiments, the spray dried solid dispersion comprising velpatasvir has a particle size ($D_{90}$) in a range from about 10 µm to about 150 µm.

Removing the solvent (e.g., ethanol) via the spray drying step b) and the optional secondary drying step c) discussed above, results in high yields across a wide range of spray-drying outlet temperatures with no material accumulation on the spray dry chamber, as described in the Examples. As also described in the Examples, velpatasvir demonstrated good chemical stability in the ethanolic feed solution.

B. Sofosbuvir

Sofosbuvir is a selective inhibitor of non-structural protein 5B (NS5B) protein (see, e.g., WO 2010/132601 and U.S. Pat. No. 7,964,580 describing the synthesis of sofosbuvir). NS5B polymerase is required for the synthesis of a double-stranded RNA from a single-stranded viral RNA that serves as a template in the replication cycle of HCV, and is thus considered an essential component in the HCV replication complex. (K. Ishi, et al, Hepatology (1999) 29:1227-1235; V. Lohmann, et al., Virology (1998) 249:108-118.) Inhibition of HCV NS5B polymerase prevents formation of the double-stranded HCV RNA and therefore constitutes an attractive approach to the development of HCV-specific antiviral therapies.

Sofosbuvir has the following chemical structure:

As discussed previously, the chemical name for sofosbuvir is (S)-isopropyl 2-(((S)-(((2R,3R,4R,5R)-5-(2,4-dioxo-3,4-dihydropyrimidin-1(2H)-yl)-4-fluoro-3-hydroxy-4-methyl-tetrahydrofuran-2-yl)methoxy)(phenoxy)phosphoryl)amino)propanoate.

In one embodiment, the pharmaceutical composition comprises sofosbuvir in a substantially crystalline form. Crystalline forms (Forms 1-8) of sofosbuvir, and methods of preparing the same, are described in U.S. Patent App. Pub. Nos.: 2010/0298257, 2011/0251152, and 2015/0175646, each of which are herein incorporated by reference in their entirety. Forms 1-8 of sofosbuvir have the following characteristic X-ray powder diffraction (XRPD) pattern 2 θ-values measured according to the XRPD methods disclosed therein (e.g., via a diffractometer using Cu—Kα radiation):

(a) 7.5, 9.6, and 18.3 °2θ±0.2 (Form 1A);
(b) 5.0, 7.3, and 18.1 °2θ±0.2 (Form 1B);
(c) 6.9, 24.7, and 25.1 °2θ±0.2 (Form 2);
(d) 19.7, 20.6, and 24.6 °2θ±0.2 (Form 3);
(e) 5.0, 6.8, and 24.9 °2θ±0.2 (Form 4);
(f) 5.2, 6.6, and 19.1 °2θ±0.2 (Form 5);
(g) 6.1, 20.1, and 20.8 °2θ±0.2 (Form 6);
(h) 12.6, 16.9 and 17.3 °2θ±0.2 (Form 7); and
(i) 8.6, 9.2 and 17.1 °2θ±0.2 (Form 8).

Form 6, as described in U.S. Patent Pub. Nos.: 2010/0298257 and 2011/0251152, may be referred to as Form 2, such as for example, by the Food and Drug Administration.

Forms 6 and 7 are alternatively characterized by the following characteristic XRPD pattern 2θ-values as measured according to the methods disclosed therein:

6.1 and 12.7 °2θ±0.2 (Form 6); and
12.6 and 13.5 2θ±0.2 (Form 7).

It is within the skill of those in the art to select sofosbuvir having a particular form for the pharmaceutical compositions disclosed herein. However, in some embodiments, the pharmaceutical composition comprises substantially crystalline sofosbuvir having at least three XRPD 2θ-reflections selected from about: 6.1, 8.2, 10.4, 12.7, 17.2, 17.7, 18.0, 18.8, 19.4, 19.8, 20.1, 20.8, 21.8, and 23.3 °2θ±0.2 (Form 6). In another embodiment, the pharmaceutical composition comprises substantially crystalline sofosbuvir having XRPD 2θ-reflections at about: 6.1, 20.1, and 20.8 °2θ±0.2 (Form 6). In yet another embodiment, the pharmaceutical composition comprises substantially crystalline sofosbuvir having XRPD 2θ-reflections at about 6.1 and 12.7 °2θ±0.2.

In some embodiments, the pharmaceutical composition comprises substantially crystalline sofosbuvir having at least three XRPD 2θ-reflections (°2θ±0.2) selected from the about: 8.2, 10.5, 12.6, 13.5, 16.9, 17.0, 17.3, 19.5, 20.2, 21.0, 23.4, and 27.3 °2θ±0.2 (Form 7). In another embodiment, the pharmaceutical composition comprises substantially crystalline sofosbuvir having XRPD 2θ-reflections (°2θ±0.2) at about: 12.6, 16.9 and 17.3 °2θ±0.2 (Form 7). In yet another embodiment, the pharmaceutical composition comprises substantially crystalline sofosbuvir having XRPD 2θ-reflections (°2θ±0.2) at about 12.6 and 13.5 °2θ±0.2.

In some embodiments, the pharmaceutical composition comprises substantially crystalline sofosbuvir having Form 6, as well as a trace amount of Form 7.

As indicated above, substantially crystalline sofosbuvir (e.g., having Form 6 and a trace amount of Form 7) may be included in the pharmaceutical composition in a therapeutically effective amount. In some embodiments, the pharmaceutical compositions comprises from about 10% to about 80% w/w of sofosbuvir. In various embodiments, the composition comprises from about 15% to about 65% w/w, about 20% to about 60% w/w, about 25% to about 55% w/w, about 30% to about 50% w/w, or about 35% to about 45% w/w of sofosbuvir. In further embodiments, the pharmaceutical composition comprises about 10% w/w, about 15% w/w, about 20% w/w, about 25% w/w, about 30% w/w, about 35% w/w, about 40%, about 45% w/w, about 50% w/w, about 55% w/w, about 60% w/w, about 65% w/w, or about 70% w/w, or about 75% w/w. In one embodiment, the pharmaceutical composition comprises about 33.3% w/w of sofosbuvir. In another embodiment, the pharmaceutical composition comprises about 27.6% w/w of sofosbuvir. In yet another embodiment, the pharmaceutical composition comprises about 30.8% w/w of sofosbuvir.

In some embodiments, the particle size of sofosbuvir may be measured by mass retained on 1000 and 1400 μm screens via an air jet sieving method. In one embodiment, the particle size of sofosbuvir is in a range from 0 to 4% mass retained on a 1000 μm screen and from 0 to 3% mass retained on a 1400 μm screen.

C. Voxilaprevir

Voxilaprevir is a pan-genotypic 5A (NS5A) protease inhibitor (see, e.g., WO 2014/008285 and U.S. Pat. No. 9,296,782 describing the synthesis of voxilaprevir). Voxilaprevir has the following chemical structure:

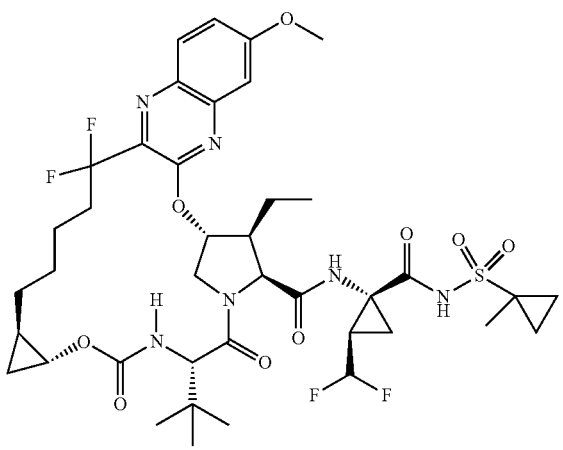

The chemical name of voxilaprevir is (1aR,5S,8S,9S,10R,22aR)-5-tert-butyl-N-{(1R,2R)-2-(difluoromethyl)-1-[(1-methylcyclopropanesulfonyl)carbamoyl]cyclopropyl}-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide.

Voxilaprevir can have any one of a variety of forms including a free acid form, crystalline forms, salts thereof, hydrates thereof, solvates thereof, and an amorphous form. The various forms of voxilaprevir, and methods of making said forms, are described in WO 2015/100144 A1 and U.S. Patent App. Pub. No. U.S. 2015/0175625 A1, both of which are herein incorporated by reference. Crystalline forms I-XXI of voxilaprevir, which may serve as the starting materials for the amorphous version, have the following characteristic XRPD pattern 2θ-values measured according to the XRPD methods disclosed therein (e.g., via a diffractometer using Cu—Kα radiation):

(a) 8.6, 11.1, and 15.5 °2θ±0.2 (Form I, ethanol solvate);
(b) 8.7, 13.0, and 17.4 °2θ±0.2 (Form I, ethyl acetate solvate)
(c) 11.1, 12.8, and 19.7 °2θ±0.2 (Form III, isopropanol solvate);
(d) 8.7, 8.9, and 16.0 °2θ±0.2 (Form IV, dehydrate);
(e) 6.2, 12.4, and 19.6 °2θ±0.2 (Form V, methanol solvate);
(f) 14.6, 15.4, and 20.0 °2θ±0.2 (Form VI, anhydrous);
(g) 6.5, 8.5, and 18.7 °2θ±0.2 (Form VII, anhydrous);
(h) 7.8, 8.2, and 20.2 °2θ±0.2 (Form VIII, anhydrous);
(i) 6.1, 9.5, and 19.4 9±0.2 (Form IX, anhydrous);
(j) 8.0, 19.0, and 20.4±0.2 (Form X, hemihydrate);
(k) 11.0, 13.9, and 20.9±0.2 (Form XI, dihydrate);
(l) 12.4, 14.6, and 19.3±0.2 (Form XII, tetrahydrate);
(m) 8.5, 11.0, and 15.4±0.2 (Form XIII, isopropyl acetate solvate);
(n) 11.2, 15.7, and 17.9±0.2 (Form XIV, tetrahydrofuran solvate);
(o) 9.7, 11.0, and 15.5±0.2 (Form XV, 2-methyltetrahydrofuran solvate);
(p) 5.8, 7.8, and 18.8±0.2 (Form XVI, toluene solvate);
(q) 7.9, 18.9, and 20.3±0.2 (Form XVII, toluene solvate);
(r) 5.6, 6.4, and 7.5±0.2 (Form XVIII, tert butyl ether solvate);
(s) 11.1, 15.5, and 19.8±0.2 (Form XIX, tert butyl ether solvate);
(t) 11.9, 14.5, and 19.1±0.2 (Form XX, dimethylacetamide solvate); and
(u) 11.7, 12.2, and 14.4±0.2 (Form XXI, dimethylformamide solvate).

It is within the skill of those in the art to select voxilaprevir having a particular form for the pharmaceutical compositions disclosed herein.

In one embodiment, the pharmaceutical composition comprises voxilaprevir having the amorphous free acid form.

Voxilaprevir may be present in the pharmaceutical composition in a therapeutically effective amount. In some embodiments, the pharmaceutical composition comprises from about 0.1% to about 50% w/w of voxilaprevir. In certain embodiments, the pharmaceutical composition comprises from about 0.1% to about 40% w/w, about 0.1% to about 35% w/w, about 0.5% to about 25% w/w, about 0.5% to about 20% w/w, about 0.5% to about 15% w/w, or about 0.5% to about 10% w/w of voxilaprevir. In further embodiments, the pharmaceutical composition comprises about 0.1% w/w, about 0.5% w/w, about 1% w/w, about 2% w/w, about 4% w/w, about 5% w/w, about 7% w/w, about 10% w/w, about 12% w/w, about 15% w/w, about 17% w/w, about 20% w/w, about 25% w/w, about 30% w/w, about 35% w/w, about 40% w/w, or about 45% w/w of voxilaprevir. In one embodiment, the pharmaceutical composition comprises about 16.7% w/w of voxilaprevir. In another embodiment, the pharmaceutical composition comprises about 15.4% w/w of voxilaprevir. In yet another embodiment, the pharmaceutical composition comprises about 13.8% w/w of voxilaprevir.

In some embodiments, the effective amount of voxilaprevir is the same as the effective amount of velpatasvir in the pharmaceutical composition. In other embodiments, the effective amount of voxilaprevir is different than the effective amount of velpatasvir in the pharmaceutical composition.

In some embodiments, the pharmaceutical composition comprises voxilaprevir formulated as a solid dispersion dispersed within a polymer matrix formed by a pharmaceutically acceptable polymer (designated polymer B). The starting material of the solid dispersion can include voxilaprevir having any of the forms (e.g., free base, crystalline, salt, hydrate, solvate, amorphous, etc.) described above. In one embodiment, the starting material may include voxilaprevir as the ethyl acetate solvate (Form II).

In various embodiments, the solid dispersion includes voxilaprevir having the free acid form. In another embodiment, the pharmaceutical composition comprises voxilaprevir, Form VI. In yet another embodiment, the pharmaceutical composition comprises voxilaprevir, Form VIII. In a further embodiment, the pharmaceutical composition comprises voxilaprevir having a substantially amorphous form. In some embodiments, the solid dispersion comprises voxilaprevir having the amorphous free acid form.

The selection of the polymer B for the solid dispersion comprising voxilaprevir is based on the stability and physical characteristics of voxilaprevir in the solution. Polyvinyl caprolactam-polyvinyl acetate-polyethylene glycol (Soluplus®) and copovidone solid dispersions both showed adequate stability and physical characteristics. Accordingly, in some embodiments, polymer B is polyvinyl caprolactam-polyvinyl acetate-polyethylene glycol (Soluplus®) or copovidone. In one embodiment, polymer B is polyvinyl caprolactam-polyvinyl acetate-polyethylene glycol (Soluplus®). In another embodiment, polymer B is copovidone.

In one embodiment, polymer B is hydrophilic. Non-limiting examples of hydrophilic polymers include polysaccharides, polypeptides, cellulose derivatives such as methyl cellulose, sodium carboxymethylcellulose, hydroxyethylcellulose, ethylcellulose, hydroxypropyl methylcellulose acetate-succinate, hydroxypropyl methylcellulose phthalate, cellulose acetate phthalate, hydroxypropylcellulose, povidone, copovidone, hypromellose, pyroxylin, polyethylene oxide, polyvinyl alcohol, and methacrylic acid copolymers.

In another embodiment, polymer B is non-ionic. Non-ionic polymers showed benefits in screening solubility experiments. Non-limiting examples of non-ionic polymers include hypromellose, copovidone, povidone, methyl cellulose, hydroxyethyl cellulose, hydroxypropyl cellulose, ethylcellulose, pyroxylin, polyethylene oxide, polyvinyl alcohol, polyethylene glycol, and polyvinyl caprolactam-polyvinyl acetate-polyethylene glycol (Soluplus®).

In yet another embodiment, polymer B is ionic. Non-limiting examples of ionic polymers include hydroxypropyl methylcellulose acetate-succinate, hydroxypropyl methylcellulose phthalate, cellulose acetate phthalate, and methacrylic acid copolymers.

In a further embodiment, polymer B is selected from the group consisting of hypromellose, hydroxypropyl cellulose, Soluplus®, copovidone, and povidone.

In some embodiments, polymer B in the solid dispersion comprising voxilaprevir is the same as polymer A in the solid dispersion comprising velpatasvir. In other embodiments, polymer B in the solid dispersion comprising voxilaprevir is different than polymer A in the solid dispersion comprising velpatasvir.

In some embodiments, the weight ratio of voxilaprevir to polymer B is from about 5:1 to about 1:5. In certain embodiments, the weight ratio of voxilaprevir to polymer B is from about 4:1 to about 1:4, about 3:1 to about 1:3, or about 2:1 to about 1:2. In some embodiments, the weight ratio of voxilaprevir to polymer B is about 5:1, 4:1, 3:1, 2:1, 1:1, 1:5, 1:4, 1:3, 1:2, 1:3, 1:4 or 1:5. In one particular embodiment, the weight ratio of voxilaprevir to polymer B is about 1:1. In another particular embodiment, the weight ratio of voxilaprevir to polymer B is about 1:2. In yet another particular embodiment, the weight ratio of voxilaprevir to polymer B is about 2:1.

In some embodiments polymer B is copovidone. In some embodiments, the weight ratio of voxilaprevir to copovidone is from about 5:1 to about 1:5. In certain embodiments, the weight ratio of voxilaprevir to copovidone is from about 4:1 to about 1:4, about 3:1 to about 1:3, or about 2:1 to about 1:2. In some embodiments, the weight ratio of voxilaprevir to copovidone is about 5:1, 4:1, 3:1, 2:1, 1:1, 1:5, 1:4, 1:3, 1:2, 1:3, 1:4 or 1:5. In one particular embodiment, the weight ratio of voxilaprevir to copovidone is about 1:1. In another particular embodiment, the weight ratio of voxilaprevir to copovidone is about 1:2. In yet another particular embodiment, the weight ratio of voxilaprevir to copovidone is about 2:1.

In some embodiments, the weight ratio of voxilaprevir to polymer B is the same as the weight ratio of velpatasvir to polymer A. In other embodiments, the weight ratio of voxilaprevir to polymer B is different than the weight ratio of velpatasvir to polymer A.

The solid dispersion comprising voxilaprevir may be present in the pharmaceutical composition in a therapeutically effective amount. In some embodiments, the pharmaceutical composition comprises from about 0.1% to about 50% w/w of the solid dispersion comprising voxilaprevir. In certain embodiments, the pharmaceutical composition comprises from about 0.1% to about 40% w/w, about 0.1% to about 35% w/w, about 0.5% to about 25% w/w, about 0.5% to about 20% w/w, about 0.5% to about 15% w/w, or about 0.5% to about 10% w/w of the solid dispersion comprising voxilaprevir. In further embodiments, the pharmaceutical composition comprises about 0.1% w/w, 0.5% w/w, 1% w/w, 2% w/w, 4% w/w, 5% w/w, about 7% w/w, about 10% w/w, about 12% w/w, about 15% w/w, about 17% w/w, about 20% w/w, about 25% w/w, about 30% w/w, about 35% w/w, about 40% w/w, or about 45% w/w of the solid dispersion comprising voxilaprevir. In one embodiment, the pharmaceutical composition comprises about 16.7% w/w of the solid dispersion comprising voxilaprevir. In another embodiment, the pharmaceutical composition comprises about 15.4% w/w of the solid dispersion comprising voxilaprevir. In yet another embodiment, the pharmaceutical composition comprises about 13.8% w/w of the solid dispersion comprising voxilaprevir.

In one embodiment, the pharmaceutical composition comprises about 15.4% w/w of the solid dispersion comprising voxilaprevir, wherein the solid dispersion comprises about 7.7% of voxilaprevir and about 7.7% of polymer B. In one embodiment, the pharmaceutical composition comprises about 15.4% w/w of the solid dispersion comprising voxilaprevir, wherein the solid dispersion comprises about 7.7% of voxilaprevir and about 7.7% of polymer B, and wherein polymer B is copovidone.

In some embodiments, the effective amount of the solid dispersion comprising voxilaprevir is the same as the effective amount of the solid dispersion comprising velpatasvir in the pharmaceutical composition. In other embodiments, the effective amount of the solid dispersion comprising voxilaprevir is different than the effective amount of the solid dispersion comprising velpatasvir in the pharmaceutical composition.

In some embodiments, the solid dispersion comprising voxilaprevir may be spray dried according to techniques known in the art and as disclosed herein. In particular embodiments, the solid dispersion comprising voxilaprevir, in some embodiments, is formulated via a spray drying process involving: a) preparing a feed solution by dissolving, in a suitable solvent, voxilaprevir (as the crystalline ethyl acetate solvate thereof) dispersed within the polymer matrix formed by polymer B; b) spray drying the solution; and c) optionally secondary drying the spray-dried particles of voxilaprevir to remove residual solvent.

Regarding step a) of the spray drying process, it is within the skill of those in the art to select an appropriate solvent based on the properties of voxilaprevir and/or polymer B such as solubility, glass transition temperature, viscosity, and molecular weight. Acceptable solvents include, but are not limited to, water, acetone, methyl acetate, ethyl acetate, chlorinated solvents, ethanol, dichloromethane, and methanol. In some embodiments, the solvent is selected from the group consisting of acetone, ethanol, dichloromethane, and methanol. In certain embodiments, the solvent is acetone or dichloromethane. In one embodiment, the solvent is acetone.

Per step b) of the spray drying process discussed above, upon solubilization of voxilaprevir and polymer B with the solvent, the solution may then be spray dried, e.g., by pumping the feed solution into a drying chamber through a nozzle that atomizes the feed solution into droplets, while concurrently introducing a heated gas to remove the solvent and produce solid particles.

In some embodiments, the spray-dried solid dispersion comprising voxilaprevir has a particle size ($D_{90}$) of less than about 500 µm, about 450 µm, about 400 µm, about 350 µm, about 300 µm, about 250 µm, about 200 µm, about 150 µm, about 100 µm, about 75 µm, about 50 µm, or about 25 µm. In certain embodiments, the spray dried solid dispersion comprising velpatasvir has a particle size ($D_{90}$) in a range from about 10 µm to about 150 µm.

Removing the solvent (e.g., ethanol) via the spray drying step b) and the optional secondary drying step c), discussed above, results in high yields across a wide range of spray-drying outlet temperatures with no material accumulation on the spray dry chamber, as described in the Examples. As also described in the Examples, voxilaprevir demonstrated good chemical stability in the acetone feed solution.

As indicated previously, the pharmaceutical composition, in some embodiments, include an effective amount of each of three active ingredients, i.e., velpatasvir (or a solid dispersion comprising velpatasvir), sofosbuvir, and voxilaprevir (or a solid dispersion comprising voxilaprevir). In such embodiments, velpatasvir may be substantially amorphous, sofosbuvir may be substantially crystalline, and voxilaprevir may be substantially amorphous.

In other embodiments, the disclosure provides a pharmaceutical composition comprising substantially amorphous voxilaprevir or a solid dispersion comprising voxilaprevir. In some embodiments, voxilaprevir has the substantially amorphous free acid form. In some embodiments, the pharmaceutical composition includes from about 0.1% to about 50% w/w of voxilaprevir as the single active ingredient. In certain embodiments, the pharmaceutical composition comprises from about 0.1% to about 40% w/w, about 0.1% to about 35% w/w, about 0.5% to about 25% w/w, about 0.5% to about 20% w/w, about 0.5% to about 15% w/w, or about 0.5% to about 10% w/w of voxilaprevir as the single active ingredient. In some embodiments, the pharmaceutical composition includes about 10% w/w of voxilaprevir as the single active ingredient.

In another embodiment in which the pharmaceutical composition comprises voxilaprevir as the single active ingredient, voxilaprevir may be present as a solid dispersion dispersed within a polymer matrix formed by a pharmaceutically acceptable polymer (e.g., polymer B disclosed herein). In some embodiments, such a solid dispersion may include voxilaprevir having the substantially amorphous free acid form. In some embodiments, the weight ratio of voxilaprevir to polymer B in the solid dispersion is from about 1:5 to about 5:1. In some embodiments, the weight ratio of voxilaprevir to polymer in the solid dispersion is about 1:1. In some embodiments, the pharmaceutical composition includes from about 0.1% to about 50% w/w of a solid dispersion of voxilaprevir as the single active ingredient. In certain embodiments, the pharmaceutical composition comprises from about 0.1% to about 40% w/w, about 0.1% to about 35% w/w, about 0.5% to about 25% w/w, about 0.5% to about 20% w/w, about 0.5% to about 15% w/w, or about 0.5% to about 10% w/w of a solid dispersion of voxilaprevir as the single active ingredient. In some embodiments, the pharmaceutical composition includes about 20% w/w of the solid dispersion of voxilaprevir as the single active ingredient.

D. Excipients

As discussed above, the pharmaceutical compositions disclosed herein may comprise: an effective amount of velpatasvir (or a solid dispersion comprising velpatasvir); and effective amount of sofosbuvir; and an effective amount of voxilaprevir (or a solid dispersion comprising voxilaprevir), wherein velpatasvir is substantially amorphous, sofosbuvir is substantially crystalline, and voxilaprevir is substantially amorphous. The pharmaceutical compositions disclosed herein may further comprise pharmaceutical excipients such as diluents, binders, fillers, glidants, disintegrants, lubricants, solubilizers, and combinations thereof. Such compositions may be prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

In some embodiments, the pharmaceutical composition comprises a diluent selected from the group consisting of dicalcium phosphate, cellulose, compressible sugars, dibasic calcium phosphate dehydrate, lactose, lactose monohydrate, mannitol, microcrystalline cellulose, starch, tribasic calcium phosphate, and combinations thereof.

In one embodiment, the pharmaceutical composition comprises lactose monohydrate in an amount ranging from about 0 to about 45% w/w, about 5 to about 40% w/w, about 5 to about 35% w/w, about 5 to about 25% w/w, or about 10 to about 20% w/w. In specific embodiments, the lactose monohydrate is present in the pharmaceutical composition at about 0% w/w, about 5% w/w, about 10% w/w, about 15% w/w, about 20% w/w, about 25% w/w, about 30% w/w, about 35% w/w, about 40% w/w, or about 45% w/w. In one exemplary embodiment, lactose monohydrate is present in the pharmaceutical composition at about 5.4% w/w. In another exemplary embodiment, lactose monohydrate is present in the pharmaceutical composition at about 6.4% w/w. In yet another embodiment, lactose monohydrate is present in the pharmaceutical composition at about 7.9% w/w. In a further exemplary embodiment, lactose monohydrate is present in the pharmaceutical composition at about 9% w/w. In an additional exemplary embodiment, lactose monohydrate is present in the pharmaceutical composition at about 12.2% w/w. In another exemplary embodiment, lactose monohydrate is present in the pharmaceutical composition at about 12.8% w/w.

In another embodiment, the pharmaceutical composition comprises microcrystalline cellulose in an amount ranging from about 0 to about 45% w/w, about 5 to about 40% w/w, about 5 to about 35% w/w, about 5 to about 25% w/w, or about 10 to about 20% w/w. In specific embodiments, the lactose monohydrate is present in the pharmaceutical composition at about 0% w/w, about 5% w/w, about 10% w/w, about 15% w/w, about 20% w/w, about 25% w/w, about 30% w/w, about 35% w/w, about 40% w/w, or about 45% w/w. In one exemplary embodiment, microcrystalline cellulose is present in the pharmaceutical composition at about 15.42% w/w. In another exemplary embodiment, microcrystalline cellulose is present in the pharmaceutical composition at about 16.4% w/w. In yet another embodiment, microcrystalline cellulose is present in the pharmaceutical composition at about 17.9% w/w. In a further exemplary embodiment, microcrystalline cellulose is present in the pharmaceutical composition at about 19% w/w. In an additional exemplary embodiment, microcrystalline cellulose is present in the pharmaceutical composition at about 22.2% w/w. In another exemplary embodiment, microcrystalline cellulose is present in the pharmaceutical composition at about 22.8% w/w.

In yet another embodiment, the pharmaceutical composition comprises a mixture of lactose monohydrate and microcrystalline cellulose in an amount ranging from about 0 to about 45% w/w, about 5 to about 40% w/w, about 5 to about 35% w/w, about 5 to about 25% w/w, or about 10 to about 20% w/w. In specific embodiments, the mixture of lactose monohydrate and microcrystalline cellulose is present in the pharmaceutical composition at about 0% w/w, about 5% w/w, about 10% w/w, about 15% w/w, about 20% w/w, about 25% w/w, about 30% w/w, about 35% w/w, about 40% w/w, or about 45% w/w. In additional embodiments, the weight ratio of lactose monohydrate to microcrystalline cellulose in the mixture is in a range from about 2:1 to 1:2. In one exemplary embodiment, the weight ratio of lactose monohydrate to microcrystalline cellulose in the mixture is about 1:1.

In some embodiments, the pharmaceutical composition comprises a disintegrant selected from the group consisting of croscarmellose sodium, crospovidone, microcrystalline cellulose, modified corn starch, povidone, pregelatinized starch, sodium starch glycolate, and combinations thereof.

In one embodiment, the pharmaceutical composition comprises croscarmellose sodium in an amount ranging from about 1 to about 20% w/w, about 1 to about 15% w/w, about 1 to about 10% w/w, about 5 to about 10% w/w, about 1 to about 8% w/w, or about 2 to about 8% w/w. In specific embodiments, the croscarmellose sodium is present in the pharmaceutical composition in an amount of about 1% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, or about 15% w/w. In one exemplary embodiment, the croscarmellose sodium is present in the pharmaceutical composition in an amount of about 2.5% w/w. In another exemplary embodiment, the croscarmellose sodium is present in the pharmaceutical composition in an amount of about 5.5% w/w. In yet another exemplary embodiment, the croscarmellose sodium is present in the pharmaceutical composition in an amount of about 8% w/w.

In some embodiments, the pharmaceutical composition comprises a glidant selected from the group consisting of colloidal silicon dioxide, talc, starch, starch derivatives, and combinations thereof.

In one embodiment, the pharmaceutical composition comprises colloidal silicon dioxide in an amount ranging from about 0 to about 5% w/w, about 0.1 to about 4.5% w/w, about 0.1 to about 4% w/w, about 0.5 to about 5.0% w/w, about 0.5 to about 3% w/w, about 0.5 to about 2% w/w, or about 0.5 to about 1.5% w/w. In specific embodiments, the colloidal silicon dioxide is present in an amount of about 0% w/w, about 0.1% w/w, about 0.5% w/w, about 0.75% w/w, about 1.25% w/w, about 1.5% w/w, or about 2% w/w. In one exemplary embodiment, the colloidal silicon dioxide is present in the pharmaceutical composition in an amount of about 1% w/w.

In some embodiments, the pharmaceutical composition comprises a lubricant selected from the group consisting of calcium stearate, magnesium stearate, polyethylene glycol, sodium stearyl fumarate, stearic acid, talc, and combinations thereof.

In one embodiment, the pharmaceutical composition comprises magnesium stearate in an amount ranging from about 0 to about 3% w/w, about 0.1 to about 2.5% w/w, about 0.5 to about 3% w/w, about 0.5 to about 2.5% w/w, about 0.5 to about 2% w/w, about 1 to about 3% w/w, or from about 1 to about 2% w/w. In specific embodiments, the magnesium stearate is present in the pharmaceutical composition in an amount of about 0.1%, about 0.5% w/w, about 0.75% w/w, about 1% w/w, about 1.5% w/w, about 2% w/w, about 2.5% w/w, or about 3% w/w. In one exemplary embodiment, the magnesium stearate is present in the pharmaceutical composition in an amount of about 0.75% w/w.

In some embodiments, the pharmaceutical composition comprises: a) about 20 to about 40% w/w of sofosbuvir; b) about 10 to about 30% w/w of the solid dispersion comprising velpatasvir; and c) about 10 to about 30% w/w of the solid dispersion comprising voxilaprevir. In some embodiments, the pharmaceutical composition further comprises: d) about 5 to about 25% w/w of microcrystalline cellulose; e) about 5 to about 15% w/w of lactose monohydrate; f) about 1 to about 15% w/w of croscarmellose sodium; g) about 0.5 to about 3% w/w of magnesium stearate; and h) about 0.5 to about 3% w/w of colloidal silicon dioxide.

In one embodiment the pharmaceutical composition comprises: a) about 30.8% w/w of sofosbuvir; b) about 15.4% w/w of the solid dispersion comprising velpatasvir; and c) about 15.4% w/w of the solid dispersion comprising voxilaprevir. In one embodiment, the solid dispersion comprising velpatasvir includes a 1:1 weight ratio of velpatasvir to polymer A (e.g., copovidone), such that velpatasvir is present at about 7.7% w/w and polymer A is present at about 7.7% w/w. In one embodiment, the solid dispersion comprising voxilaprevir includes a 1:1 weight ratio of voxilaprevir to polymer B (e.g., copovidone), such that voxilaprevir is present at about 7.7% w/w and polymer B is present at about 7.7% w/w. In one embodiment, the pharmaceutical composition further comprises: d) about 19% w/w of microcrystalline cellulose; e) about 9% w/w of lactose monohydrate; f) about 8% w/w of croscarmellose sodium; g) about 1.5% w/w of magnesium stearate; and h) about 1% w/w of colloidal silicon dioxide.

In another embodiment, the pharmaceutical composition comprises: a) about 33.3% w/w of sofosbuvir; b) about 16.7% w/w of the solid dispersion comprising velpatasvir; and c) about 16.7% w/w of the solid dispersion comprising voxilaprevir. In one embodiment, the solid dispersion comprising velpatasvir includes a 1:1 weight ratio of velpatasvir to polymer A (e.g., copovidone), such that velpatasvir is present at about 8.35% w/w and polymer is present at about 8.35% w/w. In one embodiment, the solid dispersion comprising voxilaprevir includes a 1:1 weight ratio of voxilaprevir to polymer B (e.g., copovidone), such that voxilaprevir is present at about 8.35% w/w and polymer B is present at about 8.35% w/w. In one embodiment, the pharmaceutical composition further comprises: d) about 16.4% w/w of microcrystalline cellulose; e) about 6.4% w/w of lactose monohydrate; f) about 8% w/w of croscarmellose sodium; g) about 1.5% w/w of magnesium stearate; and h) about 1% w/w of colloidal silicon dioxide.

In yet another embodiment, the pharmaceutical composition comprises: a) about 33.3% w/w of sofosbuvir; b) about 16.7% w/w of the solid dispersion comprising velpatasvir; and c) about 16.7% w/w of the solid dispersion comprising voxilaprevir. In one embodiment, the solid dispersion comprising velpatasvir includes a 1:1 weight ratio of velpatasvir to polymer A (e.g., copovidone), such that velpatasvir is present at about 8.35% w/w and polymer A is present at about 8.35% w/w. In one embodiment, the solid dispersion comprising voxilaprevir includes a 1:1 weight ratio of voxilaprevir to polymer B (e.g., copovidone), such that voxilaprevir is present at about 8.35% w/w and polymer B is present at about 8.35% w/w. In one embodiment, the pharmaceutical composition further comprises: d) about 10% w/w of microcrystalline cellulose; e) about 12.8% w/w of lactose monohydrate; f) about 8% w/w of croscarmellose sodium; g) about 1.5% w/w of magnesium stearate; and h) about 1% w/w of colloidal silicon dioxide.

In still another embodiment, the pharmaceutical composition comprises: a) about 33.3% w/w of sofosbuvir; b) about 16.7% w/w of the solid dispersion comprising velpatasvir; and c) about 16.7% w/w of the solid dispersion comprising voxilaprevir. In one embodiment, the solid dispersion comprising velpatasvir includes a 1:1 weight ratio of velpatasvir to polymer A (e.g., copovidone), such that velpatasvir is present at about 8.35% w/w and polymer A is present at about 8.35% w/w. In one embodiment, the solid dispersion comprising voxilaprevir includes a 1:1 weight ratio of voxilaprevir to polymer B (e.g., copovidone), such that voxilaprevir is present at about 8.35% w/w and polymer B is present at about 8.35% w/w. In one embodiment, the pharmaceutical composition further comprises: d) about 22.8% w/w of microcrystalline cellulose; e) about 8% w/w of croscarmellose sodium; g) about 1.5% w/w of magnesium stearate; and h) about 1% w/w of colloidal silicon dioxide.

In a further embodiment, the pharmaceutical composition comprises: a) about 33.3% w/w of sofosbuvir; b) about 16.7% w/w of the solid dispersion comprising velpatasvir; and c) about 16.7% w/w of the solid dispersion comprising voxilaprevir. In one embodiment, the solid dispersion comprising velpatasvir includes a 1:1 weight ratio of velpatasvir to polymer A (e.g., copovidone), such that velpatasvir is present at about 8.35% w/w and polymer A is present at about 8.35% w/w. In one embodiment, the solid dispersion comprising voxilaprevir includes a 1:1 weight ratio of voxilaprevir to polymer B (e.g., copovidone), such that voxilaprevir is present at about 8.35% w/w and polymer B is present at about 8.35% w/w. In one embodiment, the pharmaceutical composition further comprises: d) about 17.9% w/w of microcrystalline cellulose; e) about 7.9% w/w of lactose monohydrate; f) about 5% w/w of croscarmellose sodium; g) about 1.5% w/w of magnesium stearate; and h) about 1% w/w of colloidal silicon dioxide.

In an additional embodiment, the pharmaceutical composition comprises: a) about 33.3% w/w of sofosbuvir; b) about 16.7% w/w of the solid dispersion comprising velpatasvir; and c) about 16.7% w/w of the solid dispersion comprising voxilaprevir. In one embodiment, the solid dispersion comprising velpatasvir includes a 1:1 weight ratio of velpatasvir to polymer A (e.g., copovidone), such that velpatasvir is present at about 8.35% w/w and polymer A is present at about 8.35% w/w. In one embodiment, the solid dispersion comprising voxilaprevir includes a 1:1 weight ratio of voxilaprevir to polymer B (e.g., copovidone), such that voxilaprevir is present at about 8.35% w/w and polymer B is present at about 8.35% w/w. In one embodiment, the pharmaceutical composition further comprises: d) about 15.4% w/w of microcrystalline cellulose; e) about 5.4% w/w of lactose monohydrate; f) about 10% w/w of croscarmellose sodium; g) about 1.5% w/w of magnesium stearate; and h) about 1% w/w of colloidal silicon dioxide.

In another embodiment, the pharmaceutical composition comprises: a) about 27.6% w/w of sofosbuvir; b) about 13.8% w/w of the solid dispersion comprising velpatasvir; and c) about 13.8% w/w of the solid dispersion comprising voxilaprevir. In one embodiment, the solid dispersion comprising velpatasvir includes a 1:1 weight ratio of velpatasvir to polymer A (e.g., copovidone), such that velpatasvir is present at about 6.9% w/w and polymer A is present at about 6.9% w/w. In one embodiment, the solid dispersion comprising voxilaprevir includes a 1:1 weight ratio of voxilaprevir to polymer B (e.g., copovidone), such that voxilaprevir is present at about 6.9% w/w and polymer B is present at about 6.9% w/w. In one embodiment, the pharmaceutical composition further comprises: d) about 22.2% w/w of microcrystalline cellulose; e) about 12.2% w/w of lactose monohydrate; f) about 8% w/w of croscarmellose sodium; g) about 1.5% w/w of magnesium stearate; and h) about 1% w/w of colloidal silicon dioxide.

In yet another embodiment, the pharmaceutical composition may include: about 20.0% w/w of the solid dispersion of voxilaprevir. In one embodiment, the solid dispersion comprising voxilaprevir includes a 1:1 weight ratio of voxilaprevir to polymer B (e.g., copovidone), such that voxilaprevir is present at about 10% w/w and polymer B is present at about 10% w/w. In one embodiment, the pharmaceutical composition further comprises: d) about 34.75% w/w of microcrystalline cellulose; e) about 34.75% w/w of lactose monohydrate; f) about 8% w/w of croscarmellose sodium; g) about 1.5% w/w of magnesium stearate; and h) about 1% w/w of colloidal silicon dioxide.

3. Modes of Administration

The pharmaceutical compositions disclosed herein may be administered in either single or multiple doses by various methods including, for example, rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Another mode for administration is via inhalation. Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In some embodiments, the pharmaceutical compositions disclosed herein may be administered orally. Administration may be via, for example, tablet, capsule or enteric coated tablets. In making solid pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, sterile injectable solutions, and sterile packaged powders.

For preparing solid pharmaceutical compositions such as tablets, the principal active ingredient(s) may be mixed with a pharmaceutical excipient to form a solid preformulation composition containing a homogeneous mixture of the compounds described herein. When referring to these preformulation compositions as homogeneous, the active ingredient(s) may be dispersed evenly throughout the composition so that the composition may be readily subdivided into equally effective unit dosage forms such as tablets, pills and capsules.

In some embodiments, the pharmaceutical compositions and co-formulations disclosed herein can be formulated so as to provide quick, sustained or delayed release of the active ingredient(s) after administration to the subject by employing procedures known in the art. A "sustained release formulation" is a formulation which is designed to slowly release a therapeutic agent in the body over an extended period of time, whereas an "immediate release formulation" is a formulation which is designed to quickly release a therapeutic agent in the body over a shortened period of time. In some cases the immediate release formulation may be coated such that the therapeutic agent is only released once it reached the desired target in the body (e.g. the stomach).

In some embodiments in which the pharmaceutical compositions disclosed herein are formulated into a tablet or pill, the tablet or pill may be coated or otherwise compounded to provide a dosage form affording the advantage of prolonged/sustained action, or to protect from the acid conditions of the stomach. For example, the tablet or pill may include a time-delay material such as glyceryl monostearate or glyceryl distearate employed alone or with a wax. Additionally, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for enteric layers or coatings, such materials including a number of polymeric acids and mixtures of polymeric acids with such materials as shellac, cetyl alcohol, and cellulose acetate.

In some embodiments in which the pharmaceutical compositions disclosed herein are formulated into a tablet or pill, the tablet or pill may be coated or otherwise compounded for immediate release.

In some embodiments in which the pharmaceutical compositions disclosed herein are formulated into a tablet or pill, the tablet or pill may have a film coating configured to limit photolytic degradation. Suitable film coatings may be selected by routine screening of commercially available preparations. In one embodiment, the film coating comprises a polyvinyl alcohol-based coating. In another embodiment, the film coating comprises polyvinyl alcohol in combination with one or more of: titanium dioxide, polyethylene glycol, and talc. In yet another embodiment, the film coating is present in the pharmaceutical composition at about 3.0% w/w.

In some embodiments, the pharmaceutical compositions disclosed herein may be formulated as a monolayer tablet. Such a monolayer tablet may generally comprise the active ingredients (i.e., velpatasvir, sofosbuvir, and voxilaprevir) co-mixed in a single uniform layer. Exemplary methods for making monolayer tablets include, but are not limited to, co-dry granulation and bi-granulation. Co-dry granulation of the pharmaceutical compositions disclosed herein comprises dry granulating all the active ingredients (i.e., velpatasvir, sofosbuvir, and voxilaprevir) and excipients together. Bi-granulation of the pharmaceutical compositions disclosed herein is a multi-step process comprising (i) co-dry granulating two of the active ingredients (e.g., sofosbuvir and velpatasvir or Sofosbuvir and voxilaprevir) and excipients together to form granulation A, (ii) dry granulating the third active ingredient (e.g., voxilaprevir or velpatasvir, respectively) and excipients to form granulation B; and (iii) mixing/blending granulation A and granulation B together.

In some embodiments, a tablet comprises: an effective amount of velpatasvir, wherein velpatasvir is substantially amorphous; an effective amount of sofosbuvir, wherein sofosbuvir is substantially crystalline; an effective amount of voxilaprevir, wherein voxilaprevir is substantially amorphous; a diluent as disclosed herein, a disintegrant as disclosed herein, a lubricant as disclosed herein, a glidant as disclosed herein, or any combination thereof.

In one embodiment, a tablet comprises:

intragranular components comprising: an effective amount of velpatasvir, wherein velpatasvir is substantially amorphous; an effective amount of sofosbuvir, wherein sofosbuvir is substantially crystalline; an effective amount of voxilaprevir, wherein voxilaprevir is substantially amorphous; a diluent as disclosed herein, a disintegrant as disclosed herein, a lubricant as disclosed herein, and a glident as disclosed herein; and extragranular components comprising: a diluent as disclosed herein, a disintegrant as disclosed herein, and a lubricant as disclosed herein.

In one embodiment, the intragranular and extragranular diluents in the tablet may be the same. In one embodiment, the intragranular and extragranular diluents in the tablet may be different. In one embodiment, the intragranular and extragranular disintegrants in the tablet may be the same. In one embodiment, the intragranular and extragranular disintegrants in the tablet may be different. In one embodiment, the intragranular and extragranular lubricants in the tablet may be the same. In one embodiment, the intragranular and extragranular lubricants in the tablet may be different.

In some embodiments, a tablet comprises: a) about 20 to about 40% w/w of sofosbuvir; b) about 10 to about 30% w/w of the solid dispersion comprising velpatasvir; and c) about 10 to about 30% w/w of the solid dispersion comprising voxilaprevir. In some embodiments, the tablet further comprises: d) about 5 to about 25% w/w of microcrystalline cellulose; e) about 5 to about 15% w/w of lactose monohydrate; f) about 1 to about 15% w/w of croscarmellose sodium; g) about 0.5 to about 3% w/w of magnesium stearate; and h) about 0.5 to about 3% w/w of colloidal silicon dioxide.

In one embodiment a tablet comprises: a) about 30.8% w/w of sofosbuvir; b) about 15.4% w/w of the solid dispersion comprising velpatasvir; and c) about 15.4% w/w of the solid dispersion comprising voxilaprevir. In one embodiment, the solid dispersion comprising velpatasvir includes a 1:1 weight ratio of velpatasvir to polymer A (e.g., copovidone), such that velpatasvir is present at about 7.7% w/w and polymer A is present at about 7.7% w/w. In one embodiment, the solid dispersion comprising voxilaprevir includes a 1:1 weight ratio of voxilaprevir to polymer B (e.g., copovidone), such that voxilaprevir is present at about 7.7% w/w and polymer B is present at about 7.7% w/w. In one embodiment, the tablet further comprises: d) about 19% w/w of microcrystalline cellulose; e) about 9% w/w of lactose monohydrate; f) about 8% w/w of croscarmellose sodium; g) about 1.5% w/w of magnesium stearate; and h) about 1% w/w of colloidal silicon dioxide.

In another embodiment, a tablet comprises: a) about 33.3% w/w of sofosbuvir; b) about 16.7% w/w of the solid dispersion comprising velpatasvir; and c) about 16.7% w/w of the solid dispersion comprising voxilaprevir. In one embodiment, the solid dispersion comprising velpatasvir includes a 1:1 weight ratio of velpatasvir to polymer A (e.g., copovidone), such that velpatasvir is present at about 8.35% w/w and polymer A is present at about 8.35% w/w. In one embodiment, the solid dispersion comprising voxilaprevir includes a 1:1 weight ratio of voxilaprevir to polymer B (e.g., copovidone), such that voxilaprevir is present at about 8.35% w/w and polymer B is present at about 8.35% w/w. In one embodiment, the tablet further comprises: d) about 16.4% w/w of microcrystalline cellulose; e) about 6.4% w/w of lactose monohydrate; f) about 8% w/w of croscarmellose sodium; g) about 1.5% w/w of magnesium stearate; and h) about 1% w/w of colloidal silicon dioxide.

In yet another embodiment, a tablet comprises: a) about 33.3% w/w of sofosbuvir; b) about 16.7% w/w of the solid dispersion comprising velpatasvir; and c) about 16.7% w/w of the solid dispersion comprising voxilaprevir. In one embodiment, the solid dispersion comprising velpatasvir includes a 1:1 weight ratio of velpatasvir to polymer A (e.g., copovidone), such that velpatasvir is present at about 8.35% w/w and polymer A is present at about 8.35% w/w. In one embodiment, the solid dispersion comprising voxilaprevir includes a 1:1 weight ratio of voxilaprevir to polymer B (e.g., copovidone), such that voxilaprevir is present at about 8.35% w/w and polymer B is present at about 8.35% w/w. In one embodiment, the tablet further comprises: d) about 10% w/w of microcrystalline cellulose; e) about 12.8% w/w of lactose monohydrate; f) about 8% w/w of croscarmellose sodium; g) about 1.5% w/w of magnesium stearate; and h) about 1% w/w of colloidal silicon dioxide.

In still another embodiment, a tablet comprises: a) about 33.3% w/w of sofosbuvir; b) about 16.7% w/w of the solid dispersion comprising velpatasvir; and c) about 16.7% w/w of the solid dispersion comprising voxilaprevir. In one embodiment, the solid dispersion comprising velpatasvir includes a 1:1 weight ratio of velpatasvir to polymer A (e.g., copovidone), such that velpatasvir is present at about 8.35% w/w and polymer A is present at about 8.35% w/w. In one embodiment, the solid dispersion comprising voxilaprevir includes a 1:1 weight ratio of voxilaprevir to polymer B (e.g., copovidone), such that voxilaprevir is present at about 8.35% w/w and polymer B is present at about 8.35% w/w. In one embodiment, the tablet further comprises: d) about 22.8% w/w of microcrystalline cellulose; e) about 8% w/w of croscarmellose sodium; g) about 1.5% w/w of magnesium stearate; and h) about 1% w/w of colloidal silicon dioxide.

In a further embodiment, a tablet comprises: a) about 33.3% w/w of sofosbuvir; b) about 16.7% w/w of the solid dispersion comprising velpatasvir; and c) about 16.7% w/w of the solid dispersion comprising voxilaprevir. In one embodiment, the solid dispersion comprising velpatasvir includes a 1:1 weight ratio of velpatasvir to polymer A (e.g., copovidone), such that velpatasvir is present at about 8.35% w/w and polymer A is present at about 8.35% w/w. In one embodiment, the solid dispersion comprising voxilaprevir includes a 1:1 weight ratio of voxilaprevir to polymer B (e.g., copovidone), such that voxilaprevir is present at about 8.35% w/w and polymer B is present at about 8.35% w/w. In one embodiment, the tablet further comprises: d) about 17.9% w/w of microcrystalline cellulose; e) about 7.9% w/w of lactose monohydrate; f) about 5% w/w of croscarmellose sodium; g) about 1.5% w/w of magnesium stearate; and h) about 1% w/w of colloidal silicon dioxide.

In an additional embodiment, a tablet comprises: a) about 33.3% w/w of sofosbuvir; b) about 16.7% w/w of the solid dispersion comprising velpatasvir; and c) about 16.7% w/w of the solid dispersion comprising voxilaprevir. In one embodiment, the solid dispersion comprising velpatasvir includes a 1:1 weight ratio of velpatasvir to polymer A (e.g., copovidone), such that velpatasvir is present at about 8.35% w/w and polymer A is present at about 8.35% w/w. In one embodiment, the solid dispersion comprising voxilaprevir includes a 1:1 weight ratio of voxilaprevir to polymer B (e.g., copovidone), such that voxilaprevir is present at about 8.35% w/w and polymer B is present at about 8.35% w/w. In one embodiment, the tablet further comprises: d) about 15.4% w/w of microcrystalline cellulose; e) about 5.4% w/w of lactose monohydrate; f) about 10% w/w of croscarmellose sodium; g) about 1.5% w/w of magnesium stearate; and h) about 1% w/w of colloidal silicon dioxide.

In another embodiment, a tablet comprises: a) about 27.6% w/w of sofosbuvir; b) about 13.8% w/w of the solid dispersion comprising velpatasvir; and c) about 13.8% w/w of the solid dispersion comprising voxilaprevir. In one embodiment, the solid dispersion comprising velpatasvir includes a 1:1 weight ratio of velpatasvir to polymer A (e.g., copovidone), such that velpatasvir is present at about 6.9% w/w and polymer A is present at about 6.9% w/w. In one embodiment, the solid dispersion comprising voxilaprevir includes a 1:1 weight ratio of voxilaprevir to polymer B (e.g., copovidone), such that voxilaprevir is present at about 6.9% w/w and polymer B is present at about 6.9% w/w. In one embodiment, the tablet further comprises: d) about 22.2% w/w of microcrystalline cellulose; e) about 12.2% w/w of lactose monohydrate; f) about 8% w/w of croscarmellose sodium; g) about 1.5% w/w of magnesium stearate; and h) about 1% w/w of colloidal silicon dioxide.

In yet another embodiment, a tablet may include: about 20.0% w/w of the solid dispersion of voxilaprevir. In one embodiment, the solid dispersion comprising voxilaprevir includes a 1:1 weight ratio of voxilaprevir to polymer B (e.g., copovidone), such that voxilaprevir is present at about 10% w/w and polymer B is present at about 10% w/w. In one embodiment, the tablet further comprises: d) about 34.75% w/w of microcrystalline cellulose; e) about 34.75% w/w of lactose monohydrate; f) about 8% w/w of croscarmellose

4. Dosing

The specific dose level of the compounds disclosed herein (e.g., velpatasvir or a solid dispersion comprising velpatasvir, sofosbuvir, and/or voxilaprevir or a solid dispersion comprising voxilaprevir) for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject. The final dosing regimen is generally determined by the attending physician in view of good medical practice, and the aforementioned factors.

The dose and frequency of dosing of the compounds disclosed herein may also depend on pharmacokinetic and pharmacodynamic information. Pharmacokinetic and pharmacodynamic information about the compounds disclosed herein (e.g., sofosbuvir, velpatasvir, and/or voxilaprevir) can be collected through preclinical in vitro and in vivo studies, later confirmed in humans during the course of clinical trials. Accordingly, for the compounds disclosed herein, a therapeutically effective dose can be estimated initially from biochemical and/or cell-based assays. The dosage can then be formulated in animal models to achieve a desirable circulating concentration range effective in treating the targeted disease or condition. As human studies are conducted further information will emerge regarding the appropriate dosage levels and duration of treatment for various diseases and conditions.

The dose and frequency of dosing of the compounds disclosed herein may additionally depend on toxicity and therapeutic efficacy data. Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index", which typically is expressed as the ratio $LD_{50}/ED_{50}$. Compounds that exhibit large therapeutic indices, i.e., the toxic dose is substantially higher than the effective dose, are preferred. The data obtained from such cell culture assays and additional animal studies can be used in formulating a range of dosage for human use. The doses of such compounds lies preferably within a range of circulating concentrations that include the $ED_{50}$ with little or no toxicity.

The therapeutically effective amount of any of the compounds disclosed herein may be provided in a single dose or multiple doses to achieve the desired treatment endpoint. As used herein, "dose" refers to the total amount of an active ingredient (e.g., sofosbuvir, velpatasvir, or voxilaprevir) to be taken each time by a subject. As used herein, "subject" refers to humans, domestic animals (e.g., dogs and cats), farm animals (e.g., cattle, horses, sheep, goats and pigs), laboratory animals (e.g., mice, rats, hamsters, guinea pigs, pigs, rabbits, dogs, and monkeys), and the like.

In some embodiments, the compounds disclosed herein are formulated in a unit dosage or pharmaceutical dosage form. The term "unit dosage forms" or "pharmaceutical dosage forms" refers to physically discrete units suitable as unitary dosages for human patients and other mammals, each unit containing a predetermined quantity of active material calculated to produce the desired therapeutic effect, in association with a suitable pharmaceutical excipient (e.g., a tablet or capsule). The compounds are generally administered in a pharmaceutically effective amount.

Unit dosages of any of the compounds disclosed herein may also be administered once, twice, three, or four or more times daily, using any suitable mode described above. Additionally, administration or treatment with the compounds disclosed herein may be continued for a number of days; for example, commonly treatment would continue for at least 7 days, 14 days, or 28 days, for one cycle of treatment. Treatment cycles are well known, and are frequently alternated with resting periods of about 1 to 28 days, commonly about 7 days or about 14 days, between cycles. The treatment cycles, in other embodiments, may also be continuous.

In particular embodiments, an initial daily dose of a compound described herein (e.g., an initial dose from about 1 to 800 mg) may be administered to a subject, where the dose may be subsequently increased by increments until clinical efficacy is achieved. Increments of about 5, 10, 25, 50, or 100 mg can be used to increase the dose. The dosage can be increased daily, every other day, twice per week, or once per week, etc.

In some embodiments, unit dosages of velpatasvir are from about 1 mg to about 1000 mg. In certain embodiments, unit dosages of velpatasvir are from about 10 to about 800 mg, about 10 to about 600 mg, about 10 to about 400 mg, about 10 to about 300 mg, about 10 to about 250 mg, about 10 to about 200 mg, about 10 to about 150 mg, about 10 to about 100 mg, about 10 to about 75 mg, about 50 to about 600 mg, about 50 to about 400 mg, about 50 to about 300 mg, about 50 to about 250 mg, about 50 to about 200 mg, about 50 to about 150 mg, about 50 to about 100 mg, about 50 to about 75 mg, about 75 to about 600 mg, about 75 to about 400 mg, about 75 to about 300 mg, about 75 to about 250 mg, about 75 to about 200 mg, about 75 to about 150 mg, or about 75 to about 100 mg.

In some embodiments, a unit dosage of velpatasvir is about 5, about 10, about 15, about 25, about 50, about 75, about 100, about 125, about 150, about 175, about 200, about 225, about 250, about 275, about 300, about 350, about 400, about 450, about 500, or about 600 mg. In one embodiment, a unit dosage of velpatasvir is about 100 mg.

In some embodiments, a unit dosage of velpatasvir, as disclosed above, may be administered to a subject once daily, twice, three, or four or more times daily. For instance, in one embodiment, the unit dosage of velpatasvir is about 100 mg once daily.

In additional embodiments, velpatasvir may be administered to a subject in tablet form, wherein the tablet comprises a unit dosage of velpatasvir, as disclosed above. For instance, in one embodiment, a tablet comprises about 100 mg of velpatasvir. In another embodiment, a tablet comprises about 100 mg of velpatasvir and is administered to a subject once daily.

In some embodiments, velpatasvir is present in the pharmaceutical compositions disclosed herein as a solid dispersion, wherein velpatasvir is dispersed within a polymer matrix formed by a pharmaceutically acceptable polymer A.

Accordingly, in some embodiments, unit dosages of the solid dispersion comprising velpatasvir and polymer A are from about 1 to 1000 mg, about 10 to about 800 mg, about 10 to about 600 mg, about 10 to about 400 mg, about 10 to about 300 mg, about 10 to about 250 mg, about 10 to about 200 mg, about 10 to about 150 mg, about 10 to about 100 mg, about 10 to about 75 mg, about 50 to about 600 mg, about 50 to about 400 mg, about 50 to about 300 mg, about 50 to about 250 mg, about 50 to about 200 mg, about 50 to about 150 mg, about 50 to about 100 mg, about 50 to about 75 mg, about 75 to about 600 mg, about 75 to about 400 mg, about 75 to about 300 mg, about 75 to about 250 mg, about 75 to about 200 mg, about 75 to about 150 mg, or about 75 to about 100 mg.

In some embodiments, a unit dosage of the solid dispersion comprising velpatasvir and polymer A is about 5, about 10, about 15, about 25, about 50, about 75, about 100, about 125, about 150, about 175, about 200, about 225, about 250, about 275, about 300, about 350, about 400, about 450, about 500, or about 600 mg. In one embodiment, a unit dosage of the solid dispersion comprising velpatasvir and compound A is about 200 mg. In one embodiment in which the unit dosage of the solid dispersion comprising velpatasvir and polymer A is about 200 mg, the weight ratio of velpatasvir to polymer A may be about 1:1 (i.e., the solid dispersion comprises about 100 mg of velpatasvir and about 100 mg of polymer A).

In some embodiments, a unit dosage of the solid dispersion comprising velpatasvir, as disclosed above, may be administered to a subject once daily, twice, three, or four or more times daily. For instance, in one embodiment, the unit dosage of the solid dispersion comprising velpatasvir is about 200 mg once daily. In one embodiment in which the unit dosage of the solid dispersion comprising velpatasvir is about 200 mg once daily, the weight ratio of velpatasvir to polymer A may be about 1:1.

In additional embodiments, the solid dispersion comprising velpatasvir may be administered to a subject in tablet form, wherein the tablet comprises a unit dosage of the solid dispersion comprising velpatasvir, as disclosed above. For instance, in one embodiment, a tablet comprises about 200 mg of the solid dispersion of velpatasvir. In another embodiment, a tablet comprises about 200 mg of the solid dispersion comprising velpatasvir and is administered to a subject once daily. In one embodiment in which the tablet comprises about 200 mg of the solid dispersion comprising velpatasvir and is administered to a subject once daily, the weight ratio of velpatasvir to polymer A may be about 1:1.

In some embodiment, the unit dosage form of sofosbuvir is from about 1 to 1000 mg, about 10 to about 800 mg, about 10 to about 600 mg, about 10 to about 500 mg, about 10 to about 450 mg, about 10 to about 400 mg, about 10 to about 350 mg, about 10 to about 300 mg, about 10 to about 250 mg, about 10 to about 200 mg, about 10 to about 100 mg, about 10 to about 50 mg, about 50 to about 600 mg, about 50 to about 500 mg, about 50 to about 450 mg, about 50 to about 400 mg, about 50 to about 350 mg, about 50 to about 300 mg, about 50 to about 250 mg, about 50 to about 200 mg, about 50 to about 100 mg, about 100 to about 600 mg, about 100 to about 500 mg, about 100 to about 450 mg, about 100 to about 400 mg, about 100 to about 350 mg, about 100 to about 300 mg, about 100 to about 250 mg, about 100 to about 200 mg, about 200 to about 600 mg, about 200 to about 500 mg, about 200 to about 450 mg, about 200 to about 400 mg, about 200 to about 350 mg, about 200 to about 300 mg, about 200 to about 250 mg, about 300 to about 600 mg, about 300 to about 500 mg, about 300 to about 450 mg, about 300 to about 400 mg, or about 300 to about 350 mg.

In some embodiments, a unit dosage of sofosbuvir is about 50, about 100, about 150, about 200, about 250, about 300, about 350, about 400, about 450, about 500, about 550, about 600, about 650, about 700, about 750, or about 800 mg. In one embodiment, a unit dosage of sofosbuvir is about 400 mg.

In some embodiments, a unit dosage of sofosbuvir, as disclosed above, may be administered to a subject once daily, twice, three, or four or more times daily. For instance, in one embodiment, the unit dosage of sofosbuvir is about 400 mg once daily.

In additional embodiments, sofosbuvir may be administered to a subject in tablet form, wherein the tablet comprises a unit dosage of sofosbuvir, as disclosed above. For instance, in one embodiment, a tablet comprises about 400 mg of sofosbuvir. In another embodiment, a tablet comprises about 400 mg of sofosbuvir and is administered to a subject once daily.

In some embodiments, unit dosages of voxilaprevir are from about 1 mg to about 1000 mg. In certain embodiments, unit dosages of voxilaprevir are from about 10 to about 800 mg, about 10 to about 600 mg, about 10 to about 400 mg, about 10 to about 300 mg, about 10 to about 250 mg, about 10 to about 200 mg, about 10 to about 150 mg, about 10 to about 100 mg, about 10 to about 75 mg, about 50 to about 600 mg, about 50 to about 400 mg, about 50 to about 300 mg, about 50 to about 250 mg, about 50 to about 200 mg, about 50 to about 150 mg, about 50 to about 100 mg, about 50 to about 75 mg, about 75 to about 600 mg, about 75 to about 400 mg, about 75 to about 300 mg, about 75 to about 250 mg, about 75 to about 200 mg, about 75 to about 150 mg, or about 75 to about 100 mg.

In some embodiments, a unit dosage of voxilaprevir is about 5, about 10, about 15, about 25, about 50, about 100, about 125, about 150, about 175, about 200, about 225, about 250, about 275, about 300, about 350, about 400, about 450, about 500, or about 600 mg. In one embodiment, a unit dosage of voxilaprevir is about 100 mg.

In some embodiments, a unit dosage of voxilaprevir, as disclosed above, may be administered to a subject once daily, twice, three, or four or more times daily. For instance, in one embodiment, the unit dosage of voxilaprevir is about 100 mg once daily.

In additional embodiments, voxilaprevir may be administered to a subject in tablet form, wherein the tablet comprises a unit dosage voxilaprevir, as disclosed above. For instance, in one embodiment, a tablet comprises about 100 mg of voxilaprevir. In another embodiment, a tablet comprises about 100 mg of voxilaprevir and is administered to a subject once daily.

In some embodiments, voxilaprevir is present in the pharmaceutical compositions disclosed herein as a solid dispersion, wherein voxilaprevir is dispersed within a polymer matrix formed by a pharmaceutically polymer B. Accordingly, in some embodiments, unit dosages of the solid dispersion comprising voxilaprevir and polymer B are from about 1 to about 1000 mg, about 10 to about 800 mg, about 10 to about 600 mg, about 10 to about 400 mg, about 10 to about 300 mg, about 10 to about 250 mg, about 10 to about 200 mg, about 10 to about 150 mg, about 10 to about 100 mg, about 10 to about 75 mg, about 50 to about 600 mg, about 50 to about 400 mg, about 50 to about 300 mg, about 50 to about 250 mg, about 50 to about 200 mg, about 50 to about 150 mg, about 50 to about 100 mg, about 50 to about 75 mg, about 75 to about 600 mg, about 75 to about 400 mg, about 75 to about 300 mg, about 75 to about 250 mg, about 75 to about 200 mg, about 75 to about 150 mg, or about 75 to about 100 mg.

In some embodiments, a unit dosage of the solid dispersion comprising voxilaprevir and polymer B is about 5, about 10, about 15, about 25, about 50, about 100, about 125, about 150, about 175, about 200, about 225, about 250, about 275, about 300, about 350, about 400, about 450, about 500, or about 600 mg. In one embodiment, a unit dosage of the solid dispersion comprising voxilaprevir and compound B is about 200 mg. In one embodiment in which the unit dosage of the solid dispersion comprising voxilaprevir and polymer B is about 200 mg, the weight ratio of voxilaprevir to polymer B may be about 1:1 (i.e., the solid dispersion comprises about 100 mg velpatasvir and about 100 mg polymer B).

In some embodiments, a unit dosage of the solid dispersion comprising voxilaprevir, as disclosed above, may be administered to a subject once daily, twice, three, or four or more times daily. For instance, in one embodiment, the unit dosage of the solid dispersion comprising voxilaprevir is about 200 mg once daily. In one embodiment in which the unit dosage of the solid dispersion comprising voxilaprevir is about 200 mg once daily, the weight ratio of voxilaprevir to polymer B may be about 1:1.

In additional embodiments, the solid dispersion comprising voxilaprevir may be administered to a subject in tablet form, wherein the tablet comprises a unit dosage of the solid dispersion comprising voxilaprevir, as disclosed above. For instance, in one embodiment, a tablet comprises about 200 mg of the solid dispersion of voxilaprevir. In another embodiment, a tablet comprises about 200 mg of the solid dispersion comprising voxilaprevir and is administered to a subject once daily. In one embodiment in which the tablet comprises about 200 mg of the solid dispersion comprising voxilaprevir and is administered to a subject once daily, the weight ratio of voxilaprevir to polymer B may be about 1:1.

In some embodiments, a pharmaceutical composition, a pharmaceutical dosage form or tablet comprises from about 300 mg to about 500 mg of sofosbuvir; about 25 to about 175 mg of velpatasvir; and about 25 to about 175 mg of voxilaprevir. In one embodiment, the pharmaceutical composition, or alternatively, the pharmaceutical dosage form or tablet further comprises from about 150 to about 350 mg of microcrystalline cellulose; about 25 to about 175 mg of lactose monohydrate; about 25 to about 175 mg of croscarmellose sodium; about 1 to about 25 mg of colloidal silicon dioxide; and about 1 to about 15 mg of magnesium stearate.

In one embodiment, a pharmaceutical composition, a pharmaceutical dosage form or tablet comprises about 400 mg of sofosbuvir; about 100 mg of velpatasvir; and about 100 mg of voxilaprevir. In one embodiment, the pharmaceutical composition, or alternatively, the pharmaceutical dosage form or tablet further comprises about 246.9 mg of microcrystalline cellulose; about 116.6 mg of lactose monohydrate; about 104 mg of croscarmellose sodium; about 13 mg of colloidal silicon dioxide; and about 9.75 mg of magnesium stearate. In one embodiment, the pharmaceutical composition, or alternatively, the pharmaceutical dosage form or tablet further comprises about 39 mg of a film coating, such as a polyvinyl alcohol-based film coating.

In another embodiment, a pharmaceutical composition, a pharmaceutical dosage form or tablet comprises about 400 mg of sofosbuvir; about 200 mg of the solid dispersion comprising velpatasvir dispersed in a polymer matrix formed by a pharmaceutically acceptable polymer A; and about 200 mg of the solid dispersion of voxilaprevir dispersed in a polymer matrix formed by a pharmaceutically acceptable polymer B. In one embodiment, the weight ratio of velpatasvir to polymer A is about 1:1, such that the solid dispersion thereof comprises about 100 mg of velpatasvir and about 100 mg of polymer A. In one embodiment, the weight ratio of voxilaprevir to polymer B is about 1:1, such that the solid dispersion thereof comprises about 100 mg of voxilaprevir and about 100 mg of polymer B. In one embodiment, polymer A and/or polymer B is copovidone. In one embodiment, the pharmaceutical composition, the pharmaceutical dosage form or tablet further comprises about 246.9 mg of microcrystalline cellulose; about 116.6 mg of lactose monohydrate; about 104 mg of croscarmellose sodium; about 13 mg of colloidal silicon dioxide; and about 9.75 mg of magnesium stearate. In one embodiment, the pharmaceutical composition, or alternatively, the pharmaceutical dosage form or tablet further comprises about 39 mg of a film coating, such as a polyvinyl alcohol-based film coating.

In some embodiments, the amount or dosage of velpatasvir, sofosbuvir, and voxilaprevir, used in combination, does not exceed the level at which each agent is used individually, e.g., as a monotherapy. In certain embodiments, the amount or dosage of velpatasvir, sofosbuvir, and voxilaprevir, used in combination, is lower (e.g., at least 20%, at least 30%, at least 40%, or at least 50% lower) than the amount or dosage of each agent used individually, e.g., as a monotherapy. In other embodiments, the amount or dosage of velpatasvir, sofosbuvir, and voxilaprevir, used in combination that results in treatment of hepatitis C is lower (e.g., at least 20%, at least 30%, at least 40%, or at least 50% lower) than the amount or dosage of each agent used individually, e.g., as a monotherapy.

4. Treatment Methods and Uses

The treatment methods described herein may be applied to cell populations in vivo or ex vivo. "In vivo" means within a living individual, as within an animal or human. In this context, the treatment methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

The present disclosure, in one embodiment, provides a method for treating hepatitis C virus (HCV) in a human in need thereof, comprising administering to the human: an effective amount of velpatasvir (or a solid dispersion comprising velpatasvir); an effective amount of sofosbuvir; and an effective amount of voxilaprevir (or a solid dispersion comprising voxilaprevir), wherein velpatasvir is substantially amorphous, sofosbuvir is substantially crystalline, and voxilaprevir is substantially amorphous.

In some embodiments, the methods disclosed herein comprise administering, to the human, velpatasvir (or a solid dispersion comprising velpatasvir), sofosbuvir, and voxilaprevir (or a solid dispersion comprising voxilaprevir) in a daily dose by oral administration.

In some embodiments, velpatasvir (or a solid dispersion comprising velpatasvir), sofosbuvir, and voxilaprevir (or a solid dispersion comprising voxilaprevir) are co-formulated and administered or delivered simultaneously in a combined formulation to a human patient for the treatment of hepatitis C.

In other embodiments, velpatasvir (or a solid dispersion comprising velpatasvir), sofosbuvir, and voxilaprevir (or a solid dispersion comprising voxilaprevir) are administered or delivered in alternation or simultaneously in separate formulations to a human patient for the treatment of hepatitis C. In such embodiments, for instance, a composition of velpatasvir (or a solid dispersion comprising velpatasvir), a composition of sofosbuvir, and a composition of voxilaprevir (or a solid dispersion comprising voxilaprevir) are used separately.

In some embodiments, the methods comprising administering the combination of velpatasvir (or a solid dispersion comprising velpatasvir), sofosbuvir, and voxilaprevir (or a solid dispersion comprising voxilaprevir), provide synergy. The terms "synergy" and "synergistic effect" encompass a more than additive effect of two or more agents compared to their individual effects. In certain embodiments, synergy or synergistic effect refers to an advantageous effect of using two or more agents in combination, e.g., in a pharmaceutical composition, or in a method of treatment. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e., serially, whereas in combination therapy, effective dosages of two or more active ingredients are administered together. As used herein, the synergistic anti-HCV effect of the combination of velpatasvir (or a solid dispersion comprising velpatasvir), sofosbuvir, and voxilaprevir (or a solid dispersion comprising voxilaprevir) is greater than the predicted purely additive effects of the individual compounds of the combination.

In one embodiment, the pharmaceutical compositions, pharmaceutical dosage forms, and tablets comprising velpatasvir (or a solid dispersion comprising velpatasvir), sofosbuvir, and voxilaprevir (or a solid dispersion comprising voxilaprevir), as disclosed herein, are effective in treating one or more of genotype 1 HCV infected patients, genotype 2 HCV infected patients, genotype 3 HCV infected patients, genotype 4 HCV infected patients, genotype 5 HCV infected patients, and/or genotype 6 HCV infected patients.

In one embodiment, the pharmaceutical compositions, pharmaceutical dosage forms, and tablets comprising velpatasvir (or a solid dispersion comprising velpatasvir), sofosbuvir, and voxilaprevir (or a solid dispersion comprising voxilaprevir), as disclosed herein, are effective in treating genotype 1 HCV infected patients, including genotype 1a and/or genotype 1b.

In another embodiment, the pharmaceutical compositions, pharmaceutical dosage forms, and tablets comprising velpatasvir (or a solid dispersion comprising velpatasvir), sofosbuvir, and voxilaprevir (or a solid dispersion comprising voxilaprevir), as disclosed herein, are effective in treating genotype 2 HCV infected patients, including genotype 2a, genotype 2b, genotype 2c and/or genotype 2d.

In yet another embodiment the pharmaceutical compositions, pharmaceutical dosage forms, and tablets comprising velpatasvir (or a solid dispersion comprising velpatasvir), sofosbuvir, and voxilaprevir (or a solid dispersion comprising voxilaprevir), as disclosed herein, are effective in treating genotype 3 HCV infected patients, including genotype 3a, genotype 3b, genotype 3c, genotype 3d, genotype 3e and/or genotype 3f.

In still another embodiment, the pharmaceutical compositions, pharmaceutical dosage forms, and tablets comprising velpatasvir (or a solid dispersion comprising velpatasvir), sofosbuvir, and voxilaprevir (or a solid dispersion comprising voxilaprevir), as disclosed herein, are effective in treating genotype 4 HCV infected patients, including genotype 4a, genotype 4b, genotype 4c, genotype 4d, genotype 4e, genotype 4f, genotype 4g, genotype 4h, genotype 4i and/or genotype 4j.

In a further embodiment, the pharmaceutical compositions, pharmaceutical dosage forms, and tablets comprising velpatasvir (or a solid dispersion comprising velpatasvir), sofosbuvir, and voxilaprevir (or a solid dispersion comprising voxilaprevir), as disclosed herein, are effective in treating genotype 5 HCV infected patients, including genotype 5a.

In an additional embodiment, the pharmaceutical compositions, pharmaceutical dosage forms, and tablets comprising velpatasvir (or a solid dispersion comprising velpatasvir), sofosbuvir, and voxilaprevir (or a solid dispersion comprising voxilaprevir), as disclosed herein, are effective in treating genotype 6 HCV infected patients, including genotype 6a.

In another embodiment, the pharmaceutical compositions, pharmaceutical dosage forms, and tablets comprising velpatasvir (or a solid dispersion comprising velpatasvir), sofosbuvir, and voxilaprevir (or a solid dispersion comprising voxilaprevir), as described herein, are pangenotypic, meaning they are useful across all genotypes and drug resistant mutants thereof.

In some embodiments, the pharmaceutical compositions, pharmaceutical dosage forms, or tablets comprising velpatasvir (or a solid dispersion comprising velpatasvir), sofosbuvir, and voxilaprevir (or a solid dispersion comprising voxilaprevir), as described herein, are administered to a subject for treating HCV for about 24 weeks or less, about 22 weeks or less, about 20 weeks or less, about 18 weeks or less, about 16 weeks or less, about 12 weeks or less, about 10 weeks or less, about 8 weeks or less, about 6 weeks or less, or about 4 weeks or less. As discussed previously, the pharmaceutical composition, pharmaceutical dosage form, or tablet, as disclosed herein, may be administered once daily, twice daily, once every other day, two times a week, three times a week, or four or more times a week.

In some embodiments, administration of the pharmaceutical compositions, pharmaceutical dosage forms, or tablets comprising velpatasvir (or a solid dispersion comprising velpatasvir), sofosbuvir, and voxilaprevir (or a solid dispersion comprising voxilaprevir), as described herein, may result in a sustained virologic response at about 24 weeks, at about 20 weeks, at about 16 weeks, at about 12 weeks, at about 10 weeks, at about 8 weeks, at about 6 weeks, or at about 4 weeks, or at about 4 months, or at about 5 months, or at about 6 months, or at about 1 year, or at about 2 years.

In some embodiments, provided herein are methods for treating a human for HCV, with comorbidity, wherein the treatment is also effective in treating the comorbidity. A "comorbidity" to HCV is a disease that occurs at the same time as the HCV.

In some embodiments, provided herein are methods for treating a human for HCV, wherein the human is also suffering from cirrhosis. However, provided herein are methods for treating a human for HCV, wherein the human is not also suffering from cirrhosis.

5. Combination Therapy

In some embodiments, the pharmaceutical compositions and treatment methods disclosed herein may be further used or combined with one or more additional therapeutic agents for treating HCV and other conditions such as HIV infections. The additional therapeutic agent(s) can be any agent having a therapeutic effect when used or combined with velpatasvir (or a solid dispersion comprising velpatasvir), sofosbuvir, and voxilaprevir (or a solid dispersion comprising voxilaprevir).

Non-limiting examples of suitable additional therapeutic agents include interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs or therapeutic agents for treating HCV.

More specifically, the additional therapeutic agent(s) may be selected from the group consisting of:

1) interferons, e.g., pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), or belerofon, IFN alpha-2b XL, rIFN-alpha 2a, consensus IFN alpha, infergen, rebif, pegylated IFN-beta, oral interferon alpha, feron, reaferon, intermax alpha, r-IFN-beta, and infergen+actimmuneribavirin and ribavirin analogs, e.g., rebetol, copegus, VX-497, and viramidine (taribavirin);

2) ribavirin and its analogs, e.g., ribavirin (Rebetol, Copegus), and taribavirin (Viramidine);

3) HCV NS3 protease inhibitors, e.g., boceprevir (SCH-503034, SCH-7), TMC435350, BI-1335, BI-1230, VBY-376, GS-9256, GS-9451, AS-101, YH-5258, YH5530, MK6325, and MK2748; Compound X-8, Compound X-9, Compound X-10, ABT-450, Compound X-11 (described below), simeprevir (TMC-435), boceprevir (SCH-503034), narlaprevir (SCH-900518), vanieprevir (MK-7009), MK-5172, danoprevir (ITMN-191), sovaprevir (ACH-1625), neceprevir (ACH-2684), Telaprevir (VX-950), VX-813, VX-500, faldaprevir (BI-201335), asunaprevir (BMS-650032), BMS-605339, VBY-376, PHX-1766, YH5531, BILN-2065, and BILN-2061

4) alpha-glucosidase 1 inhibitors, e.g., celgosivir (MX-3253), Miglitol, and UT-231B;

5) hepatoprotectants, e.g., emericasan (IDN-6556), ME-3738, GS-9450 (LB-84451), silibilin, and MitoQ;

6) HCV NS5B polymerase inhibitors, e.g., valopicitabine (NM-283), and INX-189 (now BMS986094); VCH-916, VCH-222, GL60667, BILN-1941, PSI-7792, and GS-9190; Compound X-4 (described below), Compound X-5 (described below), ABT-333, Compound X-6 (described below), ABT-072, Compound X-7 (described below), tegobuvir (GS-9190), GS-9669, TMC647055, setrobuvir (ANA-598), filibuvir (PF-868554), VX-222, IDX-375, IDX-184, IDX-102, BI-207127, valopicitabine (NM-283), PSI-6130 (R1656), PSI-7851, BCX-4678, nesbuvir (HCV-796), BILB 1941, MK-0608, NM-107, R7128, VCH-759, GSK625433, XTL-2125, VCH-916, JTK-652, MK-3281, VBY-708, A-848837, GL59728, A-63890, A-48773, A-48547, BC-2329, BMS-791325, and BILB-1941;

8) HCV NS5A inhibitors, e.g., AZD-2836 (A-831), ACH-3102, ACH-2928, MK8325, MK-4882, PSI-461, IDX719, ABT-267; Compound X-1 (described below), Compound X-2 (described below), Compound X-3 (described below), JNJ-47910382, daclatasvir (BMS-790052), MK-8742, EDP-239, IDX-719, PPI-668, GSK-2336805, ACH-3102, A-831, A-689, AZD-2836 (A-831), AZD-7295 (A-689), and BMS-790052;

9) TLR-7 agonists, e.g., imiquimod, 852A, GS-9524, ANA-773, ANA-975, AZD-8848 (DSP-3025), and SM-360320;

10) cyclophillin inhibitors, e.g., DEBIO-025, SCY-635, and NIM811;

11) HCV IRES inhibitors, e.g., MCI-067;

12) pharmacokinetic enhancers, e.g., BAS-100, SPI-452, PF-4194477, TMC-41629, GS-9350, GS-9585, and roxythromycin; and 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, bavituximab, MDX-1106 (ONO-4538), oglufanide, and VX-497 (merimepodib); benzimidazole derivatives, benzo-1,2,4-thiadiazine derivatives, and phenylalanine derivatives.

In certain embodiments, the additional therapeutic agent is selected from the group consisting of non-nucleoside inhibitors of HCV NS5B polymerase (ABT-072 and ABT-333), HCV NS5A inhibitors (ABT-267, ACH-3102 and ACH-2928), and HCV NS3 protease inhibitors (ABT-450 and ACH-1625).

In one embodiment, the additional therapeutic agent is a HCV NS3 protease inhibitor, non-limiting examples of which include:

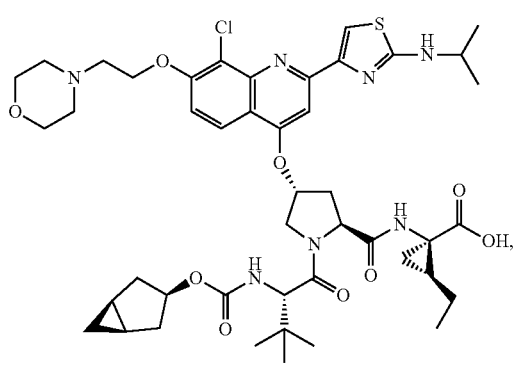
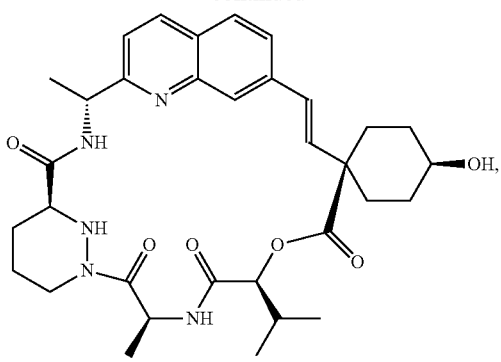
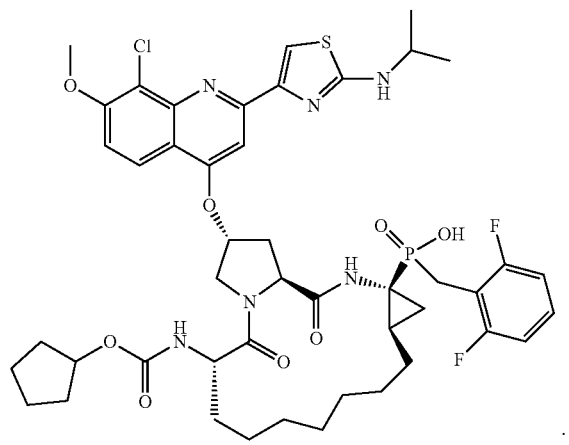
In another embodiment, the additional therapeutic agent is a cyclophillin inhibitor, such as a cyclophilin inhibitor disclosed in WO 2013/185093 Non-limiting examples of a cyclophilin inhibitor include:
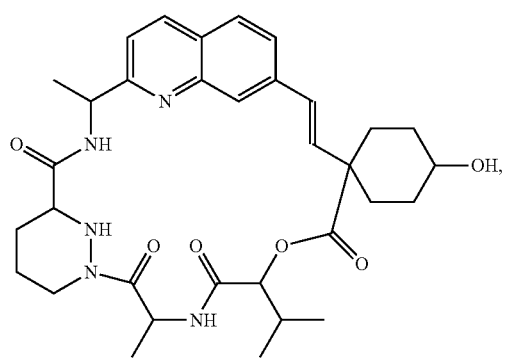
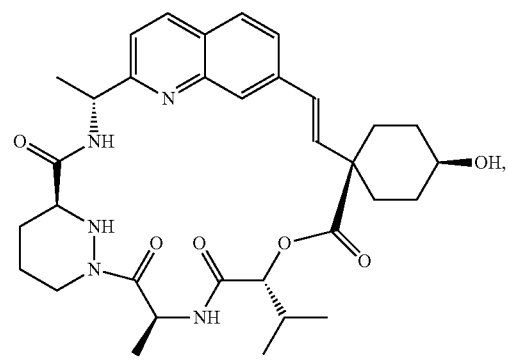
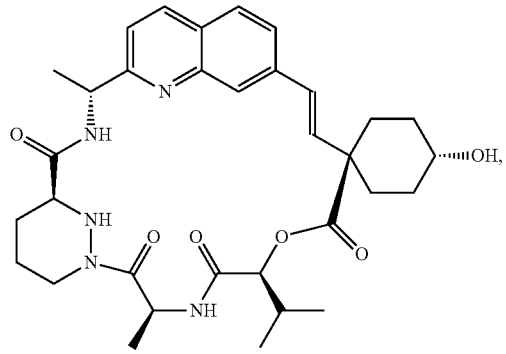
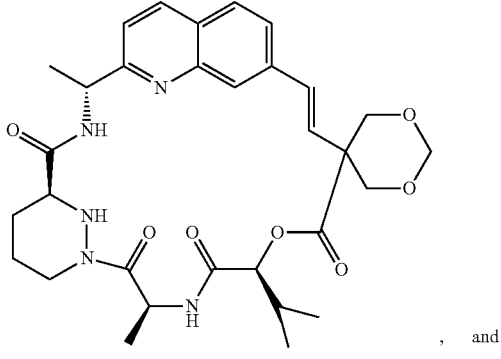
, and

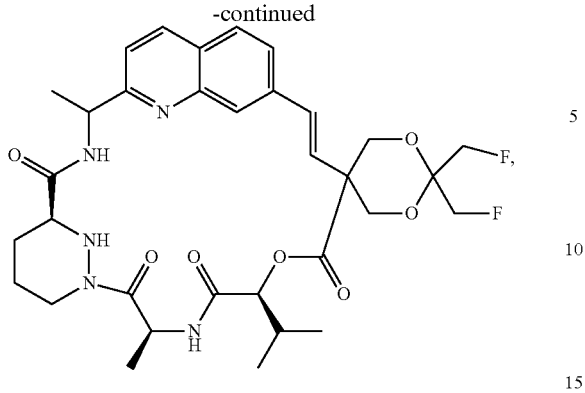

and stereoisomers and mixtures of stereoisomers thereof.

In another embodiment, the additional therapeutic agent is a non-nucleoside inhibitor of HCV NS5B polymerase, a non-limiting example of which includes GS-9669.

Compound X-1 is an inhibitor of the HCV NS5A protein and is represented by the following chemical structure:

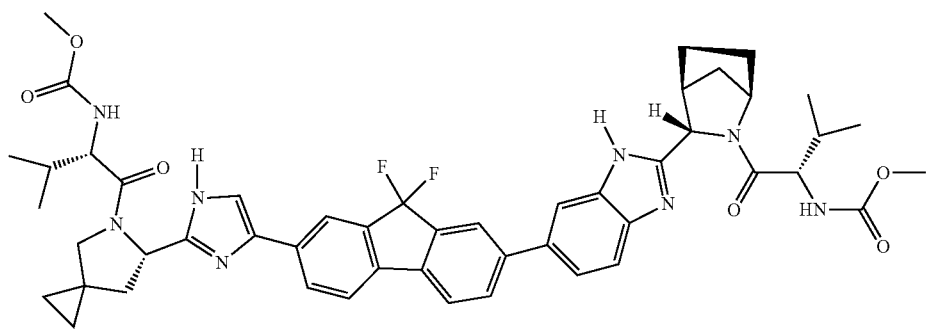

(see, e.g., U.S. Patent App. Pub. No. 2010/0310512 A1).

Compound X-2 is an NS5A inhibitor and is represented by the following chemical structure:

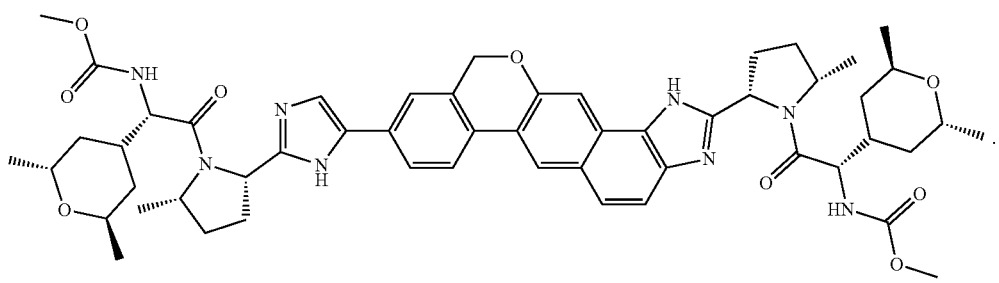

Compound X-3 is an NS5A inhibitor and is represented by the following chemical structure:

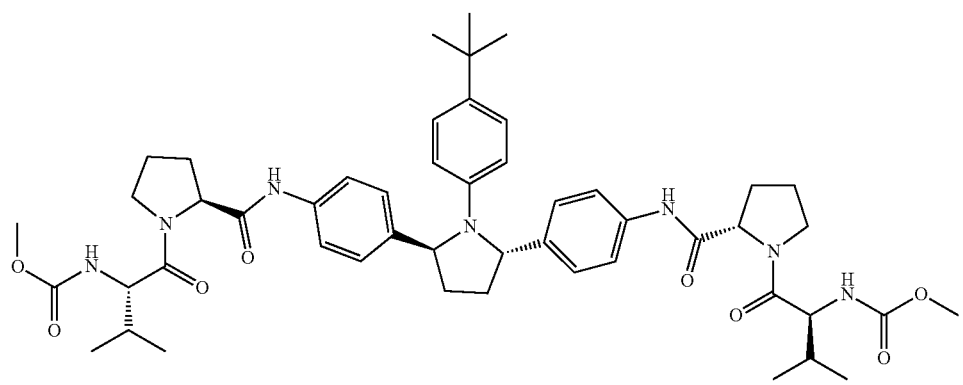 [SMILES: COC(=O)N[C@H](C(=O)N1CCC[C@H]1C(=O)Nc1ccc([C@@H]2CC[C@@H](c3ccc(NC(=O)[C@@H]4CCCN4C(=O)[C@@H](NC(=O)OC)C(C)C)cc3)N2c2ccc(C(C)(C)C)cc2)cc1)C(C)C]

(see, e.g., U.S. patent App. Pub. No. 2013/0102525 and references therein).

Compound X-4 is an NS5B Thumb II polymerase inhibitor and is represented by the following chemical structure:

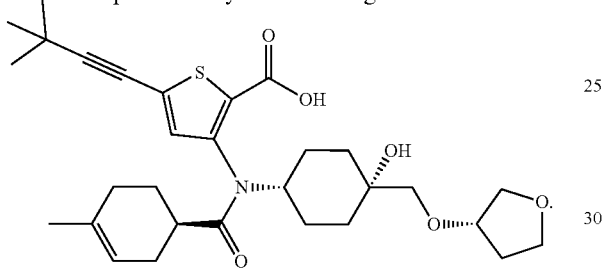

Compound X-5 is a nucleotide inhibitor prodrug designed to inhibit replication of viral RNA by the HCV NS5B polymerase, and is represented by the following chemical structure:

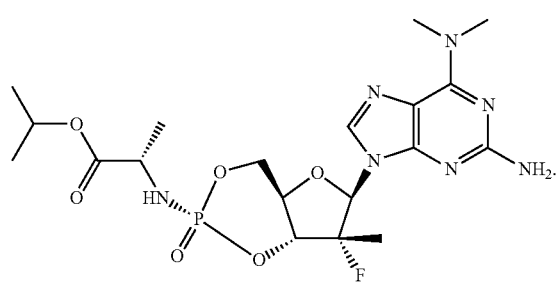 [SMILES: CC(C)OC(=O)[C@H](C)N[P@]1(=O)OC[C@H]2O[C@@H](n3cnc4c(N(C)C)nc(N)nc43)[C@](C)(F)[C@@H]2O1]

Compound X-6 is an HCV polymerase inhibitor and is represented by the following structure:

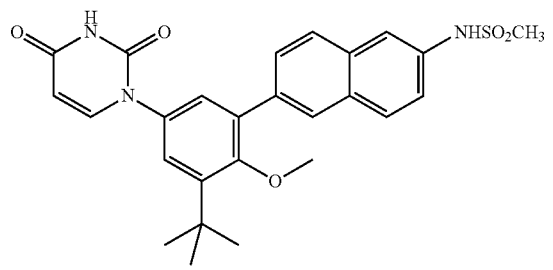

(see, e.g., U.S. Patent App. Pub. No. 2013/0102525 and references therein).

Compound X-7 is an HCV polymerase inhibitor and is represented by the following structure:

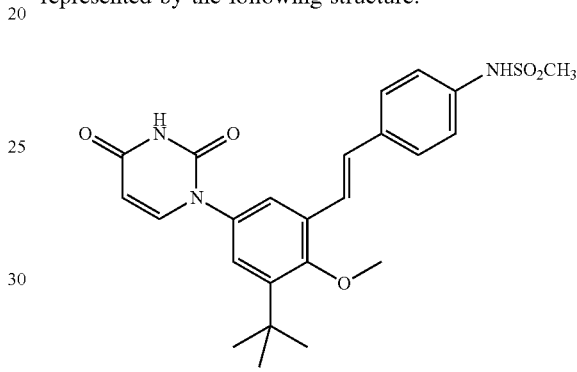

(see, e.g., U.S. Patent App. Pub. No. 2013/0102525 and references therein).

Compound X-8 is an HCV protease inhibitor and is represented by the following chemical structure:

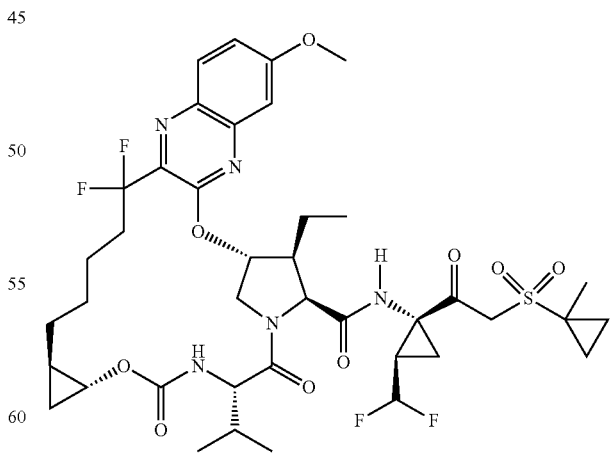

(see, e.g., U.S. Patent App. Pub. No. 2014/0017198 and references therein).

Compound X-9 is an HCV protease inhibitor and is represented by the following chemical structure:

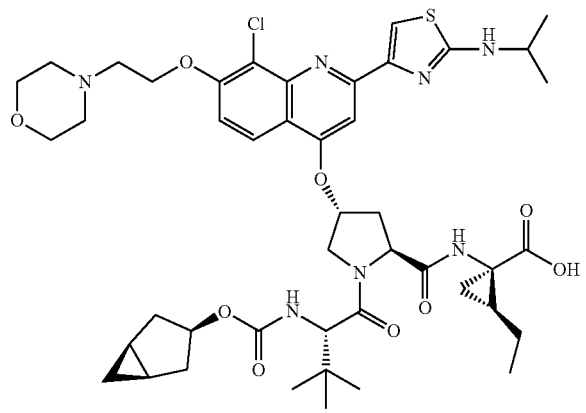

(see, e.g., U.S. Pat. No. 8,178,491 and references therein).

Compound X-10 is an HCV protease inhibitor and is represented by the following chemical structure:

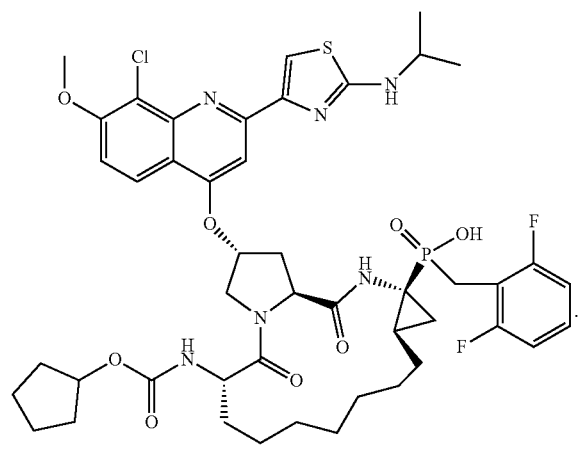 [SMILES: COc1ccc2c(O[C@@H]3C[C@H]4C(=O)N[C@]5(P(=O)(O)Cc6c(F)cccc6F)C[C@H]5CCCCCCC[C@H](NC(=O)OC5CCCC5)C(=O)N4C3)cc(-c3csc(NC(C)C)n3)nc2c1Cl]

Compound X-11 is an HCV protease inhibitor and is represented by the following chemical structure:

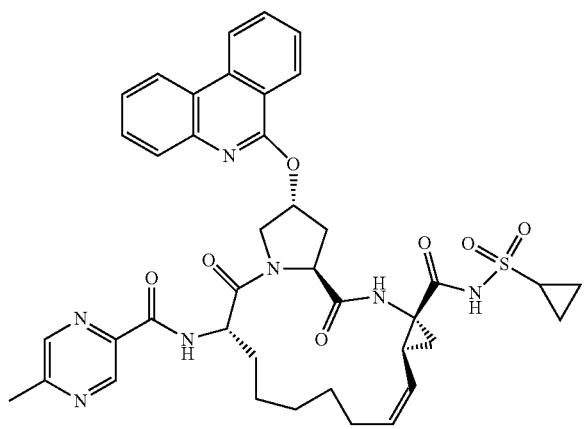 [SMILES: Cc1cnc(C(=O)N[C@H]2CCCCC/C=C\[C@@H]3C[C@@]3(C(=O)NS(=O)(=O)C3CC3)NC(=O)[C@@H]3C[C@@H](Oc4nc5ccccc5c5ccccc45)CN3C2=O)cn1]

(see, e.g., U.S. Patent App. Pub. No. 2013/0102525 and references therein).

In another embodiment, the present application provides for a method of treating hepatitis C in a human patient in need thereof comprising administering to the patient a therapeutically effective amount of a pharmaceutical composition as described herein and an additional therapeutic selected from the group consisting of: pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, albuferon, rebetol, copegus, levovirin, VX-497, viramidine (taribavirin), A-831, A-689, NM-283, valopicitabine, R1626, PSI-6130 (R1656), HCV-796, BILB 1941, MK-0608, NM-107, R7128, VCH-759, PF-868554, GSK625433, XTL-2125, SCH-503034 (SCH-7), VX-950 (Telaprevir), ITMN-191, and BILN-2065, MX-3253 (celgosivir), UT-231B, IDN-6556, ME 3738, MitoQ, and LB-84451, benzimidazole derivatives, benzo-1,2,4-thiadiazine derivatives, and phenylalanine derivatives, zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811 and a pharmaceutically acceptable carrier or excipient.

In yet another embodiment, the present application provides a composition comprising:

a) a first pharmaceutical composition comprising an effective amount of velpatasvir (or a solid dispersion comprising velpatasvir), wherein velpatasvir is substantially amorphous, an effective amount of sofosbuvir, wherein sofosbuvir is substantially crystalline, and an effective amount of voxilaprevir (of a solid dispersion comprising voxilaprevir), wherein voxilaprevir is substantially amorphous, as described herein; and b) a second pharmaceutical composition comprising at least one additional therapeutic agent selected from the group consisting of: HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, alpha-glucosidase 1 inhibitors, hepatoprotectants, non-nucleoside inhibitors of HCV, and other drugs for treating HCV, and combinations thereof.

The additional therapeutic agent may be one that treats other conditions such as HIV infections. Accordingly, the additional therapeutic agent may include, for example, HIV protease inhibiting compounds, non-nucleoside inhibitors of HIV reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin analogs, NS3 protease inhibitors, NS5b polymerase inhibitors, alpha-glucosidase 1 inhibitors, hepatoprotectants, non-nucleoside inhibitors of HCV, and other drugs for treating HCV.

More specifically, the additional therapeutic agent may be selected from the group consisting of:

1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, RO0334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 11) a CCR5 inhibitor, e.g., aplaviroc, vicriviroc, INCB9471, PRO-140, INCB15050, PF-232798, CCR5mAb004, and maraviroc, 12) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon, 13) ribavirin analogs, e.g., rebetol, copegus, levovirin, VX-497, and viramidine (taribavirin)

14) NS5a inhibitors, e.g., A-831, A-689, and BMS-790052,

15) NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-2125, 16) NS3 protease inhibitors, e.g., SCH-503034 (SCH-7), VX-950 (Telaprevir), ITMN-191, and BILN-2065, 17) alpha-glucosidase 1 inhibitors, e.g., MX-3253 (celgosivir) and UT-231B, 18) hepatoprotectants, e.g., IDN-6556, ME 3738, MitoQ, and LB-84451, 19) non-nucleoside inhibitors of HCV, e.g., benzimidazole derivatives, benzo-1,2,4-thiadiazine derivatives, and phenylalanine derivatives, 20) other drugs for treating Hepatitis C, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811, 21) pharmacokinetic enhancers, e.g., BAS-100 and SPI452, 20) RNAse H inhibitors, e.g., ODN-93 and ODN-112, and 22) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDXO10 (iplimumab), PBS119, ALG889, and PA-1050040.

It is contemplated that the additional therapeutic agent will be administered in a manner that is known in the art and the dosage and dosing frequency may be selected by someone of skill in the art. For example, the additional agent may be administered (e.g., in tablet form) in a dose from about 0.01 milligrams to about 2 grams once daily, twice daily, three times daily, or more or four times daily.

EXAMPLES

In the following examples and throughout this disclosure, abbreviations as used herein have respective meanings as follows:

| | |
|---|---|
| % CV | Percent coefficient of variation |
| AUC | Area Under the Curve |
| $AUC_{inf}$ | Area under the plasma concentration-time curve from time zero extrapolated to the infinite time |
| $AUC_{last}$ | Area under the plasma concentration-time curve from time zero to time of last measureable concentration |
| $AUC_{tau}$ | Area under the plasma concentration-time curve for a dosing interval |
| CL | Drug clearance |
| CL/F | Drug clearance following oral administration |
| $CL_{ss}/F$ | Drug clearance at steady state following oral administration |
| $C_{last}$ | Last observed plasma concentration |
| $C_{max}$ | Maximum concentration |
| cP | Centipoise |
| DCM | Dichloromethane |
| EAS | Ethyl acetate solvate |
| $EC_{50}$ | Concentration of a compound inhibiting virus replication by 50% |
| $E_{max}$ | Maximal effect range |
| F | Bioavailability |
| FDC | Fixed Dose Combination |
| h or hr | Hour |
| HFM | High-fat/high-calorie meal |
| ICH | International Conference on Harmonisation; Impurities guidelines |
| MFM | Moderate-fat/moderate-calorie meal |
| Mo | Months |
| N/A | Not applicable |
| NP | Not performed |
| ° C. | Degrees Celsius |
| PD | Pharmacodynamics |
| PE | Polyethylene |
| PEG | Polyethylene glycol |
| PK | Pharmacokinetics |
| Q1, Q3 | First quartile, third quartile |
| RH | Relative humidity |
| s | Second |
| SSD | Spray-dried solid dispersion |
| SOF | Sofosbuvir |
| SVR | Sustained virologic response |
| SVR24 | Sustained virologic response for 24 weeks |
| $t_{1/2}$ | Half-life (h) |
| $t_{last}$ | Time of last observed plasma concentration(h) |
| $t_{max}$ | Time to reach $C_{max}$ (h) |
| VEL | Velpatasvir |
| VOX | Voxilaprevir |
| w | Weight |
| μm | Micrometer |
| XRPD | X-ray powder diffraction |

Example 1: Tablet Preparation and Formulation

A. Dose Selection of Tablets i. Sofosbuvir

Sofosbuvir exhibits a variety of forms, including crystalline forms and solvates thereof (see, e.g., U.S. Patent App. Pub. Nos.: 2010/0298257, 2011/0251152, and 2015/0175646). In some embodiments, and the Examples presented herein, the tablet formulation includes sofosbuvir having Form 6 and, optionally, a trace amount of Form 7. Crystalline Forms 6 and 7 of sofosbuvir are non-hygroscopic and exhibit a similar aqueous solubility of ≥2 mg/mL at 37° C. Form 6 of sofosbuvir is the thermodynamically stable form and remains physically stable when suspended in water. Form 7 of Sofosbuvir, while physically stable in water for short periods of time, can be converted to Form 6 with prolonged stirring. Additionally, Forms 6 and 7 are not photosensitive and remain physically and chemically stable when stored in an open container for 1 month at 40° C./75% RH.

The sofosbuvir dose selected for the tablet formulation is 400 mg once daily. Support for the 400 mg sofosbuvir dose can be derived from $E_{max}$ PK/PD modeling with early virological and human exposure data which also supports the selection of a 400 mg sofosbuvir dose over others tested.

The mean sofosbuvir major metabolite $AUC_{tau}$ for the 400 mg sofosbuvir dose is associated with approximately 77% of the maximal HCV RNA change from baseline achievable as determined by this model, a value which is on the cusp of the plateau of the exposure-response sigmoidal curve. In a sigmoidal $E_{max}$ model, there is a relatively linear exposure-response relationship in the 20 to 80% maximal effect range. Therefore, given that sofosbuvir exposure with 200 mg tablets appears dose-proportional with single doses up to 1200 mg, doses below 400 mg are expected to yield considerable reductions in the magnitude of HCV RNA change from baseline. Similarly, in order to improve upon an efficacy prediction of 77% in the plateau of the exposure-response curve, substantial increases in exposure (and hence dose) would be needed for an appreciable increase in antiviral effect.

The sofosbuvir dose of 400 mg once daily was associated with higher SVR rates in genotype 1 HCV infected patients as compared to the 200 mg once daily dose when given in conjunction with additional HCV therapeutics for 24 weeks. Safety and tolerability appeared similar across both dose levels. In addition, when sofosbuvir 400 mg once daily plus other HCV therapeutics were given to genotype 2 or 3 HCV infected patients, 100% SVR24 was observed.

ii. Velpatasvir

Velpatasvir exhibits a variety of forms, including that of the free base, crystalline forms, amorphous form, salts thereof, solvates thereof, and hydrates thereof. In certain embodiments, and in the Examples presented herein, the tablets comprise the substantially amorphous fee base form of velpatasvir.

Following single and multiple oral doses of velpatasvir, maximum plasma concentrations occurred between 1.50 and 3.25 hours (median $t_{max}$). Velpatasvir exhibited nonlinear PK across the dose range of 5 to 450 mg. Increases in exposure, as assessed by AUC and $C_{max}$, were greater than dose-proportional from 5 to 50 mg and were less than dose-proportional from 50 to 450 mg. Consistent with the half-life of velpatasvir, modest accumulation was observed with time. After multiple once-daily doses of velpatasvir greater than 5 mg, the mean plasma concentrations of velpatasvir at 24 hours postdose were above the protein-adjusted concentration of a compound inhibiting virus replication by 50% ($EC_{50}$) for genotype 1 to 6 HCV replicons (Table 1).

TABLE 1

| | Single Dose (Cohorts 1-6[a]) | | | | |
|---|---|---|---|---|---|
| PK Parameter | 5 mg (N = 12) | 50 mg (N = 12) | 100 mg (N = 24) | 150 mg (N = 12) | 450 mg (N = 12) |
| $AUC_{last}$ (ng · h/mL) | 134.2 (69.6) | 2970.7 (40.1) | 4985.6 (44.8) | 4925.9 (48.0) | 9503.8 (34.5) |
| $AUC_{inf}$ (ng · h/mL) | 158.9 (64.0) | 3017.2 (40.1) | 5055.0 (45.3) | 4978.3 (47.8) | 9578.1 (34.3) |
| $C_{max}$ (ng/mL) | 22.4 (55.4) | 371.3 (32.7) | 574.9 (37.2) | 608.4 (46.7) | 1121.6 (31.7) |
| $C_{last}$ (ng/mL) | 1.40 (26.9) | 2.34 (61.4) | 2.85 (80.3) | 2.23 (40.1) | 3.28 (50.5) |
| $t_{max}$ (h) | 1.50 (1.50, 2.00) | 2.50 (2.00, 3.00) | 2.50 (2.50, 3.00) | 2.75 (2.50, 3.50) | 3.25 (2.50, 3.75) |
| $t_{last}$ (h) | 24.00 (14.00, 36.00) | 72.00 (48.00, 96.00) | 95.00 (71.50, 96.00) | 96.00 (84.02, 96.00) | 96.00 (96.00, 96.00) |
| $t_{1/2}$ (h) | 11.20 (5.40, 16.89) | 13.62 (10.62, 16.47) | 15.73 (12.63, 17.11) | 16.16 (14.55, 17.55) | 14.97 (12.91, 16.73) |
| CL/F (mL/h) | 58,398.0 (124.4) | 19,188.4 (39.2) | 24,617.9 (50.8) | 72,185.5 (196.4)[b] | 53,676.4 (42.5) |
| | Multiple Dose (Cohorts 1-4[a]) | | | | |
| PK Parameter | 5 mg (N = 12) | 50 mg (N = 12) | | 150 mg (N = 12) | 450 mg (N = 12) |
| $AUC_{tau}$ (ng · h/mL) | 172.3 (51.7) | 3032.6 (40.4) | | 4890.8 (45.4) | 9511.2 (40.9) |
| $C_{max}$ (ng/mL) | 28.3 (49.3) | 411.4 (40.7) | | 669.4 (48.1) | 1195.7 (38.0) |
| $C_{tau}$ (ng/mL) | 2.2 (76.0) | 37.9 (59.5) | | 63.4 (42.8) | 127.7 (44.3) |
| $t_{max}$ (h) | 2.00 (1.25, 2.50) | 2.50 (2.25, 3.00) | | 2.50 (2.50, 3.50) | 3.00 (2.50, 4.25) |

TABLE 1-continued

| | | | | |
|---|---|---|---|---|
| $t_{last}$ (h) | 24.00 | 24.00 | 24.00 | 24.00 |
| | (24.00, 24.00) | (24.00, 24.00) | (24.00, 24.00) | (24.00, 24.00) |
| $t_{1/2}$ (h) | 13.73 | 13.02 | 15.15 | 11.74 |
| | (13.19, 15.88) | (11.43, 16.23) | (12.03, 15.63) | (10.64, 13.12) |
| $CL_{ss}/F$ (mL/h) | 36,095.7 | 19,593.0 | 45,082.3 | 58,804.6 |
| | (46.4) | (50.5) | (88.3) | (57.3) |

Note:
All PK parameters are reported as mean (% CV), except for $t_{max}$, $t_{last}$, and $t_{1/2}$, which are reported as median (Q1, Q3).
[a] VEL dosing by cohort: Cohort 1 = 50 mg, Cohort 2 = 150 mg, Cohort 3 = 5 mg, Cohort 4 = 450 mg, Cohorts 5 and 6 (pooled in the fasted state) = 100 mg.
[b] Mean (% CV) CL/F for the VEL 150 mg group (excluding one patient) was 31,403.8 (40.5) mL/h.

iii. Voxilaprevir

Voxilaprevir exhibits various forms, as described, e.g., in WO 2015/100144 and U.S. Patent App. Pub. No. 2015/0175625 A1. Initial studies were conducted using the crystalline Form VI of voxilaprevir. As described previously, Form VI of voxilaprevir is characterized by an X-ray powder diffractogram comprising the following peaks (±0.2°): at 14.6, 15.4, and 20.0 °2θ, as determined on a diffractometer using Cu—Kα radiation. Following single and multiple oral doses of voxilaprevir, Form VI, maximum plasma concentrations occurred between 2.0 and 5.0 hours (median $t_{max}$). Voxilaprevir, Form VI exhibited substantially linear PK across the dose range of 30 to 300 mg. Voxilaprevir, Form VI exhibited a median half-life ($t_{1/2}$) of 9.37, 36.67, and 35.49 hours after single doses of 30, 100, and 300 mg doses, respectively. After multiple doses of 30, 100, and 300 mg doses, voxilaprevir, Form VI exhibited a median half-life (tin) of 40.95, 30.49, and 27.61 hours, respectively. Voxilaprevir, Form VI exhibited dose-linear pharmacokinetics after single and multiple dosing across the range of 30 to 300 mg in healthy subjects. Modestly less than dose-proportional increases in $C_{tau}$ were observed between the 100 and 300 mg doses. Steady-state concentrations of voxilaprevir, Form VI were achieved after 7 days of once-daily dosing across all dose levels (Table 2).

TABLE 2

| PK Parameter | 30 mg (N = 12) | 100 mg (N = 48) | 300 mg (N = 12) |
|---|---|---|---|
| | Single Dose | | |
| $AUC_{last}$ (ng · h/mL) | 33.0 | 188.3 | 425.3 |
| $AUC_{inf}$ (ng · h/mL) | 56.9 | 245.0 | 484.9 |
| $C_{max}$ (ng/mL) | 3.7 | 17.6 | 34.5 |
| $t_{max}$ (h) | 4.0 | 3.0 | 2.0 |
| $t_{1/2}$ (h) | 9.37 | 36.67 | 35.49 |
| | Multiple Dose | | |
| $AUC_{tau}$ (ng · h/mL) | 74.2 | 364.4 | 1030.5 |
| $C_{max}$ (ng/mL) | 7.3 | 46.0 | 155.0 |
| $C_{tau}$ (ng/mL) | 1.9 | 5.7 | 10.0 |
| $t_{max}$ (h) | 5.0 | 5.0 | 5.0 |
| $t_{1/2}$ (h) | 40.95 | 30.49 | 27.61 |

Note:
All PK parameters are reported as mean (% CV), except for $t_{max}$, $t_{last}$, and $t_{1/2}$, which are reported as median.

It was found that the crystalline Form VI of voxilaprevir was physically metastable, and converted to the crystalline Form VIII, which exhibits an aqueous solubility and oral bioavailability (in a dog model) that are approximately 50% less than those for crystalline Form VI. As described previously, Form VIII of voxilaprevir is characterized by an X-ray powder diffractogram comprising the following peaks (±0.2°): at 7.8, 8.2, and 20.2 °2θ, as determined on a diffractometer using Cu—Kα radiation.

Accordingly, a spray dried dispersion of voxilaprevir in the amorphous free acid form was selected for incorporation into the tablet formulation. As shown in Table 3, a relative bioavailability study in healthy subjects established that the administration of tablets comprising 100 mg of the amorphous free acid form of voxilaprevir achieved approximately 9% higher exposure (AUC) and 43% higher Cm, compared to the tablets (2×50 mg tablets) comprising voxilaprevir, Form VI.

TABLE 3

| | Single Dose | | |
|---|---|---|---|
| PK Parameter | Amorphous Free Acid 100 mg Healthy Subjects, Fasted (N = 15) | VOX Form VI Tablet, 2 × 50 mg | Geometric Least Square Ratio (90% CI) Amorphous Free Acid/Form VI GMR |
| $AUC_{inf}$ (ng · hr/mL) | 367 | 326 | 1.09 |
| $C_{max}$ (ng/mL) | 32.7 | 21.7 | 1.43 |

| | Amorphous Free Acid 100 mg | | |
|---|---|---|---|
| PK Parameter | Healthy Subjects, Fasted (N = 15) | Healthy Subjects, Fed (with Moderate Food) | Fed/Fasted GMR |
| $AUC_{inf}$ (n · hr/mL) | 367 | 494 | 1.53 |
| $C_{max}$ (ng/mL) | 32.7 | 44.2 | 1.50 |

B. Solid Dispersion Comprising Velpatasvir

In some embodiments, and in the Examples presented herein, the tablet formulation includes a spray-dried solid dispersion (SSD) of velpatasvir. Velpatasvir having the amorphous free base form was selected as the starting material for the formation of the substantially amorphous velpatasvir SSD.

The spray dry feed solution was prepared by solubilizing velpatasvir and copovidone in the feed solvent. In certain cases, aggressive mixing or homogenization can be used to avoid clumping of the composition.

The feed solution was initially evaluated for appropriate solvent with regard to solubility, stability, and viscosity. Ethanol, methanol, acetone, and dichloromethane all demonstrated excellent solubility. Ethanol and methanol-based feed stocks were assessed for preparation ease and spray dried at a range of inlet and outlet temperatures to assess the robustness of the spray dry process. While both solvents gave rapid dissolution of velpatasvir and copovidone, ethanol was selected for the studies described in the Examples.

An ethanolic solution of 10% velpatasvir and 10% copovidone was prepared using homogenization. Viscosity of ethanolic solutions of velpatasvir and copovidone were low. Overall, the combination of velpatasvir and copovidone in a 1:1 weight ratio demonstrated good chemical stability in the ethanolic feed solution. Unless otherwise stated, the term VEL SSD or velpatasvir SSD refers to an amorphous solid dispersion prepared by spray drying comprising a 1:1 ratio of velpatasvir and copovidone.

Spray drying the solution to remove ethanol resulted in high yields across a wide range of spray-drying outlet temperatures with no material accumulation on the spray dry chamber. Spray drying was conducted using a commercially available spray dryer (e.g., Anhydro, Buchi, or Niro spray dryer).

Organic volatile impurities, including the ethanol solvent were rapidly removed during secondary drying in a tray oven 60° C., purged with room air or via a double cone dryer. Loss on drying can be attributable to water, which can be confirmed by Karl Fischer titration. Residual ethanol was reduced below ICH guidelines of 0.5% w/w by 6 hours of drying.

C. Solid Dispersion Comprising Voxilaprevir i. Spray-Drying

In some embodiments, and in the Examples presented herein, the tablet formulation includes a spray-dried solid dispersion (SSD) of voxilaprevir. Voxilaprevir as the ethyl acetate solvate (EAS), Form II was selected as the starting material for the formation of substantially amorphous voxilaprevir SSD. As discussed previously, voxilaprevir EAS, Form II is characterized by an X-ray powder diffractogram comprising the following peaks (±0.2°): at 8.7, 13.0, and 17.4 °2θ, as determined on a diffractometer using Cu—Kα radiation.

The spray-dry process consisted of the following three sequential steps.

(1) Preparation of the feed solution by dissolving voxilaprevir EAS, Form II and copovidone in a suitable solvent.

(2) Spray-drying the feed solution to yield a primary-dried solid dispersion of voxilaprevir as the amorphous free acid. The feed solution was pumped into a drying chamber through a nozzle, which atomizes the feed solution into droplets. Hot nitrogen drying gas was introduced to the drying chamber concurrently with the atomized feed solution and supplies the energy required to evaporate the solvent from the droplets. The resulting spray-dried solid particles exited the drying chamber and were separated from the gas stream in a cyclone. Particles were collected in a vessel at the bottom of the cyclone. The nitrogen drying gas was circulated back to the drying chamber, and most of the entrained solvent vapor was removed from the gas stream by a condenser.

(3) Secondary-drying the spray-dried particles to remove water and residual solvents to yield the voxilaprevir SSD, wherein voxilaprevir SSD exhibits the amorphous free acid form. Unless stated otherwise, the term "voxilaprevir SSD" refers to an amorphous solid dispersion of voxilaprevir having a 1:1 ratio of voxilaprevir to copovidone.

The selection of a suitable solvent for the spray drying process was based on (1) the solubility of voxilaprevir EAS, Form II and copovidone in the solvent, (2) the chemical stability of voxilaprevir EAS, Form II in the presence of the solvent, and (3) the impact of the solvent on feed solution properties and particle properties of the resulting solid dispersion. Acetone and dichloromethane were evaluated as solvents for the feed solution because of their low boiling points and the high solubility of voxilaprevir EAS, Form II (>300 mg/mL) in these solvents.

The feed solution containing 15% w/w solids was prepared by dissolving 7.5% w/w voxilaprevir EAS, Form II and 7.5% w/w copovidone into acetone or DCM. Voxilaprevir EAS, Form II and copovidone dissolved rapidly in both solvents. Both acetone and DCM feed solutions were spray-dried at solid batch sizes of 150 and 360 g, respectively, on a Buchi mini spray dryer B-290. The primary-dried solid dispersion of voxilaprevir (amorphous free acid) were secondary-dried in a vacuum oven at 65° C.

A higher overall process yield was obtained for the acetone-based feed solution (84%) than for the DCM-based feed solution (70%). The resulting voxilaprevir SSD had comparable residual solvent contents (~0.3%). The spray-dried solid dispersions of substantially amorphous voxilaprevir obtained from the DCM feed solution had larger mean particle sizes (13 μm) than the spray-dried dispersions obtained from the acetone feed solution (6 μm). Overall, the spray-drying processes using both acetone and DCM feed solutions were deemed acceptable. However, acetone was selected over DCM due to the relatively high ICH limit of 5000 ppm (0.5%) for acetone as a residual solvent, compared to 600 ppm (0.06%) for DCM.

ii. Chemical and Physical Stability

Voxilaprevir SSD is hygroscopic, with a reversible weight gain of 11% when cycled between 0% and 90% RH at 25° C. Additionally, voxilaprevir SSD is not light-sensitive when exposed to 1.2 million lux-hours/200 W·hr/m². In the solid state, voxilaprevir remains substantially amorphous without an apparent phase separation or recrystallization when stored under open conditions at 40° C./75% RH for 12 months, and is chemically stable with total impurity/degradation products remaining between 2.0-2.2% w/w when stored under open conditions at 40° C./75% RH for 1 month.

The impact of copovidone peroxide content on the chemical stability of voxilaprevir SSD was evaluated. Copovidone was tested and released to a specification of not more than 400 ppm peroxides. Copovidone with typical peroxides content of ≤400 ppm (Lot A) and copovidone with high peroxides content of 665 ppm (Lot B) were both processed into voxilaprevir SSD. Voxilaprevir SSD was packaged in a designated commercial packaging configuration (i.e., polyethylene bags sealed in aluminum bags with 5% w/w desiccant) and stored for 6 months at both 25° C./60% RH and 40° C./75% RH. As shown in Table 4, voxilaprevir SSD displayed excellent stability with no increase in total voxilaprevir degradation products after 6 months of storage. The data demonstrate that the stability of voxilaprevir SSD is not impacted by copovidone peroxide levels up to and beyond the compendial specification limit of 400 ppm.

TABLE 4

| VOX SSD Lot | Peroxide Content (ppm) | Storage Condition[a] | Time (Months) | Appearance | Assay (%) | Total Imp./Deg. (%) | Water Content (%) |
|---|---|---|---|---|---|---|---|
| A | ≤400 | Initial | 0 | Conforms | 48.3 | 0.4 | 0.1 |
|   |   | 40° C./ | 1 | Conforms | 48.0 | 0.5 | 0.5 |

TABLE 4-continued

| VOX SSD Lot | Peroxide Content (ppm) | Storage Condition[a] | Time (Months) | Appearance | Assay (%) | Total Imp./Deg. (%) | Water Content (%) |
|---|---|---|---|---|---|---|---|
| | | 75% RH | 3 | Conforms | 48.0 | 0.5 | 0.5 |
| | | | 6 | Conforms | 47.6 | 0.5 | 0.7 |
| | | 25° C./ 60% RH | 3 | Conforms | 47.7 | 0.5 | 0.8 |
| | | | 6 | Conforms | 47.5 | 0.5 | 0.7 |
| B | 665 | Initial | 0 | Conforms | 47.2 | 0.4 | 0.1 |
| | | 40° C./ 75% RH | 1 | Conforms | 47.0 | 0.5 | 0.5 |
| | | | 3 | Conforms | 47.3 | 0.5 | 0.6 |
| | | | 6 | Conforms | 46.6 | 0.5 | 0.8 |
| | | 25° C./ 60% RH | 3 | Conforms | 47.2 | 0.5 | 0.5 |
| | | | 6 | Conforms | 46.5 | 0.5 | 1.1 |

[a]VOX SSD packaged in closed PE bags inside heat-sealed aluminum bags with desiccant between the PE bag and the aluminum bag. Desiccant weight was approximately 5% of the weight of the bulk powder.

The impact of voxilaprevir SSD potency on the chemical and physical stability thereof was also evaluated (Table 5). This development study compared the properties of typical voxilaprevir SSD with 50% w/w voxilaprevir/50% w/w copovidone (Lot C) to those of sub-potent voxilaprevir SSD with 40% w/w voxilaprevir/60% w/w copovidone (Lot D) and super-potent voxilaprevir SSD with 60% w/w voxilaprevir/40% w/w copovidone (Lot E). Voxilaprevir SSD was packaged in a designated commercial packaging configuration (i.e., polyethylene bags sealed in aluminum bags with 5% w/w desiccant) and stored for 6 months at both 25° C./60% RH and 40° C./75% RH. As shown in Table 5, all lots exhibited comparable properties, with VOX SSD water content ranging from 0.1 to 0.8%. All lots of voxilaprevir SSD displayed excellent stability with no increase in total voxilaprevir degradation products after 6 months of storage. All samples remained amorphous by XRPD throughout the duration of the study. The data demonstrate that the stability of voxilaprevir SSD is not impacted by voxilaprevir SSD potency levels of not less than 40% w/w and not more than 60% w/w.

The impact of reprocessed voxilaprevir SSD on the chemical and physical stability of voxilaprevir SSD was additionally evaluated. Voxilaprevir was reprocessed (re-dissolved, spray-dried, and secondary dried) twice and packaged in a designated commercial packaging configuration (i.e., polyethylene bags sealed in aluminum bags with 5% w/w desiccant) and stored for 6 months at both 25° C./60% RH and 40° C./75% RH. As shown in Table 6, all lots of voxilaprevir SSD displayed excellent stability with no increase in total voxilaprevir degradation products after 6 months of storage. All samples remained amorphous by XRPD throughout the duration of the study. The data demonstrate that the stability of voxilaprevir SSD is not impacted by reprocessing of voxilaprevir SSD.

TABLE 5

| VOX SSD (Lot) | Storage Condition[a] | Time (Months) | Appearance | Assay (%) | Total Imp./Deg. (%) | Water Content (%) | Solid-State by XRPD |
|---|---|---|---|---|---|---|---|
| C | Initial | 0 | Conforms | 48.3 | 0.4 | 0.1 | Amorphous |
| | 40° C./ 75% RH | 1 | Conforms | 48.0 | 0.5 | 0.5 | Amorphous |
| | | 3 | Conforms | 48.0 | 0.5 | 0.5 | Amorphous |
| | | 6 | Conforms | 47.6 | 0.5 | 0.7 | Amorphous |
| | 25° C./ 60% RH | 3 | Conforms | 47.7 | 0.5 | 0.8 | NP |
| | | 6 | Conforms | 47.5 | 0.5 | 0.7 | Amorphous |
| D | Initial | 0 | Conforms | 40.1 | 0.8 | 0.1 | Amorphous |
| | 40° C./ 75% RH | 1 | Conforms | 40.1 | 0.9 | 0.6 | Amorphous |
| | | 3 | Conforms | 40.0 | 1.0 | 0.7 | Amorphous |
| | | 6 | Conforms | 39.6 | 0.8 | 0.7 | Amorphous |
| | 25° C./ 60% RH | 3 | Conforms | 40.0 | 1.0 | 0.6 | NP |
| | | 6 | Conforms | 40.0 | 0.8 | 0.7 | Amorphous |
| E | Initial | 0 | Conforms | 59.9 | 0.7 | 0.1 | Amorphous |
| | 40° C./ 75% RH | 1 | Conforms | 59.6 | 0.9 | 0.5 | Amorphous |
| | | 3 | Conforms | 59.6 | 1.0 | 0.6 | Amorphous |
| | | 6 | Conforms | 59.1 | 0.8 | 0.6 | Amorphous |
| | 25° C./ 60% RH | 3 | Conforms | 59.7 | 1.0 | 0.6 | NP |
| | | 6 | Conforms | 59.1 | 0.8 | 0.7 | Amorphous |

[a]VOX SSD packaged in closed PE bags inside heat-sealed aluminum bags with desiccant between the PE bag and the aluminum bag. Desiccant weight was approximately 5% of the weight of the bulk powder.

TABLE 6

| Storage Condition[a] | Time (Months) | Appearance | Assay (%) | Total Imp./Deg. (%) | Water Content (%) | Solid-State by XRPD |
|---|---|---|---|---|---|---|
| Initial | 0 | Conforms | 49.2 | 0.3 | 0.14 | Amorphous |
| 40° C./ | 1 | Conforms | 48.9 | 0.5 | 0.60 | Amorphous |
| 75% RH | 3 | Conforms | 49.8 | 0.5 | 0.58 | Amorphous |
|  | 6 | Conforms | 48.9 | 0.5 | 0.65 | Amorphous |
| 25° C./ | 3 | Conforms | 49.2 | 0.6 | 0.47 | NP |
| 60% RH | 6 | Conforms | 48.9 | 0.5 | 0.56 | Amorphous |

[a]VOX SSD packaged in closed PE bags inside heat-sealed aluminum bags with desiccant between the PE bag and the aluminum bag. Desiccant weight was approximately 5% of the weight of the bulk powder.

D. Solid-State Compatibility

Sofosbuvir, velpatasvir SSD, and voxilaprevir SSD are chemically and physically compatible in the solid-state. The solid-state compatibility of sofosbuvir, velpatasvir SSD, and voxilaprevir SSD was evaluated by preparing a powder blend composed of 49.75% w/w sofosbuvir, 24.88% w/w of velpatasvir SSD, and 24.88% w/w of voxilaprevir SSD, and 0.25% w/w magnesium stearate (added as a lubricant). The powder blend was dry granulated using a roller compactor and then milled. The resulting granules (Lot F) contained 400 mg of sofosbuvir, 100 mg velpatasvir (as 200 mg velpatasvir SSD), and 100 mg voxilaprevir (as 200 mg voxilaprevir SSD) equivalent to the relative compositions in the sofosbuvir/velpatasvir/voxilaprevir tablet: 400/100/100 mg.

The chemical and physical stability of sofosbuvir/velpatasvir SSD/voxilaprevir SSD granules, packaged in glass vials (protected from light), was evaluated for 6 months at 25° C./60% RH and 40° C./75% RH under open and closed conditions. As summarized in Table 7, sofosbuvir, velpatasvir, and voxilaprevir were chemically stable with no increase in total impurities/degradation products of sofosbuvir (remaining at 0.0%), velpatasvir (remaining between 0.4 and 0.5%), and voxilaprevir (remaining between 1.1 and 1.4%) after a 6 month storage period. No upward trend in the content of degradation products was observed over the time period studied.

D. Tablet Preparation

The monolayer tablets comprising sofosbuvir, substantially amorphous velpatasvir SSD, and substantially amorphous voxilaprevir SSD were manufactured using one of two processes: (i) co-dry granulation and (ii) bi-granulation.

i. Co-Dry Granulation

Manufacture of the monolayer tablet via co-dry granulation involved co-dry granulating sofosbuvir, velpatasvir SSD, and voxilaprevir SSD, and subsequently compressing the co-dry granulated formulation into a monolayer tablet. The sofosbuvir/velpatasvir SSD/voxilaprevir SSD was successfully manufactured at a scale of 1.0 to 1.3 kg using a roller compaction force of 10 kN/cm, gap width of 2 mm, and a mill screen size of 1.00 mm. The final powder blend had a mean particle size of 416 μm, the percent fines (<63 μm) of 8%, bulk and tapped density of 0.58 and 0.73 g/mL, and showed acceptable flow properties (flow index of 12 mm and FT4 powder permeability pressure drop of 1.2 mbar at 15 kPa). The final powder blend was compressed to 1300 mg core tablets. Across a hardness range of 15 to 35 kp, the core tablets demonstrated the friability ≤0.2% weight loss and the disintegration time <10 minutes.

The tablets were further film-coated to reduce photolytic degradation with a polyvinylalcohol-based coating. Tablets were coated to a target 3% weight gain.

TABLE 7

| | | SOF | | VEL SSD[a] | | VOX SSD[b] | |
|---|---|---|---|---|---|---|---|
| Condition | Time (Months) | LS (%) | Total Imp./Deg. Products (%) | LS (%) | Total Imp./Deg. Products (%) | LS (%) | Total Imp./Deg. Products (%) |
| Initial | 0 | 103.5 | 0.0 | 97.9 | 0.4 | 97.7 | 1.2 |
| 40° C./75% | 1 | 99.5 | 0.0 | 95.8 | 0.4 | 97.1 | 1.2 |
| RH (Closed) | 3 | 99.4 | 0.0 | 95.8 | 0.5 | 96.2 | 1.1 |
|  | 6 | 97.2 | 0.0 | 96.0 | 0.5 | 93.5 | 1.2 |
| 40° C./75% | 1 | 101.3 | 0.0 | 99.0 | 0.4 | 97.8 | 1.2 |
| RH (Open) | 3 | 98.5 | 0.0 | 95.2 | 0.5 | 96.3 | 1.4 |
|  | 6 | 95.6 | 0.0 | 94.8 | 0.5 | 94.5 | 1.2 |
| 25° C./60% | 3 | 101.1 | 0.0 | 96.4 | 0.4 | 95.4 | 1.2 |
| RH (Closed) | 6 | 99.1 | 0.0 | 98.8 | 0.4 | 95.1 | 1.2 |

[a]Velpatasvir is incorporated as Velpatasvir SSD, consisting of 50% w/w amorphous velpatasvir free base and 50% w/w copovidone.
[b]Voxilaprevir is incorporated as Voxilaprevir SSD, consisting of 50% w/w amorphous voxilaprevir free acid and 50% w/w copovidone.
Note:
Granules were stored in glass vials and protected from light.

Intragranular Filler Compositions

Intragranular and extragranular components (e.g., excipients) were additionally included in the co-dry granulation monolayer tablets. Table 8 describes the impact of intragranular filler compositions on dissolution for various co-dry granulation formulations (Formulations A-G) of sofosbuvir, velpatasvir SSD, and voxilaprevir SSD.

As shown in Table 8 and FIG. 1, dissolution results indicated that the release of voxilaprevir SSD at 20 minutes from Formulation A comprising a 1:1 mixture of lactose monohydrate and microcrystalline cellulose was 76%, which was greater than the release of voxilaprevir from Formulation B (68%) comprising lactose monohydrate alone or Formulation C (70%) comprising microcrystalline cellulose alone.

TABLE 8

| | SOF/VEL SSD/VOX SSD Formulations[a] | | | | | | |
|---|---|---|---|---|---|---|---|
| | A | B | C | D | E | F | G[b] |
| Total Tablet Weight (mg) | 1200 | 1200 | 1200 | 1200 | 1200 | 1450 | 1300 |
| Formulation Composition (% w/w) | | | | | | | |
| Intragranular Components | | | | | | | |
| SOF | 33.33 | 33.33 | 33.33 | 33.33 | 33.33 | 27.59 | 30.77 |
| VEL SSD (1:1) | 16.67 | 16.67 | 16.67 | 16.67 | 16.67 | 13.79 | 15.38 |
| VOX SSD (1:1) | 16.67 | 16.67 | 16.67 | 16.67 | 16.67 | 13.79 | 15.38 |
| Lactose Monohydrate (Fast Flo 316) | 6.42 | 12.83 | — | 7.92 | 5.42 | 12.16 | 8.99 |
| Microcrystalline Cellulose (Avicel PH-101) | 6.42 | — | 12.83 | 7.92 | 5.42 | 12.16 | 8.99 |
| Colloidal Silicon Dioxide (Aerosil 200) | 1.00 | 1.00 | 1.00 | 1.00 | 1.00 | 1.00 | 1.00 |
| Croscarmellose Sodium (Ac-Di-Sol) | 5.50 | 5.50 | 5.50 | 2.50 | 7.50 | 5.50 | 5.50 |
| Magnesium Stearate (Hyqual Code 5712) | 0.75 | 0.75 | 0.75 | 0.75 | 0.75 | 0.75 | 0.75 |
| Extragranular Components | | | | | | | |
| Microcrystalline Cellulose (Avicel PH-102) | 10.00 | 10.00 | 10.00 | 10.00 | 10.00 | 10.00 | 10.00 |
| Croscarmellose Sodium (Ac-Di-Sol) | 2.50 | 2.50 | 2.50 | 2.50 | 2.50 | 2.50 | 2.50 |
| Magnesium Stearate (Hyqual Code 5712) | 0.75 | 0.75 | 0.75 | 0.75 | 0.75 | 0.75 | 0.75 |
| Total Tablet Core Weight (%) | 100 | 100 | 100 | 100 | 100 | 100 | 100 |
| Dissolution | | | | | | | |
| Release of SOF after 20 min at pH 5.0 w/0.5% CTAB (release for the control SOF/VEL tablet was 98%) | 100 | 102 | 102 | 98 | 97 | 96 | 101 |
| Release of VEL after 20 min at pH 5.0 w/0.5% CTAB (release for the control SOF/VEL tablet was 97%) | 96 | 95 | 95 | 93 | 94 | 96 | 97 |
| Release of VOX after 20 min at pH 4.5 w/0.15% CTAB (release for the control VOX SSD tablet was 77%) | 76 | 68 | 70 | 69 | 77 | 78 | 75 |

[a] All formulations were manufactured at compaction force of 8 kN/cm and screen size of 1.25 mm, Gap of 2 mm, roller speed of 1 rpm, and granulator speed of 90 rpm.
[b] Formulation G was processed at similar roller compaction parameters to other prototype formulations.
Note:
Dissolution conditions: 0.15% centrimonium bromide (CTAB) in 50 nM acetate buffer pH 4.5, 75 rpm, 900 mL at 37° C., USP Type II apparatus.

Comparison of Formulation A-C reveals the impact of lactose monohydrate and/or microcrystalline cellulose content on formulations comprising 33.33% w/w of sofosbuvir, 16.67% w/w of velpatasvir SSD, and 16.67% w/w of voxilaprevir w/w, with Formulation A comprising a 1:1 weight ratio of microcrystalline cellulose and lactose monohydrate, Formulation B comprising lactose monohydrate alone (i.e., no microcrystalline cellulose), and Formulation C comprising microcrystalline cellulose alone (i.e., no lactose monohydrate) or as.

Figure 2:
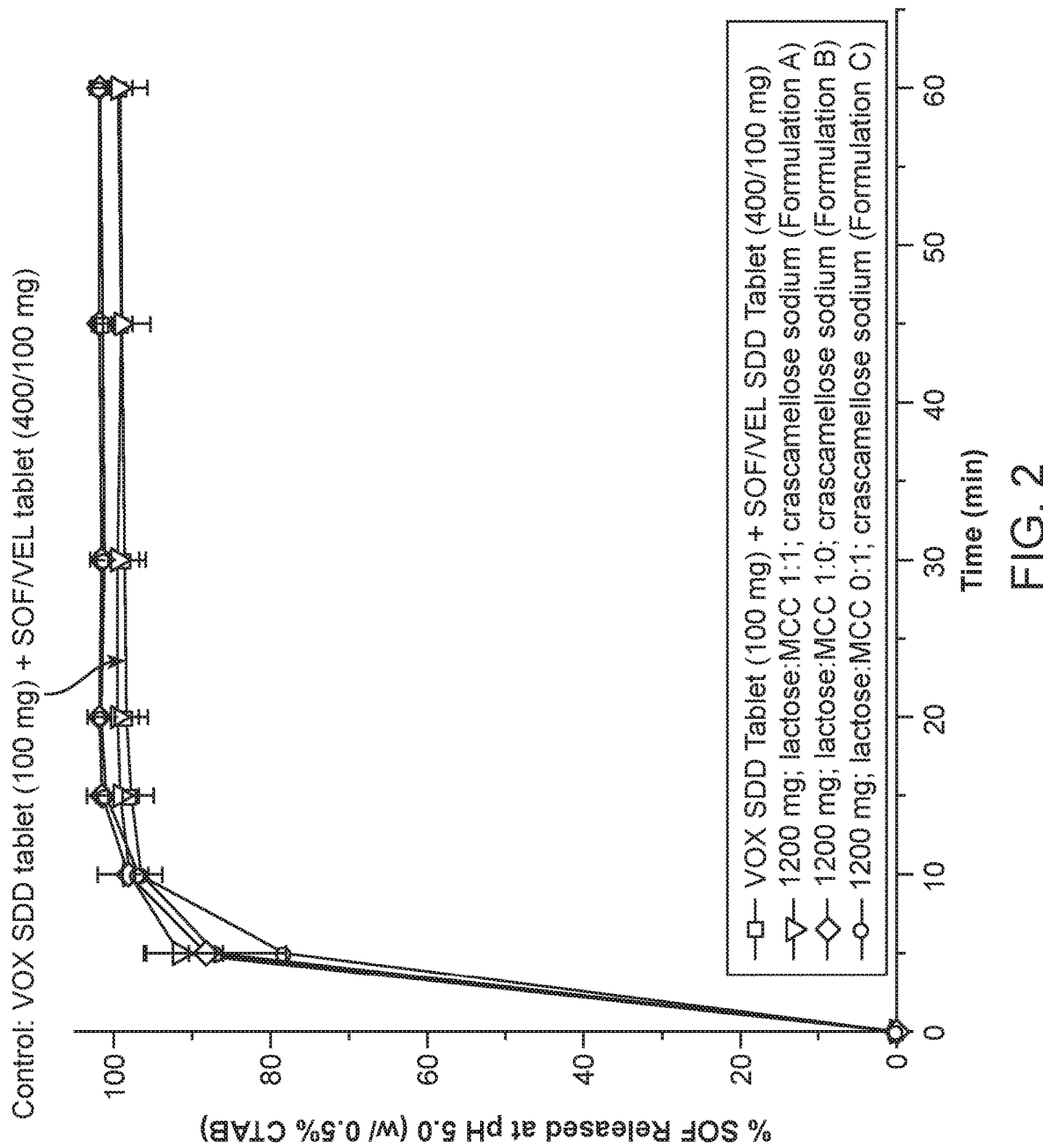
FIG. 2 depicts dissolution profiles of sofosbuvir in co-dry granulation sofosbuvir/velpatasvir/voxilaprevir tablets (400/100/100 mg) as a function of intragranular filler composition.

The lactose monohydrate and/or microcrystalline cellulose content had no impact on the dissolution profile of sofosbuvir (Table 8, FIG. 2). All three formulations (i.e., Formulations A, B, C) released 100 to 102% of sofosbuvir at 20 minutes, comparable to 98% sofosbuvir released at 20 minutes from the sofosbuvir/velpatasvir SSD tablet.

Figure 3:
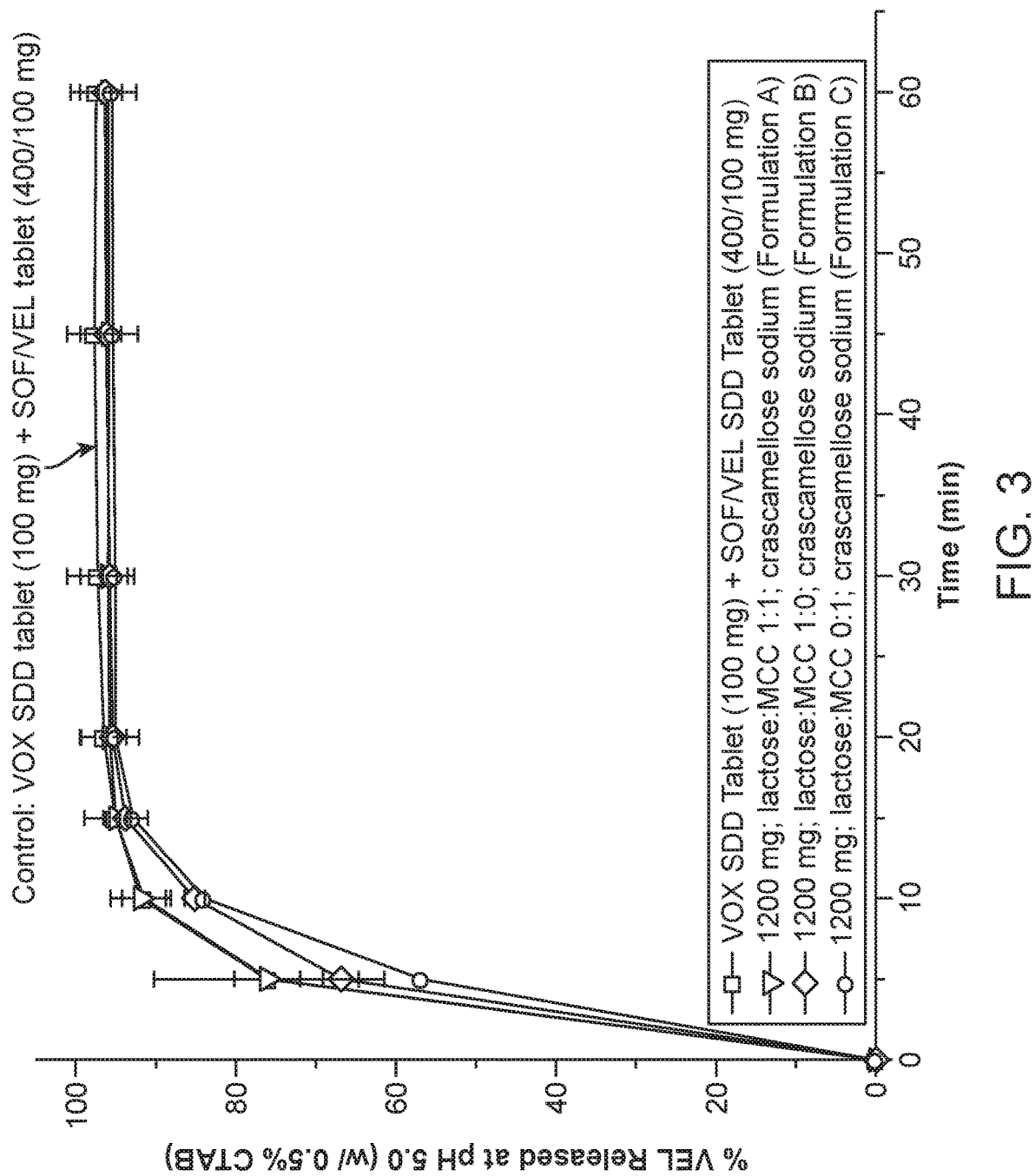
FIG. 3 depicts dissolution profiles of velpatasvir in co-dry granulation sofosbuvir/velpatasvir/voxilaprevir tablets (400/100/100 mg) as a function of intragranular filler composition.

In contrast, the dissolution profile of velpatasvir SSD at early time points (<20 minutes) was slightly slower from Formulations B and C containing lactose monohydrate alone or microcrystalline cellulose alone compared to Formulation A containing a 1:1 mixture of lactose monohydrate to microcrystalline cellulose (Table 8, FIG. 3).

Disintegrant Content

Table 8 also describes the impact of disintegrant content on dissolution for co-dry granulation formulations A, D, and E, each of which comprises 33.33% w/w of sofosbuvir, 16.67% w/w of velpatasvir SSD, and 16.67% w/w of voxilaprevir w/w. Each of these formulations were prepared using croscarmellose as disintegrant, and included 2.5% w/w extragranular croscarmellose sodium. The amount of intragranular croscarmellose sodium increased from 2.5% w/w (Formulation D), to 5.5% w/w (Formulation A) to 7.50% w/w (Formulation E).

Figure 4:
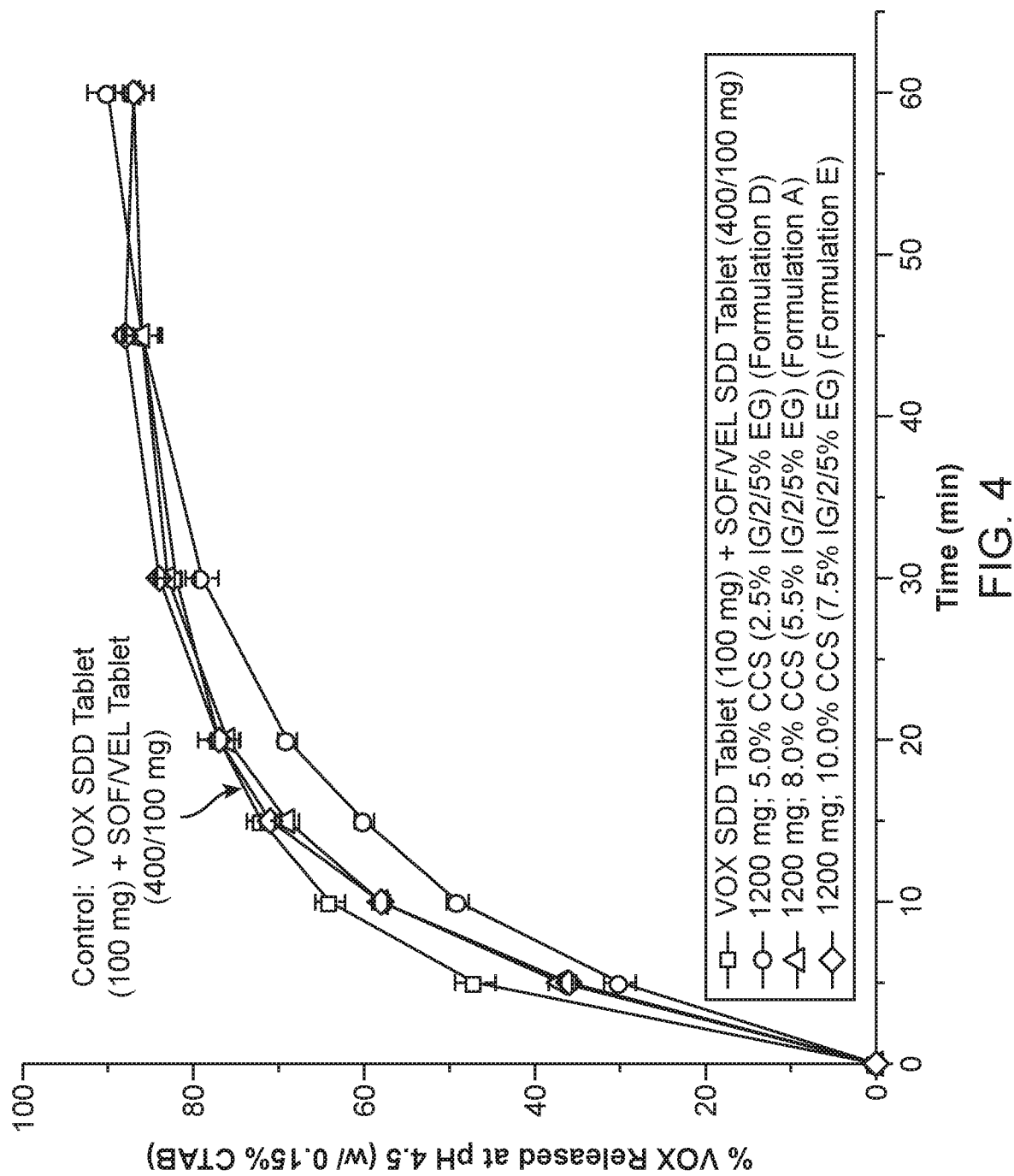
FIG. 4 depicts dissolution profiles of voxilaprevir in co-dry granulation sofosbuvir/velpatasvir/voxilaprevir tablets (400/100/100 mg) as a function of croscarmellose sodium (CCS) amount.

As shown in Table 8 and FIG. 4, dissolution results indicated that an increase in total croscarmellose sodium content from 5 to 8% w/w significantly improved dissolution performance of voxilaprevir SSD, with release at 20 minutes increasing from 69% for Formulation D containing 5% w/w croscarmellose sodium, to 78% for Formulation A containing 8% w/w croscarmellose sodium. On the other hand, an increase in total croscarmellose sodium content from 8% (Formulation A) to 10% (Formulation E) had no significant impact on the dissolution profile of voxilaprevir.

Figure 5:
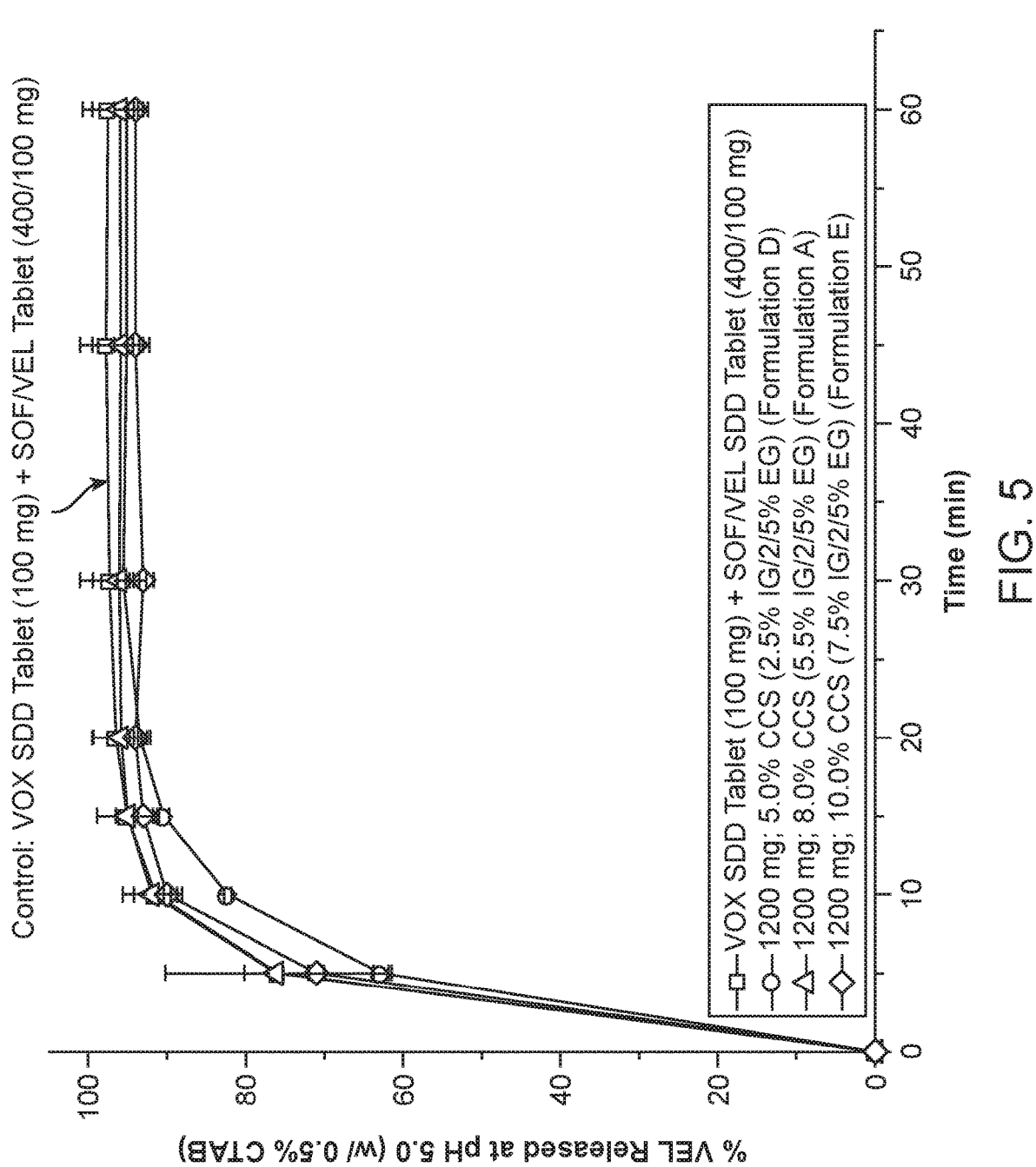
FIG. 5 depicts dissolution profiles of velpatasvir in co-dry granulation sofosbuvir/velpatasvir/voxilaprevir tablets (400/100/100 mg) as a function of croscarmellose sodium (CCS) amount.

The dissolution performance of velpatasvir SSD improved with an increase in total croscarmellose sodium content from 5 to 8% w/w, with release at 20 minutes increasing from 93% for Formulation D containing 5% w/w croscarmellose sodium, to 96% for Formulation A containing 8% w/w croscarmellose sodium (Table 8, FIG. 5). However, an increase in total croscarmellose sodium content from 8% (Formulation F) to 10% (Formulation E) resulted in a slightly slower dissolution of velpatasvir SSD voxilaprevir.

Figure 6:
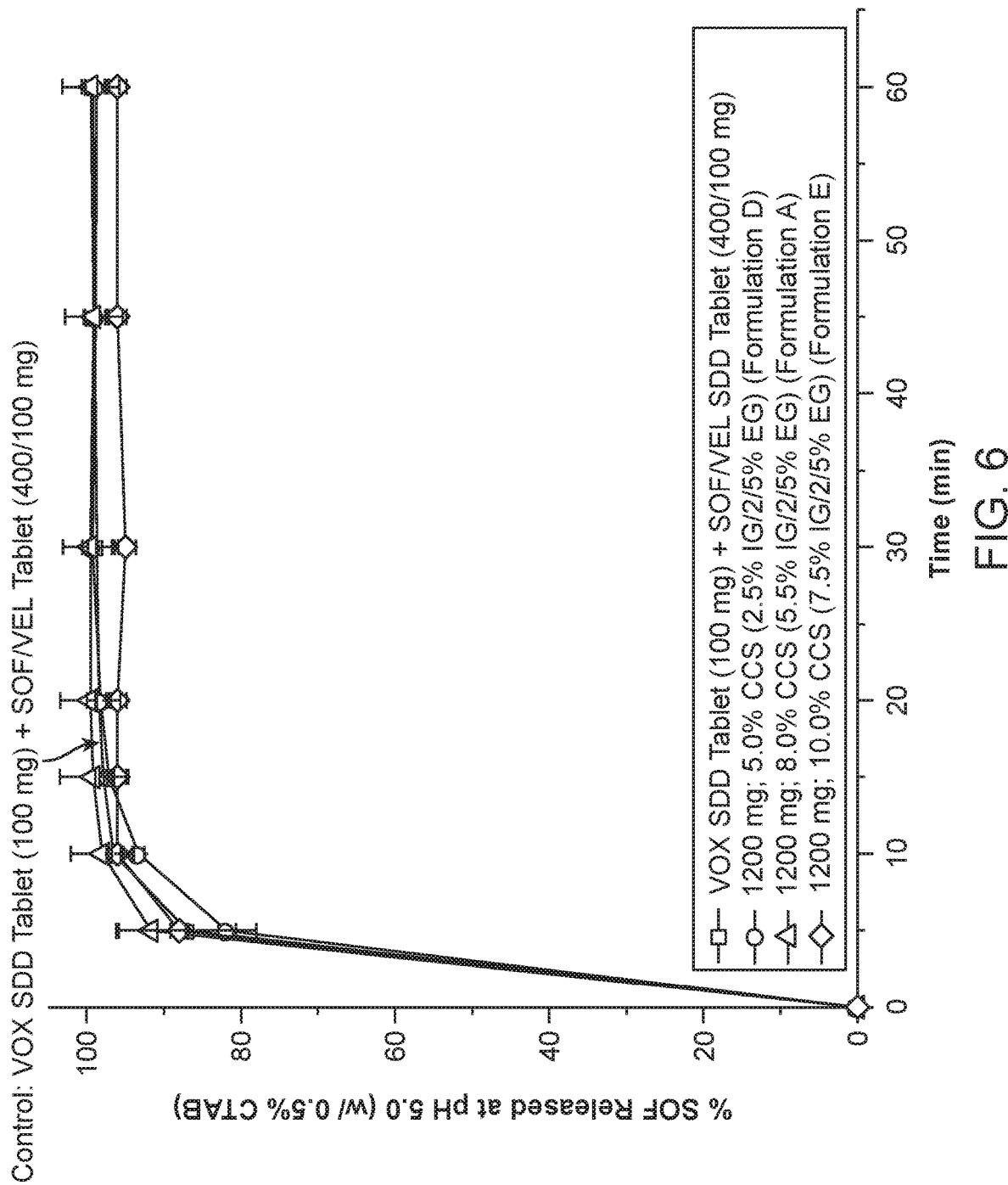
FIG. 6 depicts dissolution profiles of sofosbuvir in co-dry granulation sofosbuvir/velpatasvir/voxilaprevir tablets (400/100/100 mg) as a function of croscarmellose sodium (CCS) amount.

Dissolution of sofosbuvir was slightly slower with an increase in total croscarmellose sodium content from 5 to 8% w/w, with release at 20 minutes decreasing from 98% for Formulation D containing 5% w/w croscarmellose sodium, to 96% for Formulation A containing 8% w/w croscarmellose sodium (Table 8, FIG. 6). Increase of the total croscarmellose sodium content from 8% (Formulation A) to 10% (Formulation E) had no significant impacts on the dissolution profile of sofosbuvir.

Relative Concentrations of Sofosbuvir, Velpatasvir SSD and Voxilaprevir SSD

Table 8 additionally describes the effect of the relative concentrations of sofosbuvir, velpatasvir SSD and voxilaprevir SSD on dissolution for co-dry granulation formulations comprising: 33.33% w/w/sofosbuvir, 16.67% w/w velpatasvir SSD, and 16.67% w/w voxilaprevir SSD (Formulation A); 30.77% w/w of sofosbuvir, 15.38% w/w of velpatasvir SSD, and 15.38% w/w of voxilaprevir SSD (Formulation G); and 27.6% w/w of sofosbuvir, 13.8% w/w of velpatasvir SSD, and 13.8% w/w of voxilaprevir SSD (Formulation F).

Figure 7:
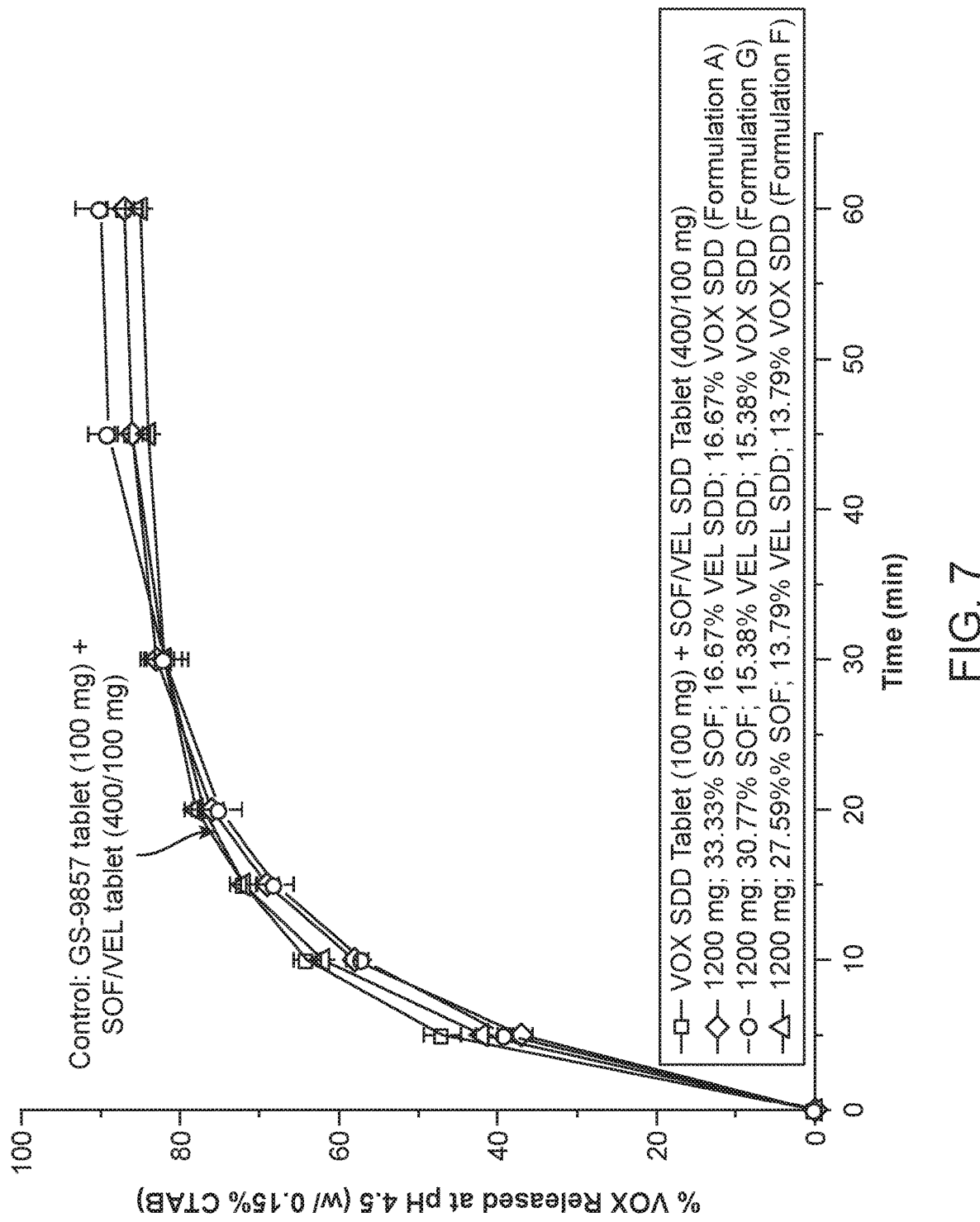
FIG. 7 depicts dissolution profiles of voxilaprevir in co-dry granulation sofosbuvir/velpatasvir/voxilaprevir tablets (400/100/100 mg) as a function of total tablet weight, and relative amounts of sofosbuvir, velpatasvir and voxilaprevir.
Figure 8:
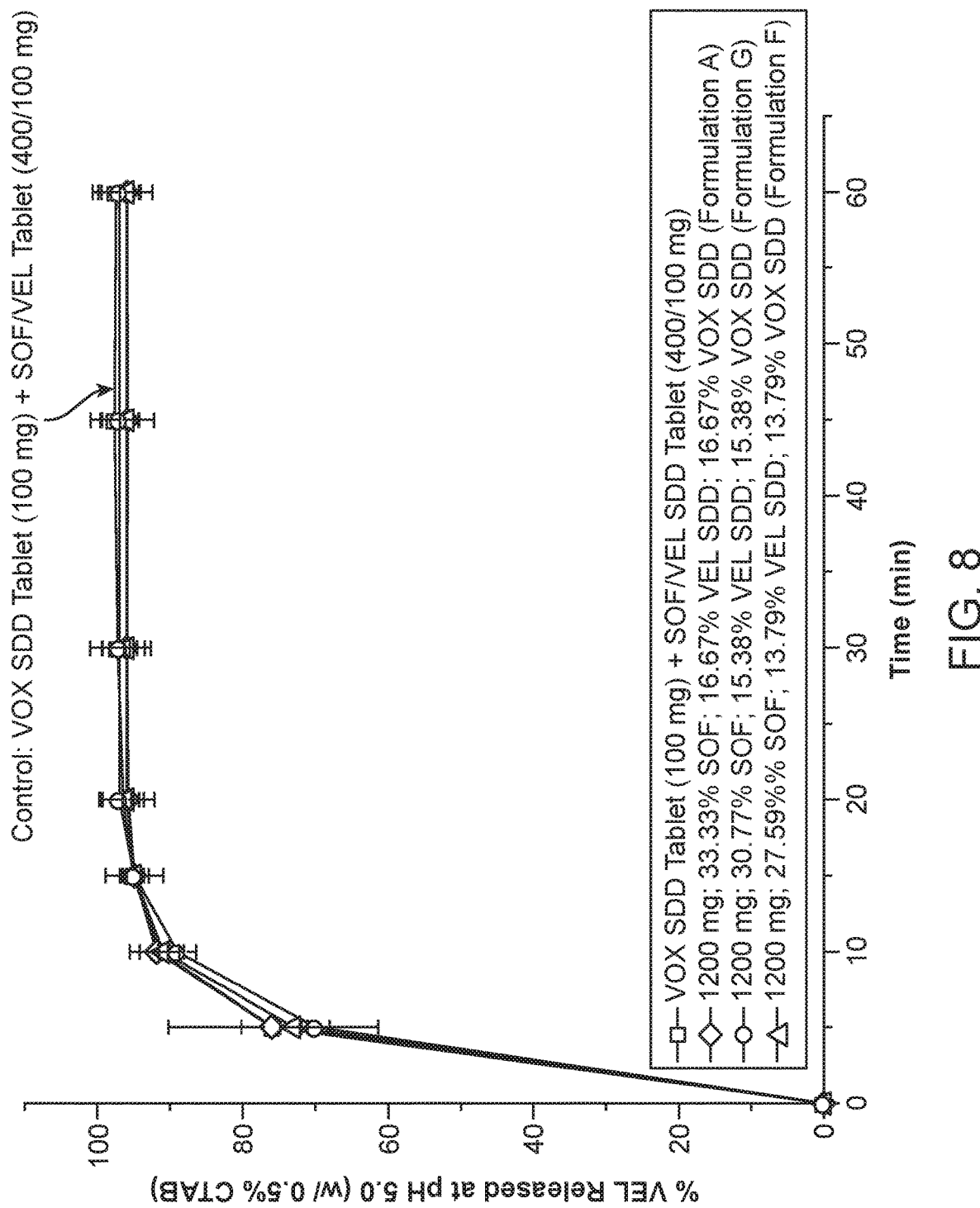
FIG. 8 depicts dissolution profiles of velpatasvir in co-dry granulation sofosbuvir/velpatasvir/voxilaprevir tablets (400/100/100 mg) as a function of total tablet weight, and relative amounts of sofosbuvir, velpatasvir and voxilaprevir.
Figure 9:
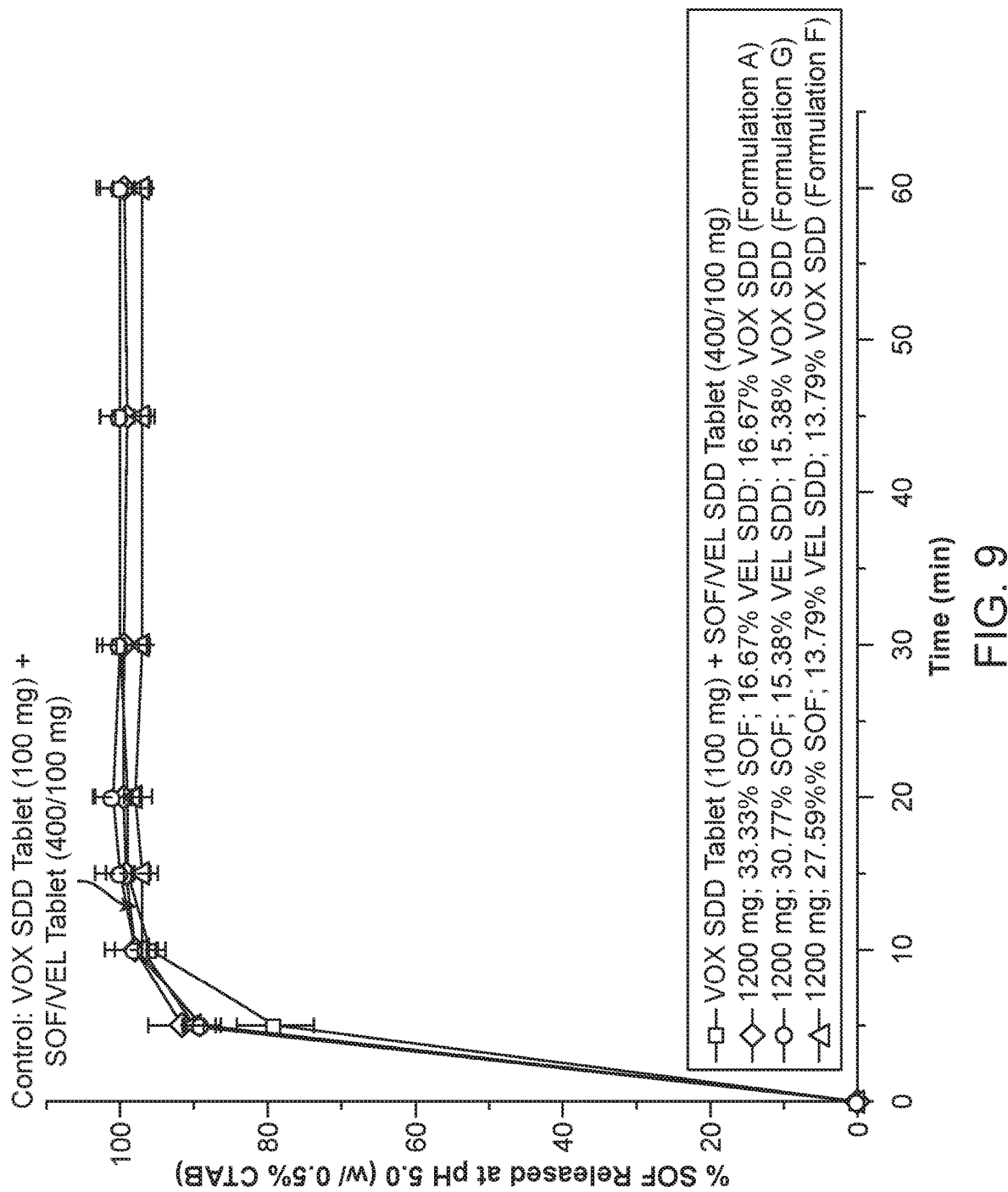
FIG. 9 depicts dissolution profiles of sofosbuvir in co-dry granulation sofosbuvir/velpatasvir/voxilaprevir tablets (400/100/100 mg) as a function of total tablet weight, and relative amounts of sofosbuvir, velpatasvir and voxilaprevir.

As shown in Table 8 and FIG. 7, dissolution results indicated that the dissolution of voxilaprevir SSD at early time points (at 20 minutes) was slightly slower from Formulations A (containing 16.67% w/w voxilaprevir SSD) and G (containing 15.38% w/w voxilaprevir SSD loading) compared to Formulation F (containing 13.8% w/w voxilaprevir SSD). Dissolution of velpatasvir SSD, as shown in Table 8 and FIG. 8, was slightly slower from Formulations A (containing 16.67% w/w velpatasvir SSD) and F (containing 13.8% w/w velpatasvir SSD) compared to Formulation G (containing 15.38% w/w velpatasvir SSD). Dissolution of sofosbuvir, as shown in Table 8 and FIG. 9, was slower from Formulations A (containing 33.3% w/w sofosbuvir) and F (containing 27.6% w/w sofosbuvir) compared to Formulation G (containing 30.8% w/w sofosbuvir).

Moreover, the release of sofosbuvir (101%), velpatasvir SSD (97%), and voxilaprevir SSD (75%) at 20 minutes from Formulation G (400/100/100 mg) was found to be comparable to the release of sofosbuvir (98%), velpatasvir SSD (97%), and voxilaprevir SSD (77%) from sofosbuvir/velpatasvir SSD (400/100 mg) and voxilaprevir SSD (100 mg) tablets, the compositions of which are provided in Table 9 and Table 10, respectively.

TABLE 9

| Ingredients | Formulation Composition (% w/w) | Unit Formula (mg) |
|---|---|---|
| Intragranular Components | | |
| SOF[a] | 40.0 | 400 |
| VEL SSD[b] | 20.0 | 200 |
| Microcrystalline Cellulose (Avicel PH-101) | 35.5 | 355 |
| Croscarmellose Sodium (Ac-Di-Sol) | 3.0 | 30 |
| Magnesium Stearate (Hyqual Code 5712) | 0.75 | 7.5 |
| Extragranular Components | | |
| Magnesium Stearate (Hyqual Code 5712) | 0.75 | 7.5 |
| Total Core Weight (mg) | 100.0 | 1000 |
| Film-Coating | | |
| Opadry II Pink 85F94644[b] | 3.0 | 30 |
| Purified Water[e] | — | — |
| Total Film-Coated Tablet Weight (mg) | — | 1030.0 |

[a]The quantity of sofosbuvir drug substance is adjusted based on the drug content factor (DCF) with concomitant adjustment in microcrystalline cellulose. The VEL SSD contains 50% w/w VEL and 50% w/w copovidone.
[b]The actual quantity of VEL SSD is adjusted based on its drug content with a concomitant adjustment to the quantity of microcrystalline cellulose
[c]Opadry II Pink 85F94644 contains Polyvinyl Alcohol (40.00% w/w), USP, Ph. Eur., Titanium Dioxide (24.95% w/w), USP, Ph. Eur., Macrogol/PEG (20.20% w/w), NF, Ph. Eur., Talc (14.80% w/w), USP, Ph. Eur., Iron Oxide Red (0.05% w/w), NF.
[d] Represents theoretical target weight gain of 3% (range of 2% to 4%).
[e] Purified Water is used during the film-coating and is removed during the process.

TABLE 10

| Ingredient | Formulation Composition (% w/w) | Unit Formula (mg) |
|---|---|---|
| Intragranular Components | | |
| VOX SSD[a,b,c] | 20.00[d] | 200.0[e] |
| Lactose Monohydrate (FastFlo 316)[c] | 34.75 | 347.5 |
| Microcrystalline Cellulose (Avicel PH 101) | 34.75 | 347.5 |
| Croscarmellose Sodium (Ac-Di-Sol) | 8.00 | 80.0 |
| Colloidal Silicon Dioxide (Aerosil 200) | 1.00 | 10.0 |
| Magnesium Stearate (Hyqual Code 5712) | 0.75 | 7.5 |
| Extragranular Components | | |
| Magnesium Stearate (Hyqual Code 5712) | 0.75 | 7.5 |
| Total Tablet Core Weight | 100.0 | 1000.0 |

TABLE 10-continued

| Ingredient | Formulation Composition (% w/w) | Unit Formula (mg) |
|---|---|---|
| Film-Coating | | |
| Opadry II Blue 85F105080[f] | 3.00 | 30.0[g] |
| Purified Water[h] | — | — |
| Total Film-Coated Tablet Weight (mg) | | 1030.0 |

[a]VOX is introduced as VOX SSD.
[b]VOX SSD contains 50% w/w VOX and 50% w/w copovidone.
[c]The actual quantity of VOX SSD is adjusted based on its drug content with a concomitant adjustment to the quantity of lactose monohydrate.
[d]Equivalent to 10% w/w of VOX.
[e]Equivalent to 100 mg of VOX.
[f]Opadry II Blue 85F105080 contains 40.00% w/w Polyvinyl Alcohol (USP, Ph. Eur.), 22.99% w/w Titanium Dioxide (USP, Ph. Eur.), 20.20% w/w Macrogol/PEG 3350 (NF, Ph. Eur.), 14.80% w/w Talc (USP, Ph. Eur.), and 2.01% w/w FD&C Blue#1/Brilliant Blue FCF Aluminum Lake.
[g]Represents a theoretical weight gain of 3% w/w with an allowable range of 2 to 4%.
[h]Purified water is used for preparation of film-coating suspension and is removed during the film-coating process.

In view of the foregoing dissolution data, the sofosbuvir/velpatasvir SSD/voxilaprevir SSD, Formulation G (with 30.77% w/w sofosbuvir, 15.38% w/w velpatasvir SSD (7.69% w/w velpatasvir and 7.69% w/w copovidone), 15.38% w/w voxilaprevir SSD (7.69% w/w voxilaprevir and 7.69% w/w copovidone), 8.97% w/w lactose monohydrate and 8.99% w/w microcrystalline cellulose as fillers, 8% w/w croscarmellose sodium as disintegrant, 1% w/w colloidal silicon dioxide as glidant, and 1.5% w/w magnesium stearate as lubricant) was selected over Formulations A and F (see Table 8).

ii. Bi-Granulation

Bi-granulation monolayer sofosbuvir/velpatasvir SSD/voxilaprevir SSD tablets, comprising 400 mg sofosbuvir, 200 mg velpatasvir SSD and 200 mg voxilaprevir SSD, were developed as alternatives to the co-dry granulation monolayer tablet approach. For the bi-granulation approach, either sofosbuvir and velpatasvir SSD or sofosbuvir and voxilaprevir SSD were co-dry granulated, and mixed with either dry-granulated voxilaprevir SSD or dry-granulated velpatasvir SSD (respectively), blended at the final blend step, and then compressed into a monolayer tablet. However, based on poor dissolution performance of velpatasvir SSD from the bi-granulation formulations, low plasma exposure of sofosbuvir and voxilaprevir SSD in pentagastrin-pretreated fasted dogs and lack of tablets content uniformity, the bi-granulation process was not selected as the desired method of tablet manufacturing.

Example 2: Chemical and Physical Stability

The chemical stability, physical stability and dissolution properties of the sofosbuvir/velpatasvir SSD/voxilaprevir SSD tablets (Formulation G) were evaluated, and summarized in Tables 11A, 11B. In some embodiments, the film-coated tablets were packaged in 75 and 100 mL white HDPE bottles (Lots A and B, respectively, as described in Tables 11A, 11B) with 1 g silica gel desiccant canisters and a polyester fiber coil. The 75 and 100 mL HDPE bottles contained fourteen and twenty eight tablets, respectively. Each HDPE bottle was capped using a white, continuous thread, child-resistant polypropylene screw cap with an introduction-sealed, aluminum-faced line. The packaged tablets (14 and 28 counts) were evaluated for stability at 40° C./75% RH and 25° C./60% RH. Additionally, the 14-count bottles (without cap) were evaluated for stability under open conditions at 40° C./75% RH.

TABLE 11A

Lot A[b]

| | | | Condition | | | | | | | |
|---|---|---|---|---|---|---|---|---|---|---|
| | | Initial | 25° C./60% RH Closed | | | 40° C./75% RH Closed | | | 40° C./75% RH Open | | |
| | Time | 0 | 1 | 3 | 6 | 1 | 3 | 6 | 1 | 3 | 6 |
| SOF | LS (%) | 100.7 | 100.9 | 101.5 | 97.9 | 101.2 | 101.6 | 99.8 | 101.2 | 101.9 | 100.9 |
| | Total Imp./Deg. (%) | 0.0 | 0.0 | 0.0 | 0.0 | 0.0 | 0.0 | 0.0 | 0.0 | 0.0 | 0.0 |
| VEL SSD | LS (%) | 98.9 | 100.2 | 100.4 | 97.2 | 100.9 | 100.6 | 98.8 | 100.9 | 100.6 | 99.6 |
| | Total Imp./Deg. (%) | 0.0 | 0.0 | 0.0 | 0.0 | 0.0 | 0.0 | 0.0 | 0.0 | 0.0 | 0.1 |
| VOX SSD | LS (%) | 98.0 | 99.9 | 99.3 | 95.8 | 100.3 | 99.4 | 97.5 | 100.0 | 99.5 | 98.3 |
| | Total Imp./Deg. (%) | 0.8 | 0.9 | 0.9 | 0.8 | 0.9 | 0.8 | 0.9 | 1.0 | 0.8 | 0.9 |
| | Water (%) | 3.3 | 1.9 | 2.3 | 2.2 | 2.0 | 2.3 | 2.3 | 5.7 | 5.8 | 5.6 |
| | Change (XRPD) | N/A | NP | NP | NP | NP | NP | NP | NP | NP | Minor[c] |
| Dissolved at 30 min (%)[a] | SOF | 103 | 98 | 103 | 103 | 100 | 100 | 100 | 98 | 101 | 100 |
| | VEL SSD | 100 | 96 | 100 | 99 | 98 | 97 | 96 | 95 | 99 | 94 |
| | VOX SSD | 99 | 95 | 99 | 100 | 97 | 96 | 97 | 95 | 98 | 95 |

[a]Dissolution condition: 1.0% w/v CTAB in 190 mM acetate buffer pH 4.0, 75 rpm, 900 mL at 37° C., USP Type II apparatus.
[b]Film-coated tablets, Lot A were packaged as: 14 ct. in 75 mL HDPE bottles in the presence of coil and 1 g desiccant. For open conditions, 14-count HDPE bottles were placed on stability without cap.
[c]A minor change (at 3.5-5.5 2θ°) observed in XRPD patterns was related to the physical form change of magnesium stearate under open conditions.

TABLE 11B

| | | Lot B[d] | | | | | | |
|---|---|---|---|---|---|---|---|---|
| | | | | Condition | | | | |
| | | Initial | 25° C./60% RH Closed | | | 40° C./75% RH Closed | | |
| | Time | 0 | 1 | 3 | 6 | 1 | 3 | 6 |
| SOF | LS (%) | 100.7 | 99.7 | 100.6 | 99.6 | 98.4 | 102.9 | 99.4 |
| | Total Imp./Deg. (%) | 0.0 | 0.0 | 0.0 | 0.0 | 0.0 | 0.0 | 0.0 |
| VEL SSD | LS (%) | 98.9 | 99.0 | 99.7 | 98.8 | 97.0 | 101.9 | 98.6 |
| | Total Imp./Deg. (%) | 0.0 | 0.0 | 0.0 | 0.0 | 0.0 | 0.0 | 0.0 |
| VOX SSD | LS (%) | 98.0 | 98.5 | 98.3 | 97.3 | 96.8 | 100.5 | 97.2 |
| | Total Imp./Deg. (%) | 0.8 | 0.9 | 0.9 | 0.9 | 0.8 | 0.8 | 0.9 |
| | Water (%) | 3.3 | 2.0 | 2.2 | 2.1 | 2.0 | 2.1 | 2.3 |
| | Change (XRPD) | N/A | NP | NP | NP | NP | NP | No change |
| Dissolved at 30 min (%)[a] | SOF | 103 | 102 | 100 | 102 | 97 | 99 | 99 |
| | VEL SSD | 100 | 99 | 98 | 97 | 95 | 96 | 95 |
| | VOX SSD | 99 | 99 | 97 | 98 | 94 | 95 | 96 |

[a]Dissolution condition: 1.0% w/v CTAB in 190 mM acetate buffer pH 4.0, 75 rpm, 900 mL at 37° C., USP Type II apparatus.
[d]Film-coated tablets, Lot B were packaged as: 28 ct. in 100 mL HDPE bottles in the presence of coil and 1 g desiccant.

The overall data presented in Tables 11A, 11B demonstrate that the packaged tablet had acceptable chemical stability at 40° C./75% RH and 25° C./60% RH for 6 months with total impurities/degradation products of sofosbuvir remaining at 0.0%, velpatasvir remaining at 0.0%, and voxilaprevir remaining between 0.8 and 0.9%. No upward trend in the content of degradation products was observed over the time period studied. The water content for the packaged tablets remained between 1.9 and 2.3% through 6 months storage at 40° C./75% RH and 25° C./60% RH.

As also shown in Tables 11A, 11B, when stored under open conditions at 40° C./75% RH for 6 months, the tablets had acceptable chemical stability with total impurities/degradation products of sofosbuvir remaining at 0.0%, velpatasvir remaining between 0.0 and 1.0%, and voxilaprevir remaining between 0.8 and 1.0%. The water content increased up to 5.8% through 6 months storage at 40° C./75% RH under open conditions.

All tablet lots showed consistent release of sofosbuvir between 98 and 103%, velpatasvir between 94 and 100%, and voxilaprevir between 95 and 100% at 30 minutes in pH 4.0 acetate buffer containing 1.0% w/v CTAB after 6 months storage at 40° C./75% RH and 25° C./60% RH under open and closed conditions.

Further, as summarized in Tables 11A, 11B, all tablets were physically stable. No change in XRPD patterns was observed for the packaged tablets (28 counts) after 6 months storage under closed conditions. A minor change (at 3.5-5.5 2θ°) in XRPD patterns, related to the physical form change of magnesium stearate, was observed for the packaged tablets (14 counts) stored under open conditions.

The impact of film-coating level of the sofosbuvir/velpatasvir SSD/voxilaprevir SSD tablets (Formulation G) on photodegradation of velpatasvir was additionally evaluated (Table 12). Tablet cores and film-coated tablets were evaluated per ICH Q1B guidelines with a total of illumination of more than 1.2 million-lux hours and a total irradiance of more than 200 W·hr/m². As shown in Table 12, the uncoated tablet cores showed up to 0.3% loss of velpatasvir and no change in sofosbuvir and voxilaprevir after exposure to light. All tablets film-coated to weight gains ranging from 2.1 to 5.4% were chemically stable and showed no increase in the level of degradation products for sofosbuvir (remaining at 0.0%), velpatasvir (remaining at 0.4%), and voxilaprevir (remaining at 0.0%). The film-coated tablets conformed to the appearance description at all coating levels. Thus, film-coating levels of ≥2% were sufficient to protect velpatasvir from photodegradation.

TABLE 12

| Film-Coating Level (% Weight Gain) | Condition[b] | SOF | | VEL SSD | | VOX SSD | |
|---|---|---|---|---|---|---|---|
| | | LS (%) | Total Imp./Deg. Products (%) | LS (%) | Total Imp./Deg. Products (%) | LS (%) | Total Imp./Deg. Products (%) |
| 0 | Protected from Light | 100.5 | 0.0 | 97.9 | 0.4 | 99.6 | 0.1 |
| | Exposed to Light | 101.5 | 0.0 | 97.1 | 0.7 | 100.4 | 0.0 |
| 2.1 | Protected from Light | 101.2 | 0.0 | 98.7 | 0.4 | 100.4 | 0.0 |
| | Exposed to Light | 101.7 | 0.0 | 98.9 | 0.4 | 100.8 | 0.0 |
| 3.4 | Protected from Light | 101.8 | 0.0 | 99.2 | 0.4 | 100.9 | 0.0 |
| | Exposed to Light | 100.6 | 0.0 | 98.0 | 0.4 | 99.6 | 0.0 |

TABLE 12-continued

| Film-Coating Level (% Weight Gain) | Condition[b] | SOF LS (%) | SOF Total Imp./Deg. Products (%) | VEL SSD LS (%) | VEL SSD Total Imp./Deg. Products (%) | VOX SSD LS (%) | VOX SSD Total Imp./Deg. Products (%) |
|---|---|---|---|---|---|---|---|
| 4.1 | Protected from Light | 101.2 | 0.0 | 98.7 | 0.4 | 100.3 | 0.0 |
|  | Exposed to Light | 102.0 | 0.0 | 99.5 | 0.4 | 101.3 | 0.0 |
| 5.4 | Protected from Light | 101.0 | 0.0 | 98.4 | 0.4 | 100.2 | 0.0 |
|  | Exposed to Light | 101.7 | 0.0 | 99.2 | 0.4 | 100.8 | 0.0 |

[a] Tablets film-coated with 2 to 5% w/w of Opadry II Beige 85F170040 containing: 40.00% w/w Polyvinyl Alcohol - Partially Hydrolyzed, USP, Ph. Eur.; 23.65% w/w Titanium Dioxide, USP, Ph. Eur.; 20.20% w/w Macrogol/PEG 3350, NF, Ph. Eur.; 14.80% w/w Talc, USP, Ph. Eur.; 1.14% w/w Iron Oxide Yellow; 0.12% w/w Iron Oxide Red, NF; 0.09% w/w Ferrosoferric Oxide, NF.
[b] Total of illumination of more than 1.2 million-lux hours and a total irradiance of more than 200 W · hr/m according to ICH Q1B guidelines.

Sofosbuvir/velpatasvir SSD/voxilaprevir SSD tablets having the formulation described in Table 13 were used in phase 1, 2, and 3 clinical studies (where such formulation is substantially equivalent to Formulation G described above in Table 8).

TABLE 13

| Ingredient, Compendial Status (Brand Name) | % w/w of Total Formulation | Unit Formula (mg/tablet) |
|---|---|---|
| Intragranular | | |
| Sofosbuvir, In-house [a] | 30.77 | 400.0 |
| VEL SDD, In-house [b] | 15.385[c] | 200.0[d] |
| VOX SDD, In-house [e] | 15.385[f] | 200.0[g] |
| Lactose Monohydrate, NF (Fast Flo 316) | 8.97 | 116.6 |
| Microcrystalline cellulose, NF (Avicel PH-101) | 8.99 | 116.9 |
| Croscarmellose sodium, NF (Ac-Di-Sol) | 5.50 | 71.5 |
| Collodial Silicon Dioxide, NF (Aerosil 200) | 1.00 | 13.0 |
| Magnesium stearate, NF (Hyqual Code 5712) | 0.75 | 9.75 |
| Extragranular | | |
| Microcrystalline cellulose, NF (Avicel PH-102) | 10.00 | 130.0 |
| Croscarmellose sodium, NF (Ac-Di-Sol) | 2.50 | 32.5 |
| Magnesium stearate, NF (Hyqual Code 5712) | 0.75 | 9.75 |
| Total Tablet Core | 100.00 | 1300.0 |
| Film-coating | | |
| Opadry II Beige 85F170040, in-house [h] | 3.0[i] | 39.0 |
| Purified Water, In-house [j] | — | — |
| Total for Film-Coated Tablets | — | 1339.0 |

[a] Actual quantity of sofosbuvir drug substance was adjusted based on the drug content factor for each lot. The quantity of lactose monohydrate was adjusted accordingly
[b] Actual quantity of VEL SDD was adjusted based on the VEL SDD drug content. The quantity of lactose monohydrate was adjusted accordingly.
[c] Equivalent to 7.6925% w/w of velpatasvir and 7.6925% w/w copovidone.
[d] Equivalent to 100 mg of velpatasvir and 100 mg of copovidone.
[e] Actual quantity of VOX SDD is adjusted based on the spray-dried dispersion drug content factor. The quantity of Lactose Monohydrate is adjusted accordingly.
[f] Equivalent to 7.6925% w/w of voxilaprevir and 7.6925% w/w of copovidone.
[g] Equivalent to 100 mg of voxilaprevir and 100 mg of copovidone.
[h] Opadry II Beige 85F170040 contains 40.00% w/w Polyvinyl Alcohol - Partially Hydrolyzed, USP, Ph. Eur.; 23.65% w/w Titanium Dioxide, USP, Ph. Eur.; 20.20% w/w Macrogol/PEG 3350, NF, Ph. Eur.; 14.80% w/w Talc, USP, Ph. Eur.; 1.14% w/w Iron Oxide Yellow; 0.12% w/w Iron Oxide Red, NF; 0.09% w/w Ferrosoferric Oxide, NF.
[i] Represents theoretical target weight gain of 3% w/w (range of 2 to 5%).
[j] Sufficient water is used for film-coating, and it is removed during the process.

Figure 10:
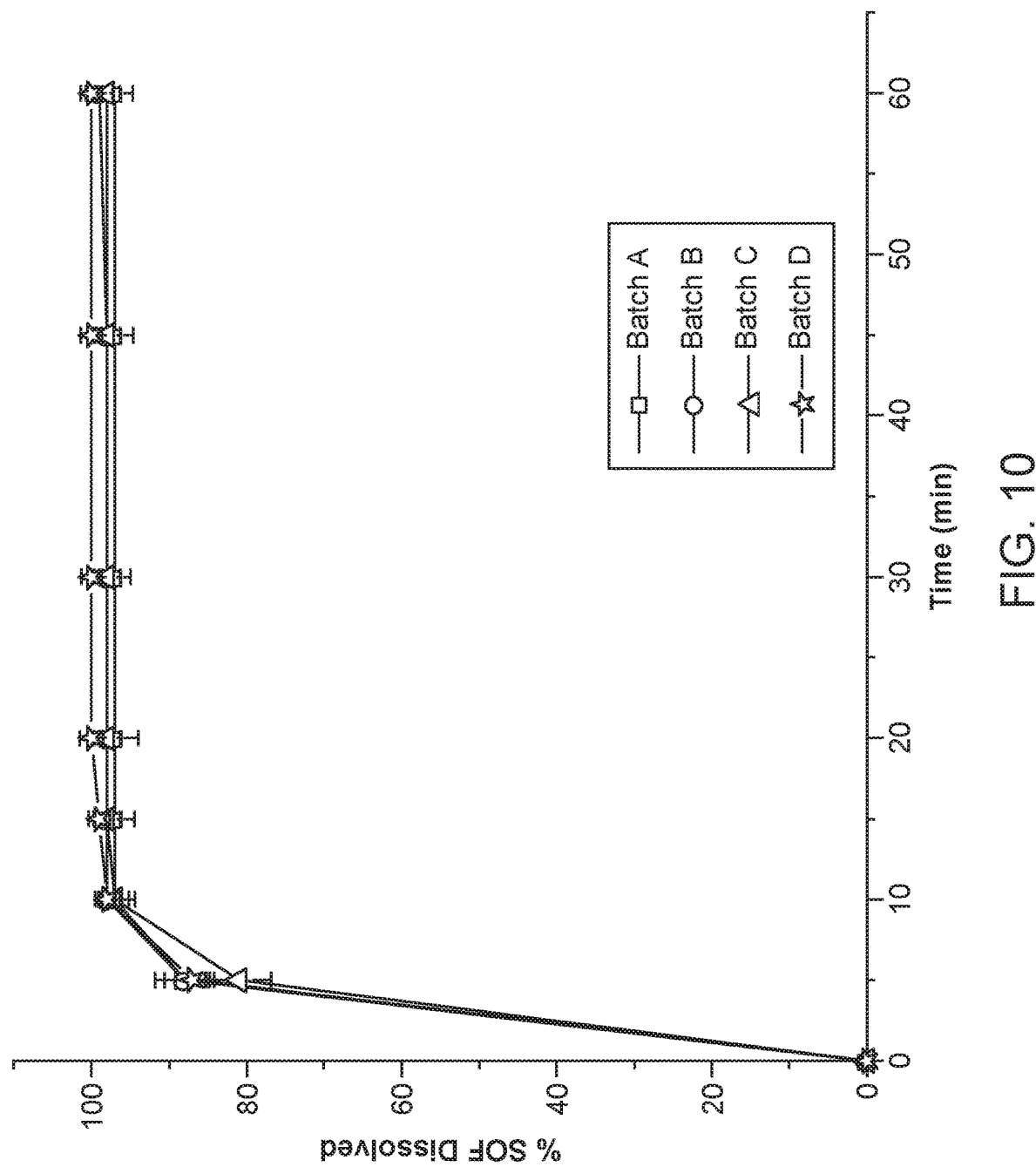
FIG. 10 depicts dissolution profiles of sofosbuvir from sofosbuvir/velpatasvir/voxilaprevir film-coated tablets used in phase 1 and phase 3 clinical studies.
Figure 11:
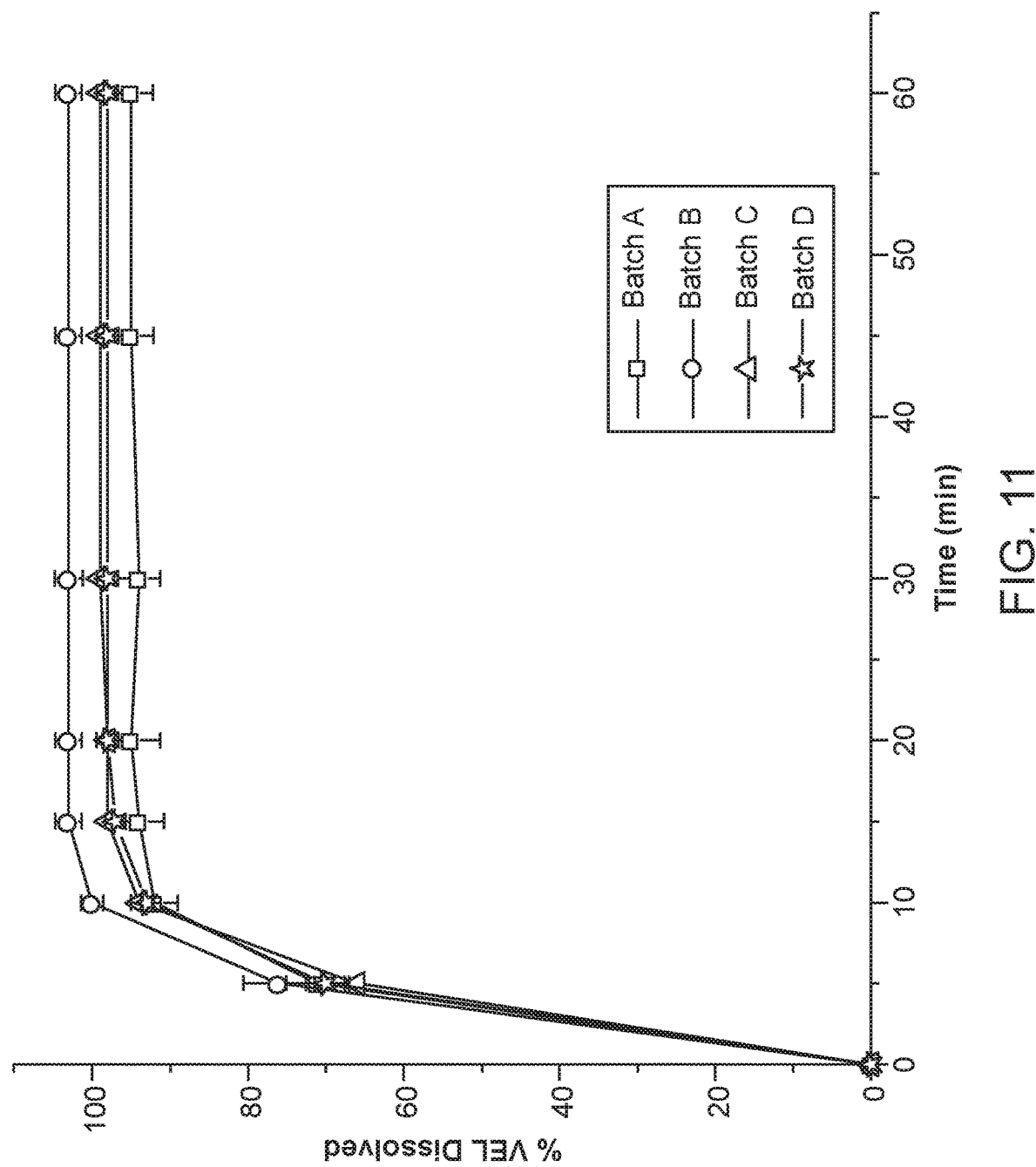
FIG. 11 depicts dissolution profiles of velpatasvir from sofosbuvir/velpatasvir/voxilaprevir film-coated tablets used in phase 1 and phase 3 clinical studies.
Figure 12:
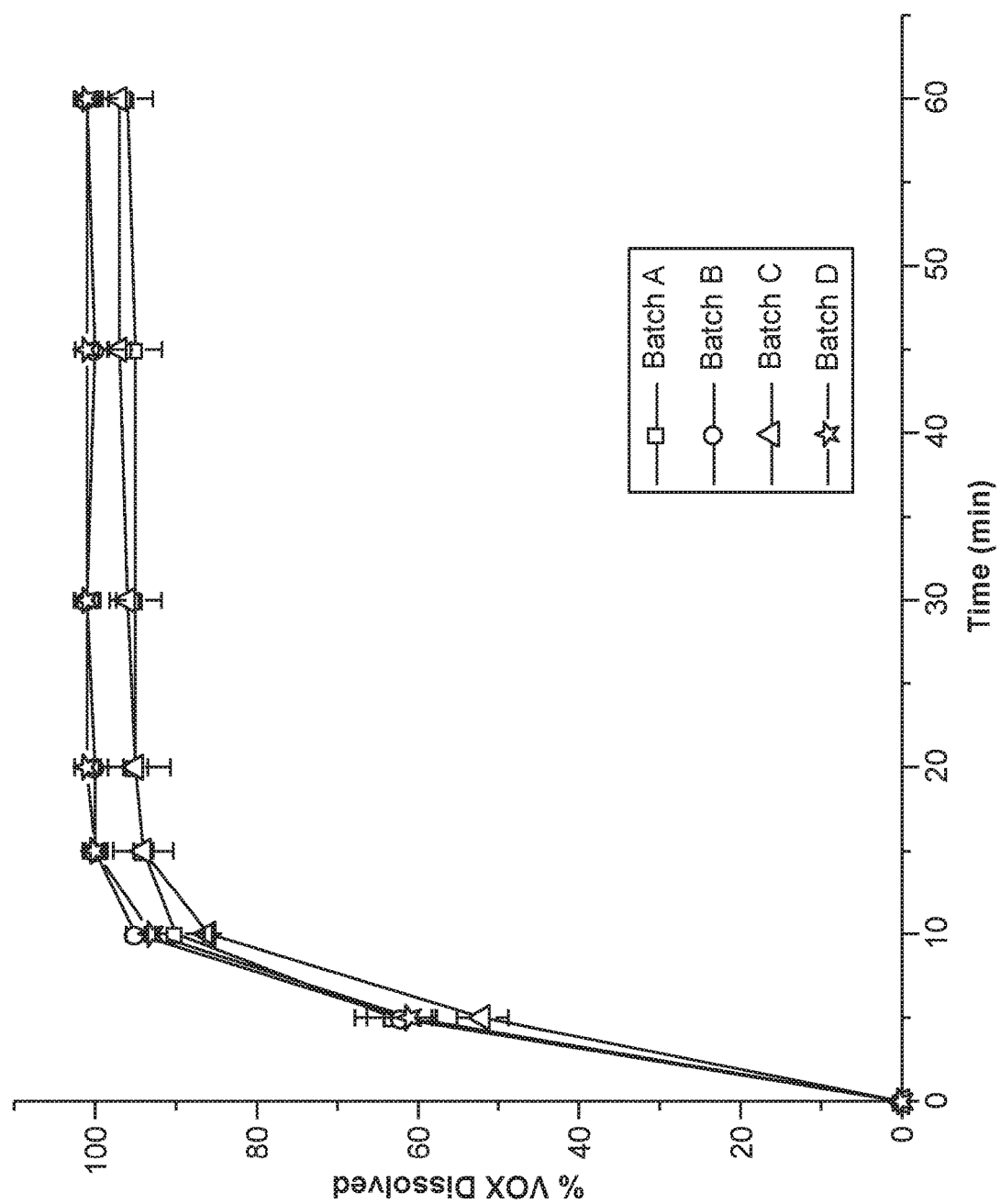
FIG. 12 depicts dissolution profiles of voxilaprevir from sofosbuvir/velpatasvir/voxilaprevir film-coated tablets used in phase 1 and phase 3 clinical studies.

FIGS. 10-12 depict additional dissolution profiles for the sofosbuvir/velpatasvir SSD/voxilaprevir SSD tablets having the formulation described in Table 13 and which were used in phase 1, 2, and 3 clinical studies, where the dissolution testing was conducted at pH 5.0 acetate buffer containing 2.0% w/v polysorbate 80. Four batches of the sofosbuvir/velpatasvir SSD/voxilaprevir SSD tablets were tested, with Batch A manufactured at 100 kg and Batches B, C and D manufactured at 145 kg. All other aspects of the formulation and manufacturing process were otherwise equivalent. The four batches were packed in the same commercial configuration: 28 count, 100 mL HPDE bottle with 1 g silica gel desiccant canister and a polyester fiber coil. Batch A exhibited good content uniformity, with mean strengths of 98.9% for sofosbuvir and 97.7% for velpatasvir SSD, and 98.6% for voxilaprevir SSD, and corresponding relative standard deviations (RSDs) of 1.8, 1.7, and 1.7%, respectively. Batches B, C and D were also found to have acceptable content uniformity with respective mean strengths between 99.9 and 100.6% for sofosbuvir, between 99.0 to 104.7% for velpatasvir SSD, and between 101.0 and 102.3% for voxilaprevir, and corresponding RSDs between 1.0 to 1.9%, 1.0 and 1.8% for velpatasvir, and 1.0 and 1.8%, respectively. Dissolution of sofosbuvir, velpatasvir SSD, and voxilaprevir SSD, as shown in FIGS. 10, 11 and 12, respectively from the sofosbuvir/velpatasvir SSD/voxilaprevir SSD film-coated tablets (Batches A-D) was complete after 15 minutes in pH 4.0 acetate buffer containing 1.0% w/v CTAB. Moreover, for Batch A, the amount dissolved at 30 min remained between 98 and 100% for sofosbuvir, between 90 and 92% for velpatasvir SSD, and between 89 and 93% for voxilaprevir SSD. For Batches B and C, the amount dissolved at 30 min remained between 98 and 101% for sofosbuvir, between 92 and 97% for velpatasvir SSD, and between 92 and 96% for voxilaprevir SSD. For Batch D, the amount dissolved at 30 min remained at 100% for sofosbuvir, between 90 and 91% for velpatasvir SSD, and between 89 and 91% for voxilaprevir SSD. Release of velpatasvir SSD and voxilaprevir SSD from the sofosbuvir/velpatasvir SSD/voxilaprevir SSD tablets associated with all four Batches was complete after 60 minutes.

Stability data associated with the sofosbuvir/velpatasvir SSD/voxilaprevir SSD film-coated tablets (Batch A) are presented in Table 14. The overall data demonstrates that the packaged tablets had acceptable chemical stability for up to 6 months under all conditions with total impurities/degradation products of sofosbuvir remaining at 0.0%, velpatasvir SSD remaining between 0.5 and 0.9%, and voxilaprevir SSD remaining at 0.0%. No upward trend in the content of degradation products was observed over the time period studied. The water content for packaged tablets remained between 1.9 and 2.3% through 6 months storage at 40° C./75% RH, 30° C./75% RH, and 25° C./60% RH. As summarized in Table 14, the packaged tablets (Batch A) were physically stable with no change in XRPD patterns after 6 months storage.

studied. The water content for packaged tablets remained between 1.8 and 2.3% through 6 months storage at 40° C./75% RH, 30° C./75% RH, and 25° C./60% RH. The packaged tablets were physically stable with no change in XRPD patterns after 6 months storage.

TABLE 14

| | | Batch A | | | | | | | |
|---|---|---|---|---|---|---|---|---|---|
| Storage Condition[a] | | Initial | 40° C./75% RH | | | 30° C./75% RH | | 25° C./60% RH | |
| | Time | 0 | 1 | 3 | 6 | 3 | 6 | 3 | 6 |
| SOF | LS (%) | 99.0 | 99.7 | 101.7 | 98.7 | 100.3 | 98.1 | 102.7 | 99.0 |
| | Total Imp./Deg. (%) | 0.0 | 0.0 | 0.0 | 0.0 | 0.0 | 0.0 | 0.0 | 0.0 |
| VEL SSD | LS (%) | 100.8 | 98.6 | 101.0 | 97.1 | 99.7 | 96.7 | 102.1 | 97.7 |
| | Total Imp./Deg. (%) | 0.9 | 0.7 | 0.8 | 0.8 | 0.9 | 0.5 | 0.9 | 0.7 |
| VOX SSD | LS (%) | 100.0 | 100.5 | 102.7 | 99.3 | 101.3 | 99.0 | 103.7 | 99.9 |
| | Total Imp./Deg. (%) | 0.0 | 0.0 | 0.0 | 0.0 | 0.0 | 0.0 | 0.0 | 0.0 |
| | Water (%) | 2.3 | 2.1 | 2.3 | 2.0 | 2.1 | 1.9 | 2.1 | 1.9 |
| | Change (XRPD) | N/A | NP | NP | No change | NP | NP | NP | NP |
| Dissolved at 30 min (%)[b] | SOF | 98 | 98 | 99 | 100 | 98 | 100 | 98 | 98 |
| | VEL SSD | 91 | 92 | 92 | 92 | 91 | 91 | 90 | 90 |
| | VOX SSD | 92 | 92 | 91 | 95 | 90 | 94 | 89 | 93 |

[a]SOF/VEL/VOX tablets Batch A were packaged in designated commercial packaging configuration: 28-count, 100 mL HPDE bottle, coil, 1 g desiccant.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.

Stability data associated with the sofosbuvir/velpatasvir SSD/voxilaprevir SSD film-coated tablets (Batches B-D) are presented in Tables 15A-15C, respectively. For Batches B and C, the overall data demonstrates that the packaged tablets had acceptable chemical stability for up to 6 months under all conditions with total impurities/degradation products of sofosbuvir remaining at 0.0%, velpatasvir SSD remaining between 0.4 and 0.7%, and voxilaprevir SSD remaining at 0.0%. No upward trend in the content of degradation products was observed over the time period For Batch D, the packaged tablets had acceptable chemical stability for up to 1 month under all conditions with total impurities/degradation products of sofosbuvir remaining at 0.0%, velpatasvir SSD remaining between 0.7 and 0.8%, and voxilaprevir SSD remaining at 0.0%. No upward trend in the content of degradation products was observed over the time period studied. The water content for packaged tablets remained between 1.9 and 2.3% through 1 month storage at 40° C./75% RH, 30° C./75% RH, and 25° C./60% RH.

TABLE 15A

| | | Batch B | | | | | | | |
|---|---|---|---|---|---|---|---|---|---|
| Storage Condition[a] | | Initial | 40° C./75% RH | | | 30° C./75% RH | | 25° C./60% RH | |
| | Time | 0 | 1 | 3 | 6 | 3 | 6 | 3 | 6 |
| SOF | LS (%) | 100.0 | 101.7 | 99.8 | 99.0 | 98.4 | 98.8 | 100.7 | 100.1 |
| | Total Imp./Deg. (%) | 0.0 | 0.0 | 0.0 | 0.0 | 0.0 | 0.0 | 0.0 | 0.0 |
| VEL SSD | LS (%) | 105.9 | 106.0 | 103.6 | 102.0 | 102.2 | 102.0 | 103.7 | 103.2 |
| | Total Imp./Deg. (%) | 0.5 | 0.7 | 0.5 | 0.5 | 0.5 | 0.5 | 0.5 | 0.5 |
| VOX SSD | LS (%) | 102.4 | 104.6 | 102.5 | 101.3 | 101.0 | 101.3 | 103.2 | 102.5 |
| | Total Imp./Deg. (%) | 0.0 | 0.0 | 0.0 | 0.0 | 0.0 | 0.0 | 0.0 | 0.0 |
| | Water (%) | 2.2 | 2.2 | 1.9 | 2.1 | 1.9 | 2.0 | 1.9 | 1.9 |
| | Change (XRPD) | N/A | NP | NP | No change | NP | NP | NP | NP |
| Dissolved at 30 min (%)[b] | SOF | 99 | 100 | 100 | 98 | 99 | 99 | 99 | 99 |
| | VEL SSD | 94 | 96 | 97 | 94 | 95 | 94 | 95 | 93 |
| | VOX SSD | 94 | 93 | 96 | 94 | 94 | 94 | 94 | 93 |

[a]SOF/VEL/VOX tablets Batch B was packaged in the designated commercial packaging configuration: 28-count, 100 mL HPDE bottle, coil, 1 g desiccant.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.

TABLE 15B

Batch C

| Storage Condition[a] | | Initial | 40° C./75% RH | | | 30° C./75% RH | | 25° C./60% RH | |
|---|---|---|---|---|---|---|---|---|---|
| Time | | 0 | 1 | 3 | 6 | 3 | 6 | 3 | 6 |
| SOF | LS (%) | 99.1 | 101.1 | 99.4 | 98.9 | 100.1 | 99.1 | 98.9 | 98.8 |
| | Total Imp./Deg. (%) | 0.0 | 0.0 | 0.0 | 0.0 | 0.0 | 0.0 | 0.0 | 0.0 |
| VEL SSD | LS (%) | 103.8 | 103.4 | 101.8 | 100.2 | 100.9 | 100.4 | 102.0 | 100.2 |
| | Total Imp./Deg. (%) | 0.5 | 0.5 | 0.5 | 0.4 | 0.5 | 0.4 | 0.5 | 0.5 |
| VOX SSD | LS (%) | 102.0 | 103.3 | 101.5 | 100.6 | 102.2 | 101.0 | 102.5 | 100.9 |
| | Total Imp./Deg. (%) | 0.0 | 0.0 | 0.0 | 0.0 | 0.0 | 0.0 | 0.0 | 0.0 |
| | Water (%) | 2.1 | 2.3 | 1.9 | 1.9 | 1.8 | 1.9 | 1.8 | 1.9 |
| | Change (XRPD) | N/A | NP | NP | No change | NP | NP | NP | NP |
| Dissolved at 30 min (%)[b] | SOF | 99 | 100 | 100 | 99 | 99 | 99 | 101 | 99 |
| | VEL SSD | 92 | 94 | 95 | 93 | 94 | 92 | 95 | 92 |
| | VOX SSD | 92 | 92 | 93 | 93 | 93 | 92 | 93 | 92 |

[a]SOF/VEL/VOX tablets Batch C was packaged in the designated commercial packaging configuration: 28-count, 100 mL HPDE bottle, coil, 1 g desiccant.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.

TABLE 15C

Batch D

| Storage Condition[a] | | Initial | 40° C./75% RH |
|---|---|---|---|
| Time | | 0 | 1 |
| SOF | LS (%) | 99.8 | 99.7 |
| | Total Imp./Deg. (%) | 0.0 | 0.0 |
| VEL SSD | LS (%) | 98.1 | 99.5 |
| | Total Imp./Deg. (%) | 0.8 | 0.7 |
| VOX SSD | LS (%) | 101.5 | 101.4 |
| | Total Imp./Deg. (%) | 0.0 | 0.0 |
| | Water (%) | 2.3 | 1.9 |
| | Change (XRPD) | N/A | NP |
| Dissolved at 30 min (%)[b] | SOF | 100 | 100 |
| | VEL SSD | 90 | 91 |
| | VOX SSD | 91 | 89 |

[a]SOF/VEL/VOX tablets Batch D was packaged in the designated commercial packaging configuration: 28-count, 100 mL HPDE bottle, coil, 1 g desiccant.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.

Example 3: Physicochemical and Biological Properties

A. Dissolution as a Function of Medium pH and Composition

Figure 13:
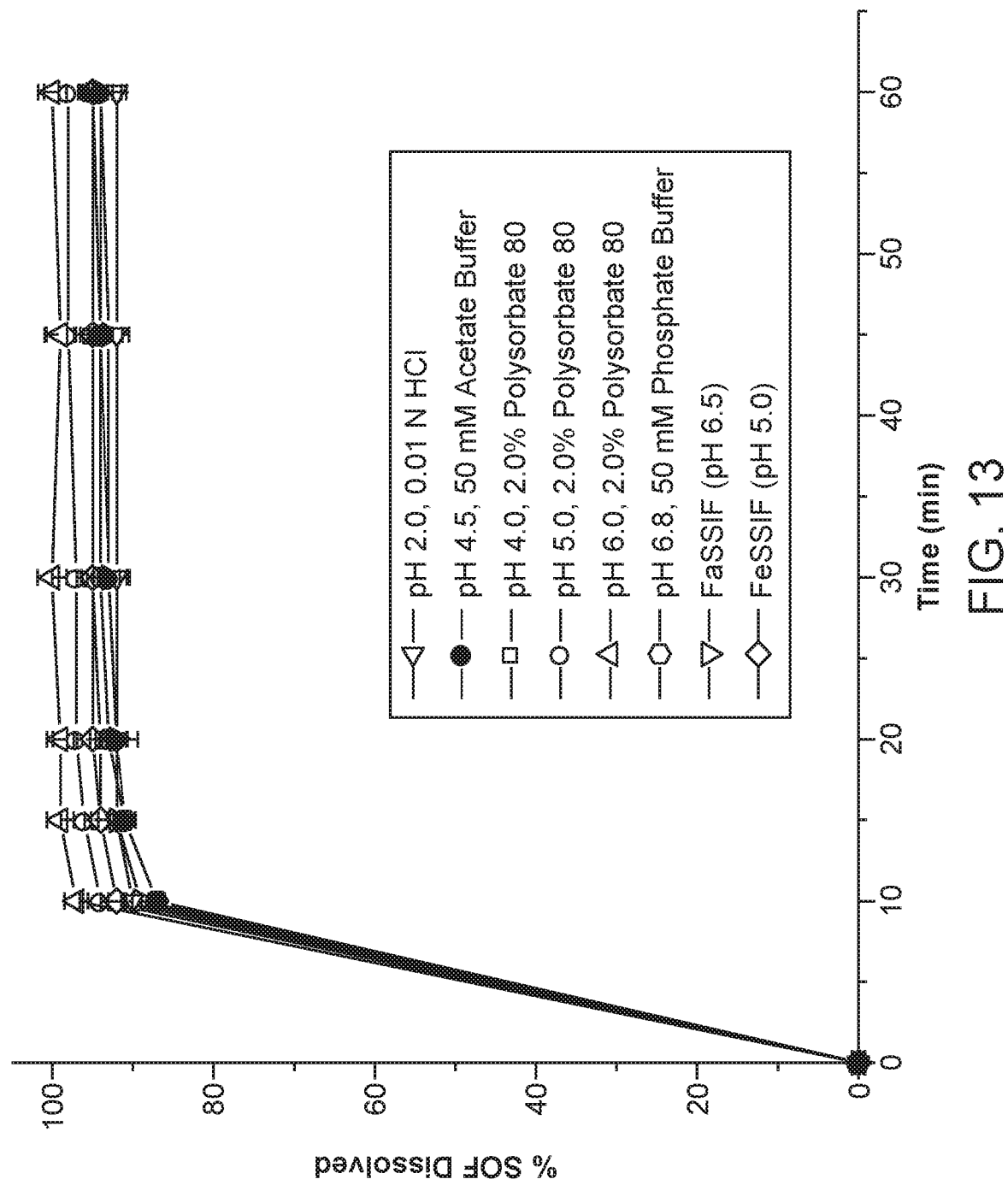
FIG. 13 depicts dissolution profiles of sofosbuvir in sofosbuvir/velpatasvir/voxilaprevir film-coated tablets as a function of pH.
Figure 14:
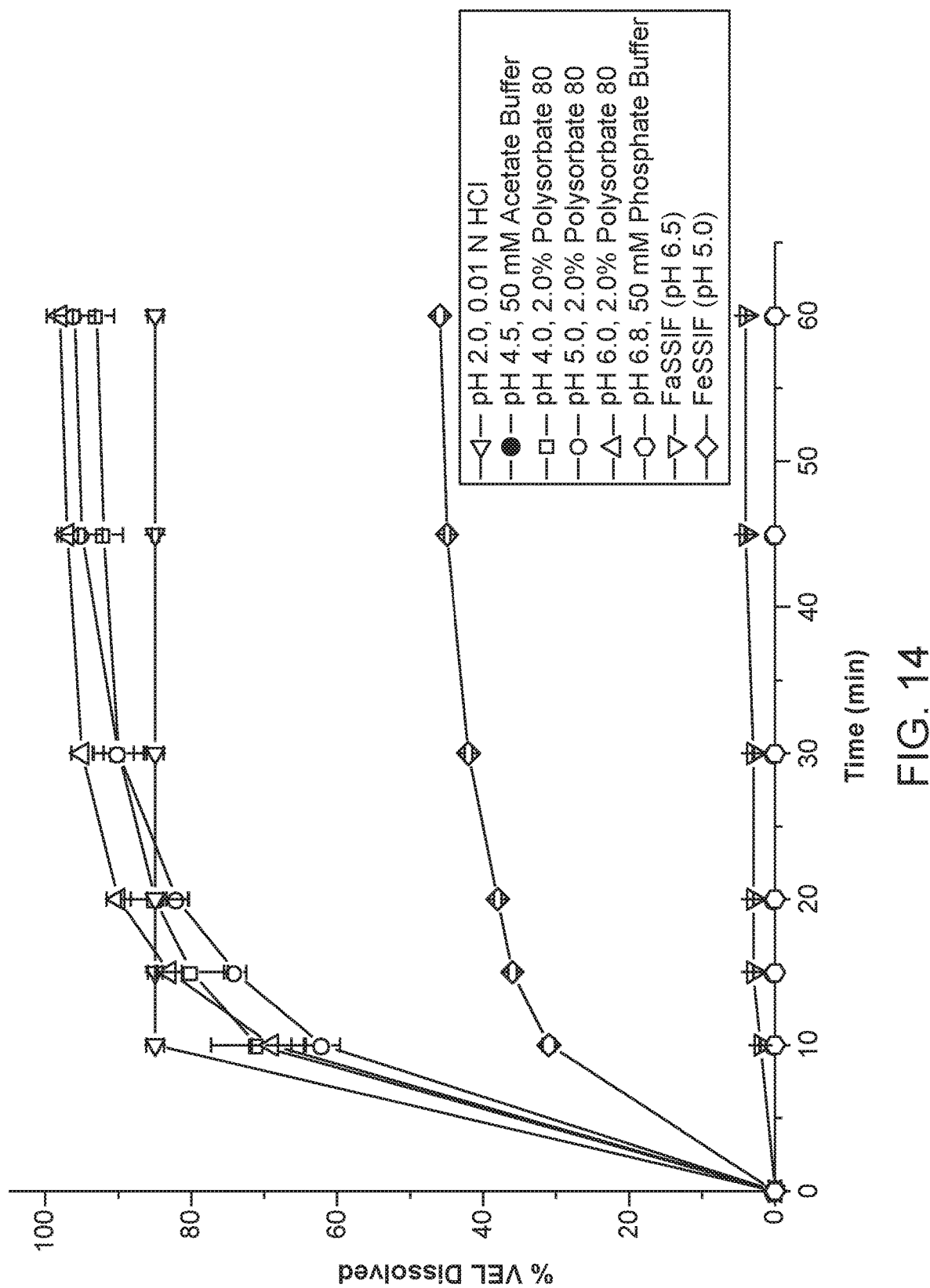
FIG. 14 depicts dissolution profiles of velpatasvir in sofosbuvir/velpatasvir/voxilaprevir film-coated tablets as a function of pH.
Figure 15:
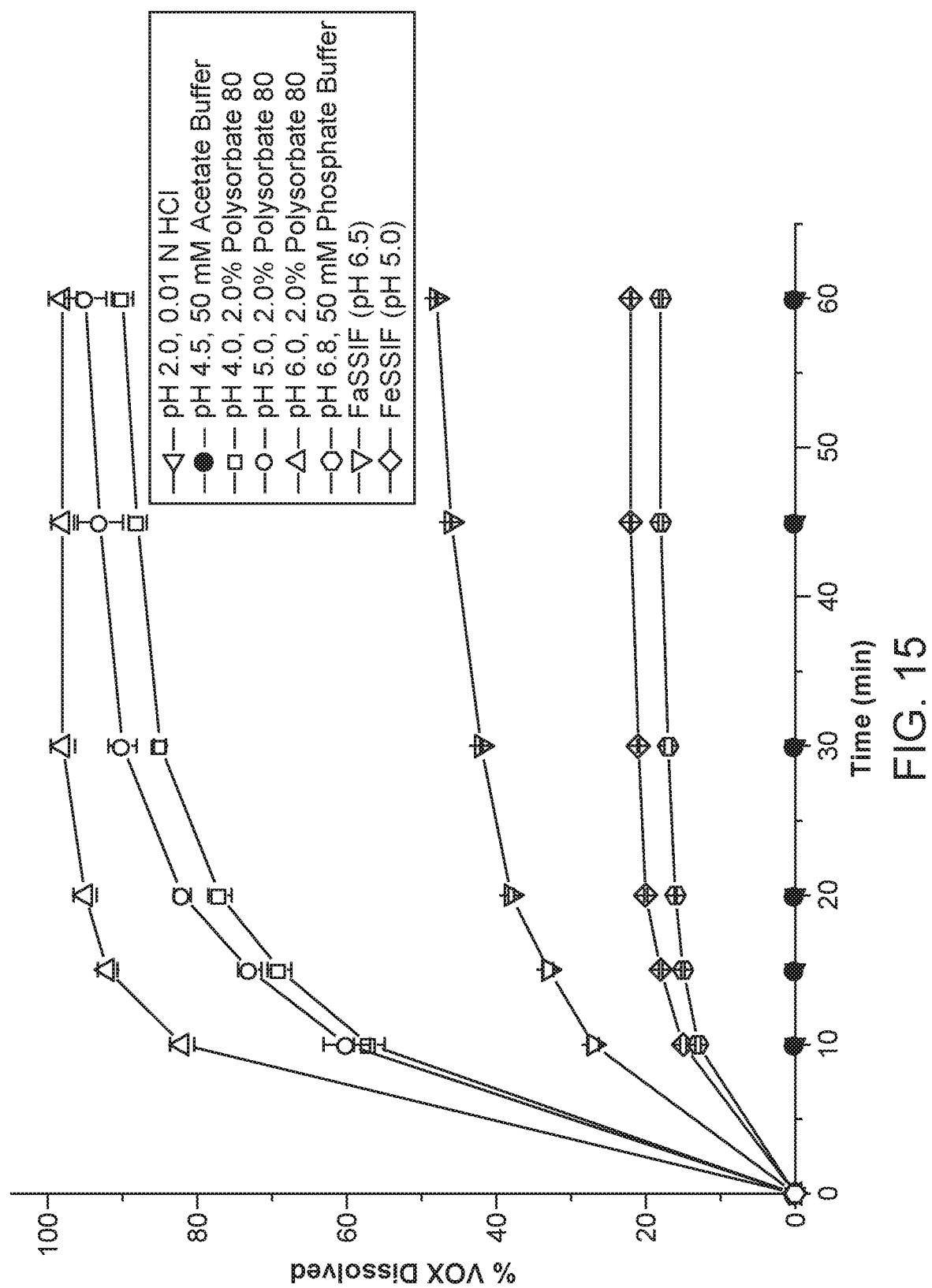
FIG. 15 depicts dissolution profiles of voxilaprevir in sofosbuvir/velpatasvir/voxilaprevir film-coated tablets as a function of pH.

Dissolution profiles of sofosbuvir, velpatasvir and voxilaprevir from the sofosbuvir/velpatasvir SSD/voxilaprevir SSD tablets (Formulation G comprising 30.77% w/w sofosbuvir, 15.38% w/w velpatasvir SSD, 15.38% w/w voxilaprevir SSD) were obtained as a function of pH in various media using Apparatus II (paddle), 75 rpm, with 900 mL medium at 37° C. (FIGS. 13-15). Sofosbuvir is a BCS Class 3 compound that exhibits high and pH-independent aqueous solubility. Velpatasvir is a BCS Class 4 compound with pH-dependent solubility. Voxilaprevir is a BCS Class 2 with pH-dependent solubility.

As shown in FIG. 13, sofosbuvir dissolution was complete within 20 minutes and was independent of medium pH and composition.

As shown in FIG. 14, the dissolution of velpatasvir from the sofosbuvir/velpatasvir SSD/voxilaprevir SSD tablets was dependent on pH and medium composition. Incomplete dissolution of velpatasvir was observed in pH 2.0, 4.5 and 6.8 buffers, fasted simulated intestinal fluid (FaSSIF), and fed-state simulated intestinal fluid (FeSSIF). When 2.0% w/v polysorbate 80 was added into pH 4.0, 5.0 and 6.0 buffers, dissolution of velpatasvir was improved. A complete dissolution of velpatasvir at 60 minutes was observed in pH 4.0 and 5.0 containing 2.0% w/v polysorbate 80.

As shown in FIG. 15, the dissolution of voxilaprevir from the sofosbuvir/velpatasvir SSD/voxilaprevir SSD tablets was dependent on pH and medium composition. Incomplete dissolution of voxilaprevir was observed in pH 2.0, 4.5, and 6.8 buffers, fasted simulated intestinal fluid (FaSSIF), and fed-state simulated intestinal fluid (FeSSIF). When 2.0% w/v polysorbate 80 was added into pH 4.0, 5.0 and 6.0 buffers, dissolution of voxilaprevir was improved. A complete dissolution of voxilaprevir at 60 minutes was observed in pH 4.0 and 5.0 containing 2.0% w/v polysorbate 80.

B. Dissolution as a Function of Crystalline Voxilaprevir Form VIII and X Contents Dissolution profiles of sofosbuvir, velpatasvir and voxilaprevir from the sofosbuvir/velpatasvir SSD/voxilaprevir SSD tablets (Formulation G comprising 30.77% w/w sofosbuvir, 15.38% w/w velpatasvir SSD, 15.38% w/w voxilaprevir SSD)) were obtained as a function of crystalline Forms VIII and X content in tablets.

The sofosbuvir/velpatasvir SSD/voxilaprevir SSD tablets were prepared from voxilaprevir SSDs spiked with 0, 5, 10, and 20% w/w crystalline voxilaprevir Form VIII and Form X (% w/w with respect to total voxilaprevir). As described previously, Form VIII of voxilaprevir is characterized by an X-ray powder diffractogram comprising the following peaks (0.2°): at 7.8, 8.2, and 20.2 °2θ, as determined on a diffractometer using Cu—Kα radiation. As also described previously, Form X of voxilaprevir is characterized by an X-ray powder diffractogram comprising the following peaks (±0.2°): at 8.0, 19.0, and 20.4 0.2 °2θ, as determined on a diffractometer using Cu—Kα radiation.

Figure 16A:
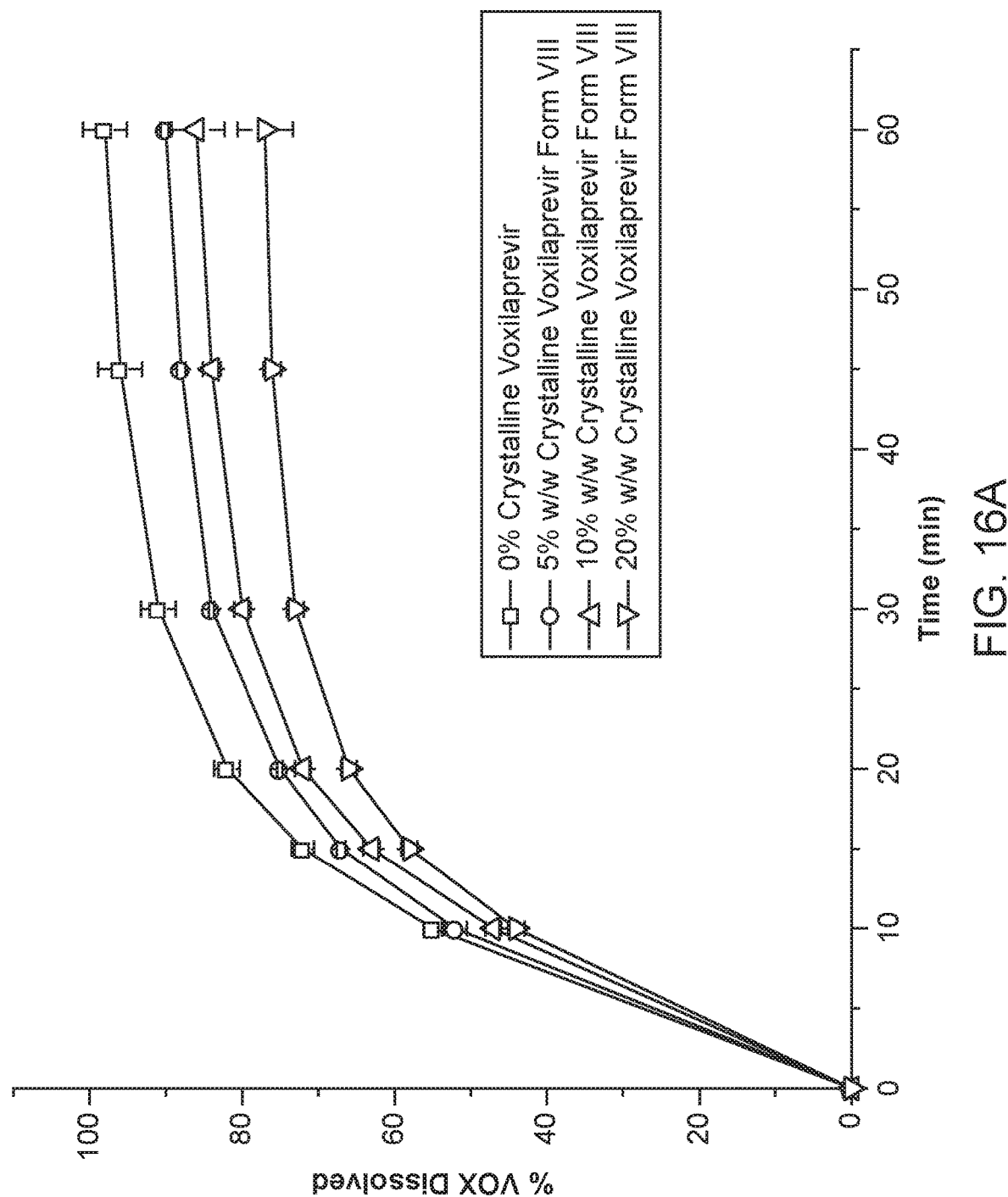
FIG. 16A depicts dissolution profiles of voxilaprevir from sofosbuvir/velpatasvir/voxilaprevir film-coated tablets as a function of crystalline voxilaprevir Form VIII content.
Figure 16B:
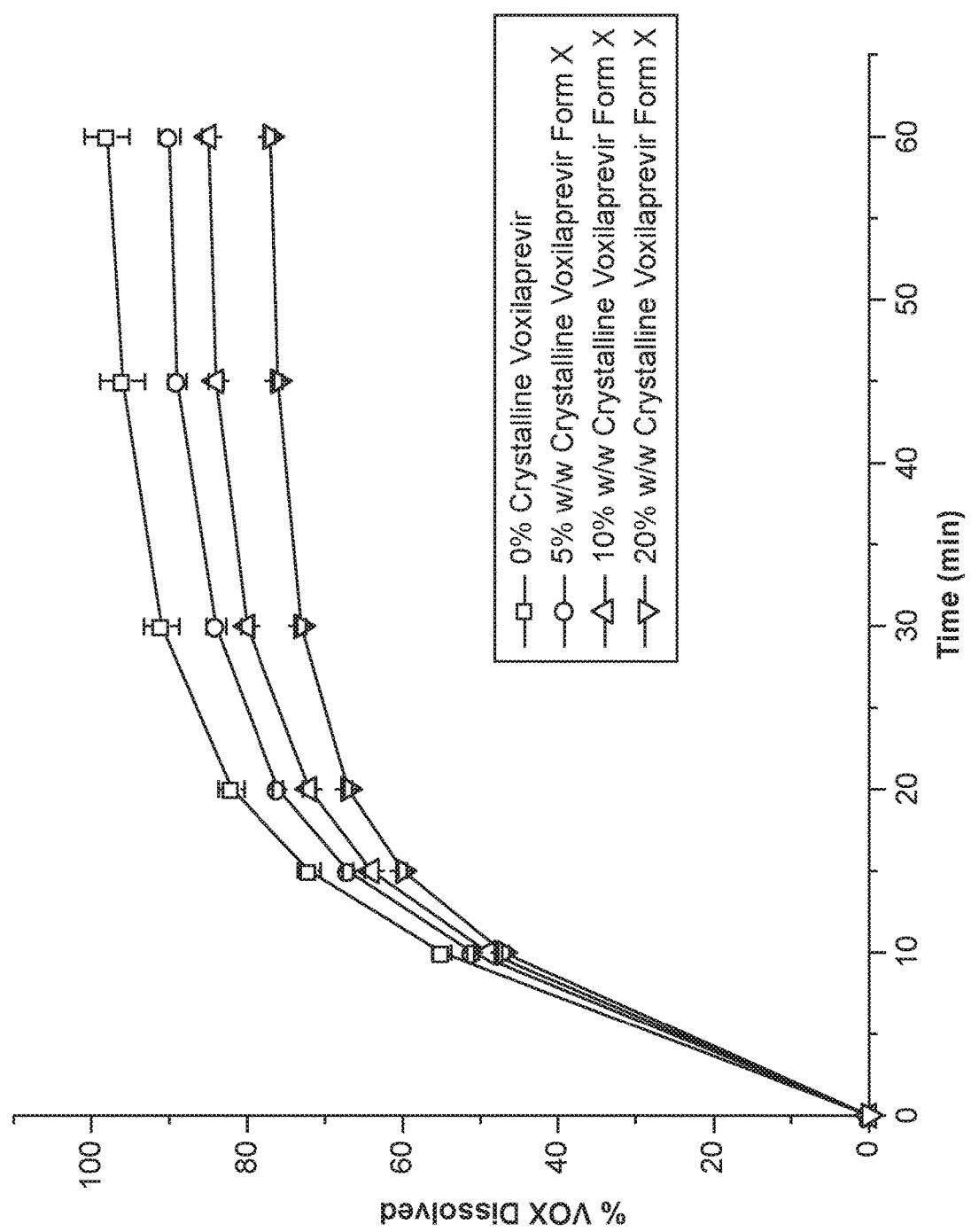
FIG. 16B depicts dissolution profiles of voxilaprevir from sofosbuvir/velpatasvir/voxilaprevir film-coated tablets as a function of crystalline voxilaprevir Form X content.

The dissolution profiles of voxilaprevir from the sofosbuvir/velpatasvir SSD/voxilaprevir SSD tablets containing 0 to 20% w/w of voxilaprevir Forms VIII and X are shown in FIGS. 16A and 16B, respectively. The sofosbuvir/velpatasvir SSD/voxilaprevir SSD tablets containing 0% w/w crystalline voxilaprevir released 91% of voxilaprevir at 30 minutes. Spiked sofosbuvir/velpatasvir SSD/voxilaprevir SSD tablets containing 5, 10, and 20% w/w Form VIII or Form X released 84, 80, and 73% of voxilaprevir at 30 minutes, respectively.

Figure 17:
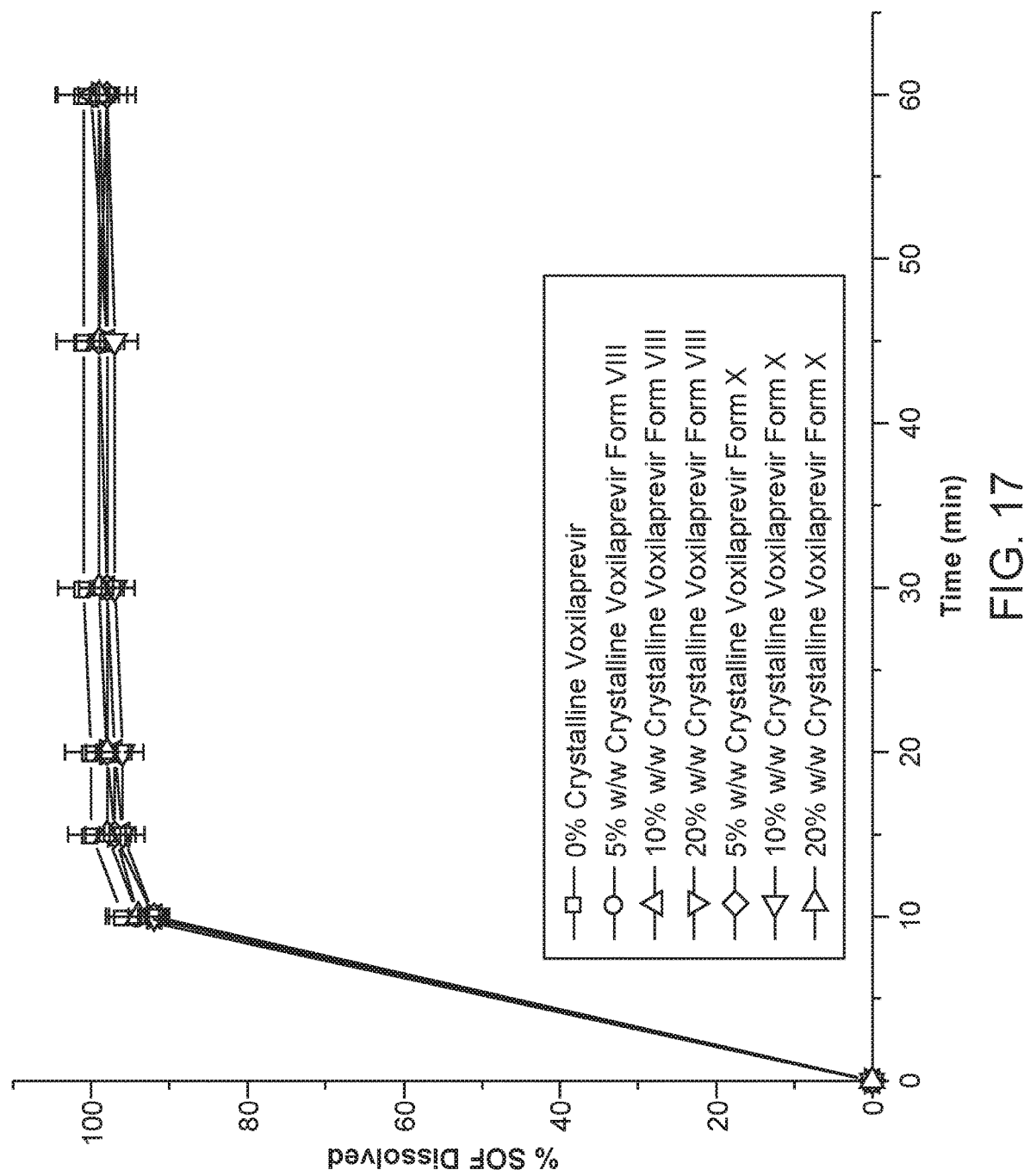
FIG. 17 depicts dissolution profiles of sofosbuvir from sofosbuvir/velpatasvir/voxilaprevir film-coated tablets as a function of crystalline voxilaprevir Form VIII and X contents.
Figure 18:
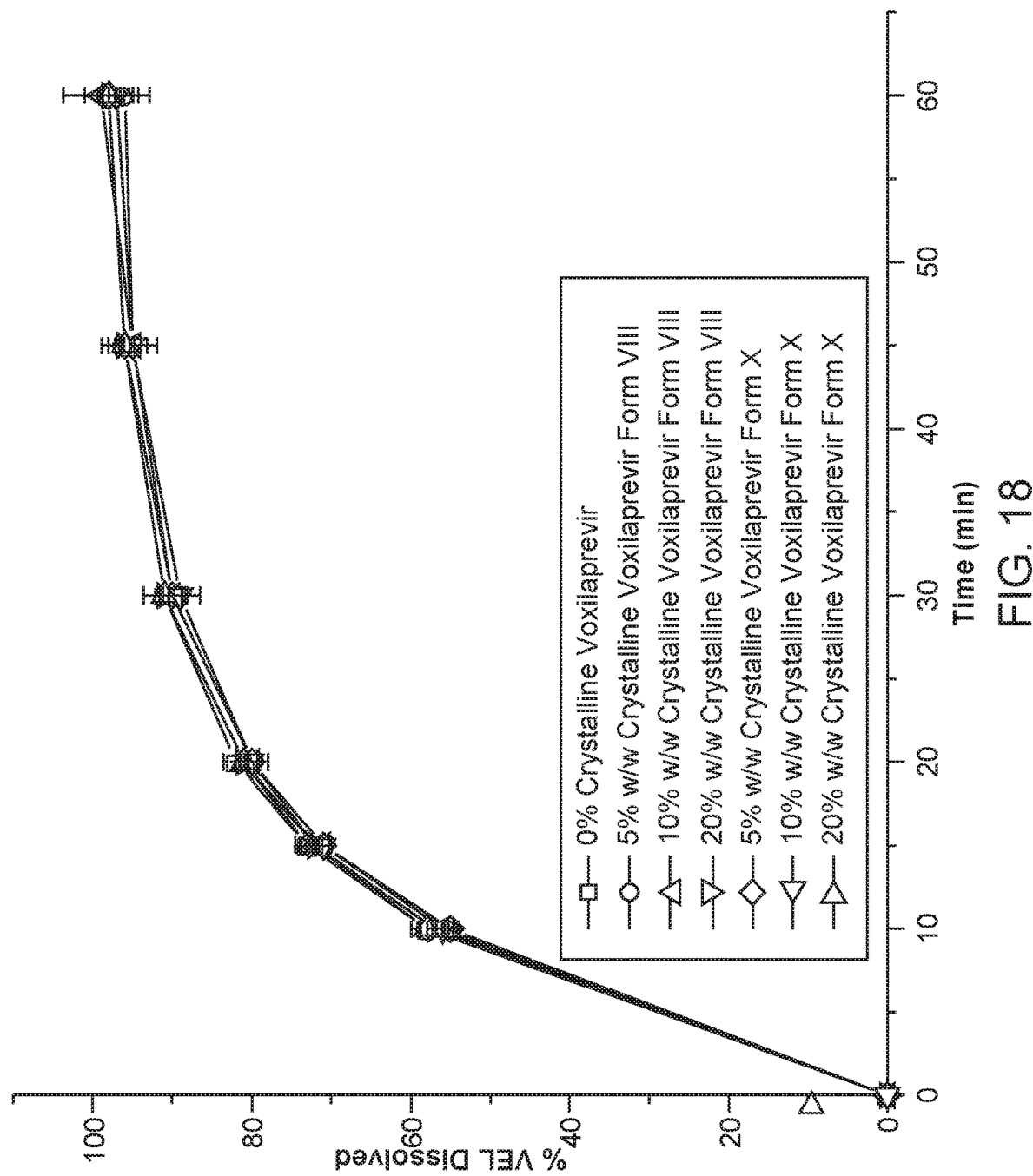
FIG. 18 depicts dissolution profiles of velpatasvir from sofosbuvir/velpatasvir/voxilaprevir film-coated tablets as a function of crystalline voxilaprevir Form VIII and X contents.

The dissolution profiles of sofosbuvir and velpatasvir from the sofosbuvir/velpatasvir SSD/voxilaprevir SSD tablets containing 0 to 20% w/w of voxilaprevir Forms VIII and X are shown in FIGS. 17 and 18, respectively. The release of sofosbuvir and velpatasvir form the spiked tablets was not impacted with the presence of crystalline voxilaprevir Form VIII and Form X (up to 20% w/w) in the tablets. All tablet lots released 97 to 101% of sofosbuvir and 89 to 91% of velpatasvir at 30 minutes.

These results indicate that the proposed dissolution method is capable of discriminating between voxilaprevir incorporated in the VOX SSD and voxilaprevir Form VIII or Form X present in the SOF/VEL/VOX tablet as neat drug substance.

C. Dissolution as a Function of Neat Amorphous Velpatasvir Free Base Content

Velpatasvir (as amorphous free base) is incorporated in the tablet formulation with copovidone in a spray-dried dispersion to improve its solubility and pharmacokinetic performance relative to that of neat amorphous velpatasvir free base drug substance. To demonstrate that incorporation of velpatasvir as velpatasvir SSD is a critical quality attribute of the drug product, dissolution of velpatasvir from the sofosbuvir/velpatasvir SSD/voxilaprevir SSD tablets containing velpatasvir SSD was compared to dissolution of velpatasvir from the sofosbuvir/velpatasvir SSD/voxilaprevir SSD tablets containing a physical mixture of neat amorphous velpatasvir free base and copovidone. All tablets contained 7.7% w/w amorphous velpatasvir free base, either in velpatasvir SSD or as neat drug substance.

Figure 19:
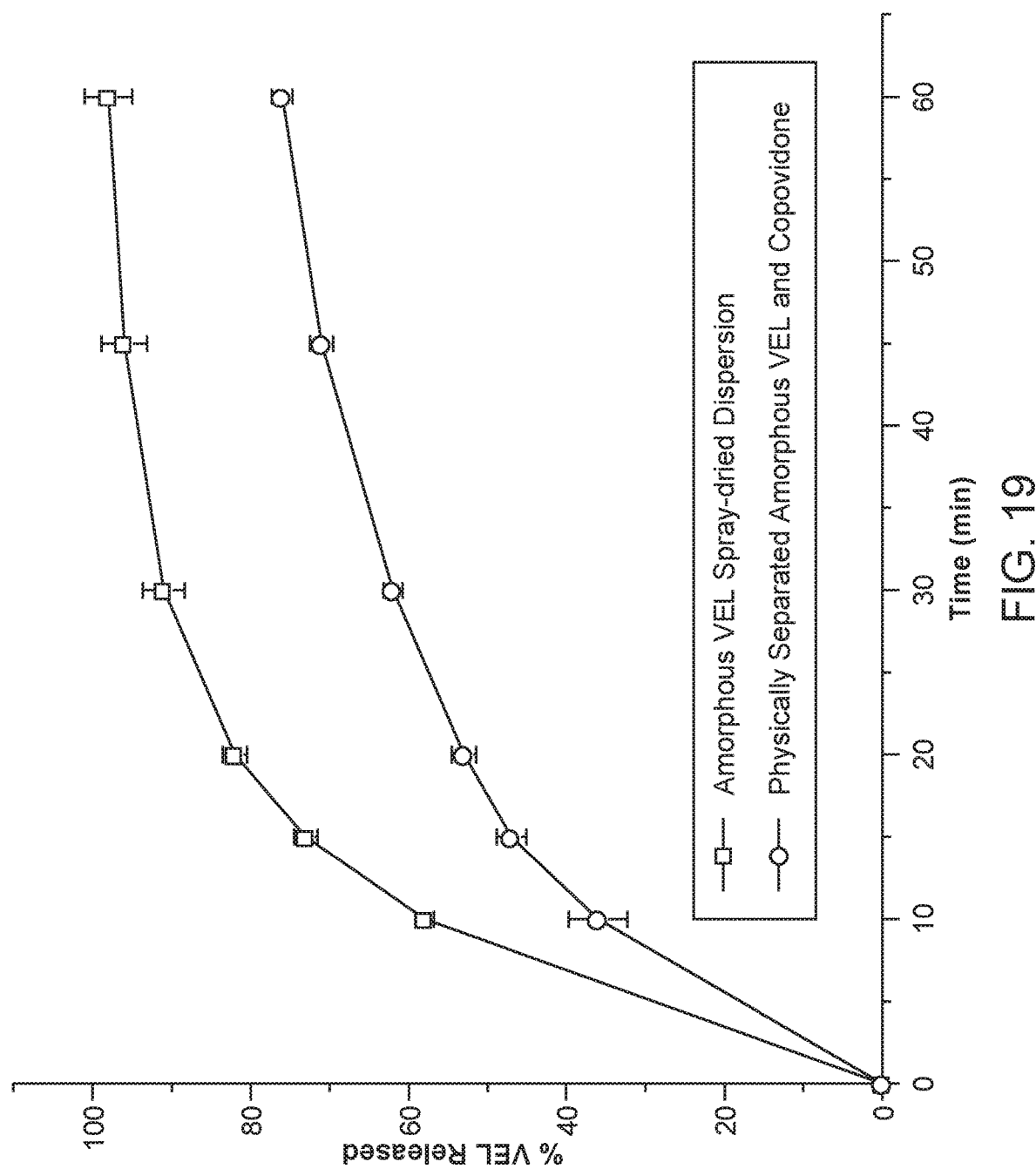
FIG. 19 depicts dissolution profiles of velpatasvir from sofosbuvir/velpatasvir/voxilaprevir film-coated tablets containing velpatasvir spray-dried solid dispersion as a function of neat amorphous velpatasvir free base.
Figure 20:
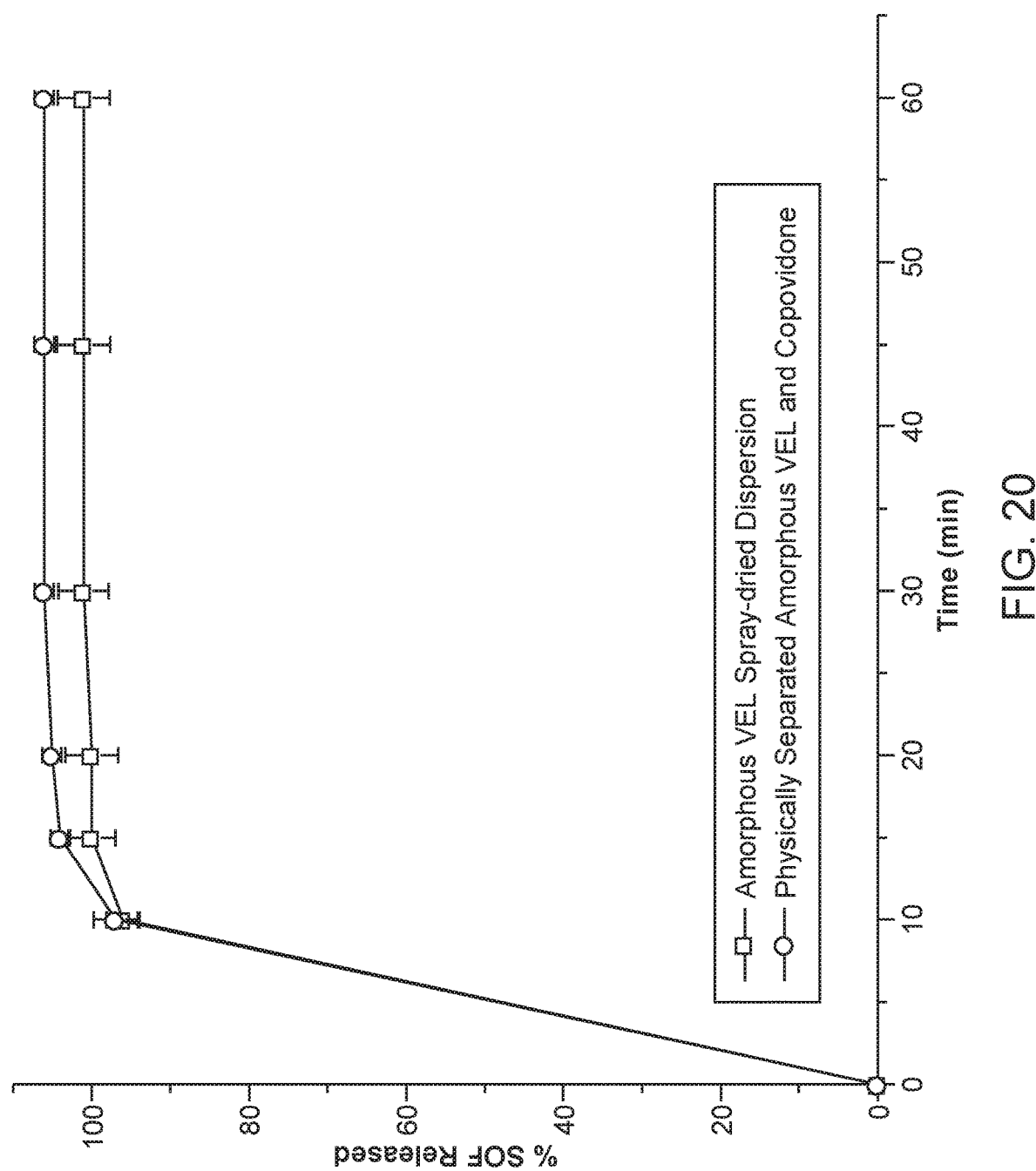
FIG. 20 depicts dissolution profiles of sofosbuvir from sofosbuvir/velpatasvir/voxilaprevir film-coated tablets containing velpatasvir spray-dried solid dispersion as a function of neat amorphous velpatasvir free base.
Figure 21:
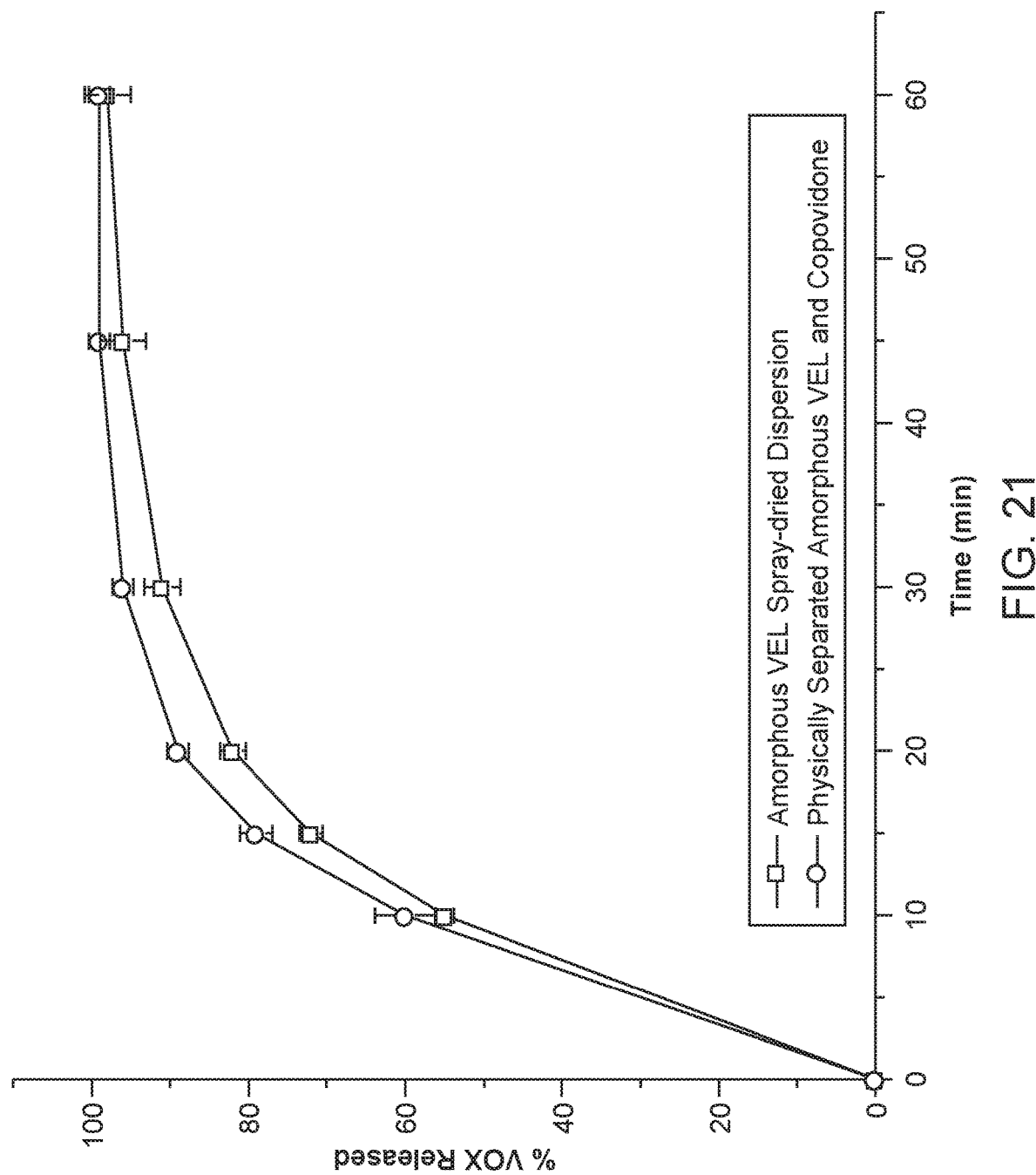
FIG. 21 depicts dissolution profiles of voxilaprevir from sofosbuvir/velpatasvir/voxilaprevir film-coated tablets containing velpatasvir spray-dried solid dispersion as a function of neat amorphous velpatasvir free base.

The dissolution profiles are shown for Velpatasvir in FIG. 19 and for sofosbuvir and voxilaprevir in FIGS. 20 and 21, respectively. As shown in FIG. 19, the release of velpatasvir from tablets containing neat amorphous velpatasvir free base was 62% at 30 minutes as compared to 91% of velpatasvir released at 30 minutes from the tablets containing velpatasvir SSD. As shown in FIGS. 20 and 21, the release of sofosbuvir and voxilaprevir from the sofosbuvir/velpatasvir SSD/voxilaprevir SSD tablets was not impacted by the presence of neat amorphous velpatasvir free base. Both tablet lots released between 101 and 106% of sofosbuvir and between 91 and 96% of velpatasvir at 30 minutes.

The results demonstrate the necessity of maintaining velpatasvir in a dispersed state for suitable drug product dissolution, and also show that the proposed dissolution method discriminates between the sofosbuvir/velpatasvir SSD/voxilaprevir SSD tablets containing velpatasvir as velpatasvir SSD and neat amorphous velpatasvir free base.

D. Dissolution as a Function of Neat Amorphous Voxilaprevir Free Acid Content

Voxilaprevir (as amorphous free acid) is incorporated in the tablet formulation with copovidone in a spray-dried dispersion to improve its solubility and pharmacokinetic performance relative to that of neat drug substance. To demonstrate that incorporation of voxilaprevir as voxilaprevir SSD is a critical quality attribute of the drug product, dissolution of voxilaprevir from the sofosbuvir/velpatasvir SSD/voxilaprevir SSD tablets containing voxilaprevir SSD was compared to dissolution of voxilaprevir from the sofosbuvir/velpatasvir SSD/voxilaprevir SSD tablets containing a physical mixture of neat amorphous voxilaprevir free acid and copovidone. All tablets contained 7.7% w/w amorphous voxilaprevir free acid, either in voxilaprevir SSD or as neat drug substance.

Figure 22:
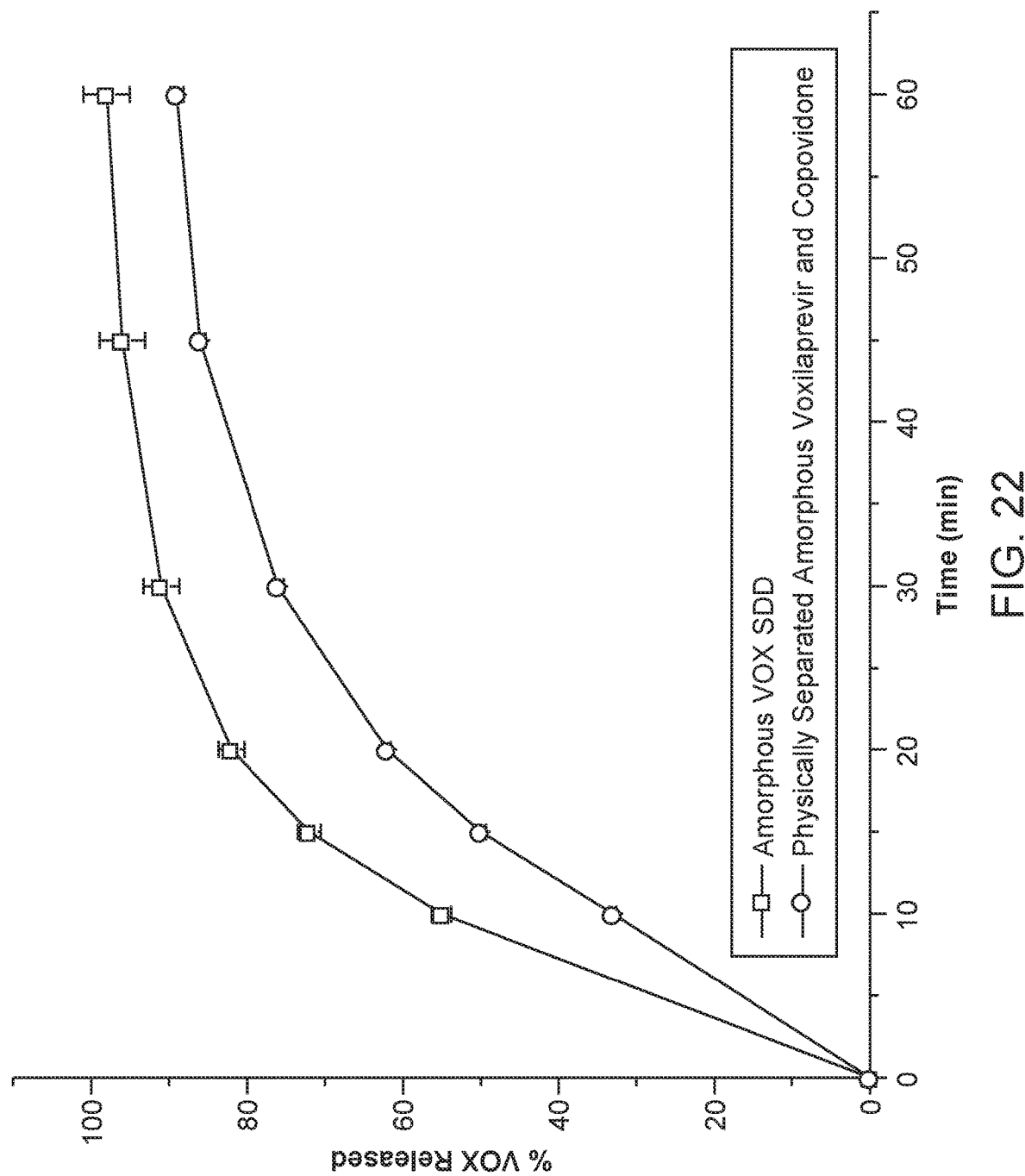
FIG. 22 depicts dissolution profiles of voxilaprevir from sofosbuvir/velpatasvir/voxilaprevir film-coated tablets containing voxilaprevir spray-dried solid dispersion as a function of neat amorphous voxilaprevir free acid.
Figure 23:
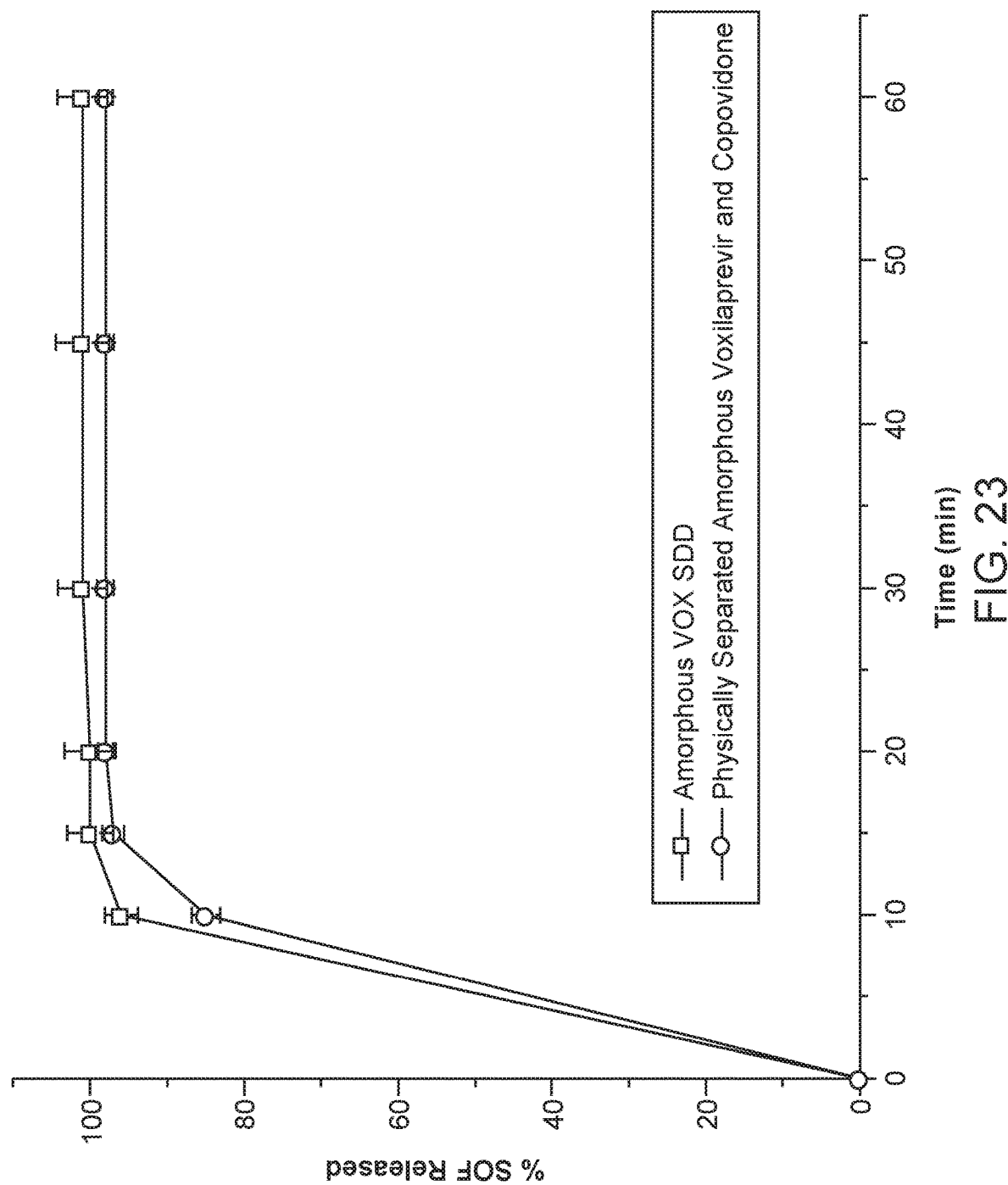
FIG. 23 depicts dissolution profiles of sofosbuvir from sofosbuvir/velpatasvir/voxilaprevir film-coated tablets containing voxilaprevir spray-dried solid dispersion as a function of neat amorphous voxilaprevir free acid.
Figure 24:
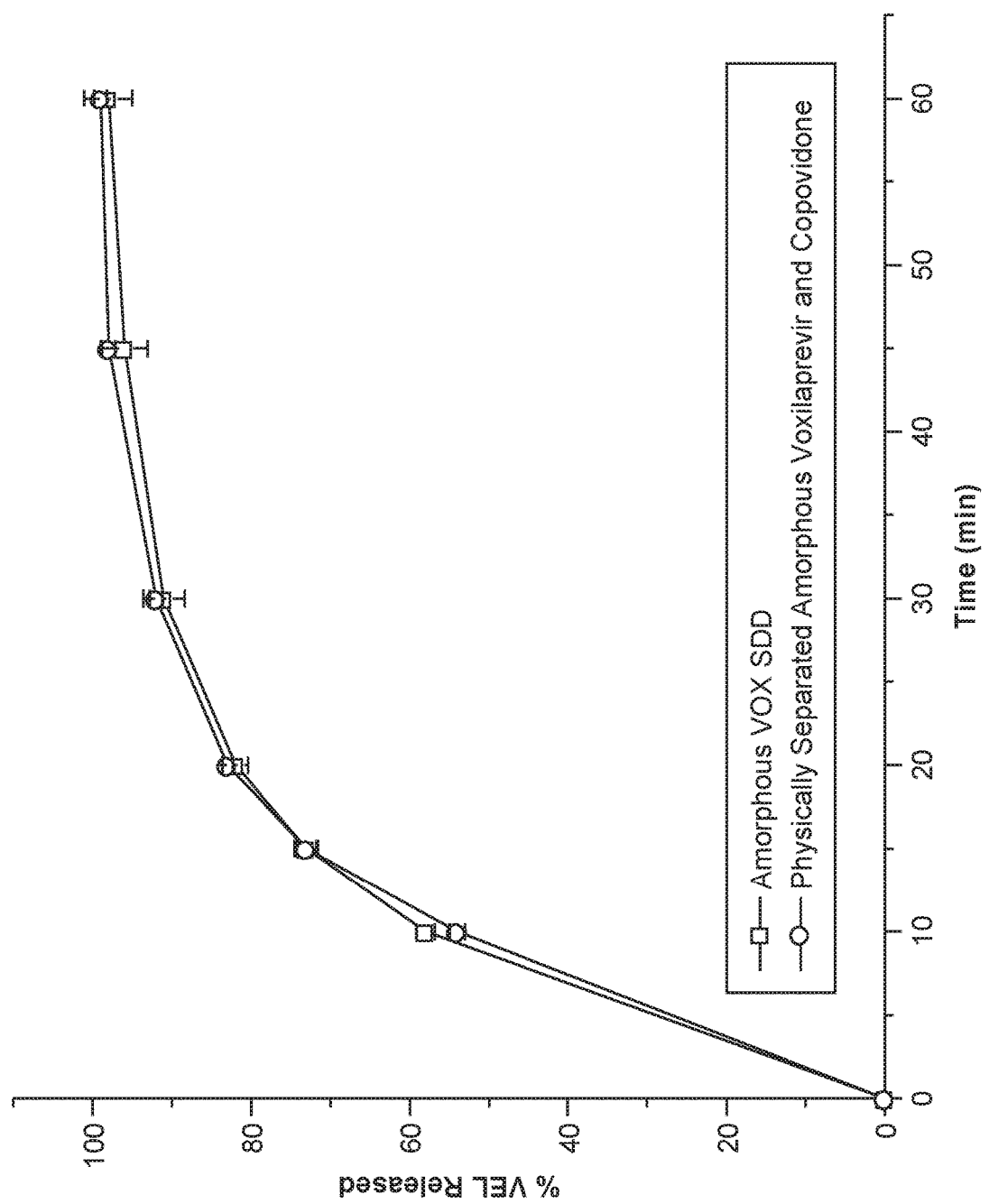
FIG. 24 depicts dissolution profiles of velpatasvir from sofosbuvir/velpatasvir/voxilaprevir film-coated tablets containing voxilaprevir spray-dried solid dispersion vs. neat amorphous voxilaprevir free acid.

The dissolution profiles are shown in FIG. 22 for voxilaprevir and in FIGS. 23 and 24 for sofosbuvir and velpatasvir, respectively. As shown in FIG. 22, the release of voxilaprevir from tablets containing neat amorphous voxilaprevir free acid was impacted. This tablet lot released 76% of voxilaprevir at 30 minutes as compared to 91% of voxilaprevir released from the tablets containing voxilaprevir SSD. As shown in FIGS. 23 and 24, the release of sofosbuvir and velpatasvir from the sofosbuvir/velpatasvir SSD/voxilaprevir SSD tablets was not impacted by the presence of neat amorphous voxilaprevir free acid. Both tablet lots released between 98 and 101% of sofosbuvir and between 91 and 92% of velpatasvir at 30 minutes.

The results demonstrate the necessity of maintaining voxilaprevir in a dispersed state for suitable drug product dissolution, and also show that the proposed dissolution method discriminates between the sofosbuvir/velpatasvir SSD/voxilaprevir SSD tablets containing voxilaprevir as voxilaprevir SSD and neat amorphous voxilaprevir free acid.

E. Stress Studies

The impact of the following stressors on the physical and chemical stability of the sofosbuvir/velpatasvir SSD/voxilaprevir SSD tablets were evaluated:

(i) Voxilaprevir SSD and velpatasvir SSD, and sofosbuvir/velpatasvir SSD/voxilaprevir SSD tablet water content;

(ii) Copovidone peroxide content in velpatasvir SSD and in voxilaprevir SSD (iii) Reprocessed velpatasvir SSD and voxilaprevir SSD;

(iv) Voxilaprevir SSD and velpatasvir SSD potency (varying the ratio of velpatasvir or voxilaprevir to copovidone); and (v) Seeding sofosbuvir/velpatasvir SSD/voxilaprevir SSD tablets with crystalline voxilaprevir Form VIII and Form X drug substances.

For each of the impact studies, the sofosbuvir/velpatasvir SSD/voxilaprevir SSD tablets were packaged in a designated commercial packaging configuration (28-count, 100 mL HPDE bottle, coil, 1 g desiccant), and stored for 12 weeks at 25° C./60% RH and 40° C./75% RH. Tablets were also packaged in open containers (28-count, 100 mL HPDE bottle without cap) and stored for 4 weeks at 40° C./75% RH and for 1 week at 50° C./92% RH.

i. Impact of Velpatasvir SSD and Voxilaprevir SSD Water Content on Sofosbuvir/Velpatasvir SSD/Voxilaprevir SSD Tablets The impact of velpatasvir SSD and voxilaprevir SSD water content on the chemical stability, physical stability, and dissolution of the sofosbuvir/velpatasvir SSD/voxilaprevir SSD tablets (Tables 16A-16B). Velpatasvir SSD with 7.0% and voxilaprevir SSD with 3.2% water content were used to produce the tablets.

Stability results are shown in Table 16A-16B. All tablets were chemically stable, under all conditions with total impurities/degradation products of sofosbuvir, velpatasvir, and voxilaprevir remaining at 0.0%. The water content remained between 2.4 and 2.7% for the tablets stored up to 12 weeks under closed conditions with 1 g desiccant at various temperature/humidity conditions. The water content increased up to 5.3% for the tablets stored up to 4 weeks at 40° C./75% RH under open conditions. All tablet lots showed consistent release of sofosbuvir between 98 and 101%, velpatasvir between 89 and 92%, and voxilaprevir between 90 and 95% at 30 minutes over the time period studied.

All tablets were physically stable, under all conditions. The peaks observed in XRPD patterns were consistent with sofosbuvir or formulation excipients. As summarized in Table 16A, no change in solid form was observed for the tablets stored up to 12 weeks under closed conditions studied with 1 g desiccant. As noted in Table 16B, a minor change (at 3.5-5.5 2θ) in XRPD patterns, related to the physical form change of magnesium stearate, was observed for the tablets stored under open conditions at 50° C./92% RH (1 week) and 40° C./75% RH (4 weeks).

As shown in Tables 16A-16B, the stability and dissolution properties of the sofosbuvir/velpatasvir SSD/voxilaprevir SSD tablets are not impacted by velpatasvir SSD water content up to 7.0% and voxilaprevir SSD water content up to 3.2%.

TABLE 16A

Closed Conditions (1 g Desiccant)

| Storage Condition[a] | | Initial | 40° C./75% RH | 25° C./60% RH |
|---|---|---|---|---|
| | Time | 0 | 4 | 12 | 12 |
| SOF | LS (%) | 100.5 | 101.6 | 100.4 | 99.9 |
| | Total Imp./Deg. (%) | 0.0 | 0.0 | 0.0 | 0.0 |
| VEL SSD | LS (%) | 101.1 | 101.9 | 98.6 | 98.3 |
| | Total Imp./Deg. (%) | 0.0 | 0.0 | 0.0 | 0.0 |
| VOX SSD | LS (%) | 101.4 | 102.6 | 101.2 | 100.7 |
| | Total Imp./Deg. (%) | 0.0 | 0.0 | 0.0 | 0.0 |
| | Water (%) | 2.7 | 2.4 | 2.5 | 2.5 |
| | Change (XRPD) | N/A | No change | No change | No change |
| Dissolved at 30 min (%)[b] | SOF | 100 | 101 | 99 | 98 |
| | VEL SSD | 89 | 92 | 92 | 89 |
| | VOX SSD | 90 | 95 | 93 | 91 |

[a]Packaging consisted of 28-count in a 100 mL HDPE bottle with 1 g desiccant and a polyester coil for closed conditions and 28-count in a 100 mL HDPE bottle without cap for open conditions.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.

TABLE 16B

Open conditions (No Desiccant)

| Storage Condition[a] | | Initial | 40° C./75% RH | 50° C./92% RH |
|---|---|---|---|---|
| | Time | 0 | 4 | 1 |
| SOF | LS (%) | 100.5 | 101.2 | NP |
| | Total Imp./Deg. (%) | 0.0 | 0.0 | NP |
| VEL SSD | LS (%) | 101.1 | 101.3 | NP |
| | Total Imp./Deg. (%) | 0.0 | 0.0 | NP |
| VOX SSD | LS (%) | 101.4 | 102.0 | NP |
| | Total Imp./Deg. (%) | 0.0 | 0.0 | NP |
| | Water (%) | 2.7 | 5.3 | NP |
| | Change (XRPD) | N/A | Change[c] | Change[c] |
| Dissolved at 30 min (%)[b] | SOF | 100 | 100 | NP |
| | VEL SSD | 89 | 90 | NP |
| | VOX SSD | 90 | 92 | NP |

[a]Packaging consisted of 28-count in a 100 mL HDPE bottle with 1 g desiccant and a polyester coil for closed conditions and 28-count in a 100 mL HDPE bottle without cap for open conditions.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.
[c]A minor change (at 3.5-5.5 2θ°) observed in XRPD patterns was related to the physical form change of magnesium stearate under open conditions.

ii. Impact of Velpatasvir SSD Residual Ethanol Content and Voxilaprevir SSD Residual Acetone Content on Sofosbuvir/Velpatasvir SSD/Voxilaprevir SSD Tablets The impact of velpatasvir SSD and voxilaprevir SSD residual solvent contents on the chemical stability, physical stability, and dissolution of sofosbuvir/velpatasvir SSD/voxilaprevir SSD tablets was evaluated (Tables 17A-17B). Development lots of velpatasvir SSD with 6.0% residual ethanol and voxilaprevir SSD with 2.1% residual acetone were used to manufacture sofosbuvir/velpatasvir SSD/voxilaprevir SSD tablets. The quantity of velpatasvir SSD and voxilaprevir SSD were adjusted based on the velpatasvir SSD and voxilaprevir SSD drug content factors, with a concomitant adjustment to the quantity of lactose monohydrate.

As shown in Tables 17A-17B, all tablets were chemically stable, under all conditions with total impurities/degradation products of sofosbuvir, velpatasvir, and voxilaprevir remaining at 0.0%. The water content remained between 2.0 and 2.1% for the tablets stored up to 12 weeks under closed conditions studied with 1 g desiccant at various temperature/humidity conditions. The water content increased to 5.2% for the tablets stored up to 4 weeks at 40° C./75% RH under open conditions. Moreover, all tablets showed consistent release of sofosbuvir between 99 and 101%, velpatasvir between 87 and 91%, and voxilaprevir between 85 and 90% at 30 minutes over the time period studied.

As also shown in Tables 17A-17B, all tablets were physically stable, under all conditions. The peaks observed in XRPD patterns were consistent with sofosbuvir or formulation excipients. No change in solid form was observed for the tablets stored up to 12 weeks under closed conditions studied with 1 g desiccant. A minor change (at 3.5-5.5 2θ°) in XRPD patterns, related to the physical form change of magnesium stearate, was observed for the tablets stored under open conditions at 50° C./92% RH (1 week) and 40° C./75% RH (4 weeks).

The data presented in Tables 17A-17B demonstrates that the stability and dissolution performance of the sofosbuvir/velpatasvir SSD/voxilaprevir SSD tablets are not impacted by 6.0% residual ethanol in velpatasvir SSD and 2.1% residual acetone in voxilaprevir SSD.

TABLE 17A

Closed Conditions (1 g Desiccant)

| Storage Condition[a] | | Initial | 40° C./75% RH | 25° C./60% RH |
|---|---|---|---|---|
| | Time | 0 | 4 | 12 | 12 |
| SOF | LS (%) | 101.2 | 101.5 | 100.9 | 100.5 |
| | Total Imp./Deg. (%) | 0.0 | 0.0 | 0.0 | 0.0 |
| VEL SSD | LS (%) | 101.6 | 101.2 | 99.0 | 98.7 |
| | Total Imp./Deg. (%) | 0.0 | 0.0 | 0.0 | 0.0 |
| VOX SSD | LS (%) | 98.8 | 99.0 | 98.5 | 98.0 |
| | Total Imp./Deg. (%) | 0.0 | 0.0 | 0.0 | 0.0 |
| | Water (%) | 2.1 | 2.0 | 2.0 | 2.0 |
| | Change (XRPD) | N/A | No change | No change | No change |
| Dissolved at 30 min (%)[b] | SOF | 99 | 101 | 100 | 101 |
| | VEL SSD | 87 | 88 | 91 | 90 |
| | VOX SSD | 85 | 86 | 90 | 89 |

[a]Packaging consisted of 28-count in a 100 mL HDPE bottle with 1 g desiccant and a polyester coil for closed condition and 28-count in a 100 mL HDPE bottle without cap for open conditions.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.

TABLE 17B

Open Conditions (No Desiccant)

| Storage Condition[a] | | Initial | 40° C./75% RH | 50° C./92% RH |
|---|---|---|---|---|
| Time | | 0 | 4 | 1 |
| SOF | LS (%) | 101.2 | 100.9 | NP |
| | Total Imp./Deg. (%) | 0.0 | 0.0 | NP |
| VEL SSD | LS (%) | 101.6 | 101.0 | NP |
| | Total Imp./Deg. (%) | 0.0 | 0.0 | NP |
| VOX SSD | LS (%) | 98.8 | 98.5 | NP |
| | Total Imp./Deg. (%) | 0.0 | 0.0 | NP |
| Water (%) | | 2.1 | 5.2 | NP |
| Change (XRPD) | | N/A | Change[c] | Change[c] |
| Dissolved at 30 min (%)[b] | SOF | 99 | 101 | NP |
| | VEL SSD | 87 | 89 | NP |
| | VOX SSD | 85 | 89 | NP |

[a]Packaging consisted of 28-count in a 100 mL HDPE bottle with 1 g desiccant and a polyester coil for closed conditions and 28-count in a 100 mL HDPE bottle without cap for open conditions.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.
[c]A minor change (at 3.5-5.5 2θ°) observed in XRPD patterns was related to the physical form change of magnesium stearate under open conditions.

iii. Impact of Copovidone Peroxide Content on Sofosbuvir/Velpatasvir SSD/Voxilaprevir SSD Tablets The impact of copovidone peroxide content on the chemical stability, physical stability, and dissolution of sofosbuvir/velpatasvir SSD/voxilaprevir SSD tablets was evaluated (Tables 18A-18B). Copovidone with 544 ppm peroxides content was incorporated in a development lot of velpatasvir SSD that was used to sofosbuvir/velpatasvir SSD/voxilaprevir SSD tablets. Copovidone with 655 ppm peroxides content was incorporated in a development lot of voxilaprevir SSD (Lot 150629401) that was used to produce sofosbuvir/velpatasvir SSD/voxilaprevir SSD tablets.

As shown in Tables 18A-18B, all tablets were chemically stable, with total impurities/degradation products of sofosbuvir and velpatasvir remaining at 0.0% and voxilaprevir between 0.2 and 0.3%. The water content remained between 2.0 and 2.2% for the tablets stored for 12 weeks under closed conditions with 1 g desiccant at various temperature/humidity conditions. The water content increased for 5.2% for the tablets stored for 4 weeks at 40° C./75% RH under open conditions. All tablet lots showed consistent release of sofosbuvir between 99 and 100%, velpatasvir between 85 and 90%, and voxilaprevir between 87 and 93% at 30 minutes over the time period studied.

As also shown in Tables 18A-18B, all tablets were physically stable, under all conditions. All peaks observed in XRPD patterns of the tablets were consistent with sofosbuvir or formulation excipients. No change in solid form was observed for the tablets stored up to 12 weeks under closed conditions studied with 1 g desiccant. A minor change (at 3.5-5.5 2θ°) in XRPD patterns, related to the physical form change of magnesium stearate, was observed for the tablets stored under open conditions at 50° C./92% RH (1 week) and 40° C./75% RH (4 weeks).

The results presented in Tables 18A-18B demonstrate that the stability and dissolution properties of sofosbuvir/velpatasvir SSD/voxilaprevir SSD tablets are not impacted by copovidone peroxides content levels exceeding the compendial specification limit of 400 ppm.

TABLE 18A

Closed Conditions (1 g Desiccant)

| Storage Condition[a] | | Initial | 40° C./75% RH | | 25° C./60% RH |
|---|---|---|---|---|---|
| Time | | 0 | 4 | 12 | 12 |
| SOF | LS (%) | 100.0 | 99.3 | 98.9 | 99.3 |
| | Total Imp./Deg. (%) | 0.0 | 0.0 | 0.0 | 0.0 |
| VEL SSD | LS (%) | 101.4 | 100.2 | 97.9 | 98.5 |
| | Total Imp./Deg. (%) | 0.0 | 0.0 | 0.0 | 0.0 |
| VOX SSD | LS (%) | 100.8 | 100.0 | 99.6 | 100.1 |
| | Total Imp./Deg. (%) | 0.3 | 0.3 | 0.2 | 0.3 |
| Water (%) | | 2.2 | 2.0 | 2.2 | 2.1 |
| Change (XRPD) | | N/A | No change | No Change | No change |
| Dissolved at 30 min (%)[b] | SOF | 99 | 99 | 99 | 99 |
| | VEL SSD | 85 | 86 | 87 | 86 |
| | VOX SSD | 87 | 90 | 89 | 88 |

[a]Packaging consisted of 28-count in a 100 mL HDPE bottle with 1 g desiccant and a polyester coil for closed condition and 28-count in a 100 mL HDPE bottle without cap for open conditions.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.

TABLE 18B

Open Conditions (No Desiccant)

| Storage Condition[a] | | Initial | 40° C./75% RH | 50° C./92% RH |
|---|---|---|---|---|
| Time | | 0 | 4 | 1 |
| SOF | LS (%) | 100.0 | 100.3 | NP |
| | Total Imp./Deg. (%) | 0.0 | 0.0 | NP |
| VEL SSD | LS (%) | 101.4 | 101.2 | NP |
| | Total Imp./Deg. (%) | 0.0 | 0.0 | NP |
| VOX SSD | LS (%) | 100.8 | 101.0 | NP |
| | Total Imp./Deg. (%) | 0.3 | 0.3 | NP |
| Water (%) | | 2.2 | 5.2 | NP |
| Change (XRPD) | | N/A | Change[c] | Change[c] |
| Dissolved at 30 min (%)[b] | SOF | 99 | 100 | NP |
| | VEL SSD | 85 | 90 | NP |
| | VOX SSD | 87 | 93 | NP |

[a]Packaging consisted of 28-count in a 100 mL HDPE bottle with 1 g desiccant and a polyester coil for closed conditions and 28-count in a 100 mL HDPE bottle without cap for open conditions.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.
[c]A minor change (at 3.5-5.5 2θ°) observed in XRPD patterns was related to the physical form change of magnesium stearate under open conditions.

iv. Impact of Reprocessed Velpatasvir SSD and Voxilaprevir SSD on Sofosbuvir/Velpatasvir SSD/Voxilaprevir SSD Tablet Stability The impact of reprocessed velpatasvir SSD and voxilaprevir SSD on the chemical stability, physical stability, and dissolution of sofosbuvir/velpatasvir SSD/voxilaprevir SSD tablets was evaluated (Tables 19A-18B). Velpatasvir SSD and voxilaprevir SSD (Lot 150629203) were reprocessed (re-dissolved, spray-dried, and secondary dried) twice and used to produce sofosbuvir/velpatasvir SSD/voxilaprevir SSD tablets.

As shown in Tables 19A-18B, all tablets were chemically stable, under all conditions with total impurities/degradation products of sofosbuvir remaining at 0.0%, velpatasvir remaining between 0.5 and 0.6%, and voxilaprevir between 0.2 and 0.3%. The water content remained between 2.0 and 2.3% for the tablets stored up to 12 weeks under closed condition with 1 g desiccant at various temperature/humidity conditions. The water content increased up to 5.2% for the tablets stored up to 4 weeks at 40° C./75% RH under open conditions. All tablet lots showed consistent release of sofosbuvir between 98 and 101%, velpatasvir between 83 and 85%, and voxilaprevir between 87 and 90% at 30 minutes over the time period studied.

As also shown in Tables 19A-19B, all tablets were physically stable, under all conditions. All peaks observed in XRPD patterns of the tablets were consistent with sofosbuvir or formulation excipients. No change in solid form was observed for the tablets stored up to 12 weeks under closed conditions studied with 1 g desiccant. A minor change (at 3.5-5.520°) in XRPD patterns, related to the physical form change of magnesium stearate, was observed for the tablets stored under open conditions at 50° C./92% RH (1 week) and 40° C./75% RH (4 weeks).

The data presented in Tables 19A-9B indicates that reprocessing of both velpatasvir SSD and voxilaprevir did not affect the chemical and physical stability of sofosbuvir/velpatasvir SSD/voxilaprevir SSD tablets under the conditions studied for 12 weeks.

TABLE 19A

Closed Conditions (1 g Desiccant)

| Storage Condition[a] | | Initial | 40° C./75% RH | 25° C./60% RH |
|---|---|---|---|---|
| Time | | 0 | 4  12 | 12 |
| SOF | LS (%) | 100.7 | 100.3  99.1 | 99.9 |
|  | Total Imp./Deg. (%) | 0.0 | 0.0  0.0 | 0.0 |
| VEL SSD | LS (%) | 98.8 | 98.2  95.2 | 95.9 |
|  | Total Imp./Deg. (%) | 0.6 | 0.5  0.5 | 0.5 |
| VOX SSD | LS (%) | 99.3 | 98.9  97.6 | 98.4 |
|  | Total Imp./Deg. (%) | 0.2 | 0.3  0.2 | 0.3 |
| Water (%) | | 2.3 | 2.0  2.1 | 2.1 |
| Change (XRPD) | | N/A | No change  No change | No Change |
| Dissolved at 30 min (%)[b] | SOF | 101 | 99  98 | 98 |
|  | VEL SSD | 83 | 83  85 | 83 |
|  | VOX SSD | 87 | 88  88 | 87 |

[a]Packaging consisted of 28-count in a 100 mL HDPE bottle with 1 g desiccant and a polyester coil for closed condition and 28-count in a 100 mL HDPE bottle without cap for open conditions.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.

TABLE 19B

Open Conditions (No Desiccant)

| Storage Condition[a] | | Initial | 40° C./75% RH | 50° C./92% RH |
|---|---|---|---|---|
| Time | | 0 | 4 | 1 |
| SOF | LS (%) | 100.7 | 96.4 | NP |
|  | Total Imp./Deg. (%) | 0.0 | 0.0 | NP |
| VEL SSD | LS (%) | 98.8 | 98.3 | NP |
|  | Total Imp./Deg. (%) | 0.6 | 0.5 | NP |
| VOX SSD | LS (%) | 99.3 | 99.2 | NP |
|  | Total Imp./Deg. (%) | 0.2 | 0.2 | NP |
| Water (%) | | 2.3 | 5.2 | NP |
| Change (XRPD) | | N/A | Change[c] | Change[c] |
| Dissolved at 30 min (%)[b] | SOF | 101 | 98 | NP |
|  | VEL SSD | 83 | 85 | NP |
|  | VOX SSD | 87 | 90 | NP |

[a]Packaging consisted of 28-count in a 100 mL HDPE bottle with 1 g desiccant and a polyester coil for closed conditions and 28-count in a 100 mL HDPE bottle without cap for open conditions.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.
[c]A minor change (at 3.5-5.5 2θ°) observed in XRPD patterns was related to the physical form change of magnesium stearate under open conditions.

v. Impact of Velpatasvir SSD and Voxilaprevir SSD Potency on Sofosbuvir/Velpatasvir SSD/Voxilaprevir SSD Tablets The impact of sub-potent velpatasvir SSD (40% w/w velpatasvir/60% copovidone; Lot A), super-potent velpatasvir SSD (55% w/w velpatasvir and 45% copovidone; Lot B), sub-potent voxilaprevir SSD (40% w/w voxilaprevir/60% copovidone; Lot C), super-potent voxilaprevir SSD (60% w/w voxilaprevir and 45% copovidone; Lot D) (Tables 20A-20D and 21A-21D). Development lots of sub-potent and super-potent velpatasvir SSD and voxilaprevir SSD were used to produce four lots of sofosbuvir/velpatasvir SSD/voxilaprevir SSD tablets (Lots A-D). The quantity of velpatasvir SSD and voxilaprevir SSD were adjusted based on the velpatasvir SSD and voxilaprevir SSD drug content factors, with a concomitant adjustment to the quantity of lactose monohydrate.

The stability results are shown in Tables 20A-20D for closed conditions and in Tables 21A-21D for open conditions. All tablet lots were chemically stable, under all conditions with total impurities/degradation products of sofosbuvir and velpatasvir remaining at 0.0% and voxilaprevir remaining at 0.7%. The water content remained between 1.8 and 2.5% for the tablets stored up to 12 weeks under closed conditions with 1 g desiccant at various temperature/humidity conditions (Tables 20A-20D). The water content increased up to 5.8% for the tablets stored up to 4 weeks at 40° C./75% RH under open conditions (Tables 21A-21D).

Lot A containing super-potent velpatasvir SSD and super-potent voxilaprevir SSD showed consistent release of sofosbuvir between 99 and 102%, velpatasvir between 90 and 92%, and voxilaprevir between 91 and 93% at 30 minutes under closed conditions studied (Table 20A). The dissolution of both velpatasvir and voxilaprevir from Lot A decreased to 86% for velpatasvir and 85% for voxilaprevir at 30 minutes after 4 weeks storage under open conditions at 40° C./75% RH (Table 21A).

Lot B containing sub-potent velpatasvir SSD and sub-potent voxilaprevir SSD showed the slowest but consistent release of sofosbuvir between 82 and 84%, velpatasvir between 61 and 63%, and voxilaprevir between 61 and 63% at 30 minutes under closed conditions studied (Table 20B). The dissolution of sofosbuvir, velpatasvir, and voxilaprevir from Lot B increased to 100% for sofosbuvir, 91% for velpatasvir, and voxilaprevir at 30 minutes after 4 weeks storage under open conditions at 40° C./75% RH (Table 21B).

Lot C containing sub-potent velpatasvir SSD and super-potent voxilaprevir SSD and Lot D containing super-potent velpatasvir SSD and sub-potent voxilaprevir SSD showed consistent release of sofosbuvir between 98 and 101%, velpatasvir between 81 and 87%, and voxilaprevir between 84 and 88% at 30 minutes under closed conditions studies (Table 20C). The dissolution of velpatasvir and voxilaprevir from C and D increased to 89-93% for velpatasvir and 92% for voxilaprevir at 30 minutes after 4 weeks storage under open conditions at 40° C./75% RH (Table 21C).

All tablets were physically stable, under all conditions. All peaks observed in XRPD patterns of the tablets were consistent with sofosbuvir or formulation excipients. As summarized in Tables 20A-20D and 21A-20D, no change in solid form was observed for the tablets stored up to 12 weeks under closed conditions studied with 1 g desiccant. A minor change (at 3.5-5.5) 20° in XRPD patterns, related to the physical form change of magnesium stearate, was observed for the tablets stored under open conditions at 50° C./92% RH (1 week) and 40° C./75% RH (4 weeks).

As a result, velpatasvir potency velpatasvir SSD and voxilaprevir potency in voxilaprevir SSD did not affect the chemical and physical stability of sofosbuvir/velpatasvir SSD/voxilaprevir SSD tablets under the conditions studied for up to 12 weeks.

TABLE 20A

Lot A

| Condition[a] | | Initial | 40° C./75% RH | | 25° C./60% RH |
|---|---|---|---|---|---|
| Time | | 0 | 4 | 12 | 12 |
| SOF | LS (%) | 100.1 | 99.9 | 99.8 | 99.0 |
| | I/D (%) | 0.0 | 0.0 | 0.0 | 0.0 |
| VEL SSD | LS (%) | 101.4 | 101.2 | 99.1 | 98.4 |
| | I/D (%) | 0.0 | 0.0 | 0.0 | 0.0 |
| VOX SSD | LS (%) | 99.6 | 99.6 | 99.2 | 98.4 |
| | I/D (%) | 0.7 | 0.7 | 0.7 | 0.7 |
| Water (%) | | 2.4 | 2.1 | 2.3 | 2.2 |
| Change (XRPD) | | N/A | No change | No change | No change |
| Dissolved at 30 min (%)[b] | SOF | 100 | 102 | 100 | 99 |
| | VEL SSD | 90 | 90 | 92 | 90 |
| | VOX SSD | 91 | 92 | 93 | 91 |

[a]Packaging consisted of 28-count in a 100 mL HDPE bottle with 1 g desiccant and a polyester coil under closed conditions.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.
Note:
I/D refers to total impurities/degradation products.

TABLE 20B

Lot B

| Condition[a] | | Initial | 40° C./75% RH | | 25° C./60% RH |
|---|---|---|---|---|---|
| Time | | 0 | 4 | 12 | 12 |
| SOF | LS (%) | 99.9 | 99.8 | 98.7 | 99.4 |
| | I/D (%) | 0.0 | 0.0 | 0.0 | 0.0 |
| VEL SSD | LS (%) | 101.1 | 101.1 | 98.0 | 98.8 |
| | I/D (%) | 0.0 | 0.0 | 0.0 | 0.0 |
| VOX SSD | LS (%) | 99.8 | 99.8 | 98.5 | 99.3 |
| | I/D (%) | 0.7 | 0.7 | 0.7 | 0.7 |
| Water (%) | | 2.1 | 1.8 | 1.9 | 1.9 |
| Change (XRPD) | | N/A | No change | No change | No change |
| Dissolved at 30 min (%)[b] | SOF | 83 | 85 | 84 | 82 |
| | VEL SSD | 63 | 62 | 62 | 61 |
| | VOX SSD | 62 | 63 | 62 | 61 |

[a]Packaging consisted of 28-count in a 100 mL HDPE bottle with 1 g desiccant and a polyester coil under closed conditions.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.
Note:
I/D refers to total impurities/degradation products.

TABLE 20C

Lot C

| Condition[a] | | Initial | 40° C./75% RH | | 25° C./60% RH |
|---|---|---|---|---|---|
| Time | | 0 | 4 | 12 | 12 |
| SOF | LS (%) | 99.5 | 99.6 | 99.1 | 99.6 |
| | I/D (%) | 0.0 | 0.0 | 0.0 | 0.0 |
| VEL SSD | LS (%) | 100.9 | 100.5 | 98.1 | 98.6 |
| | I/D (%) | 0.0 | 0.0 | 0.0 | 0.0 |
| VOX SSD | LS (%) | 99.3 | 99.3 | 98.6 | 99.0 |
| | I/D (%) | 0.7 | 0.7 | 0.7 | 0.7 |
| Water (%) | | 2.5 | 2.0 | 2.1 | 2.1 |
| Change (XRPD) | | N/A | No change | No change | No change |
| Dissolved at 30 min (%)[b] | SOF | 99 | 100 | 98 | 98 |
| | VEL SSD | 86 | 87 | 86 | 86 |
| | VOX SSD | 84 | 87 | 85 | 84 |

[a]Packaging consisted of 28-count in a 100 mL HDPE bottle with 1 g desiccant and a polyester coil under closed conditions.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.
Note:
I/D refers to total impurities/degradation products.

TABLE 20D

Lot D

| Condition[a] | | Initial | 40° C./75% RH | | 25° C./60% RH |
|---|---|---|---|---|---|
| Time | | 0 | 4 | 12 | 12 |
| SOF | LS (%) | 100.0 | 100.1 | 98.9 | 99.5 |
| | I/D (%) | 0.0 | 0.0 | 0.0 | 0.0 |
| VEL SSD | LS (%) | 101.0 | 100.8 | 97.6 | 98.3 |
| | I/D (%) | 0.0 | 0.0 | 0.0 | 0.0 |
| VOX SSD | LS (%) | 99.7 | 99.9 | 98.4 | 99.0 |
| | I/D (%) | 0.7 | 0.7 | 0.7 | 0.7 |
| Water (%) | | 2.2 | 2.0 | 2.0 | 2.0 |
| Change (XRPD) | | N/A | No change | No change | No change |
| Dissolved at 30 min (%)[b] | SOF | 101 | 98 | 98 | 98 |
| | VEL SSD | 83 | 84 | 82 | 81 |
| | VOX SSD | 87 | 88 | 85 | 84 |

[a]Packaging consisted of 28-count in a 100 mL HDPE bottle with 1 g desiccant and a polyester coil under closed condition.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.
Note:
I/D refers to total impurities/degradation products.

TABLE 21A

Lot A

| Condition[a] | | Initial | 40° C./75% RH | 50° C./92% RH |
|---|---|---|---|---|
| Time | | 0 | 4 | 1 |
| SOF | LS (%) | 100.1 | 100.3 | NP |
| | I/D (%) | 0.0 | 0.0 | NP |
| VEL SSD | LS (%) | 101.4 | 101.6 | NP |
| | I/D (%) | 0.0 | 0.0 | NP |
| VOX SSD | LS (%) | 99.6 | 99.9 | NP |
| | I/D (%) | 0.7 | 0.7 | NP |
| Water (%) | | 2.4 | 4.8 | NP |
| Change (XRPD) | | N/A | Change[c] | Change[c] |
| Dissolved at 30 min (%)[b] | SOF | 100 | 101 | NP |
| | VEL SSD | 90 | 86 | NP |
| | VOX SSD | 91 | 85 | NP |

[a]Packaging consisted of 28-count in a 100 mL HDPE bottle without cap under open conditions.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.
[c]A minor change (at 3.5-5.5 2θ°) observed in XRPD patterns was related to the physical form change of magnesium stearate under open conditions.

TABLE 21B

Lot B

| Condition[a] | | Initial | 40° C./75% RH | 50° C./92% RH |
|---|---|---|---|---|
| Time | | 0 | 4 | 1 |
| SOF | LS (%) | 99.9 | 100.1 | NP |
| | I/D (%) | 0.0 | 0.0 | NP |
| VEL SSD | LS (%) | 101.1 | 101.3 | NP |
| | I/D (%) | 0.0 | 0.0 | NP |

TABLE 21B-continued

Lot B

| Condition[a] | | Initial | 40° C./75% RH | 50° C./92% RH |
|---|---|---|---|---|
| VOX SSD | LS (%) | 99.8 | 100.1 | NP |
| | I/D (%) | 0.7 | 0.7 | NP |
| Water (%) | | 2.1 | 5.8 | NP |
| Change (XRPD) | | N/A | Change[c] | Change[c] |
| Dissolved at | SOF | 83 | 100 | NP |
| 30 min (%)[b] | VEL SSD | 63 | 91 | NP |
| | VOX SSD | 62 | 91 | NP |

[a]Packaging consisted of 28-count in a 100 mL HDPE bottle without cap under open conditions.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.
[c]A minor change (at 3.5-5.5 2θ°) observed in XRPD patterns was related to the physical form change of magnesium stearate under open conditions.

TABLE 21C

Lot C

| Condition[a] | | Initial | 40° C./75% RH | 50° C./92% RH |
|---|---|---|---|---|
| Time | | 0 | 4 | 1 |
| SOF | LS (%) | 99.5 | 99.4 | NP |
| | I/D (%) | 0.0 | 0.0 | NP |
| VEL SSD | LS (%) | 100.9 | 100.5 | NP |
| | I/D (%) | 0.0 | 0.0 | NP |
| VOX SSD | LS (%) | 99.3 | 99.1 | NP |
| | I/D (%) | 0.7 | 0.7 | NP |
| Water (%) | | 2.5 | 5.2 | NP |
| Change (XRPD) | | N/A | Change[c] | Change[c] |
| Dissolved at | SOF | 99 | 99 | NP |
| 30 min (%)[b] | VEL SSD | 86 | 93 | NP |
| | VOX SSD | 84 | 92 | NP |

[a]Packaging consisted of 28-count in a 100 mL HDPE bottle without cap under open conditions.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.
[c]A minor change (at 3.5-5.5 2θ°) observed in XRPD patterns was related to the physical form change of magnesium stearate under open conditions.

TABLE 21D

Lot D

| Condition[a] | | Initial | 40° C./75% RH | 50° C./92% RH |
|---|---|---|---|---|
| Time | | 0 | 4 | 1 |
| SOF | LS (%) | 100.0 | 99.8 | NP |
| | I/D (%) | 0.0 | 0.0 | NP |
| VEL SSD | LS (%) | 101.0 | 100.6 | NP |
| | I/D (%) | 0.0 | 0.0 | NP |
| VOX SSD | LS (%) | 99.7 | 99.5 | NP |
| | I/D (%) | 0.7 | 0.7 | NP |
| Water (%) | | 2.2 | 5.3 | NP |
| Change (XRPD) | | N/A | Change[c] | Change[c] |
| Dissolved at | SOF | 101 | 99 | NP |
| 30 min (%)[b] | VEL SSD | 83 | 89 | NP |
| | VOX SSD | 87 | 92 | NP |

[a]Packaging consisted of 28-count in a 100 mL HDPE bottle without cap under open conditions.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.
[c]A minor change (at 3.5-5.5 2θ°) observed in XRPD patterns was related to the physical form change of magnesium stearate under open conditions.

vi. Physical Stability of Sofosbuvir/Velpatasvir SSD/Voxilaprevir SSD Tablets Spiked with Crystalline Voxilaprevir Form VIII and Form X The impact of crystalline voxilaprevir Form VIII and Form X seeds on the physical stability and dissolution of sofosbuvir/velpatasvir SSD/voxilaprevir SSD tablets was evaluated (Tables 22 and 23). As described in Table 22, sofosbuvir/velpatasvir SSD/voxilaprevir SSD tablets Lots A and B were spiked with 5 and 10% w/w Form VIII (% w/w with respect to total voxilaprevir), respectively. Sofosbuvir/velpatasvir SSD/voxilaprevir SSD tablets Lots C and D, as described in Table 23, were spiked with 10 and 20% w/w Form X (% w/w with respect to total voxilaprevir), respectively.

Results for spiked tablets with 5 and 10% w/w Form VIII are summarized in Table 22. Sofosbuvir/velpatasvir SSD/voxilaprevir SSD tablets spiked with 10% w/w Form VIII showed consistent release of sofosbuvir between 98 and 100%, velpatasvir between 90 and 96%, and voxilaprevir between 80 and 85% at 30 minutes over the time period studied. All peaks observed in XRPD patterns of the tablets were consistent with sofosbuvir, Form VIII, or formulation excipients. No additional crystalline peaks were observed under closed storage conditions studied. A minor change (at 3.5-5.3 2θ°) in XRPD patterns, related to the physical form change of magnesium stearate, was observed for the samples stored under open conditions at 50° C./92% RH (1 week) and 40° C./75% RH (4 weeks).

Results for spiked tablets with 10 and 20% w/w Form X are summarized in Table 23. Sofosbuvir/velpatasvir SSD/voxilaprevir SSD tablets spiked with 10% w/w Form X showed consistent release of sofosbuvir between 97 and 100%, velpatasvir between 89 and 95%, and voxilaprevir between 80 and 85% at 30 minutes. All peaks observed in XRPD patterns of the tablets were consistent with sofosbuvir, Form X, or formulation excipients. No additional crystalline peaks were observed under closed storage conditions studied. A minor change (at 3.5-5.3 2θ°) in XRPD patterns, related to the physical form change of magnesium stearate, was observed for the samples stored under open conditions at 50° C./92% RH (1 week) and 40° C./75% RH (4 weeks).

Per the data presented in Tables 22 and 23, amorphous velpatasvir free base and amorphous voxilaprevir free acid exhibit no tendency to crystallize in the presence of pre-existing crystalline voxilaprevir.

TABLE 22

| VOX Form | Lot | % Form VIII in Tablet[a] | Condition Storage[b] | | Time Point (Weeks) | Changes observed by XRPD[c] | % Dissolved at 30 min[d] | | |
|---|---|---|---|---|---|---|---|---|---|
| | | | | | | | SOF SSD | VEL SSD | VOX SSD |
| Form VIII | A | 5.0% | | Initial | 0 | N/A | NP | NP | NP |
| | | | Closed | 25° C./ 60% RH | 12 | No new crystalline peaks | NP | NP | NP |
| | | | | 40° C./ 75% RH | 4 | No new crystalline peaks | NP | NP | NP |
| | | | | | 12 | No new crystalline peaks | NP | NP | NP |
| | | | Open | 40° C./ 75% RH | 4 | Change[e] | NP | NP | NP |
| | | | | 50° C./ 92% RH | 1 | Change[e] | NP | NP | NP |
| | B | 10.0% | | Initial | 0 | N/A | 98 | 90 | 80 |
| | | | Closed | 25° C./ 60% RH | 12 | No new crystalline peaks | 98 | 92 | 83 |
| | | | | 40° C./ 75% RH | 4 | No new crystalline peaks | 100 | 96 | 85 |
| | | | | | 12 | No new crystalline peaks | 99 | 95 | 85 |
| | | | Open | 40° C./ 75% RH | 4 | Change[e] | 100 | 95 | 83 |
| | | | | 50° C./ 92% RH | 1 | Change[e] | | | |

[a]% w/w with respect to total VOX.
[b]Packaging consisted of 28-count in a 100 mL HDPE bottle with 1 g desiccant and a polyester coil for closed conditions and 28-count in a 100 mL HDPE bottle without cap for open conditions
[c]DL (Detection Limit) is 5% for Form VIII the SOF/VEL/VOX tablets by XRPD
[d]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.
[e]A minor change (at 3.5-5.5 2θ°) in XRPD patterns of the spiked tablets was related to the physical form change of magnesium stearate under open conditions.

TABLE 23

| VOX Form | Lot | % Form X in Tablet[a] | Condition Storage[b] | | Time Point (Weeks) | Changes observed by XRPD[c] | % Dissolved at 30 min[d] | | |
|---|---|---|---|---|---|---|---|---|---|
| | | | | | | | SOF SSD | VEL SSD | VOX SSD |
| Form X | C | 10.0% | | Initial | 0 | N/A | 97 | 89 | 80 |
| | | | Closed | 25° C./ 60% RH | 12 | No new crystalline peaks | 99 | 94 | 84 |
| | | | | 40° C./ 75% RH | 4 | No new crystalline peaks | 99 | 95 | 84 |
| | | | | | 12 | No new crystalline peaks | 99 | 95 | 85 |
| | | | Open | 40° C./ 75% RH | 4 | Change[e] | 100 | 94 | 81 |
| | | | | 50° C./ 92% RH | 1 | Change[e] | | | |
| | D | 20.0% | | Initial | 0 | N/A | NP | NP | NP |
| | | | Closed | 25° C./ 60% RH | 12 | No new crystalline peaks | NP | NP | NP |
| | | | | 40° C./ 75% RH | 4 | No new crystalline peaks | NP | NP | NP |
| | | | | | 12 | No new crystalline peaks | NP | NP | NP |

TABLE 23-continued

| VOX Form | Lot | % Form X in Tablet[a] | Condition Storage[b] | Time Point (Weeks) | Changes observed by XRPD[c] | % Dissolved at 30 min[d] | | |
|---|---|---|---|---|---|---|---|---|
| | | | | | | SOF SSD | VEL SSD | VOX SSD |
| | | | Open 40° C./75% RH | 4 | Change[e] | NP | NP | NP |
| | | | 50° C./92% RH | 1 | Change[e] | NP | NP | NP |

[a]% w/w with respect to total VOX.
[b]Packaging consisted of 28-count in a 100 mL HOPE bottle with 1 g desiccant and a polyester coil for closed conditions and 28-count in a 100 mL HDPE bottle without cap for open conditions
[c]DL (Detection Limit) is 10% for Form X the SOF/VEL/VOX tablets by XRPD
[d]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.
[e]A minor change (at 3.5-5.5 2θ°) in XRPD patterns of the spiked tablets was related to the physical form change of magnesium stearate under open conditions.

F. Desiccant and Packaging Configuration on Sofosbuvir/Velpatasvir SSD/Voxilaprevir SSD Tablet Stability The impact of desiccant and packaging configuration on the physical stability, chemical stability, and dissolution of sofosbuvir/velpatasvir SSD/voxilaprevir SSD tablets was evaluated (Tables 24A-24C).

The sofosbuvir/velpatasvir SSD/voxilaprevir SSD tablets were packaged in the designated commercial packaging configuration (28-count, 100 mL HPDE bottle, coil, 1 g desiccant), and stored for 6 months at 25° C./60% RH and 40° C./75% RH.

As shown in Tables 24A-24C, all tablets lots were chemically stable, under all conditions with total impurities/degradation products of sofosbuvir remaining at 0.0%, velpatasvir remaining between 0.3 and 0.5%, and voxilaprevir remaining at 0.0%. The water content remained between 1.8 and 2.6% for the tablets stored up to 6 months under closed conditions with three (0, 1, and 3 g) desiccant levels at 25° C./60% RH and 40° C./75% RH. All tablet lots showed consistent release of sofosbuvir between 99 and 102%, velpatasvir between 90 and 96%, and voxilaprevir between 90 and 95% at 30 minutes over the time period studied. All tablets were physically stable, under all conditions. All peaks observed in XRPD patterns of the tablets were consistent with sofosbuvir or formulation excipients. No changes in solid form were observed by XRPD throughout the duration of the study.

The data presented in Tables 24A-24C demonstrates that sofosbuvir/velpatasvir SSD/voxilaprevir SSD tablets are chemically and physically stable in the presence or absence of desiccant under the conditions studied for 6 months.

TABLE 24A

| Closed Conditions (No Desiccant) | | | | | | | |
|---|---|---|---|---|---|---|---|
| Condition[a] | | Initial | 40° C./75% RH | | | 25° C./60% RH | |
| | Time | 0 | 4 | 12 | 24 | 12 | 24 |
| SOF | LS (%) | 102.1 | 101.4 | 100.3 | 100.4 | 99.3 | 100.2 |
| | I/D (%) | 0.0 | 0.0 | 0.0 | 0.0 | 0.0 | 0.0 |
| VEL SSD | LS (%) | 102.1 | 103.6 | 100.6 | 99.9 | 99.6 | 99.6 |
| | I/D (%) | 0.3 | 0.5 | 0.3 | 0.3 | 0.3 | 0.4 |
| VOX SSD | LS (%) | 102.4 | 101.4 | 100.3 | 100.3 | 99.2 | 99.9 |
| | I/D (%) | 0.0 | 0.0 | 0.0 | 0.0 | 0.0 | 0.0 |
| | Water (%) | 2.6 | 2.4 | 2.1 | 2.3 | 2.1 | 2.2 |
| | Change (XRPD) | N/A | No change | No change | No change | No change | No change |
| Dissolved at 30 min (%)[b] | SOF | 100 | 101 | 99 | 102 | 99 | 101 |
| | VEL SSD | 91 | 96 | 93 | 94 | 90 | 90 |
| | VOX SSD | 92 | 93 | 94 | 95 | 92 | 91 |

[a]Packaging consisted of 28-count in a 100 mL HDPE bottle with a polyester coil and 1 or 3 g desiccant or no desiccant.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.

TABLE 24B

| Closed Conditions (1 g Desiccant) | | | | | | | |
|---|---|---|---|---|---|---|---|
| Condition[a] | | Initial | 40° C./75% RH | | | 25° C./60% RH | |
| | Time | 0 | 4 | 12 | 24 | 12 | 24 |
| SOF | LS (%) | 102.1 | 100.0 | 99.4 | 101.7 | 99.3 | 100.4 |
| | I/D (%) | 0.0 | 0.0 | 0.0 | 0.0 | 0.0 | 0.0 |
| VEL SSD | LS (%) | 102.1 | 102.4 | 99.7 | 100.9 | 99.6 | 100.0 |
| | I/D (%) | 0.3 | 0.4 | 0.3 | 0.4 | 0.3 | 0.4 |

TABLE 24B-continued

| | Closed Conditions (1 g Desiccant) | | | | | |
|---|---|---|---|---|---|---|
| Condition[a] | | Initial | 40° C./75% RH | | 25° C./60% RH | |
| VOX SSD | LS (%) | 102.4 | 100.2 | 99.3 | 101.3 | 99.3 | 100.6 |
| | I/D (%) | 0.0 | 0.0 | 0.0 | 0.0 | 0.0 | 0.0 |
| Water (%) | | 2.6 | 2.2 | 2.0 | 2.1 | 1.9 | 2.1 |
| Change (XRPD) | | N/A | No change | No change | No change | No change | No change |
| Dissolved at 30 min (%)[b] | SOF | 100 | 99 | 99 | 100 | 101 | 101 |
| | VEL SSD | 91 | 93 | 91 | 91 | 90 | 90 |
| | VOX SSD | 92 | 90 | 92 | 92 | 92 | 91 |

[a]Packaging consisted of 28-count in a 100 mL HDPE bottle with a polyester coil and 1 or 3 g desiccant or no desiccant.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.

TABLE 24C

| | Closed Conditions (3 g Desiccant) | | | | | |
|---|---|---|---|---|---|---|
| Condition[a] | | Initial | 40° C./75% RH | | | 25° C./60% RH | |
| | Time | 0 | 4 | 12 | 24 | 12 | 24 |
| SOF | LS (%) | 102.1 | 100.0 | 99.9 | 102.3 | 100.3 | 101.6 |
| | I/D (%) | 0.0 | 0.0 | 0.0 | 0.0 | 0.0 | 0.0 |
| VEL SSD | LS (%) | 102.1 | 101.7 | 100.1 | 101.6 | 100.5 | 101.1 |
| | I/D (%) | 0.3 | 0.5 | 0.3 | 0.5 | 0.3 | 0.4 |
| VOX SSD | LS (%) | 102.4 | 99.6 | 99.6 | 102.1 | 100.1 | 101.5 |
| | I/D (%) | 0.0 | 0.0 | 0.0 | 0.0 | 0.0 | 0.0 |
| Water (%) | | 2.6 | 2.1 | 1.8 | 1.9 | 1.7 | 1.9 |
| Change (XRPD) | | N/A | No change | No change | No change | No change | No change |
| Dissolved at 30 min (%)[b] | SOF | 100 | 102 | 100 | 102 | 100 | 101 |
| | VEL SSD | 91 | 95 | 91 | 91 | 90 | 89 |
| | VOX SSD | 92 | 93 | 92 | 92 | 92 | 91 |

[a]Packaging consisted of 28-count in a 100 mL HDPE bottle with a polyester coil and 1 or 3 g desiccant or no desiccant.
[b]Dissolution condition: 50 mM sodium acetate buffer pH 5.0 containing 2.0% w/v Polysorbate 80 and 0.001% w/v BHT, 75 rpm, 900 mL at 37° C., USP Type II apparatus.

Figure 25:
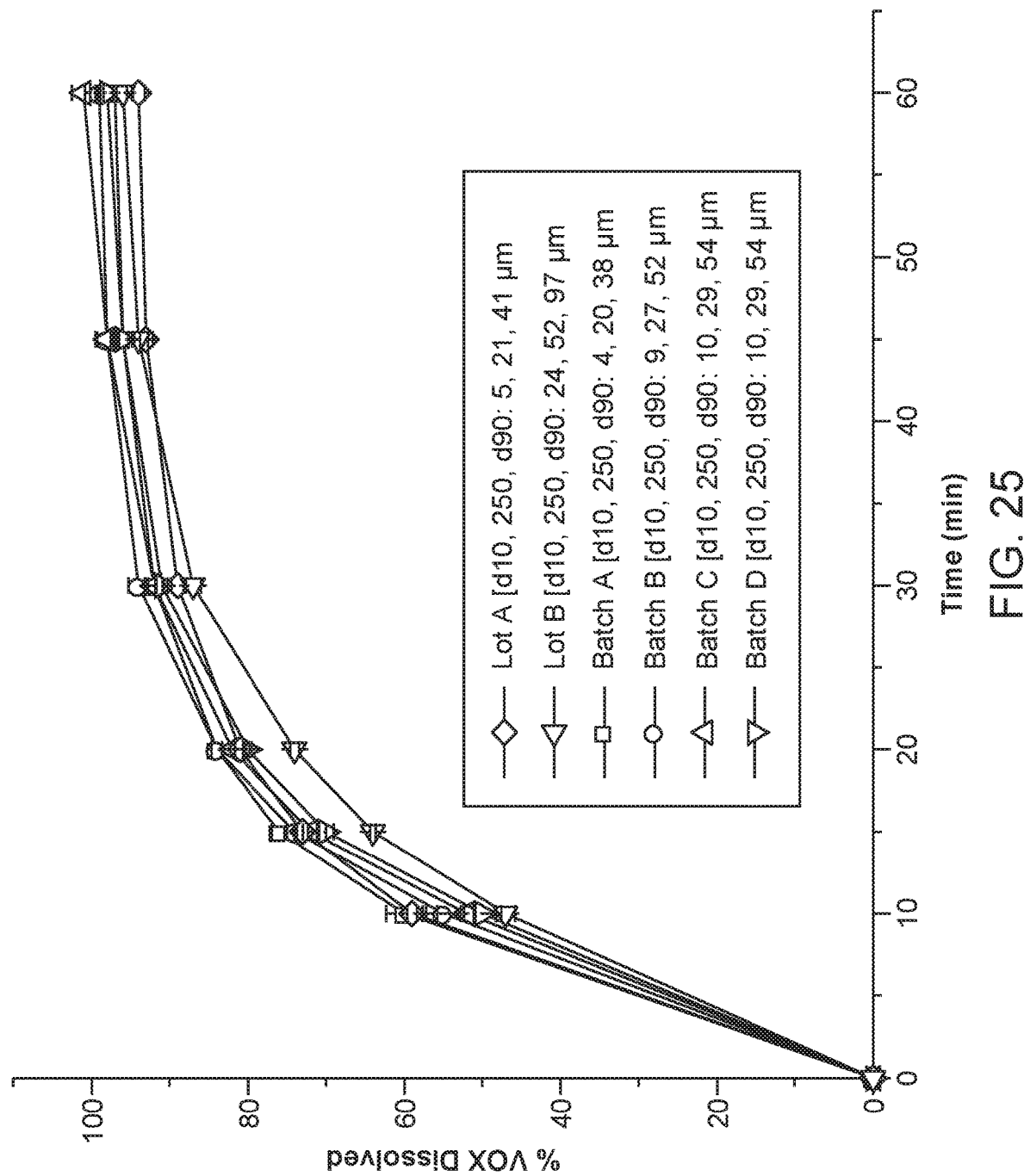
FIG. 25 depicts dissolution profiles of voxilaprevir from sofosbuvir/velpatasvir/voxilaprevir tablets containing different voxilaprevir spray-dried solid dispersion particle size distributions.
Figure 26:
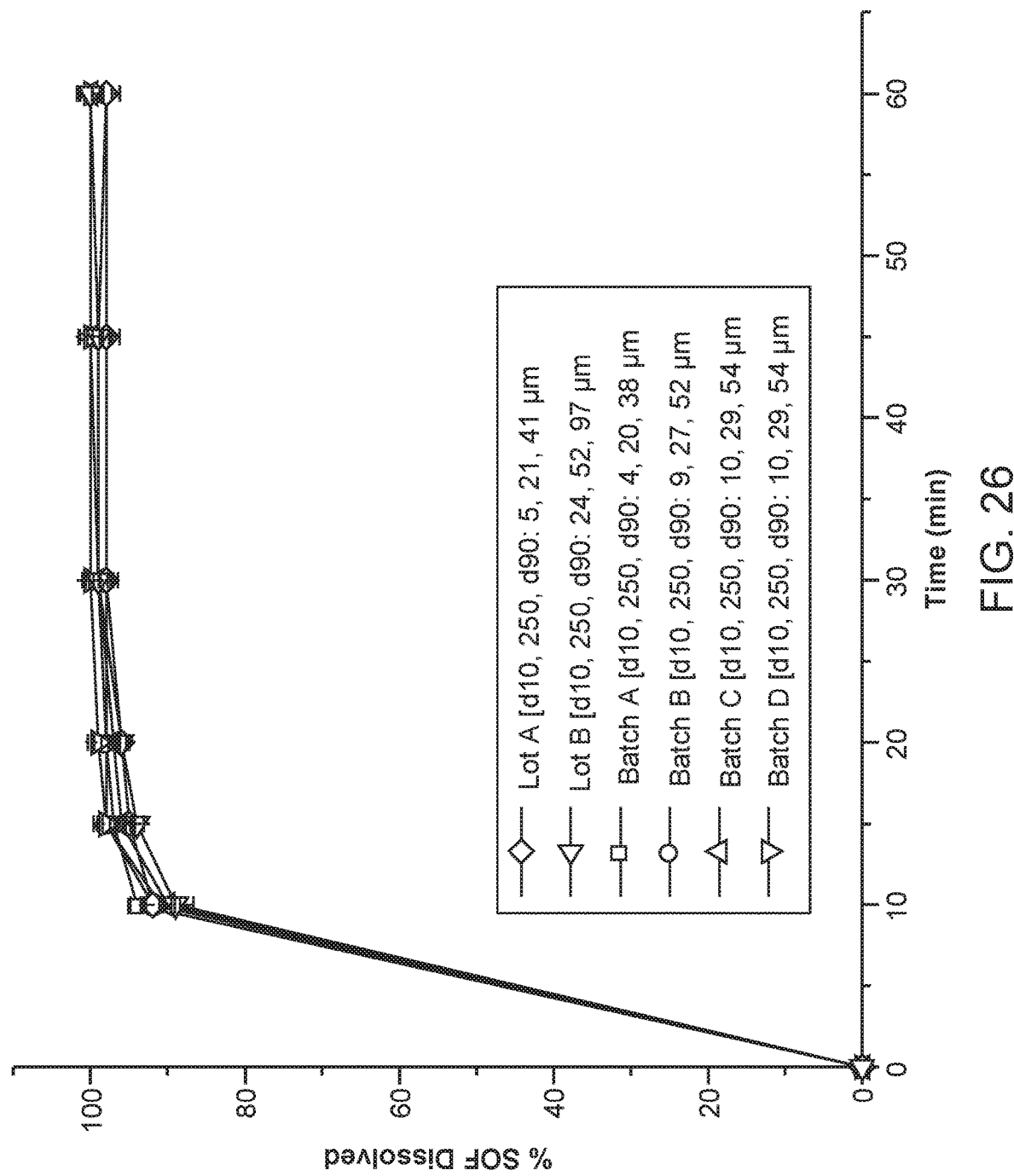
FIG. 26 depicts dissolution profiles of sofosbuvir from sofosbuvir/velpatasvir/voxilaprevir tablets containing different voxilaprevir spray-dried solid dispersion particle size distributions.
Figure 27:
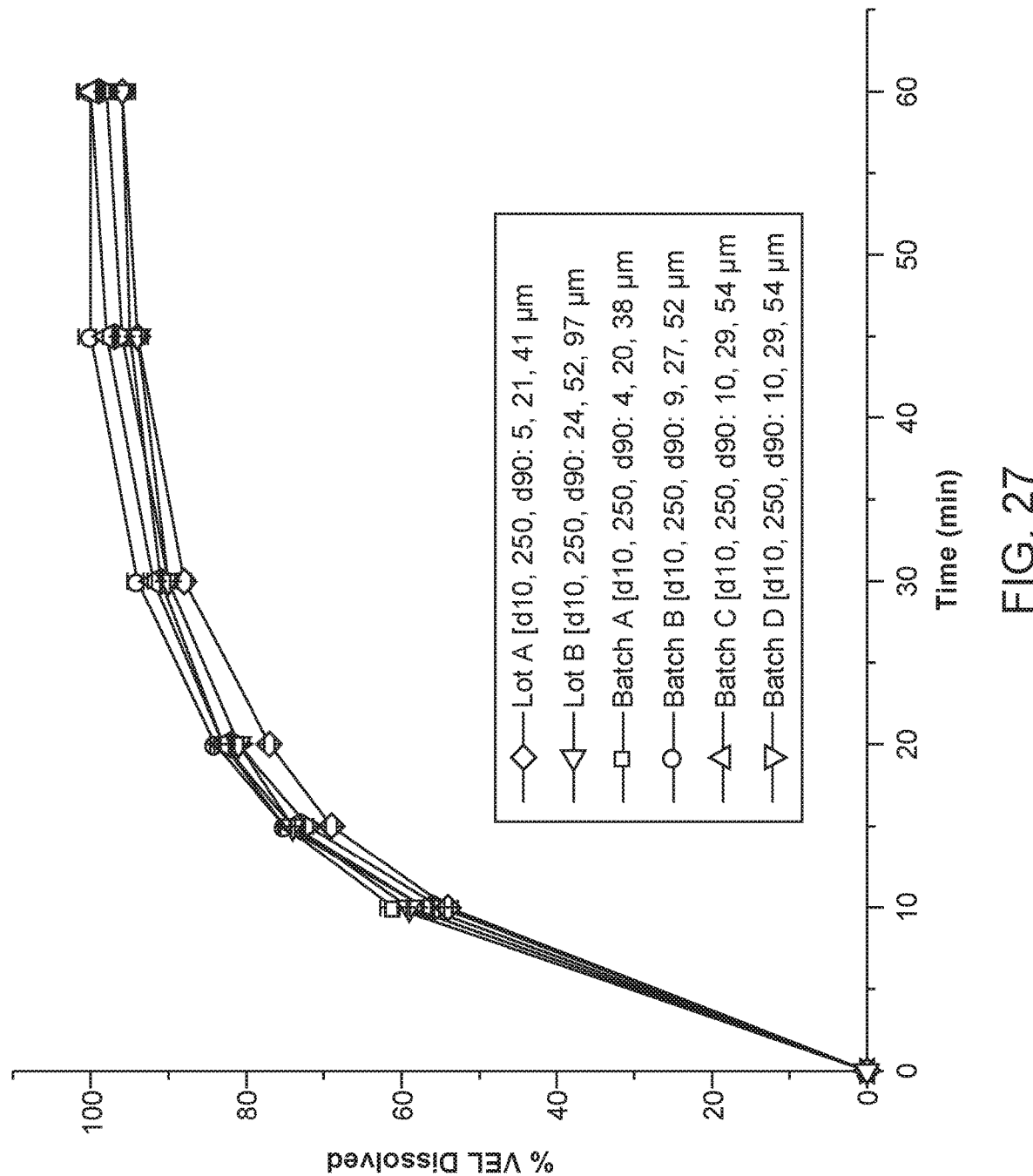
FIG. 27 depicts dissolution profiles of velpatasvir from sofosbuvir/velpatasvir/voxilaprevir tablets containing different voxilaprevir spray-dried solid dispersion particle size distributions.

G. Impact of Voxilaprevir SSD Particle Size Distribution on Sofosbuvir/Velpatasvir SSD/Voxilaprevir SSD Tablet Dissolution The effect of voxilaprevir SSD particle size was assessed on dissolution performance of sofosbuvir/velpatasvir SSD/voxilaprevir SSD tablets (FIGS. 25-27). Voxilaprevir SSD with a particle size distribution of $D_{10}$=about 3, $D_{50}$=about 17, and $D_{90}$=about 37 μm after secondary drying, was manufactured on a PSD-3 scale spray dryer at Hovione FarmaCiencia (Loures, Portugal) and used to produce sofosbuvir/velpatasvir SSD/voxilaprevir SSD tablets (Lot A in FIGS. 25-27). Voxilaprevir SSD with a particle size distribution of $D_{10}$=about 19, $D_{50}$=about 48, and $D_{90}$=about 92 μm after secondary drying, was manufactured on a PSD-4 scale spray dryer at Fuji Chemical Industry Co., Ltd. (Toyama, Japan) and used to produce sofosbuvir/velpatasvir SSD/voxilaprevir SSD tablets (Lot B in FIGS. 25-27). As shown in FIG. 25, voxilaprevir SSD particle size does not influence voxilaprevir release from sofosbuvir/velpatasvir SSD/voxilaprevir SSD tablets within the range studied. Both tablet lots released between 87 and 89% of voxilaprevir at 30 minutes.

The dissolution profiles of sofosbuvir and velpatasvir are provided in FIGS. 26 and 27, respectively. Both tablet lots (A and B) had comparable dissolution profile with consistent release of sofosbuvir between 98 and 99% and velpatasvir between 88 and 90% at 30 minutes. As shown in FIGS. 26 and 27, these sofosbuvir/velpatasvir SSD/voxilaprevir SSD tablet lots exhibited comparable dissolution profiles to the sofosbuvir/velpatasvir SSD/voxilaprevir SSD tablet batches used in the Phase 3 clinical studies (Batches A-D, as described in FIGS. 10-13 and Tables 10-14). Voxilaprevir SSD used to manufacture these clinical tablets exhibited the particle size distributions of $D_{10}$=about 4 to about 10 μm, $D_{50}$=about 20 to about 29 μm, and $D_{90}$=about 38 to about 54 μm after secondary drying. These clinical lots released between 98 and 100% of sofosbuvir, between 90 and 92% of velpatasvir, and between 91 and 92% of voxilaprevir at 30 minutes.

Figure 28:
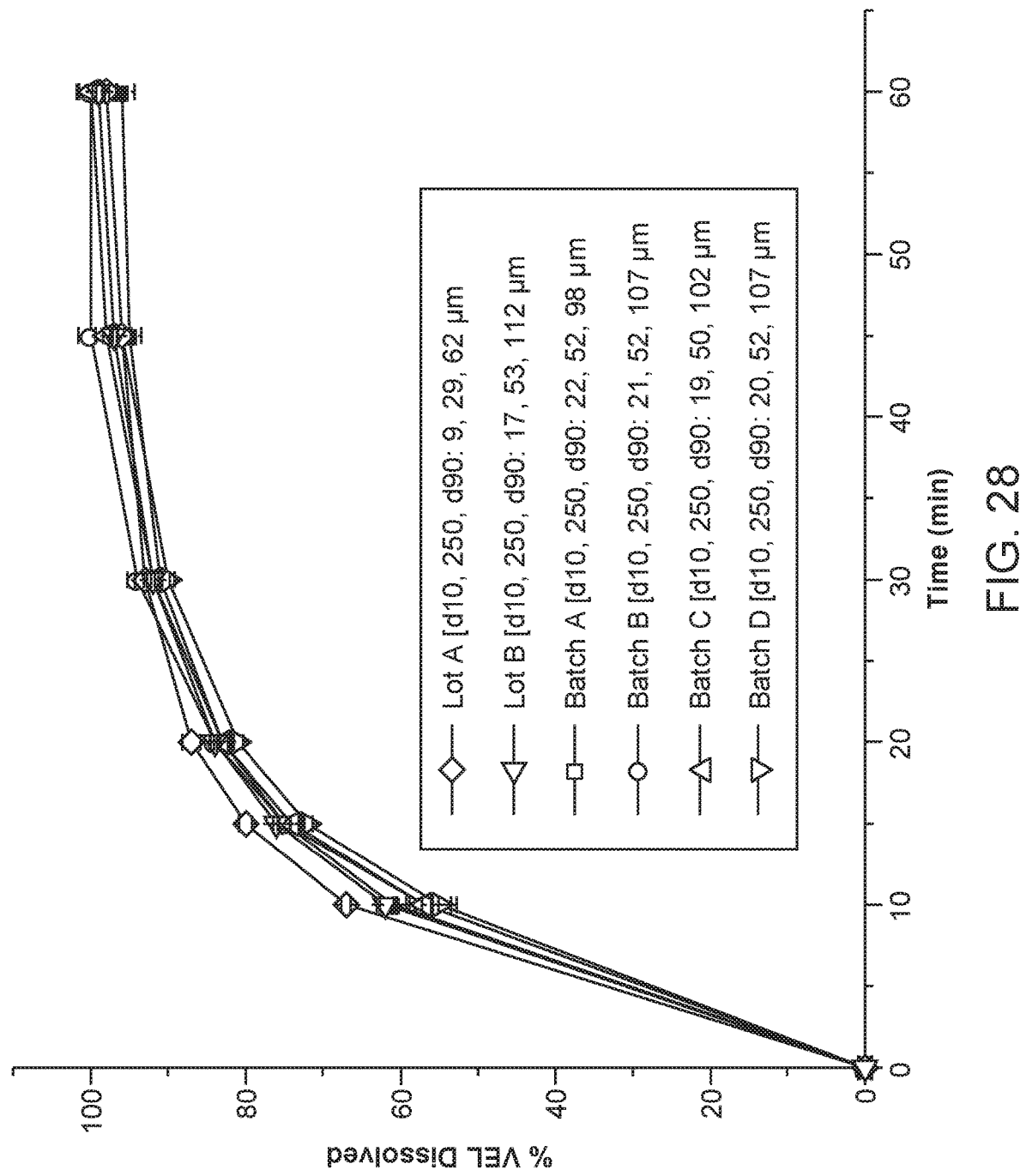
FIG. 28 dissolution profiles of velpatasvir from sofosbuvir/velpatasvir/voxilaprevir tablets containing different velpatasvir spray-dried solid dispersion particle size distributions.
Figure 29:
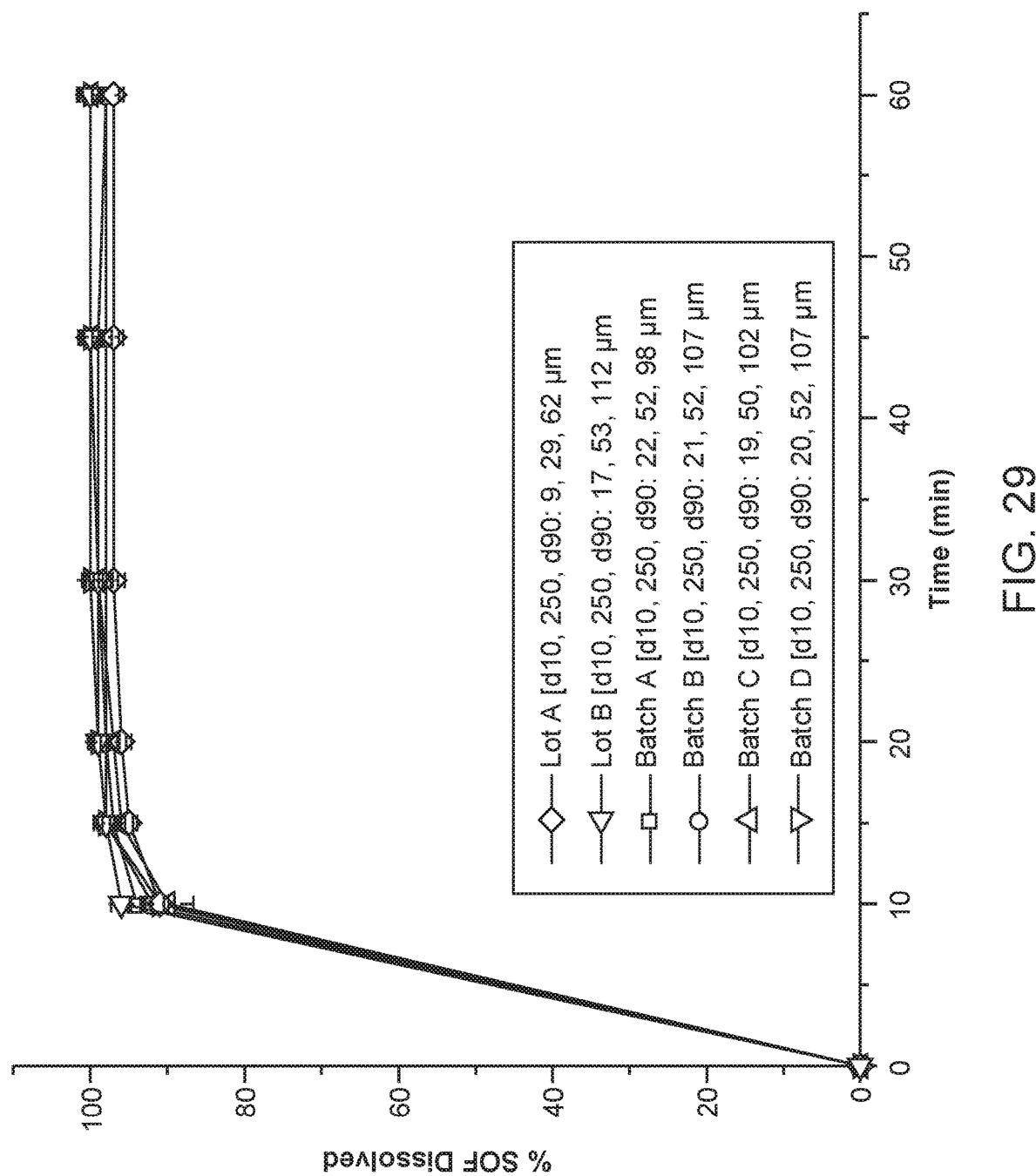
FIG. 29 depicts dissolution profiles of sofosbuvir from sofosbuvir/velpatasvir/voxilaprevir tablets containing different velpatasvir spray-dried solid dispersion particle size distributions.
Figure 30:
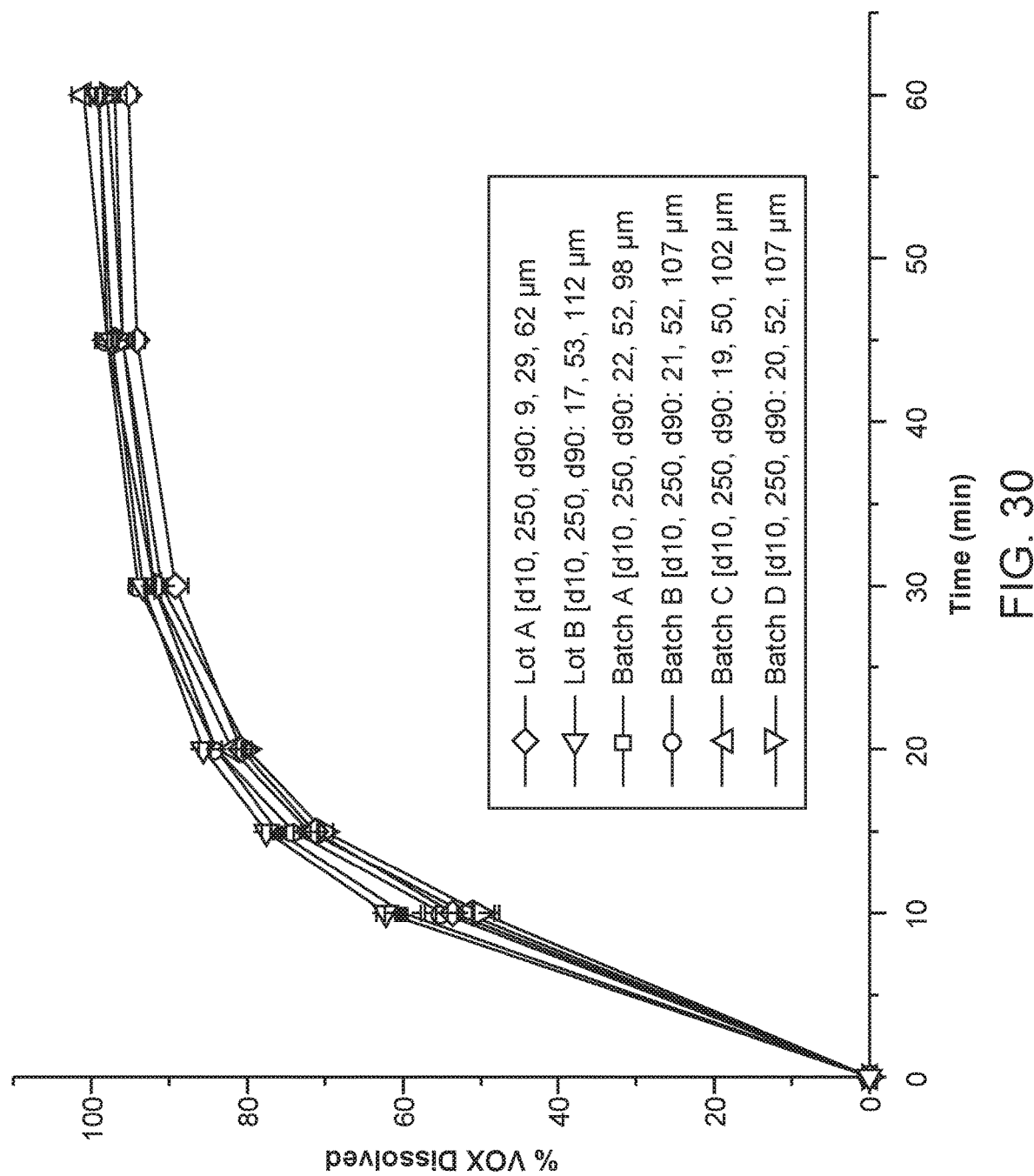
FIG. 30 depicts dissolution profiles of voxilaprevir from sofosbuvir/velpatasvir/voxilaprevir tablets containing different velpatasvir spray-dried solid dispersion particle size distributions.

H. Impact of Velpatasvir SSD Particle Size Distribution on Sofosbuvir/Velpatasvir SSD/Voxilaprevir SSD Tablet Dissolution The effect of velpatasvir SSD particle size was assessed on dissolution performance of sofosbuvir/velpatasvir SSD/voxilaprevir SSD tablets (FIGS. 28-30). Velpatasvir SSDs with a particle size distribution of $D_{10}$=9, $D_{50}$=29, and $D_{90}$=62 μm and $D_{10}$=17, $d_{50}$=53, and $D_{90}$=112 μm after secondary drying, were produced on a PSD-4 scale spray dryer at Hovione FarmaCiencia (Loures, Portugal) and used to manufacture sofosbuvir/velpatasvir SSD/voxilaprevir SSD tablets (Lots A and B, respectively, as shown in FIGS. 28-30). As shown in FIG. 28, velpatasvir SSD particle size does not affect velpatasvir release from sofosbuvir/velpatasvir SSD/voxilaprevir SSD tablets within the range studied. Both tablet lots (A and B) released between 92 and 93% of voxilaprevir at 30 minutes.

The dissolution profiles of sofosbuvir and voxilaprevir are provided in FIGS. 29 and 30, respectively. Both tablet lots (A and B) released between 97 and 99% of sofosbuvir, between 89 and 93% of velpatasvir, and between 89 and 93% of voxilaprevir at 30 minutes. As also shown in the figures, these sofosbuvir/velpatasvir SSD/voxilaprevir SSD tablets exhibited comparable dissolution profiles to the sofosbuvir/velpatasvir SSD/voxilaprevir SSD tablet lots used in the Phase 3 clinical studies (Batches A-D). Velpatasvir SSD used to manufacture these clinical tablets exhibited the particle size distributions of $D_{10}$=19 to 22 μm, $D_{50}$=50 to 52 μm, and $D_{90}$=98 to 107 μm after secondary drying. These clinical lots released between 98 and 100% of sofosbuvir, between 90 and 92% of velpatasvir, and between 91 and 92% of voxilaprevir at 30 minutes.

Figure 31:
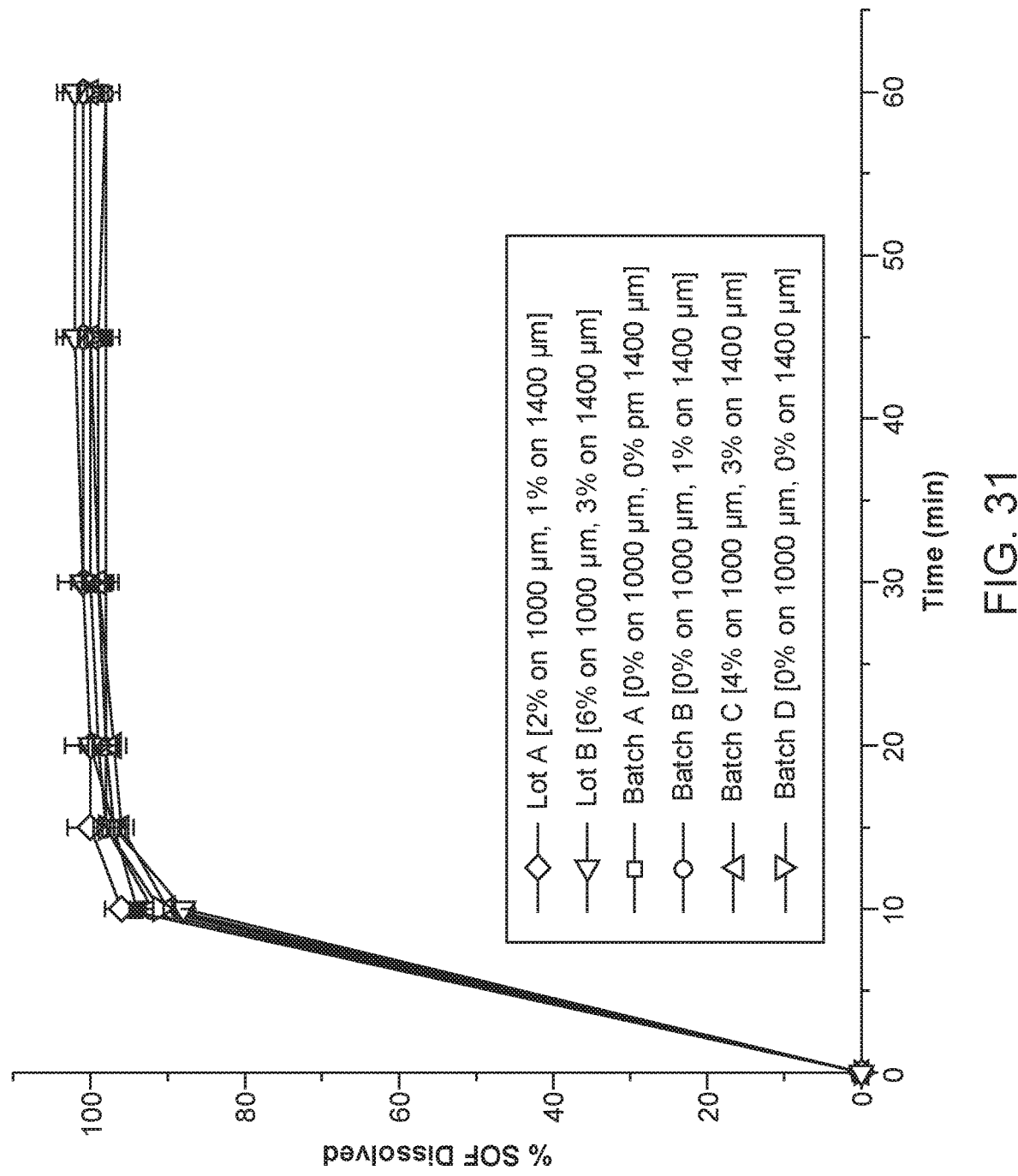
FIG. 31 depicts dissolution profiles of sofosbuvir from sofosbuvir/velpatasvir/voxilaprevir tablets containing different sofosbuvir particle size distributions.
Figure 32:
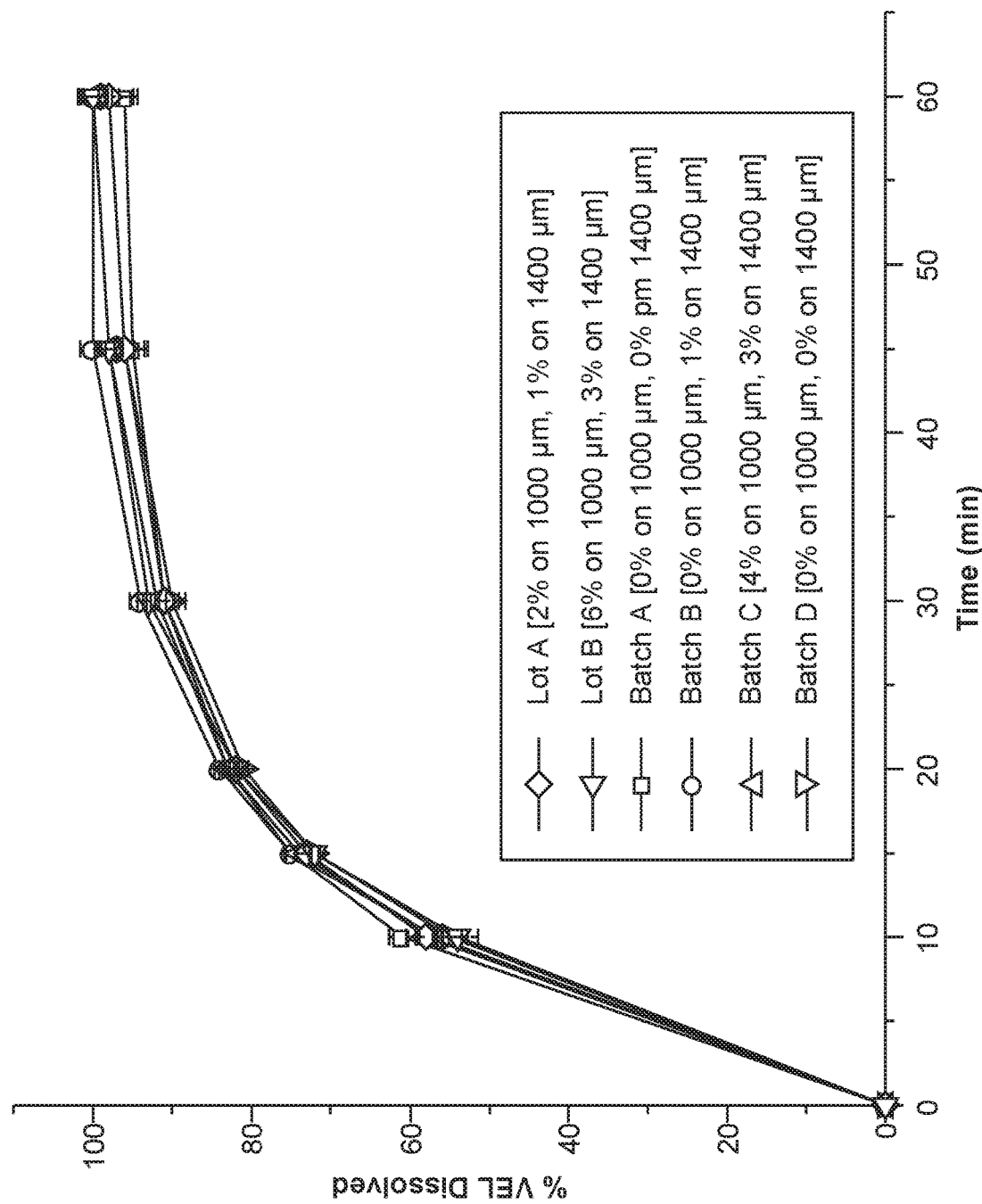
FIG. 32 depicts dissolution profiles of velpatasvir from sofosbuvir/velpatasvir/voxilaprevir tablets containing different sofosbuvir particle size distribution.
Figure 33:
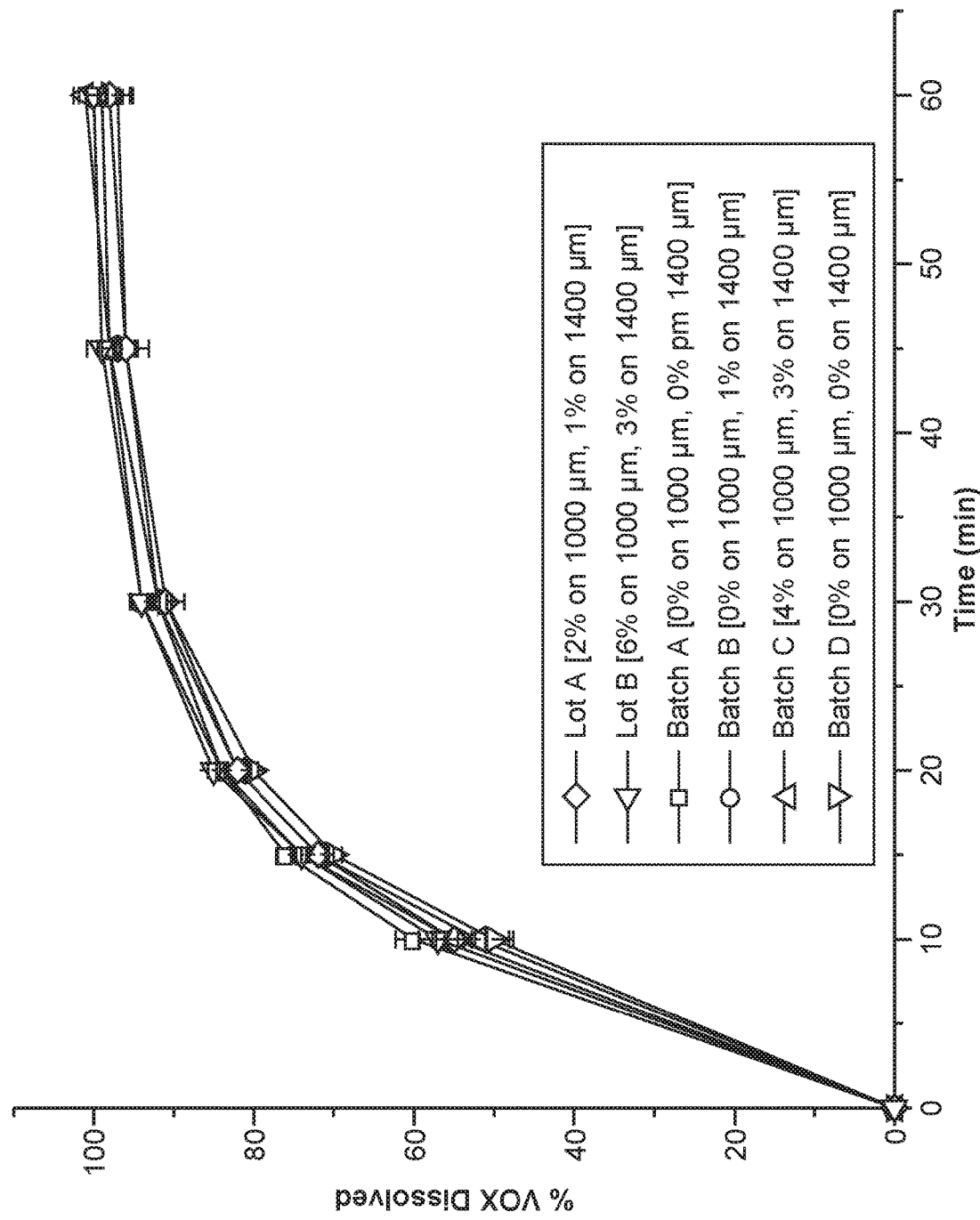
FIG. 33 depicts dissolution profiles of voxilaprevir from sofosbuvir/velpatasvir/voxilaprevir tablets containing different sofosbuvir particle size distributions.

I. Impact of Velpatasvir SSD Particle Size Distribution on Sofosbuvir/Velpatasvir SSD/Voxilaprevir SSD Tablet Dissolution The particle size of sofosbuvir drug substance is measured by mass retained on 1000 and 1400 μm screens with an air jet sieving method (FIGS. 31-33). The effect of sofosbuvir particle size on dissolution performance of sofosbuvir/velpatasvir SSD/voxilaprevir SSD tablets. Sofosbuvir with 2% mass retained on 1000 μm screen and 1% mass retained on 1400 μm screen was used to produce sofosbuvir/velpatasvir SSD/voxilaprevir SSD tablets (Lot A). Sofosbuvir with 6% mass retained on 1000 μm screen and 3% mass retained on 1400 μm screen was used to produce SOF/VEL/VOX tablets (Lot B). As shown in FIG. 31, sofosbuvir particle size does not influence sofosbuvir release from sofosbuvir/velpatasvir SSD/voxilaprevir SSD tablets within the range studied. Both tablet lots released 101% of sofosbuvir at 30 minutes.

The dissolution profiles of velpatasvir and voxilaprevir are provided FIGS. 32 and 33, respectively. Both tablet lots released between 91 and 93% of velpatasvir and between 91 and 94% of voxilaprevir at 30 minutes. As shown in said figures, lots A and B exhibited comparable dissolution profiles to the sofosbuvir/velpatasvir SSD/voxilaprevir SSD tablet lots used in the Phase 3 clinical studies (Batches A-D, as described in FIGS. 10-13 and Tables 10-13). The particle size of sofosbuvir used to manufacture these clinical tablets ranged from 0 to 4% mass retained on 1000 μm screen and 0 to 3% mass retained on 1400 μm screen. These clinical lots released between 98 and 100% of sofosbuvir, between 90 and 92% of velpatasvir, and between 91 and 92% of voxilaprevir at 30 minutes.

Example 4: Relative Bioavailability (Dog Model)

The in vivo PK performance of the sofosbuvir/velpatasvir SSD/voxilaprevir SSD tablets (Formulation G, see Table 8) as well as co-administration of a voxilaprevir SSD tablet and sofosbuvir/velpatasvir SSD tablet was evaluated in pentagastrin-pretreated fasted dogs (Tables 25, 26). As shown in Tables 25 and 26, the mean PK parameters for voxilaprevir SSD, velpatasvir SSD, sofosbuvir and metabolites after oral administration of Formulation G (100 mg sofosbuvir/25 mg velpatasvir SSD/25 mg voxilaprevir SSD) were similar to that of the control (co-administered voxilaprevir SSD and sofosbuvir/velpatasvir SSD tablets). Such metabolites include:

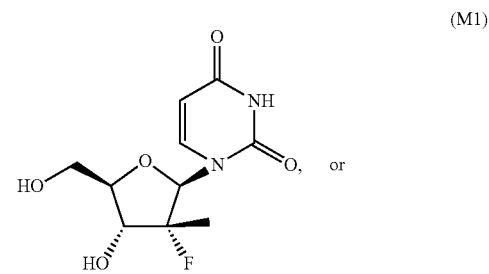

(M1)

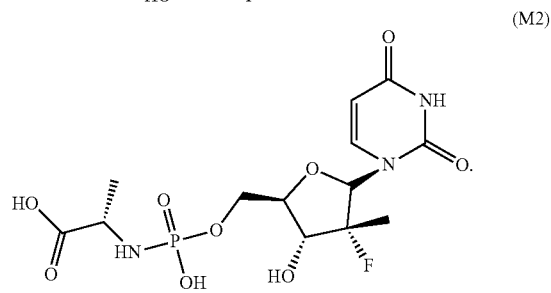

(M2)

TABLE 25

| Formulation (Process) Dose | Pentagastrin Pre-Treatment | VOX SSD | | | | VEL SSD | | | |
|---|---|---|---|---|---|---|---|---|---|
| | | $AUC_{0-last}$ (ng · hr/mL) | $C_{max}$ (ng/mL) | $t_{max}$ (hr) | F (%) | $AUC_{0-last}$ (ng · hr/mL) | $C_{max}$ (ng/mL) | $t_{max}$ (hr) | F (%) |
| Control[a] VOX SSD Tablet (25 mg); SOF/VEL SSD Tablet (100/25 mg) | Fasted | 4,120 ± 2,480 | 954 ± 662 | 4.0 ± 0.0 | 28 ± 17 | 2,140 ± 924 | 351 ± 132 | 2.3 ± 0.8 | 19 ± 9 |
| Formulation G (co-dry granulation) SOF 100 mg/VEL SSD 25 mg/VOX SSD 25 mg | Fasted Fed | 4,030 ± 1,780 6,320 ± 4,170 | 1,010 ± 532 1,530 ± 1,070 | 4.0 ± 0.0 3.3 ± 1.0 | 30 ± 14 46 ± 31 | 2,480 ± 997 2,310 ± 1,450 | 299 ± 108 305 ± 227 | 2.7 ± 1.6 3.7 ± 2.0 | 25 ± 11 22 ± 12 |
| Formulation H (Bi-granulation) SOF 100 mg/VEL SSD 25 mg/VOX SSD 25 mg | Fasted | 3,630 ± 1,840 | 931 ± 648 | 7.3 ± 8.2 | 27 ± 14 | 1,940 ± 513 | 324 ± 88 | 2.0 ± 0.0 | 19 ± 5 |

TABLE 25-continued

| Formulation (Process) Dose | Penta-gastrin Pre-Treatment | VOX SSD | | | | VEL SSD | | | |
|---|---|---|---|---|---|---|---|---|---|
| | | $AUC_{0-last}$ (ng·hr/mL) | $C_{max}$ (ng/mL) | $t_{max}$ (hr) | F (%) | $AUC_{0-last}$ (ng·hr/mL) | $C_{max}$ (ng/mL) | $t_{max}$ (hr) | F (%) |
| Formulation I (Bi-granulation) SOF 100 mg/VEL SSD 25 mg/VOX SSD 25 mg | Fasted | 2,900 ± 1,310 | 735 ± 421 | 4.0 ± 0.0 | 22 ± 10 | 1,970 ± 624 | 343 ± 125 | 1.8 ± 0.4 | 19 ± 7 |

[a] VOX SSD is composed of 20% w/w velpatasvir SSD, 34.75% w/w lactose monohydrate, 34.75% w/w microcrystalline cellulose, 8% w/w croscarmellose sodium, 1.0% w/w silicon dioxide, 1.5% w/w magnesium stearate. Sofosbuvir/voxilaprevir SSD tablet (is composed of 40% w/w SOF, 20% VEL SSD, 35.5% w/w microcrystalline cellulose, 3% w/w croscarmellose sodium, 1.5% w/w magnesium stearate.

TABLE 26

| Formulation (Process) Dose | Penta-gastrin Pre-Treatment | SOF | | | M1 | | M1 | M2 | | |
|---|---|---|---|---|---|---|---|---|---|---|
| | | $AUC_{0-last}$ (ng·hr/mL) | $C_{max}$ (ng/mL) | $t_{max}$ (hr) | $AUC_{0-last}$ (ng·hr/mL) | $C_{max}$ (ng/mL) | $t_{max}$ (hr) | $AUC_{0-last}$ (ng·hr/mL) | $C_{max}$ (ng/mL) | $t_{max}$ (hr) |
| Controls[a] VOX SSD Tablet, 25 mg SOF/VEL SSD Tablet, 100/25 mg | Fasted | 1,571 ± 743 | 870 ± 449 | 1.38 ± 1.43 | 10,366 ± 1787 | 1,099 ± 306 | 3.67 ± 1.51 | 2,372 ± 485 | 677 ± 126 | 1.75 ± 1.25 |
| Formulation G (co-dry granulation) SOF 100 mg/ VEL SSD 25 mg/VOX SSD 25 mg | Fasted Fed | 1,306 ± 523 1,542 ± 1,317 | 752 ± 350 1,079 ± 949 | 0.88 ± 0.63 1.33 ± 0.52 | 10,912 ± 2,148 9,524 ± 1,942 | 1,107 ± 324 853 ± 336 | 4.0 ± 0.0 5.0 ± 3.5 | 2,087 ± 156 2,129 ± 680 | 590 ± 35 626 ± 242 | 1.50 ± 0.55 1.83 ± 1.17 |
| Formulation H (Bi-granulation) SOF 100 mg/VEL SSD 25 mg/VOX SSD 25 mg | Fasted | 1,097 ± 396 | 713 ± 268 | 0.71 ± 0.33 | 10,450 ± 2,074 | 1,050 ± 361 | | | | |
| Formulation I (Bi-granulation) SOF 100 mg/ VEL SSD 25 mg/VOX SSD 25 mg | Fasted | 1,325 ± 372 | 993 ± 304 | 0.50 ± 0.27 | 10,440 ± 1989 | 1117 ± 330 | | | | |

TABLE 26-continued

| | | | | |
|---|---|---|---|---|
| Formulation H (Bi-granulation) SOF 100 mg/VEL SSD 25 mg/VOX SSD 25 mg | 3.33 ± 1.03 | 1,896 ± 378 | 545 ± 129 | 1.33 ± 0.52 |
| Formulation I (Bi-granulation) SOF 100 mg/VEL SSD 25 mg/VOX SSD 25 mg | 4.0 ± 0.0 | 1,865 ± 349 | 615 ± 114 | 1.25 ± 0.61 |

[a] VOX SSD is composed of 20% w/w velpatasvir SSD, 34.75% w/w lactose monohydrate, 34.75% w/w microcrystalline cellulose, 8% w/w croscarmellose sodium, 1.0% w/w silicon dioxide, 1.5% w/w magnesium stearate. Sofosbuvir/voxilaprevir SSD tablet (is composed of 40% w/w SOF, 20% VEL SSD, 35.5% w/w microcrystalline cellulose, 3% w/w croscarmellose sodium, 1.5% w/w magnesium stearate.

Example 5: Food Effect Studies (Dog Model)

The effect of food after oral administration of the sofosbuvir/velpatasvir SSD/voxilaprevir SSD tablet, Formulation G was also evaluated on pentagastrin-pretreated dogs. As also shown in Table 25 and Table 26 (reproduced above), the mean PK parameters for velpatasvir SSD, sofosbuvir and metabolites M1 and M2, described previously, after oral administration of Formulation G (100 mg sofosbuvir/25 mg velpatasvir/25 mg voxilaprevir) with high fat meal food was similar administration of Formulation G (100 mg sofosbuvir/25 mg velpatasvir/25 mg voxilaprevir) in fasted dogs. In contrast, the plasma exposure ($AUC_{0-last}$) of voxilaprevir SSD increased 1.6 fold when tablets were administered with a high fat meal.

Example 6: Relative Bioavailability (Human Subjects)

The relative bioavailability of sofosbuvir/velpatasvir SSD/voxilaprevir SSD co-dry granulation monolayer tablets and co-administered sofosbuvir/velpatasvir SSD tablets, 400/100 mg and voxilaprevir SSD tablets, 100 mg was evaluated in fasted healthy subjects. The results of the study are summarized in Table 27. The exposures of sofosbuvir, its metabolites M1 and M2, velpatasvir SSD, and voxilaprevir SSD were similar when administered as sofosbuvir/velpatasvir SSD/voxilaprevir SSD tablets or as sofosbuvir/velpatasvir SSD and voxilaprevir SSD tablets. The percent mean ratios (% GMRs) ranged from 95.3 to 113%. Based on these data, the monolayer co-dry granulated sofosbuvir/velpatasvir SSD/voxilaprevir SSD tablet was selected for Phase 3 clinical development.

TABLE 27

| Parameter (N = 68) Mean (% CV) | SOF/VEL SSD/VOX SSD (400/100/100 mg) | SOF/VEL SSD (400/100 mg) + VOX SSD (100 mg) | % GMR (SOF/VEL SSD/VOX SSD)/ (SOF/VEL SSD + VOX SSD) |
|---|---|---|---|
| SOF | | | |
| $AUC_{last}$ (ng · hr/mL) | 2510 (43.5) | 2560 (37.7) | 96.9 |
| $AUC_{inf}$ (ng · hr/mL) | 2520 (43.3) | 2570 (37.5) | 96.9 |
| $C_{max}$ (ng/mL) | 1590 (46.6) | 1580 (32.2) | 95.3 |
| M2 | | | |
| $AUC_{last}$ (ng · hr/mL) | 2800 (22.9) | 2710 (25.2) | 103 |
| $AUC_{inf}$ (ng · hr/mL) | 2870 (22.4) | 2810 (24.9) | 103 |
| $C_{max}$ (ng/mL) | 629 (26.7) | 624 (26.0) | 100 |
| M1 | | | |
| $AUC_{last}$ (ng · hr/mL) | 13,600 (22.7) | 13,300 (22.5) | 102 |
| $AUC_{inf}$ (ng · hr/mL) | 14,400 (22.9) | 14,100 (22.5) | 102 |
| $C_{max}$ (ng/mL) | 662 (26.2) | 655 (20.8) | 99.6 |
| VEL SSD | | | |
| $AUC_{last}$ (ng · hr/mL) | 6370 (30.6) | 6250 (33.3) | 105 |
| $AUC_{inf}$ (ng · hr/mL) | 6420 (30.7) | 6290 (33.2) | 104 |
| $C_{max}$ (ng/mL) | 727 (27.4) | 715 (32.1) | 104 |
| VOX SSD | | | |
| $AUC_{last}$ (ng · hr/mL) | 485 (49.0) | 457 (37.8) | 100 |
| $AUC_{inf}$ (ng · hr/mL) | 530 (45.5) | 506 (35.6) | 99.6 |
| $C_{max}$ (ng/mL) | 63.0 (73.3) | 49.8 (53.2) | 113 |

[a] SOF/VEL SSD tablet, 400/100 mg
[b] VOX SSD tablet, 100 mg

Example 7: Food Effect Studies (Human Subjects)

The effect of food (high calorie/high-fat meals) on the pharmacokinetics of sofosbuvir/velpatasvir SSD/voxilaprevir SSD tablets (400/100/100 mg). The results of the study are summarized Table 28. Administration of sofosbuvir/velpatasvir SSD/voxilaprevir SSD tablets with food does not substantially alter the plasma exposure of sofosbuvir, its metabolites M1 and M2, or velpatasvir SSD. Exposure of voxilaprevir SSD was substantially higher (% GMR: 533% for $AUC_{inf}$, 780% for $C_{max}$) upon administration of sofosbuvir/velpatasvir SSD/voxilaprevir SSD (400/100/100 mg) in the fed state compared with the fasted state. As a result, sofosbuvir/velpatasvir SSD/voxilaprevir SSD tablets are administered with food.

TABLE 28

| Parameter | SOF/VEL SSD/VOX SSD (400/100/100 mg) | | % GMR High-Calorie, |
|---|---|---|---|
| (N = 68) Mean (% CV) | High-Calorie, High-Fat Meal | Fasted | High-Fat Meal/ Fasted |
| SOF | | | |
| $AUC_{last}$ (ng · hr/mL) | 2400 (34.9) | 1572 (42.7) | 163 |
| $AUC_{inf}$ (ng · hr/mL) | 2420 (34.5) | 1580 (42.4) | 163 |
| $C_{max}$ (ng/mL) | 1440 (41.4) | 1370 (39.3) | 108 |
| M2 | | | |
| $AUC_{last}$ (ng · hr/mL) | 2800 (19.5) | 1900 (32.0) | 160 |
| $AUC_{inf}$ (ng · hr/mL) | 2860 (19.2) | 2010 (26.3) | 146 |
| $C_{max}$ (ng/mL) | 597 (24.6) | 462 (33.9) | 139 |
| M1 | | | |
| $AUC_{last}$ (ng · hr/mL) | 11,800 (18.4) | 11,800 (20.9) | 101 |
| $AUC_{inf}$ (ng · hr/mL) | 12,500 (17.9) | 12,300 (19.9) | 101 |
| $C_{max}$ (ng/mL) | 550 (17.0) | 865 (29.9) | 64.7 |
| VEL SSD | | | |
| $AUC_{last}$ (ng · hr/mL) | 5970 (38.6) | 4560 (47.5) | 143 |
| $AUC_{inf}$ (ng · hr/mL) | 6020 (38.5) | 4600 (47.1) | 143 |
| $C_{max}$ (ng/mL) | 652 (34.0) | 505 (41.4) | 139 |
| VOX SSD | | | |
| $AUC_{last}$ (ng · hr/mL) | 711 (40.6) | 159 (117) | 642 |
| $AUC_{inf}$ (ng · hr/mL) | 762 (39.9) | 194 (105) | 533 |
| $C_{max}$ (ng/mL) | 85.0 (41.7) | 16.8 (169) | 780 |

It should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

We claim:
1. A pharmaceutical composition comprising:
    a) a solid dispersion comprising about 100 mg of velpatasvir having the formula:

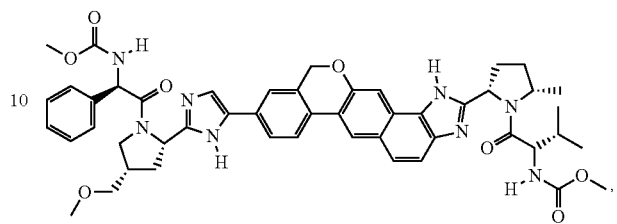

wherein velpatasvir is substantially amorphous and is dispersed within a polymer matrix comprising pharmaceutically acceptable polymer A; and wherein polymer A is hypromellose, copovidone, povidone, or polyvinyl caprolactam-polyvinyl acetate-polyethylene glycol;
    b) about 400 mg of sofosbuvir having the formula:

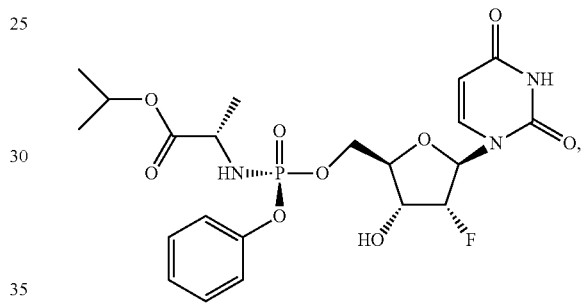

wherein sofosbuvir is substantially crystalline; and
    c) a solid dispersion comprising about 100 mg voxilaprevir having the formula:

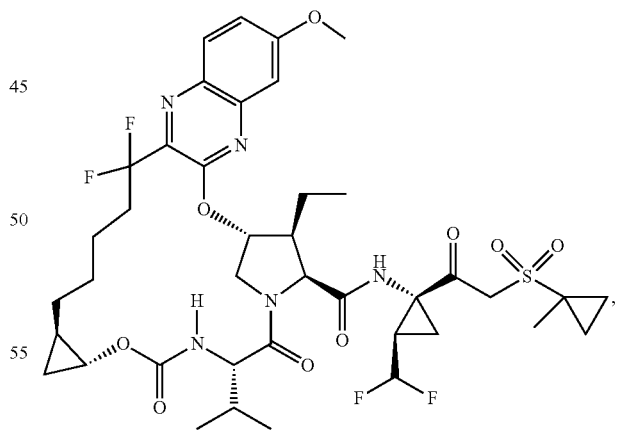

wherein voxilaprevir is substantially amorphous and is dispersed within a polymer matrix comprising pharmaceutically acceptable polymer B;
    and wherein polymer B is hypromellose, copovidone, povidone, or polyvinyl caprolactam-polyvinyl acetate-polyethylene glycol.
2. The pharmaceutical composition of claim 1, wherein polymer A is copovidone.

3. The pharmaceutical composition of claim 1, wherein the weight ratio of velpatasvir to polymer A in the solid dispersion is from about 5:1 to about 1:5.

4. The pharmaceutical composition of claim 1, wherein the weight ratio of velpatasvir to polymer A in the solid dispersion is from about 2:1 to about 1:2.

5. The pharmaceutical composition of claim 1, wherein the weight ratio of velpatasvir to polymer A in the solid dispersion is about 1:1.

6. The pharmaceutical composition of claim 1, wherein polymer B is copovidone.

7. The pharmaceutical composition of claim 1, wherein the weight ratio of voxilaprevir to polymer B in the solid dispersion is from about 5:1 to about 1:5.

8. The pharmaceutical composition of claim 7, wherein the weight ratio of voxilaprevir to polymer B in the solid dispersion is from about 2:1 to about 1:2.

9. The pharmaceutical composition of claim 8, wherein the weight ratio of voxilaprevir to polymer B in the solid dispersion is about 1:1.

10. The pharmaceutical composition according to claim 1, wherein the crystalline sofosbuvir has XRPD 2θ-reflections at about: 6.1, 20.1, and 20.8 °2θ±0.2.

11. The pharmaceutical composition of claim 10, wherein the crystalline sofosbuvir has XRPD 2θ-reflections at about 6.1, 8.2, 10.4, 12.7, 17.2, 17.7, 18.0, 18.8, 19.4, 19.8, 20.1, 20.8, 21.8, and 23.3 °2θ±0.2.

12. The pharmaceutical composition of claim 10, wherein a trace amount of crystalline sofosbuvir has XRPD 2θ-reflections at about: 12.6 and 13.5 °2θ±0.2.

13. The pharmaceutical composition of claim 1, further comprising: a diluent, a disintegrant, a lubricant, a glidant, or any combination thereof.

14. The pharmaceutical composition of claim 13, wherein the diluent is selected from the group consisting of dicalcium phosphate, cellulose, compressible sugars, dibasic calcium phosphate dehydrate, lactose, lactose monohydrate, mannitol, microcrystalline cellulose, starch, tribasic calcium phosphate, and combinations thereof.

15. The pharmaceutical composition of claim 14, wherein the diluent is a mixture of microcrystalline cellulose and lactose monohydrate and is present in an amount from about 10 to about 40% w/w.

16. The pharmaceutical composition of claim 13, wherein the disintegrant is selected from the group consisting of croscarmellose sodium, crospovidone, microcrystalline cellulose, modified corn starch, povidone, pregelatinized starch, sodium starch glycolate, and combinations thereof.

17. The pharmaceutical composition of claim 16, wherein the disintegrant is croscarmellose sodium and is present in an amount from about 1 to about 15% w/w.

18. The pharmaceutical composition of claim 13, wherein the lubricant is selected from the group consisting of calcium stearate, magnesium stearate, polyethylene glycol, sodium stearyl fumarate, stearic acid, talc, and combinations thereof.

19. The pharmaceutical composition of claim 18, wherein the lubricant is magnesium stearate and is present in an amount from about 0.5 to about 3% w/w.

20. The pharmaceutical composition of claim 13, wherein the glidant is selected from the group consisting of colloidal silicon dioxide, talc, starch, starch derivatives, and combinations thereof.

21. The pharmaceutical composition of claim 20, wherein the glidant is colloidal silicon dioxide and is present in an amount from about 0.5 to about 3% w/w.

22. The pharmaceutical composition of claim 1, further comprising
   d) about 5 to about 25% w/w of microcrystalline cellulose;
   e) about 5 to about 15% w/w of lactose monohydrate;
   f) about 1 to about 15% w/w of croscarmellose sodium;
   g) about 0.5 to about 3% w/w of magnesium stearate; and
   h) about 0.5 to about 3% w/w of colloidal silicon dioxide.

23. The pharmaceutical composition of claim 22, further comprising
   d) about 19% w/w of microcrystalline cellulose;
   e) about 9% w/w of lactose monohydrate;
   f) about 8% w/w of croscarmellose sodium;
   g) about 2% w/w of magnesium stearate; and
   h) about 1% w/w of colloidal silicon dioxide.

24. The pharmaceutical composition of claim 1, wherein the composition is formulated for immediate release.

25. A tablet comprising the pharmaceutical composition of claim 1.

26. The tablet of claim 25, further comprising a film coating.

27. A method of treating a hepatitis C virus infection in a human patient in need thereof, comprising administering to the patient a therapeutically effective amount of a tablet of claim 25.

28. The method of claim 27, wherein the tablet is administered for about 12 weeks or less.

29. The method of claim 27, wherein the tablet is administered for about 8 weeks or less.

30. The method of claim 27, wherein the tablet is administered for about 6 weeks or less.

31. The method of claim 27, wherein the tablet is administered for about 4 weeks or less.

32. The method of claim 27, wherein the tablet is administered for about 12 weeks or less and wherein the hepatitis C virus is genotype 1, 2, 3, 4, 5, or 6.

33. The method of claim 32, wherein the hepatitis C virus is genotype 1a or 1b.

34. The method of claim 27, wherein the tablet is administered for about 8 weeks or less and wherein the hepatitis C virus is genotype 1, 2, 3, 4, 5, or 6.

35. The method of claim 34, wherein the hepatitis C virus is genotype 1a or 1b.

36. The method of claim 27, wherein the tablet is administered for about 6 weeks or less and wherein the hepatitis C virus is genotype 1, 2, 3, 4, 5, or 6.

37. The method of claim 36, wherein the hepatitis C virus is genotype 1a or 1b.

38. The method of claim 27, wherein the tablet is administered for about 4 weeks or less and wherein the hepatitis C virus is genotype 1, 2, 3, 4, 5, or 6.

39. The method of claim 38, wherein the hepatitis C virus is genotype 1a or 1b.

40. The method of claim 27, wherein the tablet is administered once daily for about 12 weeks and wherein the hepatitis C virus is genotype 1a, 1b, 2a, 2b, 2c, 2d, 3a, 3b, 3c, 3d, 3e, 3f, 4a, 4b, 4c, 4d, 4e, 4f, 4g, 4h, 4i, 5a, or 6a.

41. The method of claim 27, wherein the tablet is administered once daily for about 8 weeks and wherein the hepatitis C virus is genotype 1a, 1b, 2a, 2b, 2c, 2d, 3a, 3b, 3c, 3d, 3e, 3f, 4a, 4b, 4c, 4d, 4e, 4f, 4g, 4h, 4i, 5a, or 6a.

42. The method of claim 27, wherein the method does not include administering ribavirin to the patient.

43. The method of claim 27, wherein the method does not include administering interferon or ribavirin to the patient.

44. The method of claim 27, wherein the tablet is administrable after taking food.

\* \* \* \* \*

UNITED STATES PATENT AND TRADEMARK OFFICE
CERTIFICATE OF CORRECTION

| | | |
|---|---|---|
| PATENT NO. | : 11,338,007 B2 | Page 1 of 1 |
| APPLICATION NO. | : 16/306424 | |
| DATED | : May 24, 2022 | |
| INVENTOR(S) | : Ben Chal et al. | |

It is certified that error appears in the above-identified patent and that said Letters Patent is hereby corrected as shown below:

In the Claims

In Claim 1, Column 100, Lines 41-59, please replace " 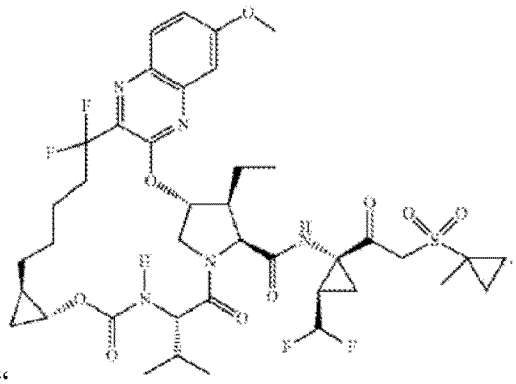 "

with -- 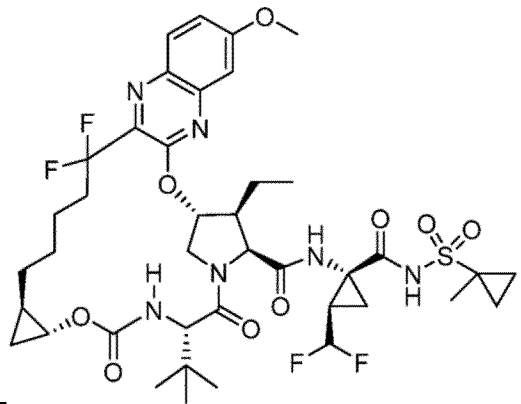 ,--

Signed and Sealed this
Twelfth Day of July, 2022

Katherine Kelly Vidal
*Director of the United States Patent and Trademark Office*